(12) United States Patent
Minami et al.

(10) Patent No.: US 7,544,758 B2
(45) Date of Patent: *Jun. 9, 2009

(54) PROPYLENE POLYMER AND COMPOSITION CONTAINING THE SAME, MOLDED OBJECT AND LAMINATE COMPRISING THESE, AND PROCESSES FOR PRODUCING PROPYLENE POLYMER AND COMPOSITION CONTAINING THE SAME

(75) Inventors: Yutaka Minami, Ichihara (JP); Masato Kijima, Ichiharashi (JP); Takuji Okamoto, Ichiharashi (JP); Yasushi Seta, Ichiharashi (JP); Yasuhiro Mogi, Ichiharashi (JP); Tsuyoshi Ota, Ichiharashi (JP); Hideo Funabashi, Ichiharashi (JP); Takashi Kashiwamura, Ichiharashi (JP); Noriyuki Tani, Ichiharashi (JP); Masami Kanamaru, Ichiharashi (JP); Koji Kakigami, Ichiharashi (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 49 days.

This patent is subject to a terminal disclaimer.

(21) Appl. No.: 11/514,257

(22) Filed: Sep. 1, 2006

(65) Prior Publication Data

US 2006/0293471 A1    Dec. 28, 2006

Related U.S. Application Data

(62) Division of application No. 10/855,964, filed on May 28, 2005, now Pat. No. 7,199,202, which is a division of application No. 09/719,552, filed as application No. PCT/JP99/03405 on Jun. 25, 1999, now Pat. No. 6,906,155.

(30) Foreign Application Priority Data

| Jun. 25, 1998 | (JP) | ................... 10-179252 |
| Jul. 24, 1998 | (JP) | ................... 10-210115 |
| Aug. 26, 1998 | (JP) | ................... 10-239872 |
| Oct. 23, 1998 | (JP) | ................... 10-302892 |
| Jan. 5, 1999 | (JP) | ................... 11-000283 |
| Mar. 3, 1999 | (JP) | ................... 11-055025 |
| Mar. 24, 1999 | (JP) | ................... 11-079694 |
| Mar. 29, 1999 | (JP) | ................... 11-086491 |
| Mar. 31, 1999 | (JP) | ................... 11/093420 |
| Apr. 12, 1999 | (JP) | ................... 11/103996 |

(51) Int. Cl.
  *C08F 110/06* (2006.01)
  *C08F 10/06* (2006.01)
(52) U.S. Cl. .................. 526/351; 526/348; 528/396
(58) Field of Classification Search ............... 526/351, 526/348, 160, 170, 127, 943, 396; 528/396; 524/351

See application file for complete search history.

(56) References Cited

U.S. PATENT DOCUMENTS

| 4,335,225 | A |  | 6/1982 | Collette et al. |
| 5,200,131 | A |  | 4/1993 | Asanuma et al. |
| 5,239,022 | A | * | 8/1993 | Winter et al. ............. 526/127 |
| 5,496,902 | A | * | 3/1996 | Evertz et al. ............. 526/127 |
| 5,539,056 | A | * | 7/1996 | Yang et al. ............. 525/240 |
| 5,556,820 | A |  | 9/1996 | Fnabashi et al. |
| 5,585,509 | A |  | 12/1996 | Langhauser et al. |
| 5,597,881 | A |  | 1/1997 | Winter et al. |
| 5,708,101 | A |  | 1/1998 | Bercaw et al. |
| 5,747,621 | A |  | 5/1998 | Resconi et al. |
| 5,756,608 | A |  | 5/1998 | Langhauser et al. |
| 5,854,165 | A | * | 12/1998 | Yabunouchi et al. ....... 502/117 |
| 6,001,933 | A | * | 12/1999 | Tsuruoka et al. ......... 525/232 |
| 6,143,846 | A | * | 11/2000 | Herrmann et al. ......... 526/170 |
| 6,339,135 | B1 | * | 1/2002 | Kashiwamura et al. .... 526/160 |
| 6,414,090 | B2 |  | 7/2002 | Minami et al. |
| 6,723,446 | B2 | * | 4/2004 | Seta et al. ............. 428/515 |
| 6,734,270 | B1 |  | 5/2004 | Minami et al. |
| 6,770,355 | B1 |  | 8/2004 | Minami et al. |
| 6,784,250 | B2 | * | 8/2004 | Kijima ............. 525/191 |
| 6,797,774 | B2 | * | 9/2004 | Kijima ............. 525/55 |
| 7,173,099 | B1 | * | 2/2007 | Minami ............. 526/351 |
| 7,199,202 | B2 | * | 4/2007 | Minami et al. ........ 526/351 |
| 7,250,211 | B1 | * | 7/2007 | Minami et al. ........ 428/355 EN |
| 2006/0293471 | A1 |  | 12/2006 | Minami et al. |

FOREIGN PATENT DOCUMENTS

| EP | 0604917 A2 | 7/1994 |
| EP | 0646624 A1 | 4/1995 |
| EP | 0 670 349 | 9/1995 |
| EP | 0682042 A1 | 11/1995 |
| EP | 0 818 458 | 1/1998 |
| EP | 0889089 A1 | 1/1999 |
| EP | 0903356 A1 | 3/1999 |
| EP | 0911349 A1 | 4/1999 |

(Continued)

OTHER PUBLICATIONS

JP 57-12046 (Jan. 1982) abstract in English.*

(Continued)

*Primary Examiner*—David Wu
*Assistant Examiner*—Rip A. Lee
(74) *Attorney, Agent, or Firm*—Oblon, Spivak, McClelland, Maier & Neustadt, P.C.

(57) ABSTRACT

A propylenic polymer according to the present invention or a composition thereof have an excellent melt flowability and contains a less amount of stickiness-causing components, and also has a low modulus and is pliable, and is capable of providing a transparent molded article, thus being useful as a substitute for a pliable vinyl chloride resin. In addition, a molded article made therefrom exhibits an excellent heat seal performance at a low temperature, and is excellent in terms of transparency and rigidity. Specifically, it has an isotactic pentad fraction (mmmm), which indicates a stereoregulariry, of 30 to 80%, a molecular weight distribution (Mw/Mn) of 3.5 or less and an intrinsic viscosity [η] of 0.8 to 5 dl/g.

3 Claims, No Drawings

FOREIGN PATENT DOCUMENTS

| | | | |
|---|---|---|---|
| EP | 0970974 A1 | | 1/2000 |
| EP | 1006149 A1 | | 6/2000 |
| JP | 42-7151 | * | 3/1966 |
| JP | 57-12046 | * | 1/1982 |
| JP | 02-206633 | | 8/1990 |
| JP | 5-112611 | | 5/1993 |
| JP | 6-100613 | | 4/1994 |
| JP | 7-102013 | | 4/1995 |
| JP | 07-126454 | | 5/1995 |
| JP | 8-20605 | | 1/1996 |
| JP | 8-231640 | | 9/1996 |
| JP | 09-509982 | | 10/1997 |
| JP | 9-309982 | | 12/1997 |
| JP | 10-259207 | | 9/1998 |
| JP | 11-1584 | | 1/1999 |
| JP | 11001584 A | | 1/1999 |
| JP | 11166084 A | | 6/1999 |
| WO | WO 95/09172 | * | 4/1995 |
| WO | WO 96/30380 | * | 10/1996 |
| WO | 9909098 A1 | | 2/1999 |
| WO | WO 02/079272 A | | 10/2002 |
| WO | WO 02/079272 A1 | | 10/2002 |

OTHER PUBLICATIONS

JP 42-7151 (Mar. 1996) abstract in English.*
Hu et al. Macromolecules 1998, 31, 6908-6916.*
Mengele, W.; Diebold, J.; Troll, C.; Roll, W.; Brintzinger, H.-H. Organometallics, 1993, 12, 1931-1935.
Veghini, D.; Henling, L. M.; Burkhardt, T. J.; Bercaw, J. E.; J. Am. Chem. Soc.; 1999, 121, 564-573.
U.S. Appl. No. 11/588,208, filed Oct. 27, 2006, Okamoto et al.
Patent Family Search for US 7,173,099 from espacenet.com dated Aug. 28, 2008, 7 pages.
Patent Family Search for US 7,199,202 from espacenet.com dated Aug. 28, 2008, 7 pages.

* cited by examiner

PROPYLENE POLYMER AND COMPOSITION CONTAINING THE SAME, MOLDED OBJECT AND LAMINATE COMPRISING THESE, AND PROCESSES FOR PRODUCING PROPYLENE POLYMER AND COMPOSITION CONTAINING THE SAME

This application is a divisional of Ser. No. 10/855,964, filed May 28, 2005, now U.S. Pat. No. 7,199,202, which is a divisional of Ser. No. 09/719,552, filed Feb. 28, 2001, now U.S. Pat. No. 6,906,155, which is a 371 of PCT/JP99/03405, filed Jun. 25, 1999.

TECHNICAL FIELD

The present invention relates to a propylenic polymer which has an excellent melt flowability, contains a less amount of stickiness-causing components, has a low modulus and is pliable, and is capable of providing a transparent molded article, thus being useful as a substitute for a pliable vinyl chloride resin, a method for producing the same, a propylenic resin composition and a molded article made therefrom; a propylenic polymer composition which is excellent in terms of heat seal performance at a low temperature and moldability, and is capable of providing a film or a molded article which is excellent in terms of transparency and rigidity, as well as a molded article, a film or a laminated article made therefrom.

More particularly, the invention relates to a polypropylenic polymer composition which is obtained by a polymerization using a metallocene catalyst, has a narrow molecular weight distribution and exhibits an excellent moldability and secondary processability (low temperature heat seal performance) and also to a film made therefrom.

Furthermore, the invention relates to a transition metal compound and a polymerization catalyst employed preferably in a polymerization of an olefinic resins mentioned above.

BACKGROUND OF THE INVENTION

A vinyl chloride resin which has widely been employed as a pliable synthetic resin is known to generate a hazardous material during a combustion process, because of which a development of a substitute of a vinyl chloride resin is desired. One substitute for a pliable vinyl chloride resin is a propylenic polymer. While a propylenic polymer is produced in the presence of various catalyst, a propylenic polymer produced using a conventional catalyst system involves a disadvantageously increased amount of stickiness-causing components as a result of an attempt to impart a pliability (i.e. a low modulus). The increase in the amount of stickiness-causing atactic polypropylenes (hereinafter referred to as APP) leads to a deteriorated surface condition of a molded article obtained.

On the other hand, an application of a molded article in a form of a sheet or a film to a food product or a medical use may involve various problems. Accordingly, a propylenic polymer having a more satisfactorily weighed relationship between a low level of the modulus and the quantity of the stickiness-causing components is desired.

Since a propylenic polymer generally has a greater supercooling degree required for initiating a crystallization when compared with an ethylenic polymer, it provides a resin characterized by a lower crystallization temperature even if it has a same melting point. Accordingly, it may cause a problematically poor molding performance especially with a heat seal grade product having a low melting point. In an attempt to reduced the heat seal temperature, a method for reducing the stereoregularity index of a propylenic polymer is employed, or a copolymer with other olefins is used. Among those produced in such attempt, a conventional low stereoregular propylenic polymer obtained by using a Ziegler catalyst system has a broad stereoregularity distribution, and an attempt to obtain a pliable polymer (i.e. having a low modulus) results in an increase in the amount of stickiness-causing components, including one derived from APP which causes a poor physical property of a low stereoregular propylenic polymer, such as a poor surface condition of a molded article once such propylenic polymer is molded. Thus, it is desired to obtain a film, a fiber, a sheet or a molded article in which a low melting point and a very narrow stereoregularity distribution possessed by a low stereoregular polymer are still preserved and which has an excellent transparency and a low temperature heat seal performance and is highly rigid.

Other disadvantageous characteristics of a propylenic polymer include a high glass transition temperature Tg (about 0° C.), due to which the impact resistance at a low temperature (e.g. −30° C.) is problematically poor.

Recently, an olefin polymer produced by using a metallocene catalyst was also proposed, but a metallocene catalyst has a limited active center, which results in a narrow molecular weight distribution of a polymer obtained, which is suitable to a precise injection molding or an ordinary injection molding and can preferably be employed to mold a fiber, but is not always satisfactory when applied to a heat molding, an extrusion, a blow molding or a molding of a foam or a film. An LLDPE (linear low density polyethylene) obtained using a metallocene also involves the problems of poor transparency and surface condition, although it has a pliability.

DISCLOSURE OF THE INVENTION

An objective of the invention is to provide a propylenic polymer which has an excellent melt flowability, contains a less amount of stickiness-causing components, has a low modulus and is pliable, and is capable of providing a transparent molded article, a method for producing the same, a propylenic resin composition and a molded article made therefrom; a propylenic polymer composition which is excellent in terms of heat seal performance at a low temperature and moldability, and is capable of providing a film or a molded article which is excellent in terms of transparency and rigidity, as well as a molded article, a resin modifier, a film or a laminated article made therefrom.

Another objective of the invention is to provide a polypropylenic polymer composition which is obtained by a polymerization using a metallocene catalyst, has a narrow molecular weight distribution and exhibits an excellent moldability and secondary processability (low temperature heat seal performance) as well as a film made threrefrom, and also to provide a transition metal compound, a polymerization catalyst and a method for production which are employed preferably in a polymerization of an olefinic resins mentioned above.

We made an effort and discovered that various parameters such as an isotactic pentad fraction (mmmm), molecular distribution, intrinsic viscosity [η] and stereoregularity index (P) are related closely to various properties of a propylenic polymer, and finally established the invention.

Thus, the present application consists of the following inventions.

I. First Invention

1. A propylenic polymer which is a propylene homopolymer having an isotactic pentad fraction (mmmm), which indicates a stereoregulariry, of 30 to 80%, a molecular weight distribution (Mw/Mn) of 3.5 or less and an intrinsic viscosity [η] of 0.8 to 5 dl/g;

2. A propylenic polymer which is a propylenic copolymer produced by copolymerising propylene and ethylene and/or an α-olefin having 4 to 20 carbon atoms having a stereoregularity index (P) of 55 to 90% by mole, a molecular weight distribution (Mw/Mn) of 3.5 or less and an intrinsic viscosity [η] of 0.8 to 5 dl/g;

3. A method for producing a propylenic polymer of above 1 wherein propylene is homopolymerized in the presence of a polymerization catalyst comprising (A) a transition metal compound represented by Formula (I)

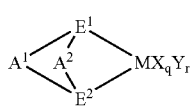 (I)

in which M denotes a metal element of Group 3 to Group 10 or of lanthanoids in the periodic table, each of $E^1$ and $E^2$ denotes a ligand selected from a substituted cyclopentadienyl group, an indenyl group, a substituted indenyl group, a heterocyclopentadienyl group, a substituted heterocyclopentadienyl group, an amide group, a phosphide group, a hydrocarbon group and a silicon-containing group, is crosslinked with each other via $A^1$ and $A^2$ and may be same to or different from each other, X denotes a σ-binding ligand, and, when two or more Xs are present they may be same or different, and each may be crosslinked with other X, $E^1$, $E^2$ or Y; Y denotes a Lewis base, and, when two or more Ys are present they may be same or different, and each may be crosslinked with other Y, $E^1$, $E^2$ or X, each of $A^1$ and $A^2$ denotes a divalent crosslinking group having two ligands including a hydrocarbon group having 1 to 20 carbon atoms, a halogen-containing hydrocarbon group having 1 to 20 carbon atoms, a silicon-containing group, a germanium-containing group, a tin-containing group, —O—, —CO—, —S—, —$SO_2$—, —Se—, —NR—, —PR—, —P(O)R—, —BR— or -AlR— wherein R is a hydrogen atom, a halogen atom, a hydrocarbon group having 1 to 20 carbon atoms and a halogen-containing hydrocarbon group having 1 to 20 carbon atoms, and each may be same to or different from each other; q is an integer of 1 to 5 and represents [(valency of M)–2], and r is an integer of 0 to 3 and (B) a component selected from (B-1) a compound capable of forming an ionic complex by reacting with a transition metal compound as a component (A) or a derivative thereof and (B-2) an aluminoxane;

4. A method for producing a propylenic polymer of above 2 wherein propylene and ethylene and/or an α-olefin having 4 to 20 carbon atoms are copolymerized in the presence of a polymerization catalyst comprising a transition metal compound represented by Formula (I) shown above and (B) a component selected from (B-1) a compound capable of forming an ionic complex by reacting with a transition metal compound as a component (A) or a derivative thereof and (B-2) an aluminoxane;

5. A molded article made from a propylenic polymer described above;

6. A propylenic polymer composition obtained by incorporating into a propylenic polymer of above 1 a nucleating agent at a level of 10 ppm or higher;

7. A propylenic polymer composition obtained by incorporating into a propylenic polymer of above 2 a nucleating agent at a level of 10 ppm or higher;

8. A propylenic polymer composition of above 6 or 7 wherein a propylenic polymer has a crystallization temperature (Tc(° C.)) and a melting point (Tm (° C.)), as determined by a differential scanning calorimeter, which are in the relationship represented by the formula: Tc≧0.75Tm–15;

9. A molded article and a film made from a propylenic polymer composition of any of 6 to 8 described above; and, 10. A laminated article comprising as at least one layer component a propylenic polymer composition of any of 6 to 8 described above.

II. Second Invention

1. A propylenic polymer satisfying the following requirements (1) and (2):
(1) the amount of the components which are dissolved out into hexane at 25° C. (H25) ranges from 0 to 80% by weight; and,
(2) no melting point (Tm(° C.)) is observed in DSC or, when any Tm is observed then the Tm and the fusion endothermic calorie ΔH(J/gr.) are in the relationship represented by the following formula:

ΔH≧6×(Tm–140)

2. A propylenic polymer satisfying the following requirements (1) to (3):
(1) the amount of the components which are dissolved out at 25° C. or lower (W25) in a temperature-raising chromatography ranges from 20 to 100% by weight;
(2) the amount of the components which are dissolved out into hexane at 25° C. (H25) ranges from 0 to 80% by weight; and,
(3) no melting point (Tm(° C.)) is observed in DSC or, when any Tm is observed then the Tm and the fusion endothermic calorie ΔH(J/gr.) are in the relationship represented by the following formula:

ΔH≧6×(Tm–140);

3. A propylene homopolymer satisfying the following requirements (1) to (3):
(1) the meso-pentad fraction (mmmm (in percentage terms by mole)) ranges from 20 to 60% by mole;
(2) the racemi-pentad fraction (rrrr) and (1–mmmm) are in the relationship represented by the following formula:

[rrrr/(1–mmmm)]≦0.1 wherein the racemi-pentad fraction (rrrr) and the meso-pentad fraction (mmmm) are not in percentage terms; and,
(3) the amount of the components which are dissolved out at 25° C. or lower (W25) in a temperature-raising chromatography ranges from 20 to 100% by weight;

4. A propylenic copolymer satisfying the following requirements (1) and (2):
(1) the stereoregularity index (P) determined by a $^{13}$C-NMR ranges from 55 to 90% by mole; and,
(2) the amount of the components which are dissolved out at 25° C. or lower (W25) in a temperature-raising chromatography ranges from 20 to 100% by weight.

5. A propylene homopolymer of above 1 or 2 or a propylenic copolymer of above 4 having a molecular weight distribution (Mw/Mn) determined by a gel permeation chromatography (GPC) of 4 or less and/or an intrinsic viscosity [η] determined in a tetralin solvent at 135° C. of 0.5 to 15.0 dl/g;

6. A method for producing a propylene homopolymer of above 1, 2, 3 or 5 wherein propylene is homopolymerized in the presence of a polymerization catalyst comprising (A) a transition metal compound represented by Formula (I) shown below and (B) a component selected from (B-1) a compound capable of forming an ionic complex by reacting with a transition metal compound as a component (A) or a derivative thereof and (B-2) an aluminoxane;

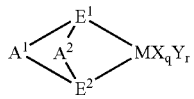

(I)

in which M denotes a metal element of Group 3 to Group 10 or of lanthanoids in the periodic table, each of $E^1$ and $E^2$ denotes a ligand selected from a substituted cyclopentadienyl group, an indenyl group, a substituted indenyl group, a heterocyclopentadienyl group, a substituted heterocyclopentadienyl group, an amide group, a phosphide group, a hydrocarbon group and a silicon-containing group, is crosslinked with each other via $A^1$ and $A^2$ and may be same to or different from each other, X denotes a σ-binding ligand, and, when two or more Xs are present they may be same or different, and each may be crosslinked with other X, $E^1$, $E^2$ or Y; Y denotes a Lewis base, and, when two or more Ys are present they may be same or different, and each may be crosslinked with other Y, $E^1$, $E^2$ or X, each of $A^1$ and $A^2$ denotes a divalent crosslinking group having two ligands including a hydrocarbon group having 1 to 20 carbon atoms, a halogen-containing hydrocarbon group having 1 to 20 carbon atoms, a silicon-containing group, a germanium-containing group, a tin-containing group, —O—, —CO—, —S—, —SO$_2$—, —Se—, —NR—, —PR—, —P(O)R—, —BR— or -AlR— wherein R is a hydrogen atom, a halogen atom, a hydrocarbon group having 1 to 20 carbon atoms and a halogen-containing hydrocarbon group having 1 to 20 carbon atoms, and each may be same to or different from each other; q is an integer of 1 to 5 and represents [(valency of M)–2], and r is an integer of 0 to 3;

7. A method for producing a propylenic copolymer of above 4 or 5 wherein propylene and ethylene and/or an α-olefin having 4 to 20 carbon atoms are copolymerized in the presence of a polymerization catalyst comprising (A) a transition metal compound represented by Formula (I) shown below and (B) a component selected from (B-1) a compound capable of forming an ionic complex by reacting with a transition metal compound as a component (A) or a derivative thereof and (B-2) an aluminoxane;

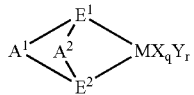

(I)

in which M denotes a metal element of Group 3 to Group 10 or of lanthanoids in the periodic table, each of $E^1$ and $E^2$ denotes a ligand selected from a substituted cyclopentadienyl group, an indenyl group, a substituted indenyl group, a heterocyclopentadienyl group, a substituted heterocyclopentadienyl group, an amide group, a phosphide group, a hydrocarbon group and a silicon-containing group, is crosslinked with each other via $A^1$ and $A^2$ and may be same to or different from each other, X denotes a σ-binding ligand, and, when two or more Xs are present they may be same or different, and each may be crosslinked with other X, $E^1$, $E^2$ or Y; Y denotes a Lewis base, and, when two or more Ys are present they may be same or different, and each may be crosslinked with other Y, $E^1$, $E^2$ or X, each of $A^1$ and $A^2$ denotes a divalent crosslinking group having two ligands including a hydrocarbon group having 1 to 20 carbon atoms, a halogen-containing hydrocarbon group having 1 to 20 carbon atoms, a silicon-containing group, a germanium-containing group, a tin-containing group, —O—, —CO—, S—, —SO$_2$—, —Se—, —NR—, —PR—, —P(O)R—, —BR— or -AlR— wherein R is a hydrogen atom, a halogen atom, a hydrocarbon group having 1 to 20 carbon atoms and a halogen-containing hydrocarbon group having 1 to 20 carbon atoms, and each may be same to or different from each other; q is an integer of 1 to 5 and represents [(valency of M)–2], and r is an integer of 0 to 3;

8. A propylenic resin composition obtained by adding a nucleating agent to a propylenic polymer, a propylene homopolymer or a propylenic copolymer of any of above 1 to 5;

9. A molded article obtained by molding a propylenic polymer, a propylene homopolymer, a propylenic copolymer or a propylenic resin composition of any of above 1 to 5 or 8; and, 10. A propylenic resin modifier comprising a propylenic polymer, a propylene homopolymer or a propylenic copolymer of any of above 1 to 5.

III. Third Invention

1. A propylenic polymer satisfying the following requirements (1) to (3):
(1) the amount of the components which are dissolved out into hexane at 25° C. (H25) ranges from 0 to 80% by weight;
(2) no melting point (Tm(° C.)) is observed in DSC or, when any Tm is observed then the Tm and the fusion endothermic calorie ΔH(J/gr.) are in the relationship represented by the following formula:

$\Delta H \geq 6 \times (Tm - 140)$; and, (3) the molecular weight distribution (Mw/Mn) determined by a gel permeation chromatography (GPC) ranges from 2.5 to 14.0 and the intrinsic viscosity [η] determined in a decalin solvent at 135° C. ranges from 0.5 to 15.0 dl/g;

2. A propylene homopolymer satisfying the following requirements (1) to (3):
(1) the meso-pentad fraction (mmmm (in percentage terms by mole)) ranges from 20 to 85% by mole;
(2) the racemi-pentad fraction (rrrr) and (1–mmmm) are in the relationship represented by the following formula:

$[rrrr/(1-mmmm)] \leq 0.1$ wherein the racemi-pentad fraction (rrrr) and the meso-pentad fraction (mmmm) are not in percentage terms; and,
(3) the molecular weight distribution (Mw/Mn) determined by a gel permeation chromatography (GPC) ranges from 2.5 to 14.0 and the intrinsic viscosity [η] determined in a decalin solvent at 135° C. ranges from 0.5 to 15.0 dl/g;

3. A propylenic copolymer satisfying the following requirements (1) and (2):
(1) the stereotegularity index (P) determined by a $^{13}$C-NMR ranges from 55 to 90% by mole; and, (2) the molecular weight distribution (Mw/Mn) determined by a gel permeation chromatography (GPC) ranges from 2.5 to 14.0 and the intrinsic viscosity [η] determined in a decalin solvent at 135° C. ranges from 0.5 to 15.0 dl/g;

4. A propylenic polymer, a propylene homopolymer or a propylenic copolymer of any of above 1 to 3 having a complex viscosity coefficient [η*] (Pa·s) and an intrinsic viscosity [η]

(dl/g) at the frequency ω, based on the frequency distribution determination of the melt viscoelasticity, of 100 rad/sec which are in the relationship represented by the formula:

$$\eta^* < 159\eta + 743;$$

5. A method for producing a propylenic polymer, a propylene homopolymer or a propylenic copolymer of any of above 1 to 4 wherein a polymerization is effected by a multi-step polymerization process comprising at least a step in which propylene is homopolymerized, or propylene and ethylene and/or an α-olefin having 4 to 20 carbon atoms are copolymerized in the presence of a polymerization catalyst comprising:

(A) a transition metal compound represented by Formula (I) shown below and (B) a component selected from (B-1) a compound capable of forming an ionic complex by reacting with a transition metal compound as a component (A) or a derivative thereof and (B-2) an aluminoxane.

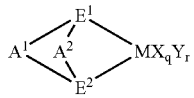

(I)

in which M denotes a metal element of Group 3 to Group 10 or of lanthanoids in the periodic table, each of $E^1$ and $E^2$ denotes a ligand selected from a substituted cyclopentadienyl group, an indenyl group, a substituted indenyl group, a heterocyclopentadienyl group, a substituted heterocyclopentadienyl group, an amide group, a phosphide group, a π-binding hydrocarbon group and a silicon-containing group, is crosslinked with each other via $A^1$ and $A^2$ and may be same to or different from each other, X denotes a σ-binding ligand, and, when two or more Xs are present they may be same or different, and each may be crosslinked with other X, $E^1$, $E^2$ or Y; Y denotes a Lewis base, and, when two or more Ys are present they may be same or different, and each may be crosslinked with other Y, $E^1$, $E^2$ or X, each of $A^1$ and $A^2$ denotes a divalent crosslinking group having two ligands including a hydrocarbon group having 1 to 20 carbon atoms, a halogen-containing hydrocarbon group having 1 to 20 carbon atoms, a silicon-containing group, a germanium-containing group, a tin-containing group, —O—, —CO—, —S—, —SO₂—, —Se—, —NR—, —PR—, —P(O)R—, —BR— or -AlR— wherein R is a hydrogen atom, a halogen atom, a hydrocarbon group having 1 to 20 carbon atoms and a halogen-containing hydrocarbon group having 1 to 20 carbon atoms, and each may be same to or different from each other; q is an integer of 1 to 5 and represents [(valency of M)–2], and r is an integer of 0 to 3; and, 6. A molded article obtained by molding a propylenic polymer, a propylene homopolymer or a propylenic copolymer of any of above 1 to 4.

IV. Fourth Invention

1. A propylenic resin composition comprising a propylene homopolymer (a) and/or a propylenic copolymer (a') and satisfying the following requirements [1] to [3]:

[1] the amount of the components extracted with a boiling diethylether ranges 1 to 99% by weight;

[2] in a propylene homopolymer (a), a component extracted with a boiling diethylether satisfies the following requirements (1) to (3):

(1) the meso-pentad fraction (mmmm (in percentage terms by mole)) ranges from 20 to 60% by mole;

(2) the racemi-pentad fraction (rrrr) and (1–mmmm) are in the relationship represented by the following formula:

$$[rrrr/(1-mmmm)] \leq 0.1$$

wherein the racemi-pentad fraction (rrrr) and the meso-pentad fraction (mmmm) are not in percentage terms; and, (3) the amount of the components which are dissolved out at 25° C. or lower (W25) in a temperature-raising chromatography ranges from 20 to 100% by weight; and,

[3] in a propylenic copolymer (a'), a component extracted with a boiling diethylether satisfies the following requirements (4) and (5):

(4) the stereoregularity index (P) determined by a ¹³C-NMR ranges from 55 to 90% by mole; and, (5) the amount of the components which are dissolved out at 25° C. or lower (W25) in a temperature-raising chromatography ranges from 20 to 100% by weight;

2. A propylenic resin composition comprising 1 to 99% by weight of a propylenic polymer [I] and 99 to 1% by weight of a polyolefin [II] in which said propylenic polymer [1] satisfies the following requirements (1) to (3):

(1) the amount of the components which are dissolved out at 25° C. or lower (W25) in a temperature-raising chromatography ranges from 20 to 100% by weight;

(2) the amount of the components which are dissolved out into hexane at 25° C. (H25) ranges from 0 to 80% by weight; and, (3) no melting point (Tm(° C.)) is observed in DSC or, when any Tm is observed then the Tm and the fusion endothermic calorie ΔH(J/gr.) are in the relationship represented by the following formula:

$$\Delta H \geq 6 \times (Tm - 140);$$

3. A propylenic resin composition comprising 1 to 99% by weight of a propylene homopolymer (a) and 99 to 1% by weight of a polyolefin [II] in which said propylene homopolymer (a) satisfies the following requirements (1) to (3):

(1) the meso-pentad fraction (mmmm (in percentage terms by mole)) ranges from 20 to 60% by mole;

(2) the racemi-pentad fraction (rrrr) and (1–mmmm) are in the relationship represented by the following formula:

$$[rrrr/(1-mmmm)] \leq 0.1$$

wherein the racemi-pentad fraction (rrrr) and the meso-pentad fraction (mmmm) are not in percentage terms; and, (3) the amount of the components which are dissolved out at 25° C. or lower (W25) in a temperature-raising chromatography ranges from 20 to 100% by weight;

4. A propylenic resin composition comprising 1 to 99% by weight of a propylenic copolymer (a') and 99 to 1% by weight of a polyolefin [II] in which said propylene homopolymer (a') satisfies the following requirements (1) and (2):

(1) the stereoregularity index (P) determined by a ¹³C-NMR ranges from 55 to 90% by mole; and, (2) the amount of the components which are dissolved out at 25° C. or lower (W25) in a temperature-raising chromatography ranges from 20 to 100% by weight;

5. A propylenic resin composition of any of above 1 to 4 in which a propylene homopolymer (a) and a propylenic copolymer (a') each independently satisfy the following requirements (1) and/or (2):

(1) the molecular weight distribution (Mw/Mn) determined by a gel permeation chromatography (GPC) is 4 or less; and, (2) the intrinsic viscosity [η] determined in a tetralin solvent at 135° C. ranges from 0.5 to 15.0 dl/g;

6. A propylenic resin composition of any of above 2 to 5 in which a polyolefin [II] has a crystallization temperature (Tc(° C.)) and consists of a propylenic polymer (b) having a Tc≧0° C. and/or an olefin polymer (b') having a glass transition temperature Tg≦−10° C.;

7. A method for producing a propylenic resin composition of any of above 1 to 6 comprising homopolymerizing propylene or copolymerizing propylene and ethylene and/or an α-olefin having 4 to 20 carbon atoms in the presence of a co-catalyst comprising a metallocene catalyst comprising:
(A) a transition metal compound represented by Formula (I) shown below and (B) (B-1) a compound capable of forming an ionic complex by reacting with a transition metal compound as a component (A) or a derivative thereof or (B-2) an aluminoxane and at least one other catalyst.

(I)

in which M denotes a metal element of Group 3 to Group 10 or of lanthanoids in the periodic table, each of $E^1$ and $E^2$ denotes a ligand selected from a substituted cyclopentadienyl group, an indenyl group, a substituted indenyl group, a heterocyclopentadienyl group, a substituted heterocyclopentadienyl group, an amide group, a phosphide group, a hydrocarbon group and a silicon-containing group, is crosslinked with each other via $A^1$ and $A^2$ and may be same to or different from each other, X denotes a σ-binding ligand, and, when two or more Xs are present they may be same or different, and each may be crosslinked with other X, $E^1$, $E^2$ or Y; Y denotes a Lewis base, and, when two or more Ys are present they may be same or different, and each may be crosslinked with other Y, $E^1$, $E^2$ or X, each of $A^1$ and $A^2$ denotes a divalent crosslinking group having two ligands including a hydrocarbon group having 1 to 20 carbon atoms, a halogen-containing hydrocarbon group having 1 to 20 carbon atoms, a silicon-containing group, a germanium-containing group, a tin-containing group, —O—, —CO—, —S—, —$SO_2$—, —Se—, —NR—, —PR—, —P(O)R—, —BR— or -AlR— wherein R is a hydrogen atom, a halogen atom, a hydrocarbon group having 1 to 20 carbon atoms and a halogen-containing hydrocarbon group having 1 to 20 carbon atoms, and each may be same to or different from each other; q is an integer of 1 to 5 and represents [(valency of M)−2], and r is an integer of 0 to 3;

8. A method for producing a propylenic resin composition of any of above 1 to 6 comprising homopolymerizing propylene or copolymerizing propylene and ethylene and/or an α-olefin having 4 to 20 carbon atoms in a multi-step polymerization process comprising at least a process employing a metallocene catalyst of above 7; and, 9. A molded article made from a propylenic resin composition of any of above 1 to 6.

V. Fifth Invention

1. A propylenic resin composition having a peak top temperature (Tc(° C.)) on the side of the maximum temperature on a crystallization curve and a differential calorie (ΔHm(J/g)) on a fusion curve, as determined by a differential scanning calorimeter (DSC), which are in the relationship represented by the following formula (1-1):

$$Tc \geq (1/4) \cdot \Delta Hm + 90 \qquad (1\text{-}1)$$

and having a frequency (ω(rad/sec)) at which the storage modulus (G'(Pa)) and the loss elasticity (G"(Pa)) based on the frequency distribution determination of the melt viscoelasticity become equal to each other and a ΔHm, which are in the relationship represented by the following formula (2-1)

$$\omega \leq (1/10) \cdot \Delta Hm + 15 \qquad (2\text{-}1)$$

2. A propylenic resin composition of above 1 comprising 1 to 99% by weight of a propylenic polymer [I] satisfying the following requirements (1) to (3) and 99 to 1% by weight of a crystalline propylenic polymer [II]:
(1) the amount of the components which are dissolved out at 25° C. or lower (W25) in a temperature-raising chromatography ranges from 20 to 100% by weight;
(2) the amount of the components which are dissolved out into hexane at 25° C. (H25) ranges from 0 to 80% by weight; and,
(3) no melting point (Tm(° C.)) is observed in DSC or, when any Tm is observed then the Tm and the fusion endothermic calorie ΔH(J/g) are in the relationship represented by the following formula:

$$\Delta H \geq 6 \times (Tm - 140);$$

3. A propylenic resin composition of above 1 comprising 1 to 99% by weight of a propylene homopolymer [a] satisfying the following requirements (1) to (3) and 99 to 1% by weight of a crystalline propylenic polymer [II]:
(1) the meso-pentad fraction (mmmm (in percentage terms by mole)) ranges from 20 to 60% by mole;
(2) the racemi-pentad fraction (rrrr) and (1−mmmm) are in the relationship represented by the following formula:

$$[rrrr/(1-mmmm)] \leq 0.1$$

wherein the racemi-pentad fraction (rrrr) and the meso-pentad fraction (mmmm) are not in percentage terms; and,
(3) the amount of the components which are dissolved out at 25° C. or lower (W25) in a temperature-raising chromatography ranges from 20 to 100% by weight;

4. A propylenic resin composition of above 2 or 3 in which a propylenic polymer [I] of above 2 or a propylene homopolymer [a] of above 3 satisfies the following requirements (1) and/or (2):
(1) the molecular weight distribution (Mw/Mn) determined by a gel permeation chromatography (GPC) is 4 or less; and,
(2) the intrinsic viscosity [η] determined in a tetralin solvent at 135° C. ranges from 0.5 to 15.0 dl/g;

5. A propylenic resin composition of any of above 2 to 4 in which a propylenic polymer [I] of above 2 or a propylene homopolymer [a] of above 3 exhibits no melting point (Tm(° C.)) in DSC;

6. A film or a sheet having a layer produced by a propylenic resin composition of any of above 1 to 5; and, 7. A film or a sheet of above 6 whose haze determined in accordance with JIS K7105 is 10% or less.

VI. Sixth Invention

1. A polypropylenic resin composition comprising (A) 99 to 50% by weight of a propylene homopolymer having the following characteristics (a1) to (a4):
(a1) the intrinsic viscosity [η] is 0.5 to 5.0 dl/g;
(a2) the molecular weight distribution (Mw/Mn) is 3.5 or less;
(a3) the isotactic pentad fraction (mmmm (in percentage terms by mole)) is 40 to 99% by mole; and,
(a4) the isotactic pentad fraction (mmmm (in percentage terms by mole)) and the melting point (Tm(° C.)) are in the relationship represented by the following formula (I):

$$Tm \leq [mmmm] + 65 \qquad (I);$$

and, (B) 1 to 50% by weight of a propylene homopolymer capable of forming an eutectic with a component (A) under a rapid cooling condition upon film formation;

2. A polypropylenic resin composition of above 1 in which the crystallization temperature (TcB ° C.) of a component (B) determined by a differential scanning calorimetry is higher by 0 to 40° C. than that (TcA ° C.) of a component (A);

3. A polypopylenic resin composition comprising (A') 99 to 50% by weight of a propylenic polymer obtained by a polymerization using a metallocene catalyst which is a propylene homopolymer and has an isotactic pentad fraction (mmmm) of 80 to 99%, an intrinsic viscosity [η] of 1.0 to 2.0 dl/g and a molecular weight distribution (Mw/Mn ratio) of 3.5 or less, and, (B') 1 to 50% by weight of a propylenic polymer obtained by a polymerization using a metallocene catalyst which is a propylene homopolymer and has an intrinsic viscosity [η] of 0.01 to 1.0 dl/g and a molecular weight distribution (Mw/Mn ratio) of 3.5 or less; and, 4. A film formed using a propylenic polymer composition of any of above 1 to 3.

VII. Seventh Invention

1. A propylenic resin comprising:

99 to 50% by weight of a propylene-α-olefin copolymer (A') having the following characteristics (a1) to (a5):

(a1) the intrinsic viscosity [η] is 0.5 to 5.0 dl/g;
(a2) the molecular weight distribution (Mw/Mn) is 3.5 or less;
(a3) the stereoregularity index (P) is 50 to 99% by mole,
(a4) it is a propylenic random copolymer produced by using propylene and ethylene and/or an α-olefin having 4 to 20 carbon atoms, in which the ethylene and/or an α-olefin having 4 to 20 carbon atoms is contained in an amount of 0.1 to 30% by mole; and,
(a5) the amount of the components which are dissolved out at 0° C. or lower in a temperature-raising fractional chromatography is 10% by weight or less;

and, 1 to 50% by weight or a propylenic polymer (B') capable of forming an eutectic with a component (A') under a rapid cooling condition upon film formation;

2. A propylenic resin of above 1 in which the crystallization temperature (T'CB ° C.) of a component (B') determined by a differential scanning calorimetry is higher by 0 to 40° C. than that (T'CA ° C.) of a component (A');

3. A propylenic resin comprising a copolymer (A) of propylene and an α-olefin having 5 or more carbon atoms and a propylenic polymer (B) having a crystallization temperature determined by a differential scanning calorimetry which is higher than that of the component (A), wherein (A) is present in an amount of 55 to 99 parts by weight and (B) in an amount of 45 to 1 parts by weight;

4. A propylenic resin of above 1 in which the crystallization temperature (Tca ° C.) of a copolymer (A) and the crystallization temperature (Tcb ° C.) of a propylenic polymer (B), as determined by a differential scanning calorimetry, are in the relationship represented by the following formula:

$$Tcb-Tca \geq 20 \qquad (1);$$

5. A propylenic resin of above 3 or 4 in which the propylenic resin, when subjected to a temperature-raising fractional chromatography, satisfies the following requirements (1), (2) and (3):

(1) when the main elution peak temperature is Tp(° C.), the amount of the components dissolved out within the temperature range from (Tp−5) ° C. to (Tp+5) ° C. is 65% by weight or more;

(2) the amount of the components dissolved out at 0° C. or lower is 3% by weight or less; and, (3) the amount of the components dissolved out at Tp+10° C. or higher is 1 to 45% by weight, based on the total weight;

6. A propylenic resin of any of above 3 to 5 wherein the peak top temperature on the side of the maximum temperature on the crystallization curve of the propylenic resin, as determined by a differential scanning calorimetry, is 85° C. or higher.

7. A propylenic resin of any of above 3 to 5 wherein the peak top temperature on the side of the minimum temperature on the fusion curve of the propylenic resin, as determined by a differential scanning calorimetry, is 150° C. or lower;

8. A propylenic resin of any of above 3 to 7 wherein a copolymer (A), when subjected to a temperature-raising fractional chromatography, satisfies the following requirements (A-1) and (A-2):

(A-1) when the main elution peak temperature is Tp, the amount of the components dissolved out within the temperature range from (Tp−5) ° C. to (Tp+5) ° C. is 70 by weight or more; and, (A-2) the amount of the components dissolved out at 0° C. or lower is 3% by weight or less;

9. A propylenic resin of any of above 3 to 8 wherein a copolymer (A) satisfies at least one of the following requirements (A-3), (A-4) and (A-5):

(A-3) a copolymer (A) contains an α-olefin unit having 5 or more carbon atoms in an amount of 0.1 to 12% by mole;

(A-4) the stereoregularity index (P) of a copolymer (A) is 85% by mole or higher; and, (A-5) a copolymer (A) has an intrinsic viscosity [η] determined in a decalin at 135° C. ranges from 0.5 to 3.0 dl/g;

10. A propylenic resin of any of above 3 to 9 wherein the α-olefin unit having 5 or more carbon atoms which is a constituent unit of a copolymer (A) is at least one of 1-octene, 1-dodecene and 1-decene;

11. A film formed using a propylenic resin of any of above 1 to 10; and,

12. A laminated article comprising as at least one layer component a propylenic polymer of any of above 1 to 10.

VIII. Eighth Invention

1. A compound of a transition metal of Group 3 to Group 10 or of lanthanoids in the periodic table represented by Formula (VIII):

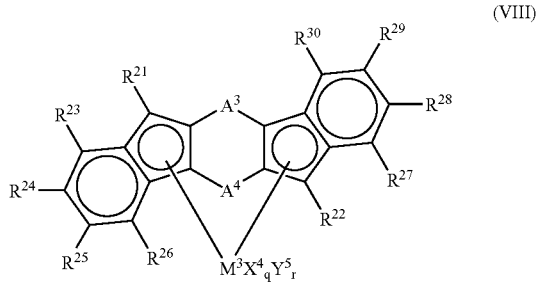

wherein each of $A^3$ and $A^4$ denotes a crosslinking consisting of Group XIV metal (C, Si, Ge, Sn) and may be same to or different from each other, $X^4$ denotes a σ-binding or π-binding ligand, and when two or more $X^4$ are present they may be same or different, $Y^5$ is a Lewis base and when two or more $Y^5$ are present they may be same or different, and each $Y^5$ may be crosslinked with other $Y^5$ or $X^4$, q is an integer of 1 to 5 and represents [(valency of $M^3$)−2], r is an integer of 0 to 3, each of $R^{21}$ to $R^{30}$ denotes a hydrogen atom, a halogen atom, a hydrocarbon group having 1 to 20 carbon atoms, a silicon-containing group and a heteroatom-containing group, and $M^3$ denotes a metal element of Group 3 to Group 10 or of lanthanoids in the periodic table;

2. An olefin-polymerizing catalyst obtained by bringing (A) a transition metal element of Group 3 to Group 10 or of lanthanoids in the periodic table of above 1 into contact with (B) a compound capable of forming an ionic complex by reacting with a transition metal compound as a component (A);

3. An olefin-polymerizing catalyst obtained by bringing (A) a transition metal element of Group 3 to Group 10 or of lanthanoids in the periodic table of above 1 into contact with (B) a compound capable of forming an ionic complex by reacting with a transition metal compound as a component (A) and with (C) an organic aluminum compound;

4. A method for producing an olefinic polymer characterized in that an olefin is polymerized in the presence of an olefin-polymerizing catalyst of above 2 or 3;

5. A method for producing an olefinic polymer of above 4 wherein an organic aluminum compound is a trialkyl aluminum; and, 6. A method for producing an olefinic polymer of above 4 or 5 wherein an olefin is propylene.

BEST MODE FOR CARRYING OUT THE INVENTION

The embodiments of the first to eighth inventions are detailed below.

[I] First invention

A propylenic polymer of the first invention consists of propylene alone or propylene and ethylene and/or an α-olefin having 4 to 20 carbon atoms. An α-olefin having 4 to 20 carbon atoms includes ethylene, 1-butene, 1-pentene, 4-methyl-1-pentene, 1-hexene, 1-octene, 1-decene, 1-dodecene, 1-tetradecene, 1-hexadecene, 1-octadecene, 1-eicocene and the like, and, in the invention, these may be employed alone or in combination with each other. A propylenic polymer of the invention is preferably a propylene homopolymer.

Among propylenic polymers according to the invention, a propylene homopolymer should have an isotactic pentad fraction (mmmm) within the range from 30 to 80%, preferably 40 to 70%, more preferably 50 to 70%. An isotactic pentad fraction less than 30% may cause an excessively reduced crystallinity which may lead to a poor moldablity, while that exceeding 80% may cause a loss of pliability, resulting in a problematic elevation of the heat seal temperature. A racemi-pentad fraction (rrrr) is a racemic moiety, represented in pentad as a unit, in a polypropylene molecule chain. A value [rrrr/(1−mmmm)] can be obtained from a fraction in pentad described above, and serves as an index for the narrowness in the regularity distribution of a propylene homopolymer. An increase in this value is associated with a broader regularity distribution, and represents a mixture of a highly regular PP and APP such as a conventional polypropylene produced using an existing catalyst system, and thus is associated with an increased stickiness and a reduced transparency. A value [rrrr/(1−mmmm)] of a propylene homopolymer of the invention which exceeds 0.1 causes a stickiness wherein the racemi-pentad fraction (rrrr) and the meso-pentad fraction (mmmm) are not in percentage terms.

(2) Determination of pentad fraction and abnormal insertion

A meso-pentad fraction (mmmm) and a racemi-pentad fraction (rrrr) referred herein were obtained in accordance with the method proposed by A. Zambelli et al in Macromolecules, 6, 925 (1973) by determining the methyl signal in a $^{13}C$ NMR spectrum and calculating an isotactic fraction and an atactic fraction, in a polypropylene molecule chain, as represented in pentad as a unit, as shown below.

<Calculation>

M=m/S×100

R=γ/S×100

S: Signal intensity of side chain methyl carbon atom in all propylene units

Pββ: 19.8 to 22.5 ppm

Pαβ: 18.0 to 17.5 ppm

Pαγ: 17.5 to 17.1 ppm

γ: Racemi-pentad chain: 20.7 to 20.3 ppm m: Meso-pentad chain: 21.7 to 22.5 ppm

With regard to (m-2, 1), (r-2, 1) and (1,3), the peaks in a $^{13}$C-NMR spectrum were assigned in accordance with the report by Grassi et al (Macromolecules, 21, p. 617 (1988)) and the report by Busico et al (Macromolecules, 27, p. 7538 (1994)) and the percentage of the content inserted in each position was calculated based on the integrated intensity of each peak. A value (m-2, 1) was obtained by calculating the ratio of the integrated intensity of a peak assigned to Pα, γ threo observed near 17.2 ppm to the integrated intensity in all methyl carbon region as a percentage of the content inserted in meso-2,1. A value (r-2, 1) was obtained by calculating the ratio of the integrated intensity of a peak assigned to Pα,γ threo observed near 15.0 ppm to the integrated intensity in all methyl carbon region as a percentage of the content inserted in rasemi-2,1. A value (1, 3) was obtained by calculating the ratio of the integrated intensity of a peak assigned to Tβ,γ+ observed near 31.0 ppm to the integrated intensity in all methine carbon region as a percentage of the content inserted in 1, 3 position. When a peak to be assigned to a meso-2, 1 insertion, a racemi-2, 1 insertion or a 1, 3 insertion could not be distinguished because of, for example, being overlapped with noises, then each heterogeneous binding content (m-2, 1), (r-2, 1) or (1, 3) was regarded as a zero value.

A $^{13}$C NMR spectrum was obtained using the following instruments under the conditions specified below.

Instrument: Nippon Densi Model JNM-EX400 $^{13}$C-NMR device

Method: Proton complete decoupling method

Concentration: 220 mg/milliliter

Solvent: A 90:10 solvent mixture (by volume) of 1,2,4-Trichlorobenzene and benzene-d6

Temperature: 130° C.

Pulse gap: 45°

Pulse interval: 4 seconds

Number of cycles: 10000 times

A comonomer unit content (mol %) in a propylenic polymer produced by copolymerizing propylene and ethylene and/or an α-olefin having 4 to 20 carbon atoms among the propylenic polymers according to the invention was obtained as described below. Thus, a $^{13}$C NMR spectrum was obtained using Nippon Densi Model JNM-EX400 $^{13}$C-NMR device under the conditions specified below and the calculation was made as described below.

Sample concentration: 220 mg/3 ml NMR solvent

NMR Solvent: 1,2,4-Trichlrobenzene/benzene-d6 (90/10 vol %)

Determination temperature: 130° C.

Pulse gap: 45°

Pulse interval: 10 seconds

Number of cycles: 4000 times (a) Ethylene Unit

A random copolymer of propylene and ethylene, when subjected to $^{13}$C-NMR, exhibited the spectrum whose signals had the chemical shifts and the assignments indicated in the table shown below.

Assignments of signals in $^{13}$C-NMR spectrum of ethylene-propylene copolymer

| Number | Chemical shift | Assignment |
|---|---|---|
| 1 | 45.1-47.3 | PPP Sαα |
| 2 | 42.3 | PPP Sαα |
| 3 | 38.6 | PPP Tαγ |
| 4 | 38. | Sαγ |
| 5 | 37.5 | Sαδ |
| 6 | 36.0 | PPP Sαβ |
| 7 | 36.0 | PPP Tαβ |
| 8 | 34.9 | EPP PEP Sαβ |
| 9 | 34.6 | EPP PEP Sαβ |
| 10 | 34.1 | EPP Tγγ |
| 11 | 33.7 | EEPP Tγδ |
| 12 | 33.3 | EPE Tδδ |
| 13 | 31.6 | PPP Tβγ |
| 14 | 31.4 | EPP Tβγ |
| 15 | 31.0 | PPE Tβδ |
| 16 | 30.7 | PPP Sαβ |
| 17 | 30.5 | PEEE Sγδ |
| 18 | 30.0 | EEE Sgg |
| 19 | 29.0 | EEE Tββ |
| 20 | 27.3 | PEE sβδ |
| 21 | 24.6 | PEP sαβ |
| 22 | 21.3-22.7 | Pββ |
| 23 | 20.6-21.3 | Pββ |
| 24 | 19.8-20.6 | Pββ |
| 25 | 17.6 | Pαβ |
| 26 | 17.2 | Pαγ |

NOTE)
E represents an ethylene unit.
NOTE)
A chemical shift is represented in ppm.

The ethylene unit content in the copolymer (α(% by mole)) was obtained in accordance with the following equation (1) based on the spectrum determined by the $^{13}$C-NMR.

$$\alpha = E/S \times 100 \quad (1)$$

wherein S and E are each represented as follows:

$$S = IEPE + IPPE + IEEE + IPPP + IPEE + IPEP$$

$$E = IEEE + 2/3(IPEE + IEPE) + 1/3(IPPE + IPEP)$$

wherein:

$$IEPE = I(12)$$

$$IPPE = I(15) + I(11) + (I(14) - I(11))/2 + I(10)$$

$$IEEP = I(18)/2 + I(17)/4$$

$$IPPP = I(19) + (I(6) + I(7))/2 + I(3) + I(13) + I(11) + (I(14) - I(11))/2$$

$$IPEE = I(20)$$

$$IPEP = (I(8) + I(9) - 2 \times I(11))/4 + I(21).$$

A isotactic triad fraction of a PPP chain was obtained as a stereoregularity index (P (% by mole)) according to the equation (2) shown below.

$$P = Im/I \times 100 \quad (2)$$

wherein Im and I are each represented as follows:

$$Im = I(22)$$

$$I = I(22) + I(23) + I(24) - \{(I(8) + I(9))/2 + I(10) + 3/2 \times I(11) + I(12) + I(13) + I(15)\}.$$

In the equation shown above, I(1), I(2) and the like represent the intensities of signal [1], signal [2] and the like, respectively.

Also a $^{13}$C NMR spectrum was obtained using Nippon Densi Model JNM-EX400 NMR device under the conditions specified below and the calculation was made as described below.

Sample concentration: 220 mg/3 ml NMR solvent
NMR Solvent: 1,2,4-Trichlorobenzene/benzene-d6 (90/10 vol %)
Determination temperature: 130° C.
Pulse gap: 45°
Pulse interval: 10 seconds
Number of cycles: 4000 times (a) 1-Butene Unit The 1-butene unit content in the copolymer (α(% by mole)) was obtained in accordance with the following equation based on the spectrum determined by the $^{13}$C-NMR.

$$\alpha = \frac{(I(2)/2 + I(4))}{\{I(1) + I(2) + I(3) + I(4) + 2 \times I(9)\}} \times 100$$

Also in accordance with the following equation, a stereoregularity index (P (% by mole)) of the copolymer was obtained.

$$P = \frac{(I(12))}{\{I(12) + I(13) + I(14)\}} \times 100$$

wherein (1), (2) and the like represent the signals of a spectrum of a copolymer of propylene and 1-butene determined by $^{13}$C-NMR. I(1), I(2) and the like represent the respective signal intensities. The signals of a spectrum of a copolymer of propylene and 1-butene determined by $^{13}$C-NMR are indicated in the table shown below.

Instead of the signal intensity of a PPP chain Sαβ carbon, the signal intensity of a PPP chain Sαβ carbon (signal intensity of (9)) was indicated as an alternative.

| Number | Chemical shift | Assignment |
|---|---|---|
| 1 | 45.7-47.4 | PP Sαα |
| 2 | 43.0-44.9 | PB Sαα |
| 3 | 42.3 | PPP Sαα |
| 4 | 40.3 | BB Sαα |
| 5 | 36.6 | PPP Tαγ |
| 6 | 36.0 | PPP Sαβ and PPP Sαβ |
| 7 | 35.5 | B unit Tββ |
| 8 | 31.6 | PPP Tβγ |
| 9 | 30.6 | PPP Sαβ |
| 10 | 28.6-29.8 | P unit Tββ |
| 11 | 27.8-28.4 | B unit side chain methylene carbon |
| 12 | 21.2-22.7 | Pββ PPP(mm), PPB(mm), BPB(mm) |
| 13 | 20.6-21.2 | Pββ PPP(mr), PPB(mr), BPB(mr), PPB(rr), BPB(rr) |
| 14 | 19.8-20.6 | Pββ PPP(rr) |
| 15 | 17.6 | Pαβ |
| 16 | 17.2 | Pαγ |
| 17 | 11.1 | B unit side chain methyl carbon |

NOTE)
B denotes a 1-butene unit.

A propylenic polymer produced by copolymerizing propylene and ethylene and/or an α-olefin having 4 to 20 carbon atoms among propylenic polymers according to the invention should have a stereoregularity index (P) within the range from 55 to 90% by mole, preferably 65 to 80% by mole. A stereoregularity index (P) less than 55% may cause an excessively reduced crystallinity which may lead to a poor moldablity, while that exceeding 90% may cause a loss of pliability, resulting in a problematic elevation of the heat seal temperature.

A propylenic polymer according to the invention has a molecular weight distribution, defined as a ratio of a weight mean molecular weight Mw to a number mean molecular weight Mn, i.e., Mw/Mn, of 3.5 or less, preferably 3.0 to 2.0. A molecular weight distribution exceeding 3.5 is too broad to achieve a sufficiently satisfactory physical properties.

An Mw/Mn defined above us a value calculated from the weight mean molecular weight Mw and the number mean molecular weight Mn, as having being converted to the values of polyethylene, by the determination by a gel permeation chromatography (GPC) method using the following instruments under the conditions specified below.

GPC instruments
Column: TOSO GMHHR-H(S) HT
Detector: RI detector for liquid chromatography, WATERS 150

GPC conditions
Solvent: 1,2,4-Trichlorobenzene
Determination temperature: 145° C.
Flow rate: 1.0 milliliter/minute
Sample concentration: 2.2 mg/milliliter
Injection volume: 160 microliter
Calibration curve: Universal Calibration
Analysis program: HT-GPC (Ver.1.0)

A propylenic polymer according to the invention should have an intrinsic viscosity [η], determined in a decalin solvent at 135° C., of 0.8 to 5 dl/g, preferably 1 to 3 dl/g, more preferably 1.5 to 2.5 dl/g. An intrinsic viscosity [η] less than 0.8 dl/g may cause a stickiness, while that exceeding 5 dl/g may cause a reduced flowability which may lead to a poor moldability.

In a propylenic polymer composition according to the invention, a propylenic polymer preferably has a crystallization temperature (Tc(° C.)) and a melting point (Tm (° C.)) of the polymer, as determined by a differential scanning calorimeter, which are in the relationship represented by the following formula:

$$Tc \geq 0.75Tm - 15.$$

A value of Tc less than 0.75Tm−15 may cause a higher tendency of a poor molding performance, due to which an inventive objective may not successfully be achieved. For the purpose of a less tendency of such poor molding performance, a relationship represented by the following formula:

$$Tc \geq 0.75Tm - 10$$

is more preferred, and a relationship represented by the following formula:

$$Tc \geq 0.75Tm - 5$$

Is particularly preferred. The values of Tm and Tc were determined in accordance with the method described in the examples.

While during an ordinary propylene polymerization process a 1,2 insertion polymerization, which means that a carbon atom of a propylene monomer on the side of a methylene undergoes a binding with an active center of a catalyst followed by a successive coordination of the propylene monomers in the same manner whereby effecting the polymerization, takes place generally, a 2,1 insertion or a 1,3 insertion may also take place at a less incidence (sometimes referred to as abnormal insertion). In a homopolymer according to the invention, it is preferable that the incidence of such 2, 1 or 1,3 insertion is low. It is also preferable that these insertion rates satisfy the relationship represented by the following formula (1):

$$[(m\text{-}2,1)+(r\text{-}2,1)+(1,3)] \leq 5.0 \tag{1}$$

wherein (m-2,1) is a % meso-2,1 insertion content determined by $^{13}$C-NMR, (r-2,1) is a % racemi-2,1 insertion content determined by $^{13}$C-NMR, and (1,3) is a % 1,3 insertion content determined by $^{13}$C-NMR, and, more preferably, they satisfy the relationship represented by the following formula (2):

$$[(m\text{-}2,1)+(r\text{-}2,1)+(1,3)] \leq 1.0 \tag{2}.$$

It is particularly preferred that they satisfy the relationship represented by the following formula (3):

$$[(m\text{-}2,1)+(r\text{-}2,1)+(1,3)] \leq 0.1 \tag{3}.$$

When the relationship represented by Formula (1) is not satisfied, the crystallinity is reduced far more than expected, and a stickiness may arise. (m-2, 1), (r-2, 1) and (1,3) are the respective % insertion contents obtained from the integrated intensities of the respective peaks after assigning the peaks in a $^{13}$C-NMR spectrum in accordance with the report by Grassi et al (Macromolecules, 21, p. 617 (1988)) and the report by Busico et al (Macromolecules, 27, p. 7538 (1994)). Thus, a value (m-2, 1) was a % meso-2,1 insertion content calculated from the ratio of the integrated intensity of a peak assigned to Pα,γ threo observed near 17.2 ppm to the integrated intensity in all methyl carbon region. A value (r-2, 1) was a % rasemi-2, 1 insertion content calculated from the ratio of the integrated intensity of a peak assigned to Pα,γ threo observed near 15.0 ppm to the integrated intensity in all methyl carbon region. A value (1, 3) was a % 1,3 insertion content calculated from the ratio of the integrated intensity of a peak assigned to Tβ,γ+ observed near 31.0 ppm to the integrated intensity in all methine carbon region.

A propylene homopolymer of the invention preferably exhibits substantially no peaks in a $^{13}$C-NMR spectrum which are assigned to a molecular chain terminal (n-butyl group) as a result of a 2,1 insertion. With regard to this molecular chain terminal as a result of a 2,1 insertion, each % insertion content is calculated from the integrated intensity of each peak after assignment of the peak in the $^{13}$C-NMR spectrum in accordance with the report by Jungling et al (J. Polym. Sci.: Part A: Polym. Chem., 33, p 1305 (1995)). In an isotactic polypropylene, a peak appearing near 18.9 ppm is assigned to a terminal methyl group carbon of an n-butyl group. The determination of a $^{13}$C-NMR for an abnormal insertion or a molecular terminal may be performed using the instruments under the conditions described above.

In addition to the characteristics discussed above, the amount of a boiling diethylether extract, which is an index for a stickiness-causing component level, of a propylenic polymer according to the invention is preferably 0 to 10% by weight, more preferably 0 to 5% by weight, for the purpose of preventing the bleeding out of a stickiness-causing component on the surface of a molded article.

The amount of the components which are dissolved out at 25° C. or lower in a temperature-raising fractionation (TREF)

which is another index for a stickiness-causing component level is preferably 20 to 100% by weight because of the same reason, more preferably 0 to 10% by weight, and particularly 0 to 5% by weight. The TREF determination was performed by the method described in the examples.

A propylenic polymer produced by copolymerizing propylene and ethylene and/or an α-olefin having 4 to 20 carbon atoms among propylenic polymers according to the invention is preferably a random copolymer. The structural unit derived from propylene exists preferably at a level of 90% by mole or higher, more preferably 85% by mole or higher.

A propylenic polymer of the invention can be produced by homopolymerizing propylene or copolymerizing propylene and ethylene and/or an α-olefin having 4 to 20 carbon atoms in the presence of a polymerization catalyst comprising (A) a transition metal compound represented by Formula (I):

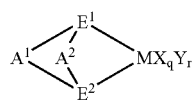

(I)

and (B) a compound capable of forming an ionic complex by reacting with a transition metal compound as a component (A) or a derivative thereof.

In Formula (I) shown above, M denotes a metal element of Group 3 to Group 10 or of lanthanoids in the periodic table, such as titanium, zirconium, hafnium, yttrium, vanadium, chromium, manganese, nickel, cobalt, palladium and lanthanoid metals, with titanium, zirconium and hafnium being preferred in view of their olefin polymerization activities. Each of E1 and E2 denotes a ligand selected from the group consisting of a substituted cyclopentadienyl group, indenyl group, a substituted indenyl group, heterocyclopentadienyl group, a substituted heterocyclopentadienyl group, amide group (—N<), phosphine group (—P<), a hydrocarbon group (>CR—, >C<) and a silicon-containing group (>SiR—, >Si<) (wherein R denotes hydrogen or a hydrocarbon group or a heteroatom-containing group having 1 to 20 carbon atom), and is crosslinked with each other via $A^1$ and $A^2$. $E^1$ and $E^2$ may be same to or different from each other. Preferred examples of $E^1$ and $E^2$ are a substituted cyclopentadienyl group, indenyl group and a substituted indenyl group.

X denotes a σ-binding ligand, and, when two or more Xs are present they may be same or different, and each may be crosslinked with other X, $E^1$, $E^2$ or Y. Examples of X include a halogen atom, a hydrocarbon atom having 1 to 20 carbon atoms, an alkoxy group having 1 to 20 carbon atoms, an arylalkoxy group having 6 to 20 carbon atoms, an amide group having 1 to 20 carbon atoms, a silicon-containing group having 1 to 20 carbon atoms, a phosphide group having 1 to 20 carbon atoms, a sulfide group having 1 to 20 carbon atoms, an acyl group having 1 to 20 carbon atoms, and the like. A halogen atom may for example be a chlorine, fluorine, bromine or iodine atom. Examples of a hydrocarbon group having 1 to 20 carbon atoms are an alkyl group such as methyl, ethyl, propyl, butyl, hexyl, cyclohexyl, octyl groups and the like, an alkenyl group such as vinyl, propenyl, cyclohexenyl groups and the like; an arylalkyl group such as benzyl, phenylethyl, phenylpropyl groups and the like; and an aryl group such as phenyl, tolyl, dimethylphenyl, trimetnylphenyl, ethylphenyl, propylphenyl, biphenyl, naphthyl, methylnaphthyl, anthracenyl, phenanthnyl groups and the like. Among those listed above, an alkyl group such as methyl, ethyl, propyl groups and the like and an aryl group such as phenyl group are preferred. Examples of an alkoxy group having 1 to 20 carbon atoms are an alkoxyl group such as methoxy, ethoxy, propoxy, butoxy groups and the like; and an aryloxy group such as phenoxy, methylphenoxy, dimethylphenoxy, naphthoxy groups and the like. Examples of an arylalkoxy group having 6 to 20 carbon atoms are phenylmethoxy, phenylethoxy groups and the like. Examples of an amide group having 1 to 20 carbon atoms are an alkylamide group such as dimethylamide, diethylamide, dipropylamide, dibutylamide, dicyclohexylamide, methylethylamide groups and the like, an alkenylamide group such as divinylamide, dipropenylamide, dicyclohexenylamide groups and the like; an arylalkylamide group such as dibenzylamide, phenylethylamide, phenylpropylamide groups and the like; and arylamide group such as diphenylamide, dinaphthylamide groups and the like. Examples of a silicon-containing group having 1 to 20 carbon atoms are a monohydrocarbon-substituted silyl group such as methylsilyl, phenylsilyl groups and the like; a dihydrocarbon-substituted silyl group such as dimethylsilyl, diphenylsilyl groups and the like; a trihydrocarbon-substituted silyl group such as trimethylsilyl, triethylsilyl, tripropylsilyl, tricyclohexylsilyl, triphenylsilyl, dimethylphenylsilyl, methylphenyldisilyl, tritolylsilyl, trinaphthylsilyl groups and the like; a silyl ether group of a hydrocarbon-substituted silyl group such as trimethylsilylether group; a silicon-substituted alkyl group such as trimethylsilylmethyl group; and a silicon-substituted aryl group such as trimethylsilylphenyl group and the like. Among those listed above, trimethylsilyl, phenethyldimethylsilyl groups are preferred. Examples of a sulfide group having 1 to 20 carbon atoms are an alkylsulfide group such as methylsulfide, ethylsulfide, propylsulfide, butylsulfide, hexylsulfide, cyclohexylsulfide, octylsulfide groups and the like and an alkenylsulfide group such as vinylsulfide, propenyl sulfide, cyclohexenylsulfide groups and the like; an arylalkylsulfide group such as benzylsulfide, phenylethylsulfide, phenylpropylsulfide groups and the like; and an arylsulfide group such as phenylsulfide, tolylsulfide, dimethylsulfide, trimethylphenylsulfide, ethylphenylsulfide, propylphenylsulfide, biphenylsulfide, naphthylsulfide, methylnaphthylsulfide, anthracenylsulfide, phenanthnylsulfide groups and the like. Examples of a sulfoxide group having 1 to 20 carbon atoms are an alkylsulfoxide group such as methylsulfoxide, methylsulfoxide, propylsulfoxide, butylsulfoxide, hexylsulfoxide, cyclohexylsulfoxide, octylsulfoxide groups and the like and an alkenylsulfoxide group such as vinylsulfoxide, propenylsulfoxide, cyclohexenylsulfoxide groups and the like; an arylalkylsulfoxide group such as benzyl sulfoxide, phenylethylsulfoxide, phenylpropylsulfoxide groups and the like; and an arylsulfoxide such as phenylsulfoxide, tolylsulfoxide, dimethylphenylsulfoxide, trimethylphenylsulfoxide, ethylphenylsulfoxide, propylphenylsulfoxide, biphenylsulfoxide, naphthylsulfoxide, methylnaphthylsulfoxide, anthracenylsulfoxide, phenanthnylsulfoxide groups and the like. Examples of an acyl group having 1 to 20 carbon atoms are an alkylacyl group such as formyl, acethyl, propionyl, butyryl, valeryl, palmitoyl, thearoyl, oleoyl groups and the like; an arylacyl group such as benzoyl, toluoyl, salicyloyl, cinnamoyl, naphthoyl, phthaloyl groups and the like; oxalyl, malonyl and succinyl groups derived from dicarboxylic acids such as oxalic acid, malonic acid and succinic acid, respectively, and the like. Y denotes a Lewis base, and, when two or more Ys are present they may be same or different, and each may be crosslinked with other Y, $E^1$, $E^2$ or X. Examples of the Lewis base represented by said Y are amines, ethers, phosphines, thioethers and the like. The amines may for example be an amine having 1 to 20 carbon atoms, and typically an alkylamine such as methylamine, ethylamine, propylamine, butylamine, cyclohexylamine, methylethylamine, dimethylamine, diethylamine, dipropylamine, dibutylamine, dicyclohexylamine, methylethylamine and the like and an alkenylamine such as vinylamine, propenylamine, cyclohexenylamine, divinylamine, dipropenylaine, dicyclohexenylamine and the like; an arylalkylamine such as phenylamine, phenylethylamine, phenylpropylamine and the like; and arylamine such as diphenylamine, dinaphthylamine and the like. Ethers may for example be an aliphatic monoether compound such as methylether, ethylether, propylether, isopropylether, butylether, isobutylether, n-amylether, isoamylether and the like; an aliphatic mixed ether compound such as methylethylether, methylptopylether, methylisopropylether, methyl-n-amylether, methylisoamylether, ethylpropylether, ethylisopropylether, ethylbutylether, ethyliobutylether, ethyl-n-amylether, ethylisoamylether and the like; an aliphatic unsaturated ether compound such as vinylether, allylether, methylvinylether, methylallylether, ethylvinylether, ethylallylether and the like; an aromatic ether compound such as anisol, phenethol, phenylether, benzylether, phenylbenzylether, α-naphthylether, β-naphthylether and the like, as well as a cyclic ether compound such as ethylene oxide, propylene oxide, trimethylene oxide, tetrahydrofuran, tetrahydropyrane, dioxane and the like. An example of the phospines may be a phosphine having 1 to 20 carbon atoms. Those included typically are an alkylphosphine including a monohydrocarbon-substituted phosphine such as methylphosphine, ethylphosphine, propylphosphine, butylphosphine, hexylphosphine, cyclohexylphosphine, octylphosphine and the like; a dihydrocarbon-substituted phosphine such as dimethylphosphine, diethylphosphine, dipropylphosphine, dibutylphosphine, dihexylphosphine, dicyclohexylphosphine, dioctylphosphine and the like; a trihydrocarbon-substituted phosphine such as dimethylphosphine, triethylphosphine, tripropylphosphine, tributylphosphine, trihexylphosphine, tricyclohexylphosphine, trioctylphosphine and the like and a monoalkenylphosphine such as vinylphosphine, propenylphosphine, cyclohexenylphosphine and the like as well as a dialkenyl phosphine whose hydrogen atoms on the phosphorus were replaced with two alkenyl groups; a trialkenyl phosphine whose hydrogen atoms on the phosphorus were replaced with three alkenyl groups; an arylalkylphosphine such as benzylphosphine, phenylethylphosphine, phenylpropylphosphine and the like; a diarylalkyl phosphine or an aryldialkylphosphine whose hydrogen atoms on the phosphorus were replaced with three aryl or alkenyl groups; phenylphosphine, tolylphosphine, dimethylphenylphosphine, trimethylphenylphosphine, ethylphenylphosphine, propylphenylphosphine, biphenylphosphine, naphthylphosphine, methylnaphthylphosphine, anthracenylphosphine, phenanthracenyl phosphine; a di(alkylaryl)phosphine whose hydrogen atoms on the phosphorus were replaced with 2 aklkylaryl groups; a tri(alkylaryl)phosphine whose hydrogen atoms on the phosphorus were replaced with 3 aklkylaryl groups, and the like. An example of the thioethers may be a sulfide mentioned above.

Each of $A^1$ and $A^2$ denotes a divalent crosslinking group having two ligands, including a hydrocarbon group having 1 to 20 carbon atoms, a halogen-containing hydrocarbon group having 1 to 20 carbon atoms, a silicon-containing group, a germanium-containing group, a tin-containing group, —O—, —CO—, —S—, —$SO_2$—, —Se—, —NR—, —PR—, —P(O)R—, —BR— or -AlR— wherein R is a hydrogen atom, a halogen atom, a hydrocarbon group having 1 to 20 carbon atoms and a halogen-containing hydrocarbon group having 1 to 20 carbon atoms, and each may be same to or different from each other. Among such crosslinking groups, at least one is a crosslinking group consisting of a hydrocarbon group having one or more carbon atoms. An example of such crosslinking group is one represented by Formula:

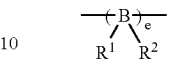

wherein B denotes an element of Group XIV in the periodic table such as carbon, silicon, germanium and tin; and each of R1 and R2 denotes a hydrogen atom or a hydrocarbon group having 1 to 20 carbon atoms, and may be same to or different from each other, or alternatively may bind to each other to form a cyclic structure; and e denotes an integer of 1 to 4, and may typically be methylene, ethylene, ethylidene, propylidene, isopropylidene, cyclohexylidene, 1,2-cyclohexylene, vinylidene ($CH2=C=$), dimethylsilylene, diphenylsilylene, methylphenylsilylene, dimethylgermylene, dimethylstannylene, tetramethyldisilylene, diphenyldisilylene groups and the like. Among those listed above, ethylene, isopropylidene and dimethylsilylene groups are preferred. q is an integer of 1 to 5 and represents [(valency of M)−2], and r is an integer of 0 to 3.

In a transient metal compound represented by Formula (I) when $E^1$ and $E^2$ are substituted cyclopentadienyl group, indenyl group or substituted indenyl group, then the crosslinking groups of $A^1$ and $A^2$ are preferably in the forms of a (1, 2') (2, 1') double crosslinking.

Among the transient metal compounds represented by Formula (I), one employed preferably is a transient metal compound having, as a ligand, a biscyclopentadienyl derivative in a double crosslinking form such as those represented by Formula (II):

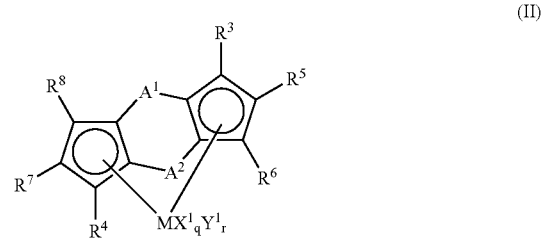

(II)

In Formula (II) shown above, M, $A^1$, $A^2$, q and r are defined as described above. $X^1$ denotes a σ-binding ligand, and, when two or more X1s are present they may be same or different, and each may be crosslinked with other $X^1$ or $Y^1$. Such $X^1$ may for example be one exemplified in the description of X in Formula (I). $Y^1$ denotes a Lewis base, and, when two or more $Y^1$s are present they may be same or different, and each may be crosslinked with other $Y^1$ or $X^1$. Such $Y^1$ may for example be one exemplified in the description of Y in Formula (I). Each of $R^3$ to $R^8$ denotes a hydrogen atom, a halogen atom, a hydrocarbon having 1 to 20 carbon atoms, a halogen-containing hydrocarbon group having 1 to 20 carbon atoms, a silicon-containing group or a heteroatom-containing group, provided that at least one of them is not a hydrogen atom. Each of $R^3$ to $R^8$ may be same to or different from each other, and any adjacent two of them may be taken together to form a ring.

This transient metal compound having as a ligand a biscyclopentadienyl derivative in a double crosslinking form has the ligand in the forms of a (1, 2') (2, 1') double crosslinking.

Examples of a transient metal compound represented by Formula (I) are (1,2'-ethylene)(2,1'-ethylene)-bis(indenyl) zirconium dichloride, (1,2'-methylene)(2,1'-methylene)-bis(indenyl)zirconium dichloride, (1,2'-isopropylidene)(2,1'-isopropylidene)-bis(indenyl)zirconium dichloride, (1,2'-ethylene)(2,1'-ethylene)-bis(3-methylindenyl)zirconium dichloride, (1,2'-ethylene) (2,1'-ethylene)-bis(4,5-benzoindenyl)zirconium dichloride, (1,2'-ethylene)(2,1'-ethylene)-bis(4-isopropylindenyl)zirconium dichloride, (1,2'-ethylene)(2,1'-ethylene)-bis(5,6-dimethylindenyl)zirconium dichloride, (1,2'-ethylene)(2,1'-ethylene)-bis(4,7-diisopropylindenyl)zirconium dichloride, (1,2'-ethylene)(2,1'-ethylene)-bis(4-phenylindenyl)zirconium dichloride, (1,2'-ethylene) (2,1'-ethylene)-bis(3-methyl-4-isopropylindenyl)zirconium dichloride, (1,2'-ethylene)(2,1'-ethylene)-bis(5,6-benzoindenyl)zirconium dichloride, (1,2'-ethylene)(2,1'-isopropylidene)-bis(indenyl)zirconium dichloride, (1,2'-methylene)(2,1'-ethylene)-bis(indenyl)zirconium dichloride, (1,2'-methylene)(2,1'-isopropylidene)-bis(indenyl)zirconium dichloride, (1,2'-dimethylsilylene)(2,1'-dimethylsilylene)bis(indenyl)zirconium dichloride, (1,2'-dimethylsilylene)(2,1'-dimethylsilylene)bis(3-methylindenyl) zirconium dichloride, (1,2'-dimethylsilylene)(2,1'-dimethylsilylene)bis(3-n-butylindenyl)zirconium dichloride, (1,2'-dimethylsilylene)(2,1'-dimethylsilylene)bis(3-I-propylindenyl)zirconium dichloride, (1,2'-dimethylsilylene)(2,1'-dimethylsilylene)bis(3-trimethylsilylmethylindenyl)zirconium dichloride, (1,2'-dimethylsilylene)(2,1'-dimethylsilylene)bis(3-phenylindenyl)zirconium dichloride, (1,2'-dimethylsilylene)(2,1'-dimethylsilylene)bis(4,5-benzoindenyl)zirconium dichloride, (1,2'-dimethylsilylene)(2,1'-dimethylsilylene)bis(4-isopropylindenyl)zirconium dichloride, (1,2'-dimethylsilylene)(2,1'-dimethylsilylene)bis(5,6-dimethylindenyl)zirconium dichloride, (1,2'-dimethylsilylene)(2,1'-dimethylsilylene)bis(4,7-di-i-propylindenyl) zirconium dichloride, (1,2'-dimethylsilylene)(2,1'-dimethylsilylene)bis(4-phenylindenyl)zirconium dichloride, (1,2'-dimethylsilylene) (2,1'-dimethylsilylene)bis(3-methyl-4-i-propylindenyl)zirconium dichloride, (1,2'-dimethylsilylene) (2,1'-dimethylsilylene)bis(5,6-benzoindenyl)zirconium dichloride, (1,2'-dimethylsilylene)(2,1'-isopropylidene)-bis(indenyl)zirconium dichloride, (1,2'-dimethylsilylene)(2,1'-isopropylidene)-bis(3-methylindenyl)zirconium dichloride, (1,2'-dimethylsilylene) (2,1'-isopropylidene)-bis(3-i-propylindenyl)zirconium dichloride, (1,2'-dimethylsilylene)(2,1'-isopropylidene)-bis(3-n-butylindenyl)zirconium dichloride, (1,2'-dimethylsilylene)(2,1'-isopropylidene)-bis(3-trimethylsilylmethylindenyl)zirconium dichloride, (1,2'-dimethylsilylene)(2,1'-isopropylidene)-bis(3-trimetylsilylindenyl)zirconium dichloride, (1,2'-dimethylsilylene)(2,1'-isopropylidene)-bis(3-phenylindenyl)zirconium dichloride, (1,2'-dimethylsilylene)(2,1'-methylene)-bis(indenyl)zirconium dichloride, (1,2'-dimethylsilylene) (2,1'-methylene)-bis(3-methylindenyl)zirconium dichloride, (1,2'-dimethylsilylene)(2,1'-methylene)-bis(3-i-propylindenyl)zirconium dichloride, (1,2'-dimethylsilylene)(2,1'-methylene)-bis(3-n-butylindenyl) zirconium dichloride, (1,2'-dimethylsilylene)(2,1'-methylene)-bis(3-trimethylsilylmethylindenyl)zirconium dichloride, (1,2'-dimethylsilylene)(2,1'-methylene)-bis(3-trimethylsilylindenyl)zirconium dichloride, (1,2'-diphenylsilylene)(2,1'-methylene)-bis(indenyl)zirconium dichloride, (1,2'-diphenylsilylene) (2,1'-methylene)-bis(3-methylindenyl)zirconium dichloride, (1,2'-diphenylsilylene)(2,1'-methylene)-bis(3-i-propylindenyl)zirconium dichloride, (1,2'-diphenylsilylene)(2,1'-methylene)-bis(3-n-butylindenyl) zirconium dichloride, (1,2'-diphenylsilylene)(2,1'-methylene)-bis(3-trimethylsilylmethylindenyl)zirconium dichloride, (1,2'-diphenylsilylene)(2,1'-methylene)-bis(3-trimethylsilylindenyl)zirconium dichloride, (1,2'-dimethylsilylene)(2,1'-dimethylsilylene)(3-methylcyclopentadienyl)(3'-methylcyclopentadienyl)zirconium dichloride, (1,2'-dimethylsilylene)(2,1'-isopropylidene)(3-methylcyclopentadienyl)(3'-methylcyclopentadienyl) zirconium dichloride, (1,2'-dimethylsilylene)(2,1'-ethylene)(3-methylcyclopentadienyl) (3'-methylcyclopentadienyl) zirconium dichloride, (1,2'-ethylene)(2,1'-methylene)(3-methylcyclopentadienyl) (3'-methylcyclopentadienyl) zirconium dichloride, (1,2'-ethylene)(2,1'-isopropylidene)(3-methylcyclopentadienyl)(3'-methylcyclopentadienyl) zirconium dichloride, (1,2'-methylene)(2,1'-methylene)(3-methylcyclopentadienyl)(3'-methylcyclopentadienyl) zirconium dichloride, (1,2'-methylene)(2,1'-isopropylidene) (3-methylcyclopentadienyl)(3'-methylcyclopentadienyl) zirconium dichloride, (1,2'-isopropylidene)(2,1'-isopropylidene)(3-methylcyclopentadienyl)(3'-methylcyclopentadienyl)zirconium dichloride, (1,2'-dimethylsilylene)(2,1'-dimethylsilylene)(3,4-dimethylcyclopentadienyl)(3',4'-dimethylcyclopentadienyl) zirconium dichloride, (1,2'-dimethylsilylene)(2,1'-isopropylidene)(3,4-dimethylcyclopentadienyl)(3',4'-dimethylcyclopentadienyl)zirconium dichloride, (1,2'-dimethylsilylene)(2,1'-ethylene)(3,4-dimethylcyclopentadienyl)(3',4'-dimethylcyclopentadienyl) zirconium dichloride, (1,2'-ethylene)(2,1'-methylene)(3,4-dimethylcyclopentadienyl)(3',4'-dimethylcyclopentadienyl) zirconium dichloride, (1,2'-ethylene)(2,1'-isopropylidene)(3,4-dimethylcyclopentadienyl)(3',4'-dimethylcyclopentadienyl)zirconium dichloride, (1,2'-methylene)(2,1'-methylene)(3,4-dimethylcyclopentadienyl) (3',4'-dimethylcyclopentadienyl)zirconium dichloride, (1,2'-methylene)(2,1'-isopropylidene)(3,4-dimethylcyclopentadienyl)(3',4'-dimethylcyclopentadienyl) zirconium dichloride, (1,2'-isopropylidene)(2,1'-isopropylidene)(3,4-dimethylcyclopentadienyl)(3',4'-dimethylcyclopentadienyl)zirconium dichloride, (1,2'-dimethylsilylene) (2,1'-dimethylsilylene)(3-methyl-5-ethylcyclopentadienyl)(3'-methyl-5'-ethylcyclopentadienyl) zirconium dichloride, (1,2'-dimethylsilylene)(2,1'-dimethylsilylene)(3-methyl-5-ethylcyclopentadienyl)(3'-methyl-5'-ethylcyclopentadienyl)zirconium dichloride, (1,2'-dimethylsilylene)(2,1'-dimethylsilylene)(3-methyl-5-isopropylcyclopentadienyl)(3'-methyl-5'-isopropylcyclopentadienyl)zirconium dichloride, (1,2'-dimethylsilylene)(2,1'-dimethylsilylene)(3-methyl-5-n-butylcyclopentadienyl)(3'-methyl-5'-n-butylcyclopentadienyl)zirconium dichloride, (1,2'-dimethylsilylene)(2,1'-dimethylsilylene)(3-methyl-5-phenylcyclopentadienyl)(3'-methyl-5'-phenylcyclopentadienyl)zirconium dichloride, (1,2'-dimethylsilylene)(2,1'-isopropylidene)(3-methyl-5-ethylcyclopentadienyl)(3'-methyl-5'-ethylcyclopentadienyl) zirconium dichloride, (1,2'-dimethylsilylene)(2,1'-isopropylidene)(3-methyl-5-i-propylcyclopentadienyl)(3'-methyl-5'-i-propylcyclopentadienyl)zirconium dichloride, (1,2'-dimethylsilylene)(2,1-isopropylidene)(3-methyl-5-n-butylcyclopentadienyl)(3'-methyl-5'-n-butylcyclopentadienyl)zirconium dichloride, (1,2'-dimethylsilylene)(2,1'-isopropylidene)(3-methyl-5-phenylcyclopentadienyl)(3'-methyl-5'-phenylcyclopentadienyl) zirconium dichloride, (1,2'-dimethylsilylene)(2,1'-ethylene)(3-methyl-5-ethylcyclopentadienyl)(3'-methyl-5'-ethylcyclopentadienyl)zirconium dichloride, (1,2'-dimethylsilylene)(2,1'-ethylene)(3-methyl-5-i-propylcyclopentadienyl)(3'-methyl-5'-i-propylcyclopentadienyl)zirconium dichloride, (1,2'-dimethylsilylene)(2,1'-ethylene)(3-methyl-5-n-butylcyclopentadienyl)(3'-methyl-5'-n-butylcyclopentadienyl)zirconium dichloride, (1,2'-dimethylsilylene)(2,1'-ethylene)(3-methyl-5-phenylcyclopentadienyl)(3'-methyl-5'-phenylcyclopentadienyl)zirconium dichloride, (1,2'-dimethylsilylene)(2,1'-methylene)(3-methyl-5-ethylcyclopentadienyl)(3'-methyl-5'-ethylcyclopentadienyl)zirconium dichloride, (1,2'-dimethylsilylene)(2,1'-methylene)(3-methyl-5-i-propylcyclopentadienyl)(3'-methyl-5'-i-propylcyclopentadienyl)zirconium dichloride, (1,2'-dimethylsilylene)(2,1'-methylene)(3-methyl-5-n-butylcyclopentadienyl)(3'-methyl-5'-n-butylcyclopentadienyl)zirconium dichloride, (1,2'-dimethylsilylene)(2,1'-methylene)(3-methyl-5-phenylcyclopentadienyl)(3'-methyl-5'-phenylcyclopentadienyl)zirconium dichloride, (1,2'-ethylene)(2,1'-methylene)(3-methyl-5-i-propylcyclopentadienyl)(3'-methyl-5'-i-propylcyclopentadienyl)zirconium dichloride, (1,2'-ethylene)(2,1'-isopropylidene)(3-methyl-5-i-propylcycldpentadienyl)(3'-methyl-5'-i-propylcyclopentadienyl)zirconium dichloride, (1,2'-methylene)(2,1'-methylene)(3-methyl-5-i-propylcyclopentadienyl)(3'-methyl-5'-i-propylcyclopentadienyl)zirconium dichloride, (1,2'-methylene)(2,1'-isopropylidene)(3-methyl-5-i-propylcyclopentadienyl)(3'-methyl-5'-i-propylcyclopentadienyl)zirconium dichloride and the like as well as the compounds obtained by replacing zirconium in the compounds listed above with titanium or hafnium. It is a matter of course that the compounds listed above are non-limiting examples. Analogous compounds of other groups or of lanthanoids may also be employed.

While a component (B-1) among the components (B) may be any ionic compound capable of forming an ionic complex by reacting with a transition metal compound as a component (A), compounds represented by Formulae (III), (IV):

(III)

(IV)

wherein $L^2$ denotes $M^2$, $R^{10}R^{11}M^3$, $R^{12}_3C$ or $R^{13}M^3$, wherein $L^1$ denotes a Lewis base, $[Z^1]^-$ denotes a non-coordinating anion $[Z^1]^-$ and $[Z^2]^-$, wherein $[Z^1]^-$ denotes an anion in which two or more groups are bound to an element, i.e., $[M^1G^1G^2 \ldots G^f]^-$, wherein $M^1$ is an element of Groups VI to XVI in the periodic table, preferably of Groups XIII to XVI in the periodic table; each of $G^1$ to $G^f$ denotes a halogen atom, an alkyl group having 1 to 20 carbon atoms, a dialkylamino group having 2 to 20 carbon atoms, an alkoxy group having 1 to 20 carbon atoms, an aryl group having 6 to 20 carbon atoms, an arylalkoxy group having 6 to 20 carbon atoms, an alkylaryl group having 7 to 40 carbon atoms, an arylalkyl group having 7 to 40 carbon atoms, a halogen-substituted hydrocarbon group having 1 to 20 carbon atoms, an acyloxy group having 1 to 20 carbon atoms, an organic metalloid group or a heteroatom-containing hydrocarbon group having 2 to 20 carbon atoms; two or more of $G^1$ to $G^f$ may be taken together to form a ring; f denotes an integer represented by [(valency of center metal $M^1$)+1], $[Z^2]^-$ denotes a conjugate base of a Brønsted acid alone or a combination of a Brønsted acid and a Lewis acid whose logarithmic number of a reciprocal number of an acid dissociation constant (pKa) is –10 or less, or a conjugate base of one generally referred to be a super acid; a Lewis base may be coordinated; $R^9$ denotes a hydrogen atom, an alkyl group having 1 to 20 carbon atoms, an aryl, alkylaryl or arylalkyl group having 6 to 20 carbon atoms, each of $R^{10}$ and $R^{11}$ is a cyclopentadienyl group, a substituted cyclopentadienyl group, an indenyl group or a fluorenyl group, $R^{12}$ denotes an alkyl, aryl, alkylaryl or arylalkyl group having 1 to 20 carbon atoms; $R^{13}$ denotes a large cyclic ligand such as tetraphenylporphyrin, phthalocyanine and the like; k denotes an integer of 1 to 3 which is an ionic valency of $[L^1-R^9]$, $[L^2]$, a denotes an integer of 1 or more, b=(k×a); $M^2$ comprises an element of Groups I to III, XI to XIII, XVII in the periodic table, and $M^2$ denotes an element of Groups VII to XII are employed preferably.

Examples of L1 are amines including ammonia, methylamine, aniline, dimethylamine, diethylamine, N-methylaniline, diphenylamine, N,N-dimethylaniline, trimethylamine, triethylamine, tri-n-butylamine, methyldiphenylamine, pyridine, p-bromo-N,N-dimethylaniline, p-nitro-N,N-dimethylaniline and the like, phosphines such as triethylphosphine, triphenylphosphine, diphenylphosphine and the like, thioethers such as tetrahydrothiophene, esters such as ethyl benzoate, nitrites such as acetonitrile, benzonitrile and the like.

$R^9$ may for example be methyl, ethyl, benzyl, trityl groups and the like, $R^{10}$ and $R^{11}$ may for example be cyclopentadienyl, methylcyclopentadienyl, ethylcyclopentadienyl, pentamethylcyclopentadienyl groups and the like. $R^{12}$ may for example be phenyl, p-tolyl, p-methoxyphenyl groups and the like, while $R^{13}$ may for example be tetraphenylporphine, phthalocyanine, allyl, methallyl groups and the like. $M^2$ may for example be Li, Na, K, Ag, Cu, Br, I, $I_3$ and the like, while $M^3$ may for example be Mn, Fe, Co, Ni, Zn and the like.

In $[Z^1]^-$, i.e. in $[M^1G^1G^2 \ldots G^f]^-$, $M^1$ may for example be B, Al, Si, P, As, Sb, preferably B and Al. $G^1$, $G^2$ to $G^f$ may for example be a dialkylamino group such as dimethylamino, diethylamino groups and the like, an alkoxy group or an arylalkoxy groups such as methoxy, ethoxy, n-butoxy, phenoxy groups and the like, a hydrocarbon group such as methyl, ethyl, n-propyl, isopropyl, n-butyl, isobutyl, n-octyl, n-eicosyl, phenyl, p-tolyl, benzyl, 4-t-butylphenyl, 3,5-dimethylphenyl groups and the like, a halogen atom such as fluorine, chlorine, bromine and iodine, a heteroatom-containing hydrocarbon group such as p-fluorphenyl, 3,5-difluorophenyl, pentachlorophenyl, 3,4,5-trifluorophenyl, pentafluorophenyl, 3,5-bis(trifluoromethyl)phenyl, bis(trimethylsilyl)methyl groups and the like, an organic metalloid group such as pentamethylantimony, trimethylsilyl, trimehylgermyl, diphenylarsine, dicyclohexylantimony groups and diphenylboron and the like.

A non-coordinating anion, i.e., $[Z^2]^-$ which is a conjugate base of a Brønsted acid alone or a combination of a Brønsted acid and a Lewis acid whose pKa is –10 or less, may for example be, trifluoromethanesulfonate anion $(CF_3SO_3)^-$, bis(trifluoromethanesulfonyl)methyl anione, bis(trifluoromethanesulfonyl)benzyl anione, bis(triphenylmethanesulfonyl)amide, perchlorite anion $(ClO_4)^-$, trifluoroacetate anion $(CF_3CO_2)^-$, hexafluoroantimony anion $(SbF_6)^-$, fluorosulfonate anione/pentafluoroantimony $(FSO_3/SbF_5)^-$, fluorosulfonate anion/pentafluoroarsenic $(FSO_3/AsF_5)^-$, trifluoromethanesulfonate/pentafluoroantimony $(CF3SO_3/SbF_5)^-$ and the like.

Examples of an ionic compound capable of forming an ionic complex by reacting with a transition metal compound as a component (A), i.e., examples of a compound as a component (B-1) are triethylammonium tetraphenylborate, tri-n-butylammonium tetraphenylborate, trimethylammonium tetraphenylborate, tetraethylammonium tetraphenylborate, methyl(tri-b-butyl)ammonium tetraphenylborate, benzyl(tri-b-butyl)ammonium tetraphenylborate, dimethylphenylammonium tetraphenylborate, triphenyl(methyl)ammonium tetraphenylborate, trimethylanilinium tetraphenylborate, methylpyridinium tetraphenylborate, benzylpyridinium tetraphenylborate, methyl(2-cyanopyridinium) tetraphenylborate, triethylammonium tetrakis(pentafluorophenyl)borate, tri-n-butylammonium tetrakis(pentafluorophenyl)borate, triphenylammonium tetrakis(pentafluorophenyl)borate, tetra-n-butylammonium tetrakis(pentafluorophenyl)borate, tetraethylammonium tetrakis(pentafluorophenyl)borate, benzyl(tri-n-butyl)ammonium tetrakis(pentafluorophenyl) borate, methyldiphenylammonium tetrakis(pentafluorophenyl)borate, triphenyl(methyl)ammonium tetrakis(pentafluorophenyl)borate, methylanilinium tetrakis (pentafluorophenyl)borate, dimethylanilinium tetrakis (pentafluorophenyl)borate, trimethylanilinium tetrakis (pentafluorophenyl)borate, methylpyridinium tetrakis (pentafluorophenyl)borate, benzylpyridinium tetrakis (pentafluorophenyl)borate, methyl(2-cyanopyridinium) tetrakis(pentafluorophenyl)borate, benzyl(2-cyanopyridinium) tetrakis(pentafluorophenyl)borate, methyl (4-cyanopyridinium)tetrakis(pentafluorophenyl)borate, triphenylphosphonium tetrakis(pentafluorophenyl)borate, dimethylanilinium tetrakis[bis(3,5-ditrifluoromethyl)phenyl]borate, ferrocenium tetraphenylborate, silver tetraphenylborate, trityl tetraphenylborate, tetraphenylporphyrinmanganese tetraphenylborate, ferrocenium tetrakis (pentafluorophenyl), (1,1'-dimethylferrocenium) tetrakis (pentafluorophenyl)borate, decamethylferrocenium tetrakis (pentafluorophenyl)borate, silver tetrakis (pentafluorophenyl)borate, trityl tetrakis(pentafluorophenyl) borate, lithium tetrakis(pentafluorophenyl)borate, sodium tetrakis(pentafluorophenyl)borate, theoraphenylporphyrinmanganese tetrakis(pentafluorophenyl)borate, silver tetrafluoroborate, silver hexafluorophosphate, silver hexafluoroarsenate, silver perchlorite, silver trifluoroacetate, silver trifluoromethanesulfonate, and the like.

Only one of or a mixture of two or more of the components (B-1), each capable of forming an ionic complex by reacting with a transition metal compound as a component (A), may be employed. A component (B-2) which is an aluminoxane may for example be a linear aluminoxane represented by Formula (V):

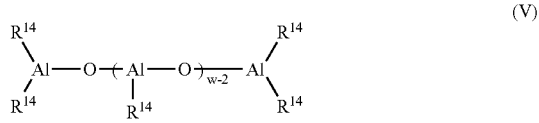

wherein $R^{14}$ is a hydrocarbon group such as an alkyl, alkenyl, aryl, arylalkyl groups having 1 to 20, preferably 1 to 12 carbon atoms or is a halogen atom, w represents a degree of polymerization which is usually an integer of 2 to 50, preferably 2 to 40; each $R^{14}$ may be same to or different from each other, and also may be a cyclic aluminoxane represented by Formula (VI):

wherein $R^{14}$ and w are defined as in Formula (V) shown above.

In a method for producing an aluminoxane described above, an alkylaluminium is brought into contact with a condensing agent such as water, while no particular procedure therefor is specified and the reaction may be in accordance with a known method. For example, [1] a method in which an organic aluminum compound is dissolved in an organic solvent and then brought into contact with water, [2] a method in which an organic aluminum compound is added upon a polymerization and water is subsequently added, [3] a method in which a water of crystallization associated with a metal or a water adsorbed onto an inorganic or organic substance is reacted with an aluminum compound, and [4] a method in which a tetraalkyldialuminoxane is reacted with a trialkylaluminium and then with water may be employed. A toluene-insoluble aluminoxane may also be employed.

Only one aluminoxane may be employed, and a combination of two or more may also be employed.

The molar ratio of a catalyst component (A) to a catalyst component (B) when employing a compound (B-1) as a catalyst component (B) is preferably 10:1 to 1:100, more preferably 2:1 to 1:10, and a ratio departing from this range is not advantageous industrially because of an increased catalyst cost per unit weight of a polymer. When a compound (B-2) is employed, the molar ratio is preferably 1:1 to 1:1000000, more preferably 1:10 to 1:10000, and particularly 1:10 to 1:1000. A ratio departing from this range is not advantageous industrially because of an increased catalyst cost per unit weight of a polymer. As a catalyst compound (B), a component (B-1) or (B-2) may be employed alone or in combination of two or more such components.

A polymerization catalyst employed in a production method according to the invention may comprise as a component C an organic aluminum compound in addition to components (A) and (B) described above.

As an organic aluminum compound as a component C may be a compound represented by Formula (VII):

Wherein R15 denotes an alkyl group having 1 to 10 carbon atoms, J denotes a hydrogen atom, an alkoxy group having 1 to 20 carbon atoms, an aryl group having 6 to 20 carbon atoms or a halogen atom, and v is an integer of 1 to 3.

Examples of a compound represented by Formula (VII) shown above are trimethylaluminium, triethylaluminium, triisopropylaluminium, triisobutylaluminium, dimethylaluminium chloride, diethylaluminium chloride, methylaluminium dichloride, ethylaluminium dichloride, dimethylaluminium fluoride, diisobutylaluminium hydride, diethylaluminium hydride, ethylaluminium sesquichloride and the like. Among those listed above, trimethylaluminium, triethylaluminium and triisobutylaluminium are preferred, and triisobutylaluminium is more preferred.

Only one organic aluminum compound listed above may be employed or a combination of two or more such compound may be employed.

The molar ratio of a catalyst component (A) to a catalyst component (C) is preferably 1:1 to 1:10000, more preferably 1:5 to 1:2000, most preferably 1:10 to 1:1000. While a catalyst component (C) serves to improve the polymerizaition activity per unit quantity of a transition metal, it remains uselessly and disadvantageously in the polymer as a large amount of surplus of the organic aluminum compound when employed in an excessive amount.

In a production method according to the invention, components (A), (B) and (C) may be subjected to a preliminary contact.

Such preliminary contact may for example be effected by bringing a component (B) into contact with a component (A)

by any known method. This preliminary contact serves to improve the catalyst activity and allows the amount of a component (B) to be reduced, thus being effective in reducing the catalyst cost. In addition to the effectiveness described above, an improvement with regard to the molecular weight can be obtained by bringing a component (A) into contact with a component (B-2).

The temperature at which a preliminary contact is effected ranges usually from −20° C. to 200° C., preferably −10° C. to 150° C., more preferably 0° C. to 80° C. In such preliminary contact, a solvent which can be employed includes inert hydrocarbons and aliphatic hydrocarbons. Among these, an aromatic hydrocarbon is particularly preferred.

In the present invention, at least one of the catalyst components may be employed as being supported on a suitable carrier. While the material for such carrier is not particularly limited and may be any of inorganic oxide carriers and other inorganic and organic carriers, an inorganic oxide carrier or other inorganic carriers are particularly preferred.

An inorganic oxide carrier may for example be $SiO_2$, $Al_2O_3$, MgO, $ZrO_2$, $TiO_2$, $Fe_2O_3$, $B_2O_3$, CaO, ZnO, BaO, $ThO_2$, as well as mixtures thereof such as silica alumina, zeolite, ferrite, glass fibers, carbons and the like. Among those listed above, $SiO_2$ and $Al_2O_3$ are particularly preferred. The inorganic oxide carriers listed above may contain small amounts of carbonates, nitrates, sulfates and the like.

Other carriers than those described above may for example be a magnesium compound represented by Formula $MgR^{16}xX^1y$, such as $MgC_{12}$, $Mg(OC_2H_5)_2$ and the like, as well as complex salts thereof. In this formula, $R^{16}$ denotes an alkyl group having 1 to 20 carbon atoms, an alkoxy group having 1 to 20 carbon atoms or an aryl group having 6 to 20 carbon atoms, $X^1$ denotes a halogen atom or an alkyl group having 1 to 20 carbon atoms, x is 0 to 2, y is 0 to 2, and x+Y=2. Each $R^{16}$ may be same or different, as may be each $X^1$.

An organic carrier may for example be a polymer such as polystyrene, a styrene-divinylbenbzene copolymer, polyethylene, propropylene, a substituted polystyrene, polyallylate and the like, as well as a starch.

One employed preferably as a carrier in the invention is $MgCl_2$, $MgCl(OC_2H_5)$, $Mg(OC_2H_5)_2$, $SiO_2$, $Al_2O_3$ and the like. While the state of a carrier may vary dependent of the type and the production method thereof, a mean particle size is usually 1 to 300 μm, preferably 10 to 200 μm, more preferably 20 to 100 μm.

A smaller particle size may result in an increase in microparticles in the polymer, while a larger particle size may result in an increase in coarse particles in the polymer, which leads to a reduced bulk density or a plugging in a hopper.

The specific surface area of a carrier is usually 1 to 1000 $m^2/g$, preferably 50 to 500 $m^2/g$, and the micropore void volume is usually 0.1 to 5 $cm^3$, preferably 0.3 to 3 $cm^3/g$.

When either of the specific surface area or the micropore void volume departs from the range specified above, the catalyst activity may be reduced. The specific surface area and the micropore void volume can for example be calculated based on the volume of the nitrogen gas adsorbed in accordance with BET method (See Journal of the American Chemical Society, Vol. 60, page 309 (1983)).

A carrier listed above is used appropriately after being sintered usually at 100 to 1000° C., preferably 150 to 800° C.

When at least one of the catalyst components is supported on a carrier listed above, at least one of catalyst components (A) and (B), preferably both of catalyst components (A) and (B) are supported.

A method for allowing at least one of a component (A) and a component (B) to be supported is not particularly limited, and those which may be exemplified are [1] a method in which at least one of a component (A) and a component (B) is mixed with a carrier, [2] a method in which a carrier is treated with an organic aluminum compound or a halogen-containing silicon compound and then mixed with at least one of a component (A) and a component (B) in an inert solvent, [3] a method in which a carrier is admixed with a component (A) and/or a component (B) together with an organic aluminum compound or a halogen-containing silicon compound, [4] a method in which a component (A) or a component (B) is supported on a carrier ant then mixed with a component (B) or a component (A), [5] a method in which a contact reaction product between a component (A) and a component (B) is mixed with a carrier, and [6] a method in which a contact reaction between a component (A) and a component (B) is effected in the presence of a carrier.

In the methods [4], [5] and [6] described above, an organic aluminum compound as a component (C) may be added.

A catalyst thus obtained may be used in a polymerization after being isolated as a solid by distilling a solvent off, or alternatively it may be subjected directly to a polymerization.

In the invention, a catalyst may be produced also by allowing at least one of a component (A) and a component (B) to be supported on a carrier within the system of polymerization. For example, at least one of a component (A) and a component (B) is admixed with a carrier, if necessary together with an organic aluminum compound as a component (C) described above, and then an olefin such as ethylene was subjected to a preliminary polymerization for 1 minutes to 2 hours at −20° C. to 200° C. under an atmospheric pressure to 20 $kg/cm^2$ to produce a catalyst particle.

In the invention, the weight ratio of a component (B-1) to a carrier is preferably 1:5 to 1:10000, more preferably 1:10 to 1:500, while the weight ratio of a component (B-2) to a carrier is preferably 1:0.5 to 1:1000, more preferably 1:1, to 1:50. When a mixture of two or more components (B) are employed, it is preferred that the weight ratio of each component (B) to a carrier is in the range specified above. The weight ratio of a component (A) to a carrier is preferably 1:5 to 1:10000, more preferably 1:10 to 1:500.

When the ratio of a component (B) [component (B-1) or component (B-2)] to a carrier or the ratio of a component (A) to a carrier is departing from the ranges specified above, the activity may be reduced. The polymerization catalyst of the invention thus prepared usually has a mean particle size of 2 to 200 μm, preferably 10 to 150 μm, particularly 20 to 100 μm, and a specific surface area usually of 20 to 1000 $m^2/g$, preferably 50 to 500 $m^2/g$. A mean particle size less than 2 μm may result in an increase in microparticles in the polymer, while that exceeding 200 μm may result in an increase in coarse particles in the polymer. A specific surface area less than 20 $m^2/g$ may result in a reduced activity, while that exceeding 100 $m^2/g$ may result in a reduced bulk density of the polymer. In an inventive catalyst, the amount of a transition metal in 100 g of a carrier is usually 0.05 to 10 g, preferably 0.1 to 2 g. An amount of a transition metal departing from the range described above may result in a reduced activity.

By means of employing a carrier as a support as described above, a polymer having industrially advantageous high bulk density and excellent particle size distribution can be obtained.

In a production method according to the present invention, a polymerization catalyst described above is employed to homopolymerize propylene, or copolymerize propylene and ethylene and/or an α-olefin having 4 to 20 carbon atoms.

While a polymerization method is not particularly limited in the invention and may be a slurry polymerization, a vapor phase polymerization, a bulk polymerization, a solution polymerization, a suspension polymerization and the like, those particularly preferred are a slurry polymerization and a vapor phase polymerization.

A polymerization condition involves a polymerization temperature usually of −100 to 250° C., preferably −50 to 200° C., more preferably 0 to 130° C. The ratio of a catalyst to a reactant, represented as starting monomer/component (A) (molar ratio), is preferably 1 to $10^8$, particularly 100 to $10^5$. A polymerization time usually of 5 minutes or longer, and a reaction pressure preferably of atmospheric pressure to 200 kg/cm²G, particularly atmospheric pressure to 100 kg/cm²G are employed.

The molecular weight of a polymer may be adjusted by appropriately selecting the types of respective catalyst components, the amounts and the polymerization temperature, or by performing a polymerization in the presence of hydrogen.

When a polymerization solvent is used, it may for example be an aromatic hydrocarbon such as benzene, toluene, xylene, ethylbenezene and the like, an alicyclic hydrocarbon such as cyclopentane, cyclohexane, methylcyclohexane and the like, an aliphatic hydrocarbon such as pentane, hexane, heptane, octane and the like, a halogenated hydrocarbon such as chloroform, dichloromethane and the like. Only one of these solvents may be employed, or a combination of two or more may be employed. A monomer such as an α-olefin may also be employed as a solvent. A certain polymerization procedure may need no use of a solvent.

Upon polymerization, a polymerization catalyst described above may be used to perform a preliminary polymerization. While a preliminary polymerization may for example be conducted by bringing a small amount of an olefin into contact with a solid catalyst component, the procedure for such contact is not particularly limited and may be any known procedure. An olefin employed in a preliminary polymerization is not particularly limited, and may be any of those listed above, such as ethylene, an α-olefin having 3 to 20 carbon atoms, or a mixture thereof, while it is advantageous to use an olefin similar to that employed in a main polymerization.

A preliminary polymerization may be performed usually at −20 to 200° C., preferably −10 to 130° C., more preferably 0 to 80° C. A solvent which may be used in a preliminary polymerization is an inert hydrocarbon, an aliphatic hydrocarbon, an aromatic hydrocarbon, a monomer and the like. Among these, an aliphatic hydrocarbon is particularly preferred. A preliminary polymerization may be performed without using any solvent.

The conditions of a preliminary polymerization may preferably be adjusted so that the intrinsic viscosity [η] (determined in a decalin at 135° C.) is 0.2 dL/g or higher, particularly 0.5 dl/g or higher and the amount of a preliminary polymerization product per 1 millimole of a transition metal component in a catalyst ranges from 1 to 10000 g, particularly 10 to 1000 g.

A propylenic polymer according to the invention thus obtained can be formed into a molded article by a press molding. It may be used also as a modifier for imparting a resin with a pliability.

A propylenic polymer composition according to the invention is obtained by admixing a propylene homopolymer described above [component (a)] or a propylenic polymer produced by copolymerizing a propylene and ethylene and/or an α-olefin having 4 to 20 carbon described above [component (a')] with a nucleating agent (b) at a level of 10 ppm or higher.

A nucleating agent as a component (b) may be any of those capable of inducing a crystalline nucleation rapidly and lowering the supercooling degree required for initiating a crystallization without affecting the physical properties of a propylenic polymer adversely.

Examples of a nucleating agent used in the invention are a high melting polymer, an organic carboxylic acid or its metal salt, an aromatic sulfonate or its metal salt, an organic phosphorus compound or its metal salt, a dibenzylidene sorbitol or its derivative, a rosinic acid partial metal salt, an inorganic microparticle, imides, amides, quinacridones, quinones as well as mixtures thereof.

A high melting polymer may for example be a polyolefin such as polyethylene and polypropylene, a polyvinylcycloalkane such as polyvinylcyclohexane and polyvinylcyclopentane, as well as poly 3-methylpentene-1, poly 3-methylbutene-1, polyalkenylsilanes and the like. A metal salt may for example be aluminum benzoate, aluminum p-t-butylbenzoate, sodium adipate, sodium thiophenecarboxylate, sodium pyrrole carboxylate and the like. A dibenzylidene sorbitol and its derivative may for example be dibenzylidene sorbitol, 1,3:2,4-bis(o-3,4-dimethylbenzylidene)sorbitol, 1,3:2,4-bis(o-2,4-dimethylbenzylidene)sorbitol, 1,3:2,4-bis(o-4-ethylbenzylidene)sorbitol, 1,3:2,4-bis(o-4-chlorobenzylidene) sorbitol, 1,3:2,4-dibenzylidene sorbitol and the like. Typically, GELOL MD or GELOL MD-R (trade names) available from SHINNIPPON RIKA (KK) may also be exemplified.

A rosinic acid partial metal salt may for example be PINECRYSTAL KM1600, PINECRYSTAL KM1500, PINECRYSTAL KM1300 (trade names) and the like which are available from ARAKAWA KAGAKU KOGYO (KK).

An inorganic microparticle may for example be talc, clay, mica, asbestos, glass fiber, glass flake, glass bead, calcium silicate, montmorillonite, bentonite, graphite, aluminium powder, alumina, silica, kieselguhr, titanium oxide, magnesium oxide, pumice powder, pumice balloon, aluminum hydroxide, magnesium hydroxide, basic magnesium carbonate, dolomite, calcium sulfate, potassium titanate, barium sulfate, calcium sulfite, molybdenum sulfite and the like. Among these substances, an organic metal phosphate represented by Formula (VIII) and an inorganic microparticle such as talc are preferable when an inventive propylenic polymer composition is applied to a food product because of their reduced odor generation.

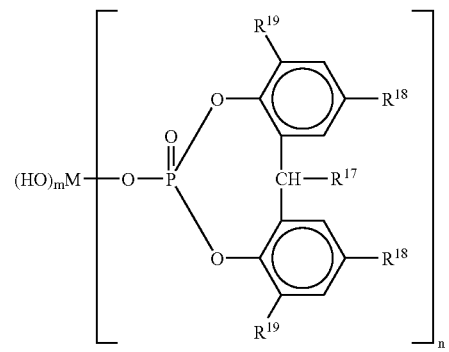

(VIII)

wherein $R^{17}$ denotes a hydrogen atom or an alkyl group having 1 to 4 carbon atoms, each of $R^{18}$ and $R^{19}$ denotes a hydrogen atom, an alkyl group having 1 to 12 carbon atoms, cycloalkyl, aryl or aralkyl group; M denotes an alkaline metal, an alkaline earth metal, aluminum or zinc, and in case that M is an alkaline metal then m is 0 and n is 1, and in case that M is a divalent metal then n is 1 or 2 and m is 1 when n is 1 and m is 0 when n is 2, and in case that M is aluminium then m is 1 and n is 2.

In addition, since a film formed by molding a propylenic polymer composition containing an inorganic microparticle such as talc also has an excellent slipperiness, it gives an improvement in a secondary processing performance such as bag making or printing performance, due to which it is suitable as a general-purpose packaging film subjected to a high speed bag making machine including various automatic filling-packaging laminators.

A film produced by molding a propylenic polymer composition containing a dibenzylidene sorbitol or its derivative as a nucleating agent has a particularly excellent transparency which is highly display-oriented, and which makes it to be suitable as a package film of a toy or a stationery.

Examples of a dibenzylidene sorbitol are 1,3:2,4-bis(o-3, 4-dimethylbenzylidene)sorbitol, 1,3:2,4-bis(o-2,4-dimethylbenzylidene)sorbitol, 1,3:2,4-bis(o-4-ethylbenzylidene)sorbitol, 1,3:2,4-bis(o-4-chlorobenzylidene)sorbitol, 1,3:2,4-dibenzylidene sorbitol and the like.

A film produced by molding a propylenic polymer composition containing an amide compound as a nucleating agent has a particularly excellent rigidity and a less problematic wrinkling when being wound during a high speed bag making, due to which it is suitable as a general-purpose packaging film subjected to a high speed bag making machine.

An amide compound may for example be dianilide adipate, dianilide suberate and the like.

The amount of an nucleating agent added is usually 10 ppm or higher, preferably 50 to 3000 ppm based on a propylenic copolymer. An amount less than 10 ppm does not improve a low temperature heat seal performance, while an increase in a nucleating agent may fail to exhibit a corresponding increase in the effect.

In view of the transparency and the impact resistance of a propylenic polymer composition, the amount of a nucleating agent to be added is 1000 ppm or less, particularly 500 ppm or less, although it may vary depending on the type of the nucleating agent. Typically wen a sorbitol-based nucleating agent is employed, dibenzylidene sorbitol, in this case, is added at 3000 ppm or less, more preferably 1500 ppm or less, and most preferably 500 ppm or less. In the case where bis(p-methyl-benzylidene)sorbitol or bis(dimethylbenzylidne)sorbitol is employed, it is added preferably at 1200 ppm or less, more preferably 600 ppm or less, particularly 300 ppm or less. In the case where sodium organophosphate which is one of the metal organophosphates, it is added preferably at 50 ppm or less, more preferably 200 ppm or less, particularly 125 ppm or less. An aluminium organophosphate is added preferably at 1900 ppm or less, more preferably 1500 ppm or less, particularly 500 ppm or less. When a talc is employed, talc MMR produced by ASADA SEIFUN, for example in this case, is added preferably at 4000 ppm or less, more preferably 2000 ppm or less, particularly 1000 ppm or less. When an amide-based compound is employed, N-GESTER-NU-100 produced by SHINNPPON RIKA, for example in this case, is added preferably at 3000 ppm or less, more preferably 1500 ppm or less, particularly 500 ppm or less.

To a propylenic polymer, a propylenic polymer composition, a molded article or a film according to the invention, customary additives such as antioxidant, neutralizing agent, slipperiness-imparting agent, anti-blocking agent, anti-frosting agent, decomposing agent, foaming agent, antistatic agent and the like may be incorporated as desired.

A film produced by a propylenic polymer composition of the invention is produced first by kneading of a propylenic polymer and a nucleating agent together with necessary various additives using a single- or twin-screw extruder, Banbury mixer and the like into a pellet which is then formed into a film by a cast molding. Alternatively, a propylenic polymer, a nucleating agent and necessary additives are dry-blended in Henschel mixer or an equivalent, and then formed into a film by a cast molding.

When a high melting polymer is used as a nucleating agent, the high melting polymer may be produced simultaneously or sequentially during the production of a propylenic polymer in a reactor, whereby obtaining a propylenic polymer composition.

[II] Second Invention

The second invention consisting of a propylenic polymer [1], a method for producing the same [2], a propylenic resin composition [3], a molded article [4] and a propylenic resin modifier [5] is detailed below.

[1] Propylenic Polymer

An inventive propylenic polymer is a propylenic polymer satisfying the following requirements (1) and (2):
(1) the amount of the components which are dissolved out into hexane at 25° C. (H25) ranges from 0 to 80% by weight; and,
(2) no melting point (Tm(° C.)) is observed in DSC or, when any Tm is observed then the Tm and the fusion endothermic calorie ΔH (J/g) are in the relationship represented by the following formula:

$$\Delta H \geq 6 \times (Tm - 140).$$

In addition, an inventive propylenic polymer is a propylenic polymer satisfying the following requirements (1) to (3):
(1) the amount of the components which are dissolved out at 25° C. or lower (W25) in a temperature-raising chromatography ranges from 20 to 100% by weight;
(2) the amount of the components which are dissolved out into hexane at 25° C. (H25) ranges from 0 to 80% by weight; and,
(3) no melting point (Tm(° C.)) is observed in DSC or, when any Tm is observed then the Tm and the fusion endothermic calorie ΔH (J/g) are in the relationship represented by the following formula:

$$\Delta H \geq 6 \times (Tm - 140).$$

By satisfying the requirements described above, an inventive propylenic polymer provides a molded article exhibiting well-balanced amount of the stickiness-imparting components, low modulus and transparency. Thus, it exhibits a low modulus and an excellent softness (referred to as pliability), contains a reduced amount of a stickiness-imparting component and has an excellent surface characteristics (for example those experienced as a less bleeding and a less migration of a stickiness-imparting component into other products), and is also associated with an advantageously excellent transparency.

The requirements described above are discussed below.

A propylenic polymer has an amount of the components which are dissolved out at 25° C. or lower (W25) in a temperature-raising chromatography which ranges from 20 to 100% by weight, preferably 30 to 100% by weight, more preferably 50 to 100% by weight. W25 is an index for the softness of a propylenic polymer. An increase in this value is associated with an increase in the component having a higher modulus and/or a broader reoregularity distribution. In the invention, a value W25 less than 20% is not preferable since it results in the loss of the pliability. A value W25 is the amount (% by weight) of the components which are dissolved out, instead of adsorbed onto a packing, at the TREF column temperature of 25° C., as observed on a elution curve determined by a temperature-raising chromatography performed by the operating procedure with the instruments under the operating conditions specified below.

(a) Operating Procedure

A sample solution is introduced into a TREF column adjusted at 135° C. and then the temperature is lowered gradually at the lowering rate of 5° C./hour to 0° C., at which the temperature is held for 30 minutes to effect a crystallizaiton of a sample on the surface of the packing. Subsequently, the column temperature is raised at the raising rate of 40° C./hour to 135° C. to obtain an elution curve.

(b) Instruments

TREF column: Manufactured by GL SCIENCE, Silica gel column (4.6φ×150 mm)
Flow cell: Manufactured by GL SCIENCE, path length 1 mm, KBr cell
Feed pump: Manufactured by SENSHU KAGAKU, Pump Model SSC-3100
Valve oven: Manufactured by GL SCIENCE, Oven model 554 (high temperature type)
TREF oven: Manufactured by GL SCIENCE
Dual-system thermostat: Manufactured by RIKAGAKU KOGYO, Thermostat model REX-C100
Detector: Infrared detector for HPLC, Manufactured by FOXBORO CORP., Model MIRAN 1A CVF
10-way valve: Manufactured by VALCO, Electric valve
Loop: Manufactured by VALCO, 500 μL Loop (C) Operating Conditions Solvent: o-Dichlorobenzene
Sample concentration: 7.5 g/L
Injeciton volume: 500 μL
Pumping rate: 2.0 mL/min
Detection wave number: 3.41 μm
Column packing: CHROMOSOLVE P (30 to 60 mesh)
Column temperature deviation: Within ±0.2° C.

In a propylenic polymer according to the invention, the amount of the components which are dissolved out into hexane at 25° C. (H25) ranges from 0 to 80% by weight. Preferably, it is 0 to 50% by weight, particularly 0 to 25% by weight. H25 is an index for the level of a stickiness-imparting component which causes a reduced transparency, and a higher H25 indicates an increased amount of a stickiness-imparting component. With a level of H25 exceeding 80% by weight, a stickiness-imparting component exists in a large amount, which may cause problematic blocking and transparency characteristics, because of which the use in a food or medical product is not acceptable.

A level of H25 is a % reduction in weight which is obtained by determining the weight of a propylenic polymer (W0) and the weight of the same after allowing to stand in 200 mL of hexane at 25° C. for 3 days or longer followed by drying (W1) and then calculating in accordance with the equation shown below.

$$H25 = [(W0 - W1)/W0] \times 100(\%)$$

In a propylenic polymer according to the invention, no melting point (Tm(° C.)) is observed in DSC, or, when any Tm is observed then the Tm and the fusion endothermic calorie ΔH(J/G) are in the relationship represented by the following formula:

$$\Delta H \geq 6 \times (Tm - 140),$$

more preferably, $$\Delta H \geq 3 \times (Tm - 120),$$

particularly, $$\Delta H \geq 2 \times (Tm - 100).$$

The vales of Tm and ΔH are determined in DSC. Thus, using a differential scanning calorimeter (Perkin Elmer, DSC-7), 10 mg of a sample is fused for 3 minutes at 230° C. under a nitrogen atmosphere and then the temperature is lowered to 0° C. at the rate of 10° C./minutes. After holding at 0° C. for 3 minutes, the temperature is raised at the rate of 10° C./minutes to obtain a fusion endothermic curve, in which the peak top of the maximum peak represents the melting point: Tm and the fusion endothermic calorie in this case is represented as ΔH(J/g).

A propylenic polymer according to the invention is not particularly limited, provided that it can satisfy the requirements described above, and may for example be a propylene homopolymer or a propylenic copolymer. Specifically, a propylenic polymer according to the invention described above can more preferably be embodied by a propylene homopolymer [a] or a propylene copolymer [a'] described below.

[a] Propylene Homopolymer

A propylene homopolymer of the invention is a polymer satisfying the following requirements (1) to (3):

(1) the meso-pentad fraction (mmmm (in percentage terms by mole)) ranges from 20 to 60% by mole;
(2) the racemi-pentad fraction (rrrr) and (1−mmmm) are in the relationship represented by the following formula:

$$[rrrr/(1-mmmm)] \leq 0.1$$

wherein the racemi-pentad fraction (rrrr) and the meso-pentad fraction (mmmm) are not in percentage terms; and,
(3) the amount of the components which are dissolved out at 25° C. or lower (W25) in a temperature-raising chromatography ranges from 20 to 100% by weight.

When a propylene homopolymer according to the invention satisfies the requirements described above, a resultant molded article exhibits well-balanced amount of the stickiness-imparting components, low modulus and transparency. Thus, it exhibits a low modulus and an excellent softness (referred to as pliability), contains a reduced amount of a stickiness-imparting component and has an excellent surface characteristics (for example those experienced as a less bleeding and a less migration of a stickiness-imparting component into other products), and is also associated with an advantegously excellent transparency.

A % meso-pentad (% mmmm) employed in the present invention is the same to that discussed in the first invention. A meso-pentad fraction (mmmm) of an inventive propylene homopolymer less than 20% by mole may cause a stickiness. One exceeding 60% by mole may represent disadvantageously high modulus. A % racemi-pentad (% rrrr) is a % racemic moiety, represented in pentad as a unit, in a polypropylene molecule chain. A value [rrrr/(1−mmmm)] can be obtained from a % in pentad described above, and serves as an index for the narrowness in the regularity distribution of a propylene homopolymer. An increase in this value is associated with a broader regularity distribution, and represents a mixture of a highly regular PP and APP such as a conventional polypropylene produced using an existing catalyst system, and thus is associated with an increased stickiness and a reduced transparency. A value [rrrr/(1−mmmm)] of a propylene homopolymer of the invention which exceeds 0.1 causes a stickiness. A $^{13}$C-NMR spectrum is obtained similarly as in the first invention.

The meanings and the determination method of a W25 with regard to a propylene homopolymer are similar to those with regard to the propylenic polymer [1] described above. A W25 of an inventive propylene homopolymer less than 20% results in the loss of pliability.

A propylenic homopolymer is further preferred when it satisfies, among the requirements descrived above, the following requirements:

(4) the meso-pentad fraction (mmmm (in percentage terms by mole)) ranges from 30 to 50% by mole;
(5) the racemi-pentad fraction (rrrr) and (1−mmmm) are in the relationship represented by the following formula:

$$[rrrr/(1-mmmm)] \leq 0.08$$

wherein the racemi-pentad fraction (rrrr) and the meso-pentad fraction (mmmm) are not in percentage terms; and, (6) the amount of the components which are dissolved out at 25° C. or lower (W25) in a temperature-raising chromatography ranges from 30 to 100% by weight;

and is particularly preferred when it satisfies the following requirements:

(7) the racemi-pentad fraction (rrrr) and (1−mmmm) are in the relationship represented by the following formula:

$$[rrrr/(1-mmmm)] \leq 0.06$$

wherein the racemi-pentad fraction (rrrr) and the meso-pentad fraction (mmmm) are not in percentage terms; and, (8) the amount of the components which are dissolved out at 25° C. or lower (W25) in a temperature-raising chromatography ranges from 50 to 100% by weight.

A propylene homopolymer according to the invention is preferred when it satisfies, in addition to the requirements described above, that the molecular weight distribution (Mw/Mn) determined by a gel permeation chromatography (GPC) is 4 or less and/or the intrinsic viscosity [η] determined in a tetralin solvent at 135° C. ranges from 0.5 to 15.0 dl/g, with a Mw/Mn of 3.5 or less and/or a [η] of 1.0 to 5.0 dl/g being more preferred and a Mw/Mn of 3 or less and/or a [η] of 1.0 to 3.0 dl/g being particularly preferred. A molecular weight distribution (Mw/Mn) exceeding 4 may cause a stickiness, and an intrinsic viscosity [η] less than 0.5 dl/g may also cause a stickiness. A [η] exceeding 15.0 dl/g results in a reduced flowability which may lead to a poor molding performance.

A Mw/Mn described above may be understood similarly as in the first invention.

In addition to the requirements described above, a fusion endothermic calorie ΔH determined by DSC of 20 J/gr. or less allows an inventive propylene homopolymer to be more pliable and thus be more preferred. A value of ΔH is an index for the softness, and a higher value represents a higher modulus and a reduced softness. A ΔH is obtained as described above.

While an inventive propylenic homopolymer may have or may not have a melting point (Tm) and a crystallization temperature (Tc), it is preferred for the purpose of the softness that such values do not exist or do exist only as low values, with a Tm not higher than 100° C. being preferred. The values of Tm and Tc are determined by DSC. Thus, using a differential scanning calorimeter (Perkin Elmer, DSC-7), 10 mg of a sample is fused for 3 minutes at 230° C. under a nitrogen atmosphere and then the temperature is lowered to 0° C. at the rate of 10° C./minutes. The peak top of the maximum curve in the crystallization exothermic curve obtained during this course is the crystallization temperature:Tc. After holding at 0° C. for 3 minutes, the temperature is raised at the rate of 10° C./minutes to obtain a fusion endothermic curve, in which the peak top of the maximum peak represents the melting point: Tm.

While during an ordinary propylene polymerization process a 1,2 insertion polymerization, which means that a carbon atom of a propylene monomer on the side of a methylene undergoes a binding with an active center of a catalyst followed by a successive coordination of the propylene monomers in the same manner whereby effecting the polymerization, takes place generally, a 2,1 insertion or a 1,3 insertion may also take place at a less incidence (sometimes referred to as abnormal insertion) In a homopolymer according to the invention, it is preferable that the incidence of such 2, 1 or 1,3 insertion is low. It is also preferable that these insertion rates satisfy the relationship represented by the following formula (1):

$$[(m\text{-}2,1)+(r\text{-}2,1)+(1,3)] \leq 5.0 \tag{1}$$

wherein (m-2,1) is a % meso-2,1 insertion content determined by $^{13}$C-NMR, (r-2,1) is a % racemi-2,1 insertion content determined by $^{13}$C-NMR, and (1,3) is a % 1,3 insertion content determined by $^{13}$C-NMR, and, more preferably, they satisfy the relationship represented by the following formula (2):

$$[(m\text{-}2,1)+(r\text{-}2,1)+(1,3)] \leq 1.0 \tag{2}$$

It is particularly preferred that they satisfy the relationship represented by the following formula (3):

$$[(m\text{-}2,1)+(r\text{-}2,1)+(1,3)] \leq 0.1 \tag{3}$$

When the relationship represented by Formula (1) is not satisfied, the crystallinity is reduced far more than expected, and a stickiness may arise.

(m-2, 1), (r-2, 1) and (1,3) are understood similarly as in the first invention.

A propylene homopolymer of the invention preferably exhibits substantially no peaks in a $^{13}$C-NMR spectrum which are assigned to a molecular chain terminal (n-butyl group) as a result of a 2,1 insertion. With regard to this molecular chain terminal as a result of a 2,1 insertion, each % insertion content is calculated from the integrated intensity of each peak after assignment of the peak in the $^{13}$C-NMR spectrum in accordance with the report by Jungling et al (J. Polym. Sci.: Part A: Polym. Chem., 33, p 1305 (1995)).

In addition to the requirements described above, a % boiling diethylether extract, which is an index for the modulus, of 5% by weight or higher allows a propylene homopolymer in the invention to be further preferred. A % boiling diethylether extract can be determined using a Soxlet extractor under the conditions specified below.

Extraction sample: 1 to 2 g
State of sample: Powder (a pellet should be pulverized into a powder before use)
Extraction solvent: Diethylether
Extraction duration: 10 hours
Extraction times: 180 times or more
Calculation of extract: As shown below

[Amount extracted into diethylether (g))/Charged powder weight (g)]×100

Further preferably, an inventive propylene homopolymer has a tensile elastic modulus of 100 MPa or less, more preferably 70 MPa or less.

[a'] Propylenic Copolymer

A propylenic copolymer according to the invention is a copolymer of propylene and ethylene and/or an α-olefin having 4 to 20 carbon atoms which satisfies the following requirements:

(1) the stereoregularity index (P) determined by a $^{13}$C-NMR ranges from 55 to 90% by mole; and,
(2) the amount of the components which are dissolved out at 25° C. or lower (W25) in a temperature-raising chromatography ranges from 20 to 100% by weight.

When a propylenic copolymer according to the invention satisfies the requirements described above, a resultant molded article exhibits well-balanced amount of the stickiness-imparting components, low modulus and transparency. Thus, it exhibits a low modulus and an excellent softness (referred to as pliability), contains a reduced amount of a stickiness-imparting component and has an excellent surface characteristics (for example those experienced as a less bleeding and a less migration of a stickiness-imparting component into other products), and is also associated with an advantegously excellent transparency. A stereoregularity index (P) in the invention is a value obtained by determining a $^{13}$C-NMR spectrum similarly as in the first invention using Nippon Densi Model JNM-EX400 $^{13}$C-NMR device described above and then calculating a % meso-triad (mmm) of a propylene chain. An increase in this value is associated with a higher stereoregularity. A propylenic copolymer according to the invention preferably has a stereoregularity index (P) of 65 to 80% by mole. A stereoregularity index (P) less than 55% by weight results in a too reduced modulus, which may lead to a poor molding performance. At 90% by mole or higher, a rigidness may arise and a softness is lost. It is further preferred that the W25 is 30 to 100% by weight, with 50 to 100% by weight being particularly preferred. A W25 less than 20% by weight results in a loss of pliability. The meanings and the determination method of a W25 are as described above.

A propylenic copolymer according to the invention is preferred when it satisfies, in addition to the requirements described above, that the molecular weight distribution (Mw/Mn) determined by a gel permeation chromatography (GPC) is 4 or less and/or the intrinsic viscosity [η] determined in a tetralin solvent at 135° C. ranges from 0.5 to 15.0 dl/g, with a Mw/Mn of 3.5 or less and/or a [η] of 1.0 to 5.0 dl/g being more preferred and a Mw/Mn of 3 or less and/or a [η] of 1.0 to 3.0 dl/g being particularly preferred. A molecular weight distribution (Mw/Mn) exceeding 4 may cause a stickiness. An intrinsic viscosity [η] less than 0.5 dl/g may also cause a stickiness, and one exceeding 15.0 dl/g results in a reduced flowability which may lead to a poor molding performance. The determination method of this Mw/Mn is as described above.

In addition to the requirements described above, a fusion endothermic calorie ΔH determined by DSC of 20 J/gr. or less allows an inventive propylenic copolymer to be more pliable and thus be more preferred. While an inventive propylenic copolymer may have or may not have a melting point (Tm) and a crystallization temperature (Tc), it is preferred for the purpose of the softness that such values do not exist or do exist only as low values, with a Tm not higher than 100° C. being preferred. ΔH, Tm and Tc are obtained as described above. In addition to the requirements described above, a % boiling diethylether extract, which is an index for the modulus, of 5% by weight or higher allows a propylenic copolymer in the invention to be further preferred. The boiling diethylether extract is determined as described above.

In addition, the tensile elastic modulus is preferably 100 MPa or less, more preferably 70 MPa or less.

In conjunction with a propylenic copolymer according to the invention, an α-olefin having 4 to 20 carbon atoms may for example be ethylene, 1-butene, 1-pentene, 4-methyl-1-pentene, 1-hexene, 1-octene, 1-decene, 1-dodecene, 1-tetradecene, 1-hexadecene, 1-octadecene, 1-eicocene and the like, and, in the invention, these may be employed alone or in combination with each other.

A propylenic copolymer according to the invention is preferably a random copolymer. The structural unit derived from propylene exists preferably at a level of 90% by mole or higher, more preferably 95% by mole or higher.

[Method for Producing Propylene Homopolymer (a) and Propylenic copolymer (a')]

A method for producing a propylene homopolymer (a) and a propylenic copolymer (a') according to the invention may be a method in which a catalyst system called a metallocene catalyst is used to homopolymerize propylene or to copolymerize propylene and ethylene and/or an α-olefin having 4 to 20 carbon atoms. A metallocene-based catalyst may for example be those described in JP-A-58-19309, JP-A-61-130314, JP-A-3-163088, JP-A-4-300887, JP-A-4-211694, JP-W-1-502036 and the like, such as a catalyst derived from a transition metal compound having, as its one or two ligands, cyclopentadienyl group, substituted cyclopentadienyl group, indenyl group, substituted indenyl group and the like or and a tansition metal compound in which said ligands are controlled geometrically in combination with a promoter.

In the invention, among metallocene catalysts, one derived from a transition metal compound whose ligand forms a crosslinking structure via a crosslinking group is preferred, and a particularly preferred method involves a use of a metallocene catalyst obtained by combining a transition metal compound whose crosslinking structure is formed via 2 crosslinking groups with a promoter whereby effecting a homopolymerization of propylene or a copolymerization of propylene and ethylene and/or an α-olefin having 4 to 20 carbon atoms.

Typically, a catalyst consists of the following components.

(A) a transition metal compound (B) a component (B-1) which is a compound capable of forming an ionic complex by reacting with a transition metal compound as a component (A) and a component (B-2) which is an aluminoxane.

In addition to a component (A) and a component (B), an organic aluminum compound can be used as a component (C).

Components (A), (B) and (C) are similar to those described in the first invention, and each of components (B) and (C) may be used alone or in combination of two or more. The amount of each component to be used is also similar to that employed in the first invention.

In a production method according to the invention, components (A), (B) and (C) may be subjected to a preliminary contact. Such preliminary contact may for example be effected by bringing a component (B) into contact with a component (A) in a manner similar to that described in the first invention.

In the present invention, at least one of the catalyst components may be employed as being supported on a suitable carrier. A carrier employed in this invention is similar to that in the first invention. A method for allowing at least one of the catalyst components to be supported on a carrier is also similar to that in the first invention.

In the present invention, a catalyst may be prepared by irradiating a dynamic wave upon contact between components (A), (B) and (C). Such elastic wave is usually a sound wave, preferably an ultrasonic wave. Typically, an ultrasonic wave at a frequency of 1 to 1000 kHz, preferably 10 to 500 kHz may be exemplified.

A catalyst thus obtained may be used in a polymerization after being isolated as a solid by distilling a solvent off, or alternatively it may be subjected directly to a polymerization.

In the invention, as is discussed already in the first invention, a catalyst may be produced also by allowing at least one of a component (A) and a component (B) to be supported on a carrier within the system of polymerization.

In this invention, the ratio of a component (B-1) to a carrier, the ratio of a component (B-2) to a carrier and the ratio of a component (A) to a carrier are similar to those in the first invention.

The polymerization catalyst of the invention thus prepared usually has a mean particle size of 2 to 200 µm, preferably 10 to 150 µm, particularly 20 to 100 µm, and a specific surface area usually of 20 to 1000 m$^2$/g, preferably 50 to 500 m$^2$/g. In an inventive catalyst, the amount of a transition metal in 100 g of a carrier is usually 0.05 to 10 g, preferably 0.1 to 2 g. An amount of a transition metal departing from the range described above may result in a reduced activity.

By means of employing a carrier as a support as described above, a polymer having industrially advantageous high bulk density and excellent particle size distribution can be obtained.

A propylenic polymer according to the invention is produced by using a polymerization catalyst described above to homopolymerize propylene, or to copolymerize propylene and ethylene and/or an α-olefin having 4 to 20 carbon atoms.

While a polymerization method is not particularly limited and may be a slurry polymerization, a vapor phase polymerization, a bulk polymerization, a solution polymerization, a suspension polymerization and the like, those particularly preferred are a slurry polymerization and a vapor phase polymerization.

A polymerization condition involves a polymerization temperature usually of −100 to 250° C., preferably −50 to 200° C., more preferably 0 to 130° C. The ratio of a catalyst to a reactant, represented as starting monomer/component (A) (molar ratio), is preferably 1 to $10^8$, particularly 100 to $10^5$. A polymerization time usually of 5 minutes to 10 hours, and a reaction pressure preferably of atmospheric pressure to 200 kg/cm$^2$G, particularly atmospheric pressure to 100 kg/cm$^2$G are employed.

The molecular weight of a polymer may be adjusted by a manner similar to that in the first invention.

When a polymerization solvent is employed, the types of the solvents may be similar to those in the first invention.

Upon polymerization, a polymerization catalyst described above may be used to perform a preliminary polymerization. Such preliminary polymerization may be similar to that in the first invention.

[3] Propylenic Resin Composition

A propylenic resin composition according to the invention is a resin composition obtained by adding a nucleating agent to a propylenic polymer [1], a propylene homopolymer [a] or a propylenic copolymer [a'] described above. In general, the crystallizaiton of a propylenic polymer involves 2 processes, namely, a nucleation process and a crystal growth process, and it is understood that in the nucleation process the nucleation rate varies dependend on the state factors such as the difference from the crystallization temperature or the orientation of a molecular chain. Especially when a substance having a molecular chain orientation promoting effect via a adsorption of the molecular chain is present, the nucleation rate is increased markedly. As a nucleating agent in the invention, one having a nucleation rate accelerating effect is employed. The substance having a nucleation rate accelerating effect may for example be one having a molecular chain orientation promoting effect via a adsorption of the molecular chain of a polymer.

A nucleating agent in this invention is similar to that in the first invention, and only one or a combination of two or more of nucleating agents may be employed.

A propylenic resin compisition in this invention which employs a metal organophosphate and/or an inorganic microparticle such as talc is preferred because of a reduced generation of an odor. Such propylenic resin composition is applied preferably to a food product.

A propylenic resin composition in this invention which employs as a nucleating agent an inorganic microparticle such as talc as described above, it exhibits an excellent slipperiness when molded into a film and provides an improvement in the film characteristics such as printability. When a dibenzylidene sorbitol or its derivative described above is employed as a nucleating agent, an advantageously excellent transparency is achieved. Also when an amide compound described above is employed as a nucleating agent, an advantageously excellent rigidity is achieved.

An inventive propylenic resin composition may be one obtained by dry-blending a propylenic polymer [1], a propylene homopolymer [a] or a propylenic copolymer [a'] with a nucleating agent, together with various additives if desired, using a mixer such as Henschel mixer. Alternatively, a kneading may be effected using a single- or twin-screw extruder, Banbury mixer and the like. When a high melting polymer is used as a nucleating agent, the high melting polymer may be added to a reactor simultaneously or sequentially during the production of a propylenic polymer. Additives employed if necessary are antioxidant, neutralizing agent, slipperiness-imparting agent, anti-blocking agent, anti-frosting agent and antistatic agent and the like.

The amount of a nucleating agent added in the invention is 10 ppm or higher, preferably 10 to 10000 ppm, more preferably 10 to 5000 ppm, particularly 10 to 2500 ppm, based on a propylenic polymer [1], a propylene homopolymer [a] or a propylenic copolymer [a']. An amount less than 10 ppm provides no improvement in the moldability, while an amount exceeding 10000 ppm fails to exhibit corresponding increase in the effect.

[4] Molded Article

A molded article in this invention is a molded article obtained by molding a propylenic polymer [1], a propylene homopolymer [a], a propylenic copolymer [a'] or a propylenic resin composition [3] described above. An inventive molded article has a softness (also referred to as pliability) and a high % elasticity recovery (ability of recovery after being stretched), and is characterized by a less stickiness in spite of its high softness, i.e., a low modulus, as well as an excellent transparency.

A molded article in this invention may for example be films, sheets, containers, automobile interior parts, electricity power line housings and the like. Films may for example be films for food product packagings and films for agricultural uses (such as for green houses). Containers may for example be clear cases, clear boxes, decorated boxes utilizing their excellent transparency.

A molded article may be produced by injection molding, compression molding, injection stamping, gas-assisted injection molding, extrusion molding, blow molding and the like.

The molding conditions may not particularly be limited, provided that a temperature capable of allowing a resin to be molten and to flow is employed, and a usual case involves a resin temperature of 50° C. to 300° C. and a mold temperature of 60° C. or lower.

When a film is formed as a molded article in this invention, a method which may be employed includes ordinary compression molding, extrusion molding, blow molding, cast molding and the like. The film obtained may be oriented or may not be oriented. When oriented, it is preferred to be biaxially oriented. The biaxially orienting conditions involve the parameters described below.

[1] Sheet Molding Conditions

Resin temperature of 50 to 200° C., chill roll temperature of 50° C. or lower

[2] Lengthwise Orienting Conditions

Orienting magnitude of 3 to 7 times, orienting temperature of 50 to 100° C.

[3] Widthwise Orienting Conditions

Orienting magnitude of 6 to 12 times, orienting temperature of 50 to 100° C.

A film may be surface-treated if necessary to enhance its surface energy or to impart the surface with a polarity. For example, corona discharge treatment, chromic acid treatment, flame treatment, hot gas treatment, ozone- or UV irradiation treatment may for example be employed. The surface may be embossed by, for example, sand-blast method or solvent treatment.

To a film, a customary additives such as antioxidant, neutralizing agent, slipperiness-imparting agent, anti-blocking agent, anti-frosting agent, antistatic agent and the like may be incorporated as desired.

A film further containing an inorganic microparticle such as talc exhibits an excellent slipperiness, which leads to an improvement in secondary processing performances such as bag making or printing performance, due to which it is suitable as a general-purpose packaging film subjected to a high speed machine including various automatic filling-packaging laminators.

A film produced by molding a propylenic resin composition containing a dibenzylidene sorbitol or its derivative as a nucleating agent has a particularly excellent transparency which is highly display-oriented, and which makes it suitable as a package film of a toy or a stationery.

A film produced by molding a propylenic resin composition containing an amide compound as a nucleating agent has a particularly excellent rigidity and exhibits a less problematic wrinkling when being wound during a high speed bag making, due to which it is suitable as a general-purpose packaging film subjected to a high speed bag making machine.

[5] Propylenic Resin Modifier

A propylenic resin modifier is a resin modifier comprising a propylenic polymer [1], a propylene homopolymer [a] or a propylenic copolymer [a'] described above. An inventive propylenic resin modifier is characterized by an ability of providing a molded article having a softness, a less stickiness and an excellent compatibility with a polyolefin resin. Thus, an inventive propylenic resin modifier exhibits a less stickiness when compared with a conventional modifier which is a soft polyolefin resin, since it comprises specified propylene homopolymer and specified propylenic polymer and is associated partially with a crystallinity especially in a polypropylene chain moiety. In addition, an inventive propylenic resin modifier is excellent in terms of the compatibility with an olefin resin, especially with a polypropylenic resin. As a result, it exhibits a less deterioration of the surface condition (such as stickiness) and a higher transparency, when compared with a conventional modifier which is an ethylenic rubber. The characteristics discussed above makes an inventive propylenic resin modifier to be used preferably as an agent for modifying physical properties such as pliability and transparency.

[III] Third Invention

The third invention consisting of a propylenic polymer [1], a method for producing the same [2], and a molded article [3] is detailed below.

[1] Propylenic Polymer

An inventive propylenic polymer is a propylenic polymer satisfying the following requirements (1) to (3):

(1) the amount of the components which are dissolved out into hexane at 25° C. (H25) ranges from 0 to 80% by weight;

(2) no melting point (Tm(° C.)) is observed in DSC or, when any Tm is observed then the Tm and the fusion endothermic calorie $\Delta H$ (J/g) are in the relationship represented by the following formula:

$$\Delta H \geq 6 \times (Tm - 140); \text{ and,}$$

(3) the molecular weight distribution (Mw/Mn) determined by a gel permeation chromatography (GPC) ranges from 2.5 to 14.0 and the intrinsic viscosity [η] determined in a decalin solvent at 135° C. ranges from 0.5 to 15.0 dl/g.

By satisfying the requirements described above, an inventive propylenic polymer exhibits an excellent melt flowability and provides a molded article having a less stickiness as well as excellent softness and transparency.

The requirements described above are detailed below.

In a propylenic polymer according to the invention, the amount of the components which are dissolved out into hexane at 25° C. (H25) ranges from 0 to 80% by weight. Preferably, it is 0 to 50% by weight, particularly 0 to 25% by weight. H25 is an index for the level of a stickiness-imparting component which causes a reduced transparency, and a higher H25 indicates an increased amount of a stickiness-imparting component. With a level of H25 exceeding 85% by weight, a stickiness-imparting component exists in a large amount, which may cause deterioration in blocking and transparency characteristics.

H25 can be understood similarly as in the second invention. Furthermore in a propylenic polymer according to the invention, no melting point (Tm(° C.)) is observed in DSC, or, when any Tm is observed then the Tm and the fusion endothermic calorie $\Delta H(J/G)$ are in the relationship represented by the following formula:

$$\Delta H \geq 6 \times (Tm - 140),$$

more preferably, $$\Delta H \geq 3 \times (Tm - 120),$$

particularly, $$\Delta H \geq 2 \times (Tm - 100).$$

Tm and $\Delta H$ can also be understood similarly as in the second invention.

A propylenic copolymer according to the invention has a molecular weight distribution (Mw/Mn) determined by a gel permeation chromatography (GPC) of 2.5 to 14.0 and an intrinsic viscosity [η] determined in a decalin solvent at 135° C. of 0.5 to 15.0 dl/g. An Mw/Mn of 3.0 to 12.0 and a [η] of 1.0 to 5.0 dl/g are more preferred, and an Mw/Mn of 4.0 to 10.0 and a [η] of 1.0 to 3.0 dl/g is particularly preferred. A molecular weight distribution (Mw/Mn) less than 2.5 results in a poor moldability, while that exceeding 14.0 may cause a stickiness. An intrinsic viscosity [η] less than 0.5 dl/g may also cause a stickiness, and one exceeding 15.0 dl/g results in a reduced flowability which may lead to a poor molding performance. GPC is determined similarly as in the first invention.

In addition to the requirements described above, a complex viscosity coefficient (η*)(Pa·s) and an intrinsic viscosity [η] (dl/g) at the frequency ω of 100 rad/sec in determination of the frequency distribution of the melt viscoelasticity, which are in the relationship represented by the formula:

$$\eta^* < 159\eta + 743;$$

more preferably, $$\eta^* < 159\eta + 600;$$

particularly, $$\eta^* < 159\eta + 500;$$

allows an inventive propylenic copolymer to have an improved melt flowability and thus be more preferred.

A value of (η*)(Pa·s) is obtained by determining a frequency distribution of a melt viscoelasticity using a rotary rheometer (ARES) manufactured by RHEOMETRIX together with a parallel plate (25 mm in diameter, 1 mm in gap) at the temperature of 230° C. and at the initial strain of 20% or less. (η*) is an index for the flowability of a molten resin upon molding fabrication, and a lower value indicates a higher flowability and a higher molding fabrication performance.

A propylenic polymer according to the invention is not particularly limited, provided that it can satisfy the requirements described above, and may for example be a propylene homopolymer or a propylenic copolymer. Specifically, a propylenic polymer according to the invention described above can more preferably be embodied by a propylene homopolymer [a] or a propylene copolymer [a'] described below.

[a] Propylene Homopolymer

A propylene homopolymer of the invention is a polymer satisfying the following requirements (1) to (3):

(1) the meso-pentad fraction (mmmm (in percentage terms by mole)) ranges from 20 to 85% by mole;
(2) the racemi-pentad fraction (rrrr) and (1−mmmm) are in the relationship represented by the following formula:

$$[rrrr/(1-mmmm)] \leq 10.1$$

wherein the racemi-pentad fraction (rrrr) and the meso-pentad fraction (mmmm) are not in percentage terms; and,
(3) the molecular weight distribution (Mw/Mn) determined by a gel permeation chromatography (GPC) ranges from 2.5 to 14.0 and the intrinsic viscosity [η] determined in a decalin solvent at 135° C. ranges from 0.5 to 15.0 dl/g.

When a propylene homopolymer according to the invention satisfies the requirements described above, a resultant molded article exhibits an excellent melt flowability, a less stickiness, and excellent softness and transparency.

A % meso-pentad (% mmmm) and a % racemi-pentad (% rrrr) referred herein were similar to those described in the first invention. An inventive propylene homopolymer has a % meso-pentad (% mmmm) which is preferably 30 to 70%, particularly 35 to 60%. A meso-pentad fraction (mmmm) of an inventive propylene homopolymer less than 20% by mole may cause a stickiness. One exceeding 85% by mole results in a disadvantageously higher modulus. An inventive propylene homopolymer is preferred when [rrrr/(1−mmmm)]≦0.08, and is particularly preferred when [rrrr/(1−mmmm)]≦0.06. A value of [rrrr/(1−mmmm)] exceeding 0.1 may cause a stickiness.

A propylene homopolymer according to the invention has a molecular weight distribution (Mw/Mn) determined by a gel permeation chromatography (GPC) of 2.5 to 14.0 and an intrinsic viscosity [η] determined in a decalin solvent at 135° C. of 0.5 to 15.0 dl/g. An Mw/Mn of 3.0 to 12.0 and a [η] of 1.0 to 5.0 dl/g are more preferred, and an Mw/Mn of 4.0 to 10.0 and a [η] of 1.0 to 3.0 dl/g is particularly preferred. A molecular weight distribution (Mw/Mn) less than 2.5 results in a poor moldability, while that exceeding 14.0 may cause a stickiness. An intrinsic viscosity [η] less than 0.5 dl/g may also cause a stickiness, and one exceeding 15.0 dl/g results in a reduced flowability which may lead to a poor molding performance.

In addition to the requirements described above, a complex viscosity coefficient (η*)(Pa·s) and an intrinsic viscosity [η] (dl/g) at the frequency ω of 100 rad/sec in determination of the frequency distribution of the melt viscoelasticity, which are in the relationship represented by the formula:

$$\eta^* < 159\eta + 743;$$

more preferably, $$\eta^* < 159\eta + 600;$$

particularly, $$\eta^* < 159\eta + 500;$$

allows an inventive propylene homopolymer to have an improved melt flowability and thus be more preferred.

The meaning of (η*)(Pa·s) is understood as discussed above.

In addition, it is preferred that in a propylene homopolymer according to the invention the amount of the components which are dissolved out at 25° C. or lower (W25) in a temperature-raising chromatography ranges from 20 to 100% by weight. More preferably, such amount ranges from 30 to 100% by weight, and most preferably 50 to 100% by weight. W25 is an index for the softness of a propylenic polymer. An increase in this value is associated with an increase in the component having a higher modulus and/or a broader stereoregularity distribution. In the invention, a value W25 less than 20% may result in the loss of the pliability. A value W25 is the amount (% by weight) of the components which are dissolved out, instead of adsorbed onto a packing, at the TREF column temperature of 25° C., as observed on a elution curve determined by a temperature-raising chromatography performed by the operating procedure with the instruments under the operating conditions described in the examples. In the invention, a value W25 less than 20% may result in the loss of the pliability.

Furthermore, a fusion endothermic calorie ΔH determined by DSC of 20 J/gr. or less allows an inventive propylene homopolymer to be excellent in terms of the pliability and thus be more preferred. A value of ΔH is an index for the softness, and a higher value represents a higher modulus and a reduced softness. A ΔH is obtained as described above.

In addition, while an inventive propylenic homopolymer may have or may not have a melting point (Tm) and a crystallization temperature (Tc), it is preferred for the purpose of the softness that such values do not exist or do exist only as low values, with a Tm not higher than 100° C. being preferred.

The values of Tm and Tc are determined by DSC, and may be understood as described in the second invention.

While during an ordinary propylene polymerization process a 1,2 insertion polymerization, which means that a carbon atom of a propylene monomer on the side of a methylene undergoes a binding with an active center of a catalyst followed by a successive coordination of the propylene monomers in the same manner whereby effecting the polymerization, takes place generally, a 2,1 insertion or a 1,3 insertion may also take place at a less incidence (sometimes referred to as abnormal insertion). In a homopolymer according to the invention, it is preferable that the incidence of such 2, 1 or 1,3 insertion is low. It is also preferable that these insertion rates satisfy the relationship represented by the following formula (1):

$$[(m\text{-}2,1)+(r\text{-}2,1)+(1,3)] \leq 5.0 \quad (1)$$

wherein (m-2,1) is a % meso-2,1 insertion content determined by $^{13}$C-NMR, (r-2,1) is a % racemi-2,1 insertion content determined by $^{13}$C-NMR, and (1,3) is a % 1,3 insertion content determined by $^{13}$C-NMR, and, more preferably, they satisfy the relationship represented by the following formula (2):

$$[(m\text{-}2,1)+(r\text{-}2,1)+(13)] \leq 1.0 \quad (2).$$

It is particularly preferred that they satisfy the relationship represented by the following formula (3):

$$[(m\text{-}2,1)+(r\text{-}2,1)+(1,3)] \leq 0.1 \quad (3).$$

When the relationship represented by Formula (1) is not satisfied, the crystallinity is reduced far more than expected, and a stickiness may arise. (m-2, 1), (r-2, 1) and (1,3) are understood similarly as in the first invention.

A propylene homopolymer of the invention preferably exhibits substantially no peaks in a $^{13}$C-NMR spectrum which are assigned to a molecular chain terminal (n-butyl group) as a result of a 2,1 insertion. With regard to this molecular chain terminal as a result of a 2,1 insertion, each % insertion content is calculated from the integrated intensity of each peak after assignment of the peak in the $^{13}$C-NMR spectrum in accordance with the report by Jungling et al (J. Polym. Sci.: Part A: Polym. Chem., 33, p 1305 (1995)).

In addition to the requirements described above, a % boiling diethylether extract, which is an index for the modulus, of 5% by weight or higher allows a propylene homopolymer in the invention to be further preferred. A % boiling diethylether extract can be determined as described in the second invention.

Further preferably, an inventive propylene homopolymer has a tensile elastic modulus of 100 MPa or less, more preferably 70 MPa or less.

[a'] Propylenic Copolymer

A propylenic copolymer according to the invention is a copolymer of propylene and ethylene and/or an α-olefin having 4 to 20 carbon atoms which satisfies the following requirements:

(1) the stereoregularity index (P) determined by a $^{13}$C-NMR ranges from 55 to 90% by mole; and (2) the molecular weight distribution (Mw/Mn) determined by a gel permeation chromatography (GPC) ranges from 2.5 to 14.0 and the intrinsic viscosity [η] determined in a decalin solvent at 135° C. ranges from 0.5 to 15.0 dl/g.

By satisfying the requirements described above, an inventive propylenic polymer exhibits an excellent melt flowability and provides a molded article having a less stickiness as well as excellent softness and transparency.

A stereoregularity index (P) in the invention is a value obtained by determining a $^{13}$C-NMR spectrum and then calculating a % meso-triad (mm) of a propylene chain, and an increase in this value is associated with a higher stereoregularity. A propylenic copolymer according to the invention preferably has a stereoregularity index (P) of 65 to 80% by mole. A stereoregularity index (P) less than 55% by weight results in a too reduced modulus, which may lead to a poor molding performance. At 90% by mole or higher, a softness is lost.

$^{13}$C-NMR spectrum is determined in a manner similar to that described in the first invention.

Furthermore, a propylenic copolymer in this invention has a molecular weight distribution (Mw/Mn), determined by a gel permeation chromatography (GPC) described in the examples, of 2.5 to 14.0 and an intrinsic viscosity [η] determined in a decalin solvent at 135° C. of 0.5 to 15.0 dl/g. An Mw/Mn of 3.0 to 12.0 and a [η] of 1.0 to 5.0 dl/g are more preferred, and an Mw/Mn of 4.0 to 10.0 and a [η] of 1.0 to 3.0 dl/g is particularly preferred. A molecular weight distribution (Mw/Mn) less than 2.5 results in a poor moldability, while that exceeding 14.0 may cause a stickiness. An intrinsic viscosity [η] less than 0.5 dl/g may also cause a stickiness, while that exceeding 15.0 dl/g results in a reduced flowability which may lead to a poor molding performance. GPC is determined by a method described in the first invention.

In addition to the requirements described above, a complex viscosity coefficient (η*)(Pa·s) and an intrinsic viscosity [η] (dl/g) at the frequency ω of 100 rad/sec in determination of the frequency distribution of the melt viscoelasticity, which are in the relationship represented by the formula:

$$\eta^* < 159\eta + 743;$$

more preferably, $$\eta^* < 159\eta + 600;$$

particularly, $$\eta^* < 159\eta + 500;$$

allows an inventive propylenic copolymer to have an improved melt flowability and thus be more preferred.

The meaning of (η*) (Pa·s) is understood as discussed above.

In addition, it is preferred that in a propylenic copolymer according to the invention the amount of the components which are dissolved out at 25° C. or lower (W25) in a temperature-raising chromatography ranges from 20 to 100% by weight. More preferably, such amount ranges from 30 to 100% by weight, and most preferably 50 to 100% by weight. A value W25 less than 20% may result in the loss of the pliability. The meaning and the determination method of W 25 are as described above.

Furthermore, a fusion endothermic calorie ΔH determined by DSC of 20 J/gr. or less allows an inventive propylenic copolymer to be excellent in terms of the pliability and thus be more preferred. In addition, while an inventive propylenic copolymer may have or may not have a melting point (Tm) and a crystallization temperature (Tc), it is preferred for the purpose of the softness that such values do not exist or do exist only as low values, with a Tm not higher than 100° C. being preferred. The determination methods of ΔH, Tm and Tc are as described above.

In addition to the requirements described above, a % boiling diethylether extract, which is an index for the modulus, of 5% by weight or higher allows a propylenic copolymer in the invention to be further preferred.

In addition, the tensile elastic modulus is preferably 100 MPa or less, more preferably 70 MPa or less.

In conjunction with a propylenic copolymer according to the invention, an α-olefin having 4 to 20 carbon atoms may for example be ethylene, 1-butene, 1-pentene, 4-methyl-1-pentene, 1-hexene, 1-octene, 1-decene, 1-dodecene, 1-tetradecene, 1-hexadecene, 1-octadecene, 1-eicocene and the like, and, in the invention, these may be employed alone or in combination with each other.

A propylenic copolymer according to the invention is preferably a random copolymer. The structural unit derived from propylene exists preferably at a level of 90% by mole or higher, more preferably 95% by mole or higher.

[Method for Producing Propylene Homopolymer [a] and Propylenic Copolymer [a']]

A method for producing a propylene homopolymer [a] and a propylenic copolymer [a'] according to the invention may be a method in which a propylene is homopolymerized or copolymerized by a multi-step polymerization process comprising at least a step in which propylene is homopolymerized, or propylene and ethylene and/or an α-olefin having 4 to 20 carbon atoms are copolymerized in the presence of a catalyst system called a metallocene catalyst. A metallocene catalyst may for example be those described in the second invention. In the invention, among metallocene catalysts, one derived from a transition metal compound whose ligand forms a crosslinking structure via a crosslinking group is preferred, and a particularly preferred method involves a multi-step polymerization process comprising at least a step in which propylene is homopolymerized, or propylene and ethylene and/or an α-olefin having 4 to 20 carbon atoms are copolymerized in the presence of a metallocene catalyst obtained by combining a transition metal compound whose crosslinking structure is formed via 2 crosslinking groups with a promoter.

Typically, a catalyst consists of the following components.

(A) a transition metal compound (B) a component (B-1) which is a compound capable of forming an ionic complex by reacting with a transition metal compound as a component (A) and a component (B-2) which is an aluminoxane.

In addition to a component (A) and a component (B), an organic aluminium compound can be used as a component (C).

Components (A), (B) and (C) are similar to those described in the first invention, and each of components (B) and (C) may be used alone or in combination of two or more. The amount of each component to be used is also similar to that employed in the first invention.

In a production method according to the invention, components (A), (B) and (C) may be subjected to a preliminary contact. Such preliminary contact may for example be effected by bringing a component (B) into contact with a component (A). Such preliminary contact may be performed in a manner similar to that described in the first invention.

In the present invention, at least one of the catalyst components may be employed as being supported on a suitable carrier. A carrier employed is similar to that in the first invention. A method for allowing at least one of the catalyst components to be supported on a carrier is also similar to that in the first invention.

In the present invention, a catalyst may be prepared by irradiating a dynamic wave upon contact between components (A), (B) and (C). Such elastic wave is usually a sound wave, preferably an ultrasonic wave. Typically, an ultrasonic wave at a frequency of 1 to 1000 kHz, preferably 10 to 500 kHz may be exemplified.

A catalyst thus obtained may be used in a polymerization after being isolated as a solid by distilling a solvent off, or alternatively it may be subjected directly to a polymerization.

In the invention, as is discussed already in the first invention, a catalyst may be produced also by allowing at least one of a component (A) and a component (B) to be supported on a carrier within the system of polymerization.

The ratio of each component to a carrier is also the same to that employed in the first invention. The polymerization catalyst of the invention thus prepared usually has a mean particle size of 2 to 200 μm, preferably 10 to 150 μm, particularly 20 to 100 μm, and a specific surface area usually of 20 to 1000 $m^2/g$, preferably 50 to 500 $m^2/g$. In an inventive catalyst, the amount of a transition metal in 100 g of a carrier is usually 0.05 to 10 g, preferably 0.1 to 2 g. An amount of a transition metal departing from the range described above may result in a reduced activity.

A propylene homopolymer [a] and a propylenic copolymer [a'] according to the invention are produced by a method in which a propylene is homopolymerized or copolymerized by a multi-step polymerization process comprising at least a step in which propylene is homopolymerized, or propylene and ethylene and/or an α-olefin having 4 to 20 carbon atoms are copolymerized in the presence of a metallocene catalyst. An inventive production method may be a method in which a propylene is homopolymerized or copolymerized by a multi-step polymerization process comprising at least a step in which propylene is homopolymerized, or propylene and ethylene and/or an α-olefin having 4 to 20 carbon atoms are copolymerized in the presence of a co-catalyst comprising a metallocene catalyst containing a component (A) described above and a component (B) and at least one other catalyst. The copolymerization may be performed as a multi-step polymerization or may not. Preferably, a multi-step polymerization is employed for the polymerization.

In a production method in this invention a polymerization method is not particularly limited and may be a slurry polymerization, a vapor phase polymerization, a bulk polymerization, a solution polymerization, a suspension polymerization and the like, and those particularly preferred are a slurry polymerization and a vapor phase polymerization.

A polymerization condition of a multi-step polymerization or a single-stage polymerization involves a polymerization temperature usually of −100 to 250° C., preferably −50 to 200° C., more preferably 0 to 130° C. The ratio of a catalyst to a reactant, represented as starting monomer/component (A) (molar ratio), is preferably 1 to $10^8$, particularly 100 to $10^5$. A polymerization time usually of 5 minutes to 10 hours, and a reaction pressure preferably of atmospheric pressure to 200 $kg/cm^2G$, particularly atmospheric pressure to 100 $kg/cm^2G$ are employed.

The molecular weight of a polymer may be adjusted by appropriately selecting the type and the amount of each catalyst component and the polymerization temperature, or by performing the polymerization in the presence of a chain transfer agent. In this context, the description in the second invention can analogously be applied. In the case of a multi-step polymerization, it is preferred to use the polymerization conditions, such as temperature, pressure, polymerization time, amount of a chain transfer agent, monomer composition ratio and the like, in the second stage which are different from those in the first stage.

When a polymerization solvent is employed, the types of the solvents may be similar to those in the first invention. A monomer such as an α-olefin may also be employed as a solvent. Some polymerization methods need no use of solvents.

Upon polymerization, a polymerization catalyst described above may be used to perform a preliminary polymerization. Such preliminary polymerization may be similar to that in the first invention.

A propylenic polymer, a propylene homopolymer [a] and a propylenic copolymer [a'] in this invention may be supplemented with a nucleating agent. Such nucleating agent is understood similarly as in the first invention.

As a nucleating agent in this invention, a metal organophosphate and/or an inorganic microparticle such as talc, as described in the first invention, is preferred because of a reduced generation of an odor and can be applied preferably to a food product.

In this invention, the use of an inorganic microparticle such as talc as described above as a nucleating agent results in an excellent slipperiness of a molded film and provides an improvement in the characteristics such as printability. When a dibenzylidene sorbitol or its derivative described above is employed as a nucleating agent, an advantageously excellent transparency is achieved. Also when an amide compound described above is employed as a nucleating agent, an advantageously excellent rigidity is achieved.

In this invention, a nucleating agent and various desirable additives are dry-blended using a mixer such as Henschel mixer. Alternatively, a kneading may be effected using a single- or twin-screw extruder, Banbury mixer and the like. When a high melting polymer is used as a nucleating agent, the high melting polymer may be added to a reactor simultaneously or sequentially during the production of a propylenic polymer. Additives employed if necessary are antioxidant, neutralizing agent, slipperiness-imparting agent, anti-blocking agent, anti-frosting agent and antistatic agent and the like.

The amount of a nucleating agent added in the invention is 10 ppm or higher, preferably 10 to 10000 ppm, more preferably 10 to 5000 ppm, particularly 10 to 2500 ppm, based on a propylenic polymer [1], a propylene homopolymer [a] or a propylenic copolymer [a']. An amount less than 10 ppm provides no improvement in the moldability, while an amount exceeding 10000 ppm fails to exhibit corresponding increase in the effect.

[3] Molded Article

A molded article in this invention is a molded article obtained by molding a propylenic polymer [1], a propylene homopolymer [a] or a propylenic copolymer [a'] described above (hereinafter also referred to as inventive propylenic polymers). An inventive molded article has a softness (also referred to as pliability) and a high % elasticity recovery (ability of recovery after being stretched), and is characterized by a less stickiness in spite of its high softness, i.e., a low modulus, as well as an excellent transparency.

A molded article in this invention may for example be films, sheets, containers, automobile interior parts, electricity power line housings and the like. Films may for example be films for food product packagings and films for agricultural uses (such as for green houses). Containers may for example be clear cases, clear boxes, decorated boxes utilizing their excellent transparency.

A molded article may be produced by injection molding, compression molding, injection stamping, gas-assisted injection molding, extrusion molding, blow molding and the like.

The molding conditions may not particularly be limited, provided that a temperature capable of allowing a resin to be molten and to flow is employed, and in this context, the description in the second invention can analogously be applied. The film may be oriented or may not be oriented. When oriented, it is preferred to be biaxially oriented. The biaxially orienting conditions involve the parameters described in the second invention.

A film may be surface-treated if necessary to enhance its surface energy or to impart the surface with a polarity.

To a film, a customary additives such as antioxidant, neutralizing agent, slipperiness-imparting agent, anti-blocking agent, anti-frosting agent, antistatic agent and the like may be incorporated as desired.

A film further containing an inorganic microparticle such as talc exhibits an excellent slipperiness, which leads to an improvement in secondary processing performances such as bag making or printing performance, due to which it is suitable as a general-purpose packaging film subjected to a high speed machine including various automatic filling-packaging laminators.

A film produced by molding a propylenic polymers containing a dibenzylidene sorbitol or its derivative as a nucleating agent has a particularly excellent transparency which is highly display-oriented, and which makes it suitable as a package film of a toy or a stationery.

A film produced by molding a propylenic polymers containing an amide compound as a nucleating agent has a particularly excellent rigidity and exhibits a less problematic wrinkling when being wound during a high speed bag making, due to which it is suitable as a general-purpose packaging film subjected to a high speed bag making machine.

An inventive propylenic polymers are used preferably also as propylenic resin modifiers.

[IV] Fourth Invention

The fourth invention consisting of a propylenic resin composition [1], a method for producing the same [2], and a molded article [3] is detailed below.

[1] Propylenic Resin Composition

A propylenic resin composition in this invention consists of a propylene homopolymer (a) and/or a propylenic copolymer (a'), and is a resin composition (hereinafter also referred to as a propylenic resin composition of the first invention] which satisfies the following requirements [1] to [3]:

[1] the amount of the components extracted with a boiling diethylether ranges 1 to 99% by weight;

[2] in a propylene homopolymer (a), a component extracted with a boiling diethylether satisfies the following requirements (1) to (3):

(1) the meso-pentad fraction (mmmm (in percentage terms by mole)) ranges from 20 to 60% by mole;

(2) the racemi-pentad fraction (rrrr) and (1−mmmm) are in the relationship represented by the following formula:

$$[rrrr/(1-mmmm)] \leq 0.1$$

wherein the racemi-pentad fraction (rrrr) and the meso-pentad fraction (mmmm) are not in percentage terms; and, (3) the amount of the components which are dissolved out at 25° C. or lower (W25) in a temperature-raising chromatography ranges from 20 to 100% by weight; and,

[3] in a propylenic copolymer (a'), a component extracted with a boiling diethylether satisfies the following requirements (4) and (5):

(4) the stereoregularity index (P) determined by a $^{13}$C-NMR ranges from 55 to 90% by mole; and, (5) the amount of the components which are dissolved out at 25° C. or lower (W25) in a temperature-raising chromatography ranges from 20 to 100% by weight.

A propylene homopolymer (a) and a propylene copolymer in this invention are as described below.

(a) Propylene Homopolymer

A propylene homopolymer in this invention is a polymer which satisfies the following requirements (1) to (3):

(1) the meso-pentad fraction (mmmm (in percentage terms by mole)) ranges from 20 to 60% by mole;

(2) the racemi-pentad fraction (rrrr) and (1−mmmm) are in the relationship represented by the following formula:

[rrrr/(1−mmmm))] ≦ 0.1 wherein the racemi-pentad fraction (rrrr) and the meso-pentad fraction (mmmm) are not in percentage terms; and, (3) the amount of the components which are dissolved out at 25° C. or lower (W25) in a temperature-raising chromatography ranges from 20 to 100% by weight.

By satisfying the requirements described above, an inventive propylene homopolymer provides a molded article exhibiting well-balanced amount of the stickiness-impartihg components, low modulus and transparency. Thus, it exhibits a low modulus and an excellent softness (referred to as pliability), contains a reduced amount of a stickiness-imparting component and has an excellent surface characteristics (for example those experienced as a less bleeding and a less migration of a stickiness-imparting component into other products), and is also associated with an advantageously excellent transparency.

A % meso-pentad (% mmmm) employed in the present invention and a % racemi-pentad (% rrrr) are the same to those discussed in the first invention. A meso-pentad fraction (mmmm) of an inventive propylene homopolymer less than 20% by mole may cause a stickiness. One exceeding 60% by mole may represent disadvantageously high modulus. A value of [rrrr/(1−mmmm)] of an inventive propylene homopolymer which exceeds 0.1 may cause a stickiness.

A $^{13}$C-NMR spectrum is obtained similarly as in the first invention.

A propylene homopolymer in this invention has an amount of the components which are dissolved out at 25° C. or lower (W25) in a temperature-raising chromatography ranging from 20 to 100% by weight. More preferably, such amount ranges from 30 to 100% by weight, and most preferably 50 to 100% by weight. The description with regard to W 25 is similar to those in the second invention.

In this invention, a propylenic homopolymer described above is further preferred when it satisfies, among the requirements described above, the following requirements:

(4) the meso-pentad fraction (mmmm (in percentage terms by mole)) ranges from 30 to 50% by mole;

(5) the racemi-pentad fraction (rrrr) and (1−mmmm) are in the relationship represented by the following formula:

[rrrr/(1−mmmm)] ≦ 0.08 wherein the racemi-pentad fraction (rrrr) and the meso-pentad fraction (mmmm) are not in percentage terms; and, (6) the amount of the components which are dissolved out at 25° C. or lower (W25) in a temperature-raising chromatography ranges from 30 to 100% by weight;

and is particularly preferred when it satisfies the following requirements:

(7) the racemi-pentad fraction (rrrr) and (1−mmmm) are in the relationship represented by the following formula:

[rrrr/(1−mmmm)] ≦ 0.06 wherein the racemi-pentad fraction (rrrr) and the meso-pentad fraction (mmmm) are not in percentage terms; and, (8) the amount of the components which are dissolved out at 25° C. or lower (W25) in a temperature-raising chromatography ranges from 50 to 100% by weight.

A propylene homopolymer according to the invention is preferred when it satisfies, in addition to the requirements described above, that the molecular weight distribution (Mw/Mn) determined by a gel permeation chromatography (GPC) is 4 or less and/or the intrinsic viscosity [η] determined in a tetralin solvent at 135° C. ranges from 0.5 to 15.0 dl/g, with an Mw/Mn of 3.5 or less and/or a [η] of 1.0 to 5.0 dl/g being more preferred and an Mw/Mn of 3 or less and/or a [η] of 1.0 to 3.0 dl/g being particularly preferred. A molecular weight distribution (Mw/Mn) exceeding 4 may cause a stickiness, and an intrinsic viscosity [η] less than 0.5 dl/g may also cause a stickiness. A [η] exceeding 15.0 dl/g results in a reduced flowability which may lead to a poor molding performance.

An Mw/Mn described above may be understood similarly as in the first invention.

In addition to the requirements described above, a fusion endothermic calorie ΔH determined by DSC of 20 J/gr. or less allows an inventive propylene homopolymer to be more pliable and thus be more preferred. A value of ΔH is an index for the softness, and a higher value represents a higher modulus and a reduced softness. A ΔH is a fusion endothermic calorie obtained using a differential scanning calorimeter (Perkin-Elmer, DSC-7) by fusing 10 mg of a sample for 3 minutes at 230° C. under a nitrogen atmosphere followed by lowering the temperature to 0° C. at the rate of 10° C./minutes, followed by holding at 0° C. for 3 minutes, and followed by raising the temperature at the rate of 10° C./minutes.

While an inventive propylene homopolymer may have or may not have a melting point (Tm) and a crystallization temperature (Tc), it is preferred for the purpose of the softness that such values do not exist or do exist only as low values, with a Tm not higher than 100° C. being preferred. The values of Tm and Tc are determined similarly as in the first invention.

While during an ordinary propylene polymerization process a 1,2 insertion polymerization, which means that a carbon atom of a propylene monomer on the side of a methylene undergoes a binding with an active center of a catalyst followed by a successive coordination of the propylene monomers in the same manner whereby effecting the polymerization, takes place generally, a 2,1 insertion or a 1,3 insertion may also take place at a less incidence (sometimes referred to as abnormal insertion). In a homopolymer according to the invention, it is preferable that the incidence of such 2, 1 or 1,3 insertion is low. It is also preferable that these insertion rates satisfy the relationship represented by the following formula (1):

[(m-2,1)+(r-2,1)+(1,3)] ≦ 5.0    (1)

wherein (m-2,1) is a % meso-2,1 insertion content determined by $^{13}$C-NMR, (r-2,1) is a % racemi-2,1 insertion content determined by $^{13}$C-NMR, and (1,3) is a % 1,3 insertion content determined by $^{13}$C-NMR, and, more preferably, they satisfy the relationship represented by the following formula (2):

[(m-2,1)+(r-2,1)+(1,3)] ≦ 1.0    (2).

It is particularly preferred that they satisfy the relationship represented by the following formula (3):

[(m-2,1)+(r-2,1)+(1,3)] ≦ 0.1    (3).

When the relationship represented by Formula (1) is not satisfied, the crystallinity is reduced far more than expected, and a stickiness may arise.

(m-2, 1), (r-2, 1) and (1,3) are understood similarly as in the first invention.

A propylene homopolymer of the invention preferably exhibits substantially no peaks in a $^{13}$C-NMR spectrum which are assigned to a molecular chain terminal (n-butyl group) as a result of a 2,1 insertion. With regard to this molecular chain terminal as a result of a 2,1 insertion, each % insertion content is calculated from the integrated intensity of each peak after assignment of the peak in the $^{13}$C-NMR spectrum in accordance with the report by Jungling et al (J. Polym. Sci. Part A: Polym. Chem., 33, p 1305 (1995)).

In addition to the requirements described above, a % boiling diethylether extract, which is an index for the modulus, of 5% by weight or higher allows a propylene homopolymer in the invention to be further preferred. A % boiling diethylether extract can be determined by the method similar to that described in the first invention.

In addition to the requirements described above, a tensile elastic modulus of 100 MPa or less, more preferably 70 MPa or less is associated with an inventive propylene homopolymer.

(a') Propylenic Copolymer

A propylenic copolymer in this invention is a copolymer of propylene and ethylene and/or an α-olefin having 4 to 20 carbon atoms which satisfies the following requirements (1) to (2):

(1) the stereoregularity index (P) determined by a $^{13}$C-NMR ranges from 55 to 90% by mole; and,
(2) the amount of the components which are dissolved out at 25° C. or lower (W25) in a temperature-raising chromatography ranges from 20 to 100% by weight.

By satisfying the requirements described above, an inventive propylenic copolymer provides a molded article exhibiting well-balanced amount of the stickiness-imparting components, low modulus and transparency. Thus, it exhibits a low modulus and an excellent softness (referred to as pliability), contains a reduced amount of a stickiness-imparting component and has an excellent surface characteristics (for example those experienced as a less bleeding and a less migration of a stickiness-imparting component into other products), and is also associated with an advantageously excellent transparency. A stereoregularity index (P) in the invention is a value obtained by determining a $^{13}$C-NMR spectrum and then calculating a % meso-triad (mm) of a propylene chain similarly as in the first invention. An increase in this value is associated with a higher stereoregularity. A propylenic copolymer according to the invention preferably has a stereoregularity index (P) of 65 to 80% by mole. A stereoregularity index (P) less than 55% by weight results in a too reduced modulus, which may lead to a poor molding performance. At 90% by mole or higher, a softness is lost. It is further preferred that the W25 is 30 to 100% by weight, with 50 to 10% by weight being particularly preferred. A W25 less than 20% by weight results in a loss of pliability. The meanings and the determination method of a W25 are as described above.

A propylenic copolymer according to the invention is preferred when it satisfies, in addition to the requirements described above, that the molecular weight distribution (Mw/Mn) determined by a gel permeation chromatography (GPC) is 4 or less and/or the intrinsic viscosity [η] determined in a tetralin solvent at 135° C. ranges from 0.5 to 15.0 dl/g, with an (Mw/Mn) of 3.5 or less and/or a [η] of 1.0 to 5.0 dl/g being more preferred and an (Mw/Mn) of 3 or less and/or a [η] of 1.0 to 3.0 dl/g being particularly preferred. A molecular weight distribution (Mw/Mn) exceeding 4 may cause a stickiness. An intrinsic viscosity [η] less than 0.5 dl/g may also cause a stickiness, and one exceeding 15.0 dl/g results in a reduced flowability which may lead to a poor molding performance. The determination method of this Mw/Mn is as described above.

In addition to the requirements described above, a fusion endothermic calorie ΔH determined by DSC of 20 J/gr. or less allows an inventive propylenic copolymer to be more pliable and thus be more preferred. While a melting point (Tm) and a crystallization temperature (Tc) may exist or may not, it is preferred for the purpose of the softness that such values do not exist or do exist only as low values, with a Tm not higher than 100° C. being preferred. ΔH, Tm and Tc are obtained as described above.

In addition to the requirements described above, a % boiling diethylether extract, which is an index for the modulus, of 5% by weight or higher allows a propylenic copolymer in the invention to be further preferred. The boiling diethylether extract is determined as described above.

In addition, the tensile elastic modulus is preferably 100 MPa or less, more preferably 70 MPa or less.

In conjunction with a propylenic copolymer according to the invention, an α-olefin having 4 to 20 carbon atoms may for example be ethylene, 1-butene, 1-pentene, 4-methyl-1-pentene, 1-hexene, 1-octene, 1-decene, 1-dodecene, 1-tetradecene, 1-hexadecene, 1-octadecene, 1-eicocene and the like, and, in the invention, these may be employed alone or in combination with each other.

A propylenic copolymer according to the invention is preferably a random copolymer. The structural unit derived from propylene exists preferably at a level of 90% by mole or higher, more preferably 95% by mole or higher.

(2) Propylenic Resin Composition

A propylenic resin composition in this invention consists of 1 to 99% by weight of a propylenic polymer [I] and 99 to 1% by weight of a polyolefin [II] in which said propylenic polymer [I] satisfies the following requirements (1) to (3):
(1) the amount of the components which are dissolved out at 25° C. or lower (W25) in a temperature-raising chromatography ranges from 20 to 100% by weight;
(2) the amount of the components which are dissolved out into hexane at 25° C. (H25) ranges from 0 to 80% by weight; and,
(3) no melting point (Tm(° C.)) is observed in DSC or, when any Tm is observed then the Tm and the fusion endothermic calorie ΔH(J/gr.) are in the relationship represented by the following formula:

$$\Delta H \geq 6 \times (Tm - 140).$$

A propylenic polymer [I] in this invention is discussed first. By satisfying the requirements described above, an inventive propylenic polymer [I] provides a molded article exhibiting well-balanced amount of the stickiness-imparting components, low modulus and transparency. Thus, it exhibits a low modulus and an excellent softness (referred to as pliability), contains a reduced amount of a stickiness-imparting component and has an excellent surface characteristics (for example those experienced as a less bleeding and a less migration of a stickiness-imparting component into other products), and is also associated with an advantageously excellent transparency.

The requirements described above are discussed below. A propylenic polymer in this invention has an amount of the components which are dissolved out at 25° C. or lower (W25) in a temperature-raising chromatography which ranges from 20 to 100% by weight. Such amount is preferably 30 to 100% by weight, more preferably 50 to 100% by weight. In this invention, a value of W25 less than 20% by weight results in a disadvantageous loss of pliability. The meanings and the determination method of a W25 are as described above. Also in a propylenic polymer in this invention, the amount of the components which are dissolved out into hexane at 25° C. (H25) ranges from 0 to 80% by weight. Preferably, it is 0 to 50% by weight, particularly 0 to 25% by weight. H25 can be understood as described in the second invention. With a level of H25 exceeding 80% by weight, a stickiness-imparting component exists in a large amount, which may cause problematic blocking and transparency characteristics, because of which the use in a food or medical product is not acceptable.

Also in an inventive propylenic polymer, no melting point (Tm(° C.)) is observed in DSC or, when any Tm is observed then the Tm and the fusion endothermic calorie ΔH(J/gr.) are in the relationship represented by the following formula:

$$\Delta H \geq 6 \times (Tm-140)$$

preferably by the following formula:

$$\Delta H \geq 3 \times (Tm-120); \text{ and,}$$

particularly by the following formula:

$$\Delta H \geq 2 \times (Tm-100).$$

Tm and ΔH can also be understood similarly as in the second invention.

A propylenic polymer [I] in this invention is not particularly limited, provided that it can satisfy the requirements described above, and may for example be a propylene homopolymer or a propylenic copolymer. Specifically, a propylenic polymer [I] in this invention described above can more preferably be embodied by a propylene homopolymer (a) or a propylene copolymer (a') described below.

A polyolefin [II] in this invention is discussed further later.

(3) Propylenic Resin Composition

A propylenic resin composition in this invention consists of 1 to 99% by weight of a propylene homopolymer (a) and 99 to 1% by weight of a polyolefin [II] in which said propylene homopolymer (a) satisfies the following requirements (1) to (3):

(1) the meso-pentad fraction (mmmm (in percentage terms by mole)) ranges from 20 to 60% by mole;
(2) the racemi-pentad fraction (rrrr) and (1−mmmm) are in the relationship represented by the following formula:

$$[rrrr/(1-mmmm)] \leq 0.1$$

wherein the racemi-pentad fraction (rrrr) and the meso-pentad fraction (mmmm) are not in percentage terms; and,
(3) the amount of the components which are dissolved out at 25° C. or lower (W25) in a temperature-raising chromatography ranges from 20 to 100% by weight.

A propylene homopolymer (a) in this invention is understood as described above.

A polyolefin [II] in this invention is discussed further later.

(4) Propylenic Resin Composition

A propylenic resin composition in this invention consists of 1 to 99% by weight of a propylenic copolymer (a') and 99 to 1% by weight of a polyolefin [II] in which said propylenic copolymer (a) satisfies the following requirements (1) to (2):
(1) the stereoregularity index (P) determined by a $^{13}$C-NMR ranges from 55 to 90% by mole; and,
(2) the amount of the components which are dissolved out at 25° C. or lower (W25) in a temperature-raising chromatography ranges from 20 to 100% by weight.

A propylenic copolymer (a') in this invention is understood as described above.

A polyolefin [II] in this invention is discussed further later.

A propylene homopolymer (a) and a propylenic copolymer (a') in the sections (2) to (4) described above may for example be produced by the following method.

[Method for Producing Propylene Homopolymer (a) and Propylenic Copolymer (a')]

A method for producing a propylene homopolymer (a) and a propylenic copolymer (a') according to the invention may be a method in which a catalyst system called a metallocene catalyst is used to homopolymerize propylene or to copolymerize propylene and ethylene and/or an α-olefin having 4 to 20 carbon atoms. A metallocene catalyst may for example be those described in the second invention. In the invention, among metallocene catalysts, one derived from a transition metal compound whose ligand forms a crosslinking structure via a crosslinking group is preferred, and a particularly preferred method involves a multi-step polymerization process comprising at least a step in which propylene is homopolymerized, or propylene and ethylene and/or an α-olefin having 4 to 20 carbon atoms are copolymerized in the presence of a metallocene catalyst obtained by combining a transition metal compound whose crosslinking structure is formed via 2 crosslinking groups with a promoter.

Typically, a catalyst consists of the following components.

(A) a transition metal compound (B) a component (B-1) which is a compound capable of forming an ionic complex by reacting with a transition metal compound as a component (A) and a component (B-2) which is an aluminoxane.

In addition to a component (A) and a component (B), an organic aluminium compound can be used as a component (C).

Components (A), (B) and (C) are similar to those described in the first invention, and each of components (B) and (C) may be used alone or in combination of two or more. The amount of each component to be used is also similar to that employed in the first invention.

In a production method according to the invention, components (A), (B) and (C) may be subjected to a preliminary contact. Such preliminary contact may be performed in a manner similar to that described in the first invention.

In the present invention, at least one of the catalyst components may be employed as being supported on a suitable carrier. A carrier employed is similar to that in the first invention. A method for allowing at least one of the catalyst components to be supported on a carrier is also similar to that in the first invention.

In the present invention, a catalyst may be prepared by irradiating a dynamic wave upon contact between components (A), (B) and (C). Such elastic wave is usually a sound wave, preferably an ultrasonic wave. Typically, an ultrasonic wave at a frequency of 1 to 1000 kHz, preferably 10 to 500 kHz may be exemplified.

A catalyst thus obtained may be used in a polymerization after being isolated as a solid by distilling a solvent off, or alternatively it may be subjected directly to a polymerization.

As is discussed already in the second invention, a catalyst may be produced by allowing at least one of a component (A) and a component (B) to be supported on a carrier within the system of polymerization.

Also in this invention, as is discussed already in the first invention, a catalyst may be produced by allowing at least one of a component (A) and a component (B) to be supported on a carrier within the system of polymerization.

The ratio of each component to a carrier is also the same to that employed in the first invention. The polymerization catalyst of the invention thus prepared usually has a mean particle size of 2 to 200 μm, preferably 10 to 150 μm, particularly 20 to 100 μm, and a specific surface area usually of 20 to 1000 m$^2$/g, preferably 50 to 500 m$^2$/g. In an inventive catalyst, the amount of a transition metal in 100 g of a carrier is usually 0.05 to 10 g, preferably 0.1 to 2 g. An amount of a transition metal departing from the range described above may result in a reduced activity.

A propylenic polymer employed in this invention can be produced using a polymerization catalyst described above by homopolymerizing a propylene or by copolymerizing propylene and ethylene and/or an α-olefin having 4 to 20 carbon atoms.

In such procedure, a polymerization method is not particularly limited and may be a slurry polymerization, a vapor phase polymerization, a bulk polymerization, a solution polymerization, a suspension polymerization and the like, and those particularly preferred are a slurry polymerization and a vapor phase polymerization.

A polymerization condition involves a polymerization temperature usually of −100 to 250° C., preferably −50 to 200° C., more preferably 0 to 130° C. The ratio of a catalyst to a reactant, represented as starting monomer/component (A) (molar ratio), is preferably 1 to $10^8$, particularly 100 to $10^5$. A polymerization time usually of 5 minutes to 10 hours, and a reaction pressure preferably of atmospheric pressure to 200 kg/cm$^2$, particularly atmospheric pressure to 100 kg/cm are employed.

The molecular weight of a polymer may be adjusted by appropriately selecting the type and the amount of each catalyst component and the polymerization temperature, or by performing the polymerization in the presence of hydrogen.

When a polymerization solvent is employed, the types of the solvents may be similar to those in the first invention. A monomer such as an α-olefin may also be employed as a solvent. Some polymerization methods need no use of solvents.

Upon polymerization, a polymerization catalyst described above may be used to perform a preliminary polymerization. Such preliminary polymerization may be similar to that in the first invention.

On the other hand, a polyolefin [II] in the sections (2) to (4) described above is one which is detailed below.

A polyolefin [II] in this invention is not particularly limited, and may be a homopolymer of an olefin or a copolymer of two or more olefins as well as mixtures thereof. A component [II] is preferably a propylenic polymer (b) having a crystallization temperature (Tc(° C.)) in which Tc≧0° C., and/or an olefin polymer (b') having a glass transition temperature (Tg(° C.)) in which Tg≦−10° C.

(b) Propylenic Polymer

A propylenic polymer (b) having a crystallization temperature (Tc(° C.)) in which Tc≧0° C. may for example be a general-purpose polypropylene. Such general purpose polypropylene may for example be a propylene homopolymer (1) and a propylenic copolymer (2).

(1) Propylene Homopolymer

As a propylene homopolymer, a high stereoregular isotactic polypropylene is preferred. Typically, one having a % isotactic pentad, which is an index for a stereoregularity, of 85% by mole or higher, more preferably 90% by mole or higher, and particularly 95% mole or higher. In this context, a % isotactic pentad is a % isotactic moiety in a triad unit determined by $^{13}$C-NMR, and is a value obtained as a ratio of the signal intensity of 21.7 to 22.5 ppm to the total signal intensity of 19.8 to 22.5 ppm. $^{13}$C-NMR is determined as described above.

(2) Propylenic Copolymer

A propylenic copolymer may for example be a random polypropylene or a block polypropylene obtained by copolymerizing propylene and ethylene or an α-olefin having 4 to 20 carbon atoms. An α-olefin having 4 to 20 carbon atoms may for example be an α-olefin which is straight, branched, or substituted with an aromatic ring. Those exemplified typically are a straight monoolefin such as 1-hexene, 1-octene, 1-nonene, 1-decene, 1-undecene, 1-dodecene and the like, a branched monoolefin such as 3-methylbutene-1, 3-methylpentene-1, 4-methylpentene-1, 2-ethylhexene-1,2,2,4-trimethylpentene-1 and the like, and a monoolefin substituted with an aromatic ring such as styrene. Each α-olefin may be employed alone or in combination with two or more.

A propylenic copolymer preferably has a high stereoregularity of a propylene chain moiety. A stereoregularity index of the propylene chain moiety of 90% or higher is more preferred. A higher crystallinity in spite of a low melting point is further preferred. These characteristics are associated for example with a propylenic polymer whose crystallization temperature Tc is elevated as a result of the addition of a nucleating agent.

Examples of a propylenic copolymer are an ethylene/propylene copolymer, an ethylene/1-butyne/propylene copolymer, 1-butene/propylene copolymer and the like.

Ethylene/propylene copolymers which are employed preferably are those described in JP-A-10-130336 and JP-A-10-142431. Thus, a preferable ethylene/propylene copolymer satisfies the following requirements [1] to [6]:

[1] The ethylene unit content (χ(wt %)) in a copolymer is 0.2 to 15 wt %;

[2] The melt index (MI (g/10 min) of a copolymer is 0.1 to 15 g/10 min;

[3] The boiling diethylether extract (Ext (wt %)) and χ are in the relationship represented the formula (1) or (2):

$$Ext \leq 0.2\chi + 1.0 (0.2 \leq \chi < 5) \quad (1)$$

$$Ext \leq 2.0 (5 \leq \chi < 15) \quad (2);$$

[4] The melting point (Tm(° C.)) determined by a differential scanning calorimeter and χ are in the relationship represented by the formula (3) or (4):

$$Tm \leq 140 (0.2 \leq \chi < 4) \quad (1)$$

$$Tm \leq 160 - 5\chi (4 \leq \chi < 15) \quad (4);$$

[5] The % isotactic triad (mm (mol %)) of a PPP chain moiety determined by $^{13}$C-NMR is 90% by mole or higher; and,

[6] The % PEP chain moiety (R(mol %)) determined by $^{13}$C-NMR and χ are in the relationship represented by the formula (5):

$$R \geq 0.5\chi + 1 \quad (5).$$

The meanings and the method for determination of each variant are in accordance with the descriptions of the publications listed above.

An ethylene/1-butene/propylene copolymer which is employed preferably is one described in JP-A-11-60639. Thus, it is a copolymer of propylene, ethylene and 1-butene and is a propylenic random copolymer which satisfies the following requirements [1] to [6]:

[1] The ethylene unit content in a copolymer (α mol %) and the 1-butene unit content (β mol %) are in the relationship represented by the formula (1):

$$4 \leq \alpha + \beta \leq 15 \quad (1)$$

[2] The melt index of a copolymer (MI (g/10 min) is 1 to 12 g/10 min;

[3] The boiling diethylether extract (E) and (α+β) are in the relationship represented by the formula (2) when (α+β)≦12 and by the formula (3) when (α+β)>12:

$$E \leq 0.2(\alpha+\beta)+0.6 \quad (2)$$

$$E \leq 3.0 \quad (3)$$

[4] The melting point (Tm(° C.)) determined by a differential scanning calorimeter and (α+β) are in the relationship represented by the formula (4):

$$Tm \leq 164-3.6(\alpha+\beta) \quad (4)$$

[5] The stereoregularity index P (mol %) determined by $^{13}$C-NMR is 98% by mole or higher; and,

[6] The ratio (Mw/Mn) of the weight mean molecular weight (Mw) to the number mean molecular weight (Mn) determined by a gel permeation chromatography (GPC) is 6 or less.

A method for producing a propylene homopolymer (1) or a propylenic copolymer (2) described above is not particularly limited, and various olefin polymerization catalyst may be employed in the production. For example, a highly active Ziegler-Natta catalyst comprising a catalyst component obtained by bringing a carrier such as a magnesium compound and a compound of a transition metal of Group IV in the periodic table into contact in the presence or absence of an electron donor and an organic aluminium compound (JP-A-53-43094, JP-A-55-135102, JP-A-55-135103, JP-A-56-18606 and the like), or a catalyst called a metallocene catalyst (JP-A-58-19309, JP-A-2-167307 and the like) may be employed.

A highly active Ziegler-Natta catalyst may for example be a catalyst obtained by bringing the following components:

(A) a solid titanium catalyst comprising:
a. titanium;
b. magnesium; and,
c. an electron donor;

and, (B) an organic aluminium compound, optionally together with (C) an organic silane compound into contact. Alternatively, a catalyst obtained by subjecting the catalyst described above to a preliminary polymerization with olefins followed by bringing into contact with an organic aluminium compound optionally together with (C) an organic silane compound may be exemplified.

A metallocene catalyst which may be exemplified as a preferred example is a metallocene catalyst disclosed in JP-A-10-260376. Thus, an olefin polymerization catalyst obtained by bringing at least an aluminoxane into contact with a compound of a transition metal of Groups IV to VI in the periodic table optionally with an organic aluminium compound may be exemplified. In addition, an olefin polymerization catalyst may for example be an olefin polymerization catalyst in which at least one of the catalyst component is supported on a carrier. A compound of a transition metal of Groups IV to VI in the periodic table is preferably one represented by any of the following formulae (1) to (3):

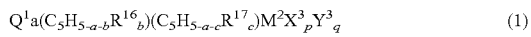

Wherein $Q^1$ denotes a binding group which crosslinks two conjugate 5-membered ring ligands $(C_5H_{5-a-b}R^{16}_b)$ and $(CH_5H_{5-a-c}R^{17}_c)$, $Q^2$ denotes a binding group which crosslinks a conjugate 5-membered ring ligand $(C_5H_{5-a-d}R^{18}_d)$ and $Z^1$ group; each of $R^{16}$, $R^{17}$ and $R^{18}$ is a hydrocarbon group, a halogen atom, an alkoxy group, a silicon-containing hydrocarbon group, a phosphorus-containing hydrocarbon group, a nitrogen-containing hydrocarbon group or a boron-containing hydrocarbon group, and a is 0, 1 or 2; each of b, c and d is an integer of 0 to 5 when a=0, an integer of 0 to 4 when a=1, and an integer of 0 to 3 when a=2; p+q=the valency of $M^2$–2, r=the valency of $M^2$; $M^2$ denotes a transition metal of Groups IV to VI in the periodic table; each of $X^3$, $Y^3$ and $Z^1$ denotes a covalent-binding or ionic-binding ligand, $X^4$ is a covalent-binding ligand; or, $X^3$ and $Y^3$ may be taken together to form a cyclic structure.

(b') Olefin Polymer

An olefin polymer (b') having a glass transition temperature (Tg(° C.)) in which Tg≦−10° C. in a polyolefin [II] may for example be an ethylenic polymer. Such ethylenic polymer is not particularly limited provided that it contains at least an ethylene component. Such ethylenic polymer may for example be a high density polyethylene, a low density polyethylene, a linear low density polyethylene, an ethylene-α-olefin copolymer and the like.

A preferred ethylene-α-olefin copolymer satisfies the following requirements (1) to (3).

(1) α-Olefin

An α-olefin employed in an ethylene-α-olefin copolymer may for example be a straight, branched or aromatic ring-substituted α-olefin having 3 to 18, preferably 6 to 18, particularly 6 to 18 carbon atoms. A number of carbon atoms less than 6 results in a reduced tensile elongation at break, which may leads to an elevated brittleness temperature. An α-olefin having 3 to 18 carbon atoms may typically be a straight monoolefin such as propylene, 1-butene, 1-hexene, 1-octene, 1-nonene, 1-decene, 1-undecene, 1-dodecene and the like, a branched monoolefin such as 3-methylbutene-1,3-methylpentene-1,4-methylpentene-1,2-ethylhexene-1,2,2,2-trimethylpentene-1 and the like, as well as a monoolefin substituted with an aromatic ring such as styrene. Each α-olefin may be employed alone or in combination with two or more.

(2) α-Olefin Content

The α-olefin content in an ethylene-α-olefin copolymer is 10 to 60% by weight, preferably 20 to 50% by weight. A content less than 10% by weight may result in a reduced impact strength. A content exceeding 60% by weight may result in a reduced rigidity of a resin composition.

(3) Characteristics of Ethylene-α-Olefin Copolymer

1) Melt Index (MI)

The melt index of an ethylene-α-olefin copolymer employed in this invention is 0.05 to 150 g/10 min, preferably 0.1 to 100 g/10 minutes, more preferably 1 to 70 g/10 minutes. A melt index less than 150 g/10 minutes may result in a reduced impact strength. A measurement was in accordance with JIS-K-7210 (determined with a load of 2160 g at 190° C.).

2) Maximum Melting Point (Tm(° C.))

The maximum melting point (Tm(° C.)) of an ethylene-α-olefin copolymer employed in this invention is 90° C. or lower, preferably 85° C. or lower, more preferably 80° C. or lower. A Tm exceeding 90° C. may result in a reduced impact strength. A measurement was conducted as follows. About 10 mg of a sample was heated for 3 minutes at 190° C. using a differential scanning calorimeter (DSC-7: Perkin-Elmer) and then cooled slowly at 10° C./min to 25° C. to effect crystallization, and the sample temperature was raised from 25° C. to 160° C. at the raising rate of 10° C./min to obtain a fusing curve. The highest temperature of the peak obtained in this procedure was regarded as the maximum melting point.

3) Weight Mean Molecular Weight/Number Mean Molecular Weight (Mw/Mn)

The weight mean molecular weight/number mean molecular weight (Mw/Mn) of an ethylene-α-olefin copolymer is 3.0 or less, preferably 2.5 or less. A value exceeding 3.0 results in a reduced tensile elongation at break. A measurement was conducted as follows. A solution of 10 mg of sample in 20 ml of 1,2,4-trichlorobenzene was supplemented with an antioxidant 2,6-di-t-butyl-p-cresol (commonly referred to as BHT) at 0.1 w/v % and heated at 150° C. in a conical flask and then stirred for 1 hour to effect dissolution. This solution was subjected to a gel permeation chromatography using a device manufactured by Waters (model: 150C-ALC/GPC) and the weight mean molecular weight (Mw) and the number mean molecular weight (Mn) were calculated as being converted to the values of a standard polystyrene having a known molecular weight (Mono-distributed polystyrene manufactured by TOSO), whereby obtaining the value of Mw/Mn of the sample. The column TOSO GMH6-HT was used with the sample injection volume of 400 µl at the flow rate of 1.0 ml/min at 135° C.

A method for producing an ethylene-α-olefin copolymer is not particularly limited, and various olefin polymerization catalysts may be employed in the production. For example, an olefin polymerization catalyst disclosed in JP-A-9-87479 can be employed.

While an inventive propylenic resin composition [I] is embodied more typically by a resin composition in which a propylene homopolymer (a) and/or a propylenic copolymer (a') described above is combined with a polyolefin [II] described above at a weight ratio of 1:99 to 99:1, an inventive propylenic resin composition [I] may be supplemented with a nucleating agent. Such nucleating agent may typically be any of those described in the first invention.

In this invention, the use of an inorganic microparticle such as talc as described above as a nucleating agent results in an excellent slipperiness of a molded film and provides an improvement in the characteristics such as printability.

An inventive propylenic resin may be mixed with a nucleating agent and various desirable additives by means of a dry-blending using a mixer such as Henschel mixer. Alternatively, a kneading may be effected using a single- or twin-screw extruder, Banbury mixer and the like. When a high melting polymer is used as a nucleating agent, the high melting polymer may be added to a reactor simultaneously or sequentially during the production of a propylenic polymer. Additives employed if necessary are antioxidant, neutralizing agent, slipperiness-imparting agent, anti-blocking agent, anti-frosting agent and antistatic agent and the like.

The amount of a nucleating agent added in the invention is 10 ppm or higher, preferably 10 to 10000 ppm, more preferably 10 to 5000 ppm, particularly 10 to 2500 ppm, based on a propylenic resin. An amount less than 10 ppm provides no improvement in the moldability, while an amount exceeding 10000 ppm fails to exhibit corresponding increase in the effect.

[2] Method for Producing Propylenic Resin Composition

A method for producing an inventive propylenic resin composition [1] is typically a blending of a propylene homopolymer (a) and/or a propylenic copolymer (a') with a polyolefin [II] described above. A procedure for blending may for example be a powder blending method using a kneader. A kneader may be Banbury mixer and a twin-screw kneader and the like. A reactor blending method in which a blending is effected in a polymerization reaction vessel may also be employed. Preferably, a reactor blending method capable of blending each component sufficiently is employed.

A reactor blending method may be a multi-step polymerization in which two or more polymerization steps are employed or a polymerization method in which a co-catalyst comprising two or more transition metal compounds is employed (also referred to as a multi-stage polymerization). Such multi-step polymerization may for example be a polymerization method comprising at least a step for producing a propylenic resin [1] described above, i.e., a polymerization step employing at least a low stereoregular metallocene catalyst. A low stereoregular metallocene catalyst means a metallocene catalyst which provides a component (a) or (a') described above. Representatives are the catalysts exemplified as the catalysts for producing a component (a) or (a') described above. A multi-step polymerization may for example be a multi-step sequential polymerization employing a high activity-supporting Ziegler-Natta catalyst and a low stereoregular metallocene catalyst or a multi-step sequential polymerization employing a high stereoregular metallocene catalyst and a low stereoregular metallocene catalyst. A preferred high activity-supporting Ziegler-Natta catalyst is a high activity-supporting Ziegler-Natta catalyst capable of providing a polypropylene having a meso-pentad fraction (mmmm) exceeding 60% by mole, and those listed above are exemplified typically. A high stereoregular metallocene catalyst means a metallocene catalyst capable of providing a polypropylene having a meso-pentad fraction (mmmm) exceeding 60% by mole. Examples of a high stereoregular metallocene catalyst are, as listed above, those described in JP-A-58-19309, JP-A-61-130314, JP-A-3-163088, JP-A-4-300887, JP-A-4-211694, JP-W-1-502036 and the like, such as a catalyst derived from a transition metal compound having, as its one or two ligands, cyclopentadienyl group, substituted cyclopentadienyl group, indenyl group, substituted indenyl group and the like or and a transition metal compound in which said ligands are controlled geometrically in combination with a promoter.

A polymerization method employing a co-catalyst may for example be a polymerization method employing a co-catalyst at least one component of which consists of a low stereoregular metallocene catalyst. One which can be exemplified is a polymerization method employing a co-catalyst comprising a high stereoregular metallocene catalyst and a low stereoregular metallocene catalyst. A co-catalyst may be supported on a carrier. One which can be exemplified is a polymerization method employing a co-supported-catalyst obtained by allowing a high stereoregular metallocene catalyst and a low stereoregular metallocene catalyst to be supported on a carrier. A low stereoregular metallocene catalyst may be a metallocene catalyst which provides a component (a) or (a') described above.

Among those described above, a polymerization method employing a co-catalyst is preferred as an inventive production method, and a polymerization method employing a co-supported-catalyst is particularly preferred.

[3] Molded Article

A molded article in this invention is a molded article obtained by molding a propylenic resin composition [1] described above. An inventive molded article has a softness (also referred to as pliability)

And is characterized by a less stickiness in spite of its high softness, and is excellent also in terms of heat resistance. An inventive molded article is pliable and has a high % elasticity recovery (ability of recovery after being stretched), and is excellent also in terms of low temperature impact resistance, with such characteristics being well-balanced.

A molded article in this invention may for example be films, sheets, fibers, containers, automobile interior parts, housings of home electric devices. Films may for example be films for food product packagings and films for agricultural uses (such as for green houses). Containers may for example be cases, boxes, decorated boxes and the like.

A propylenic resin composition according to the invention is suitable to an extrusion molded article, particularly as a film and a sheet. Such film and sheet may be laminated. Since an inventive propylenic resin composition is characterized also by its broad composition distribution which allows the molding temperature range upon orientation to be wider and the moldability to be improved, it is applied preferably also to an oriented film and a fiber and the like.

A method for molding into an article may for example be an injection molding, compression molding, injection stamping, gas-assisted injection molding, extrusion molding, blow molding, calendering and the like. A molding method employing an inventive propylenic resin composition gives a broader composition distribution which leads to an improved moldability, and also provides a higher crystallization rate when employing a blending of a highly crystalline resin (resin having a higher Tc), resulting in an improved molding cycle. Also in a calendering, a broader composition distribution allows the viscosity to be less dependent on the temperature, resulting in an improved moldability.

The molding conditions may not particularly be limited, provided that a temperature capable of allowing a resin to be molten and to flow is employed, and a usual case involves a resin temperature of 50° C. to 300° C. and a mold temperature of 60° C. or lower.

When a film is formed as a molded article in this invention, a method which may be employed includes ordinary compression molding, extrusion molding, blow molding, cast molding and the like. The film obtained may be oriented or may not be oriented. When oriented, it is preferred to be biaxially oriented. The biaxially orienting conditions involve the parameters described below.

[1] Sheet Molding Conditions

Resin temperature of 50 to 200° C., chill roll temperature of 50° C. or lower

[2] Lengthwise Orienting Conditions

Orienting magnitude of 3 to 7 times, orienting temperature of 50 to 100° C.

[3] Widthwise Orienting Conditions

Orienting magnitude of 6 to 12 times, orienting temperature of 50 to 100° C.

A film may be surface-treated if necessary to enhance its surface energy or to impart the surface with a polarity. For example, corona discharge treatment, chromic acid treatment, flame treatment, hot gas treatment, ozone- or UV irradiation treatment may for example be employed. The surface may be embossed by, for example, sand-blast method or solvent treatment.

To a film, a customary additives such as antioxidant, neutralizing agent, slipperiness-imparting agent, anti-blocking agent, anti-frosting agent, antistatic agent and the like may be incorporated as desired.

A film further containing an inorganic microparticle such as talc exhibits an excellent slipperiness, which leads to an improvement in secondary processing performances such as bag making or printing performance, due to which it is suitable as a general-purpose packaging film subjected to a high speed machine including various automatic filling-packaging laminators.

A film produced by molding a propylenic resin composition containing a dibenzylidene sorbitol or its derivative as a nucleating agent has a particularly excellent transparency which is highly display-oriented, and which makes it suitable as a package film of a toy or a stationery.

A film produced by molding a propylenic resin composition containing an amide compound as a nucleating agent has a particularly excellent rigidity and exhibits a less problematic wrinkling when being wound during a high speed bag making, due to which it is suitable as a general-purpose packaging film subjected to a high speed bag making machine.

[V] Fifth Invention

The fifth invention consisting of a propylenic resin composition [1] and a film and a sheet made therefrom are detailed below.

[1] Propylenic Resin Composition

An inventive propylenic resin composition [1] consists substantially of a propylene homopolymer and/or a propylenic copolymer, and a resin composition having a peak top temperature ($Tc$(° C.)) on the side of the maximum temperature on a crystallization curve and a differential calorie ($\Delta Hm$ (J/g)) on a fusion curve, as determined by a differential scanning calorimeter (DSC), which are in the relationship represented by the following formula:

$$Tc \geq (1/4) \cdot \Delta Hm + 90 \quad (1\text{-}1)$$

and having a frequency ($\omega$(rad/sec)) at which the storage modulus (G'(Pa)) and the loss elasticity (G"(Pa)) based on the frequency distribution determination of the melt viscoelasticity become equal to each other and a $\Delta Hm$, which are in the relationship represented by the following formula:

$$\omega \leq (1/10) \cdot \Delta Hm + 15 \quad (2\text{-}1)$$

By satisfying the requirements described above, an inventive propylenic resin composition provides a film or sheet whose pliability and transparency are excellent and whose heat seal strength is improved substantially. For example, a film having a tensile elastic modulus of 1000 MPa or less, a haze of 5% or less and a heat seal strength of 1000 gf/15 mm or higher can be obtained. Especially with regard to the heat seal strength, a film having a far more excellent heat seal strength even at a high sealing temperature, e.g. at 160° C. or higher, can advantageously be obtained. Another advantageous properties are a higher heat seal temperature and a higher heat resistance when compared with those possessed by other propylenic resin composition having a comparable pliability.

In addition to a sheet or film, a laminated film or sheet formed by lamination or co-extrusion may preferably employ an inventive propylenic resin composition as at least one layer component thereof.

When the requirement (1-1) described above is not satisfied, the pliability of a resultant film or sheet is reduced, and the transparency is also reduced. When the requirement (2-1) described above is not satisfied, a resultant film or sheet fails to exhibit an improved heat seal strength or excellent transparency, although it has a certain pliability.

As a propylenic resin composition in this invention, a resin composition satisfying:

$$Tc \geq (1/4) \cdot \Delta Hm + 92 \quad (1\text{-}2); \text{and,}$$

$$\omega \leq (1/10) \cdot \Delta Hm + 13 \quad (2\text{-}2),$$

is more preferred since it provides a film or sheet having excellent pliability and transparency as well as an improved seal strength.

A peak top temperature (Tc(° C.)) on the side of the maximum temperature on a crystallization curve and a differential calorie (ΔHm(J/g)) on a fusion curve as determined by a differential scanning calorimeter (DSC) in this invention are determined as described in the fourth invention. A frequency (ω(rad/sec)) at which the storage modulus (G'(Pa)) and the loss elasticity (G"(Pa)) based on the frequency distribution determination of the melt viscoelasticity become equal to each other is determined by the procedure described below. Thus, a rotary rheometer manufactured by RHEOMETRIX is used together with a cone plate (25 mm in diameter, 0.10 radian in cone angle) at the temperature of 175° C. with the initial strain of 20% to perform the frequency distribution determination of the melt viscosity, and the storage modulus (G'(Pa)), the loss elasticity (G"(Pa)) and the frequency (ω(rad/sec)) giving G'=G" are determined. A complex modulus of elasticity G* (iω) at a frequency (ω(rad/sec)) can be represented by a stress σ* and a strain γ* as shown below.

$$G^*(i\omega)=\sigma^*/\gamma^*=G'(\omega)+iG''(\omega)$$

wherein i is an imaginary number unit.

A propylenic resin composition in this invention is not particularly limited as far as the requirements described above are satisfied. For example, a propylenic resin composition comprising 1 to 99% by weight of a propylenic polymer [I] satisfying the following requirements:

(1) the amount of the components which are dissolved out at 25° C. or lower (W25) in a temperature-raising chromatography ranges from 20 to 100% by weight;
(2) the amount of the components which are dissolved out into hexane at 25° C. (H25) ranges from 0 to 80% by weight; and,
(3) no melting point (Tm(° C.)) is observed in DSC or, when any Tm is observed then the Tm and the fusion endothermic calorie ΔH(J/gr.) are in the relationship represented by the following formula:

$$\Delta H \geq 6 \times (Tm-140);$$

and 99 to 1% by weight of a crystalline propylenic polymer [II] may be exemplified.

By satisfying the requirements shown above, a propylenic polymer [I] in this invention provides a resultant film or sheet whose amount of the stickiness-imparting components, low modulus and transparency are well-balanced. Thus, it exhibits a low modulus and an excellent softness (referred to as pliability), contains a reduced amount of a stickiness-imparting component and has an excellent surface characteristics (for example those experienced as a less bleeding and a less migration of a stickiness-imparting component into other products), and is also associated with an advantageously excellent transparency.

The requirements described above to be satisfied by a propylenic polymer [I] in this invention are discussed below. In a propylenic copolymer [I] in this invention, the amount of the components which are dissolved out at 25° C. or lower (W25) in a temperature-raising chromatography ranges from 20 to 100% by weight. More preferably, such amount ranges from 30 to 100% by weight, a most preferably 50 to 100% by weight. W25 is an index for the softness of a propylenic polymer [I]. An increase in this value is associated with an increase in the component having a higher modulus and/or a broader stereoregularity distribution. In this invention, a value W25 less than 20% may result in a disadvantageous loss of the pliability. The meanings of W25 are as described in the second invention.

Also in a propylenic polymer [I] in this invention, the amount of the components which are dissolved out into hexane at 25° C. (H25) ranges from 0 to 80% by weight. Preferably, it is 0 to 50% by weight, particularly 0 to 25% by weight. H25 can also be understood as described in the second invention.

Also in an inventive propylenic polymer [I], no melting point (Tm(° C.)) is observed in DSC or, when any Tm is observed then the Tm and the fusion endothermic calorie ΔH(J/g) are in the relationship represented by the following formula:

$$\Delta H \geq 6 \times (Tm-140);$$

preferably by the following formula:

$$\Delta H \geq 3 \times (Tm-120);$$ and, particularly by the following formula:

$$\Delta H \geq 2 \times (Tm-100).$$

Tm and ΔH can also be understood similarly as in the second invention.

A propylenic polymer [I] in this invention is not particularly limited, provided that it can satisfy the requirements described above, and may for example be a propylene homopolymer or a propylenic copolymer. Specifically, a propylenic polymer [I] in this invention described above can more preferably be embodied by a propylene homopolymer [a] or a propylene copolymer [a'] described below.

[a] Propylene Homopolymer

A propylene homopolymer [a] in this invention is a polymer satisfying the following requirements (1) to (3):
(1) the meso-pentad fraction (mmmm (in percentage terms by mole)) ranges from 20 to 60% by mole;
(2) the racemi-pentad fraction (rrrr) and (1−mmmm) are in the relationship represented by the following formula:

$$[rrrr/(1-mmmm)] \leq 0.1$$

wherein the racemi-pentad fraction (rrrr) and the meso-pentad fraction (mmmm) are not in percentage terms; and,
(3) the amount of the components which are dissolved out at 25° C. or lower (W25) in a temperature-raising chromatography ranges from 20 to 100% by weight.

When a propylene homopolymer [a] in this invention satisfies the requirements described above, a resultant film or sheet exhibits well-balanced amount of the stickiness-imparting components, low modulus and transparency. Thus, it exhibits a low modulus and an excellent softness (also referred to as pliability), contains a reduced amount of a stickiness-imparting component and has an excellent surface characteristics (for example those experienced as a less bleeding and a less migration of a stickiness-imparting component into other products), and is also associated with an advantageously excellent transparency.

A % meso-pentad (% mmmm) and a racemi-pentad fraction (rrrr) referred in this invention are the same to those discussed in the first invention. A meso-pentad fraction (mmmm) of an inventive propylene homopolymer [a] less than 20% by mole may cause a stickiness. One exceeding 60% by mole may represent disadvantageously high modulus. A value [rrrr/(1−mmmm)] of a propylene homopolymer [a] in this invention which exceeds 0.1 causes a stickiness. A $^{13}$C-NMR spectrum is obtained similarly as in the first invention. A W25 of an inventive propylene homopolymer [a] less than 20% results in the loss of pliability.

A propylenic homopolymer [a] described above is further preferred when it satisfies, among the requirements described above, the following requirements:
(3) the meso-pentad fraction (mmmm (in percentage terms by mole)) ranges from 30 to 50% by mole;
(4) the racemi-pentad fraction (rrrr) and (1−mmmm) are in the relationship represented by the following formula:

$$[rrrr/(1-mmmm)] \leq 0.08$$

wherein the racemi-pentad fraction (rrrr) and the meso-pentad fraction (mmmm) are not in percentage terms; and,
(6) the amount of the components which are dissolved out at 25° C. or lower (W25) in a temperature-raising chromatography ranges from 30 to 100% by weight;

and is particularly preferred when it satisfies the following requirements:
(7) the meso-pentad fraction (mmmm (in percentage terms by mole)) ranges from 30 to 50% by mole;
(8) the racemi-pentad fraction (rrrr) and (1−mmmm) are in the relationship represented by the following formula:

$$[rrrr/(1-mmmm)] \leq 0.06$$

wherein the racemi-pentad fraction (rrrr) and the meso-pentad fraction (mmmm) are not in percentage terms; and,
(9) the amount of the components which are dissolved out at 25° C. or lower (W25) in a temperature-raising chromatography ranges from 50 to 100% by weight.

A propylene homopolymer [a] in this invention is preferred when it satisfies, in addition to the requirements described above, that the molecular weight distribution (Mw/Mn) determined by a gel permeation chromatography (GPC) is 4 or less and/or the intrinsic viscosity [η] determined in a tetralin solvent at 135° C. ranges from 0.5 to 15.0 dl/g, with an Mw/Mn of 3.5 or less and/or a [η] of 1.0 to 5.0 dl/g being more preferred and an Mw/Mn of 3 or less and/or a [η] of 1.0 to 3.0 dl/g being particularly preferred. A molecular weight distribution (Mw/Mn) exceeding 4 may cause a stickiness in a film or sheet. An intrinsic viscosity [η] less than 0.5 dl/g may also cause a stickiness, while that exceeding 15.0 dl/g results in a gel or a fish eye in a film or sheet.

An Mw/Mn described above may be understood similarly as in the first invention.

In addition to the requirements described above, a fusion endothermic calorie ΔH determined by DSC of 20 J/g or less allows an inventive propylene homopolymer [a] to be more pliable and thus be more preferred.

In addition a propylene homopolymer [a] in this invention is further preferred when it exhibits no crystallization peak in the crystallization curve obtained by a differential scanning calorimetry (DSC).

While during an ordinary propylene polymerization process a 1,2 insertion polymerization, which means that a carbon atom of a propylene monomer on the side of a methylene undergoes a binding with an active center of a catalyst followed by a successive coordination of the propylene monomers in the same manner whereby effecting the polymerization, takes place generally, a 2,1 insertion or a 1,3 insertion may also take place at a less incidence (sometimes referred to as abnormal insertion). In a homopolymer in this invention, it is preferable that the incidence of such 2, 1 or 1,3 insertion is low. It is also preferable that these insertion rates satisfy the relationship represented by the following formula (1):

$$[(m\text{-}2,1)+(r\text{-}2,1)+(1,3)] \leq 5.0 \tag{1}$$

wherein (m-2,1) is a % meso-2,1 insertion content determined by $^{13}$C-NMR, (r-2,1) is a % racemi-2,1 insertion content determined by $^{13}$C-NMR, and (1,3) is a % 1,3 insertion content determined by $^{13}$C-NMR, and, more preferably, they satisfy the relationship represented by the following formula (2):

$$[(m\text{-}2,1)+(r\text{-}2,1)+(1,3)] \leq 1.0 \tag{2}$$

It is particularly preferred that they satisfy the relationship represented by the following formula (3):

$$[(m\text{-}2,1)+(r\text{-}2,1)+(1,3)] \leq 0.1 \tag{3}$$

When the relationship represented by Formula (1) is not satisfied, the crystallinity is reduced far more than expected, and a stickiness may arise.

(m-2, 1), (r-2, 1) and (1,3) are understood similarly as in the first invention.

A propylene homopolymer in this invention preferably exhibits substantially no peaks in a $^{13}$C-NMR spectrum which are assigned to a molecular chain terminal (n-butyl group) as a result of a 2,1 insertion. With regard to this molecular chain terminal as a result of a 2,1 insertion, each % insertion content is calculated from the integrated intensity of each peak after assignment of the peak in the $^{13}$C-NMR spectrum in accordance with the report by Jungling et al (J. Polym. Sci. Part A: Polym. Chem., 33, p 1305 (1995)).

In addition to the requirements described above, a % boiling diethylether extract, which is an index for the modulus, of 5% by weight or higher allows a propylene homopolymer [a] in the invention to be further preferred. A % boiling diethylether extract can be determined by the method similar to that described in the second invention.

In addition to the requirements described above, a tensile elastic modulus of 100 MPa or less, more preferably 70 MPa or less is associated with an inventive propylene homopolymer [a].

[η] Propylenic Copolymer

A propylenic copolymer [a'] in this invention is a copolymer of propylene and ethylene and/or an α-olefin having 4 to 20 carbon atoms which satisfies the following requirements (1) to (2)
(1) the stereoregularity index (P) determined by a $^{13}$C-NMR ranges from 55 to 90% by mole; and,
(2) the amount of the components which are dissolved out at 25° C. or lower (W25) in a temperature-raising chromatography ranges from 20 to 100% by weight.

By satisfying the requirements described above, an inventive propylenic copolymer [a'] provides a film or sheet exhibiting well-balanced amount of the stickiness-imparting components, low modulus and transparency. Thus, it exhibits a low modulus and an excellent softness (referred to as pliability), contains a reduced amount of a stickiness-imparting component and has an excellent surface characteristics (for example those experienced as a less bleeding and a less migration of a stickiness-imparting component into other products), and is also associated with an advantageously excellent transparency. A stereoregularity index (P) in the invention is a value obtained by determining a $^{13}$C-NMR spectrum using Nippon Densi Model JNM-EX400 $^{13}$C-NMR device under the conditions described in the first invention followed by calculating a % meso-triad (mm) of a propylene chain. An increase in this value is associated with a higher stereoregularity. A propylenic copolymer [a'] in this invention preferably has a stereoregularity index (P) of 65 to 80% by mole. A stereoregularity index (P) less than 55% by weight results in a too reduced modulus, which may lead to a poor molding performance. At 90% by mole or higher, a rigidness may arise and a softness is lost. It is further preferred that the W25 is 30 to 100% by weight, with 50 to 100% by weight being particularly preferred. A W25 less than 20% by weight results in a loss of pliability. The meanings and the determination method of a W25 are as described above.

A propylenic copolymer [a'] in this invention is preferred when it satisfies, in addition to the requirements described above, that the molecular weight distribution (Mw/Mn) determined by a gel permeation chromatography (GPC) is 4 or less and/or the intrinsic viscosity [η] determined in a tetralin solvent at 135° C. ranges from 0.5 to 15.0 dl/g, with an Mw/Mn of 3.5 or less and/or a [η] of 1.0 to 5.0 dl/g being more preferred and an Mw/Mn of 3 or less and/or a [η] of 1.0 to 3.0 dl/g being particularly preferred. A molecular weight distribution (Mw/Mn) exceeding 4 may cause a stickiness in a film or sheet. An intrinsic viscosity [η] less than 0.5 dl/g may also cause a stickiness, while that exceeding 15.0 dl/g results in a gel or a fish eye in a film or sheet.

An Mw/Mn described above may be understood similarly as in the first invention.

In addition to the requirements described above, a fusion endothermic calorie ΔH determined by DSC of 20 J/g or less allows an inventive propylenic copolymer [a'] to be more pliable and thus be more preferred. In addition, a propylenic copolymer [a'] in this invention is further preferred when it exhibits no crystallization peak in the crystallization curve obtained by a differential scanning calorimetry (DSC). One exhibiting any crystallization peak in the crystallization curve obtained by a differential scanning calorimetry (DSC) may result in no film or sheet having an excellent pliability. ΔH, Tm and Tc are obtained as described above.

In addition to the requirements described above, a % boiling diethylether extract, which is an index for the modulus, of 5% by weight or higher allows a propylenic copolymer [a'] in this invention to be further preferred. The boiling diethylether extract is determined as described above.

In addition, the tensile elastic modulus is preferably 100 MPa or less, more preferably 70 MPa or less.

In conjunction with a propylenic copolymer [a'] in this invention, an α-olefin having 4 to 20 carbon atoms may for example be ethylene, 1-butene, 1-pentene, 4-methyl-1-pentene, 1-hexene, 1-octene, 1-decene, 1-dodecene, 1-tetradecene, 1-hexadecene, 1-octadecene, 1-eicocene and the like, and, in the invention, these may be employed alone or in combination with each other.

A propylenic copolymer [a'] in this invention is preferably a random copolymer. The structural unit derived from propylene exists preferably at a level of 90% by mole or higher, more preferably 95% by mole or higher.

[Method for Producing Propylene Homopolymer [a] and Propylenic Copolymer [a']]

A method for producing a propylene homopolymer [a] and a propylenic copolymer [a'] in this invention may be a method in which a catalyst system called a metallocene catalyst is used to homopolymerize propylene or to copolymerize propylene and ethylene and/or an α-olefin having 4 to 20 carbon atoms. In this invention, among metallocene catalysts, one derived from a transition metal compound whose ligand forms a crosslinking structure via a crosslinking group is preferred, and a particularly preferred method involves a use of a metallocene catalyst obtained by combining a transition metal compound whose crosslinking structure is formed via 2 crosslinking groups with a promoter whereby effecting a homopolymerization of propylene or a copolymerization of propylene and ethylene and/or an α-olefin having 4 to 20 carbon atoms.

Typically, a catalyst consists of the following components.

(A) a transition metal compound (B) a component (B-1) which is a compound capable of forming an ionic complex by reacting with a transition metal compound as a component (A) and a component (B-2) which is an aluminoxane.

In addition to a component (A) and a component (B), an organic aluminium compound can be used as a component (C).

Components (A), (B) and (C) are similar to those described in the first invention, and each of components (B) and (C) may be used alone or in combination of two or more. The amount of each component to be used is also similar to that employed in the first invention.

In a production method according to the invention, components (A), (B) and (C) may be subjected to a preliminary contact. Such preliminary contact may be understood as discussed in the first invention.

In the present invention, at least one of the catalyst components may be employed as being supported on a suitable carrier. A carrier employed in this invention is similar to that in the first invention. A method for allowing at least one of the catalyst components to be supported on a carrier is also similar to that in the first invention.

In the present invention, a catalyst may be prepared by irradiating a dynamic wave upon contact between components (A) (B) and (C). Such elastic wave is usually a sound wave, preferably an ultrasonic wave. Typically, an ultrasonic wave at a frequency of 1 to 1000 kHz, preferably 10 to 500 kHz may be exemplified.

A catalyst thus obtained may be used in a polymerization after being isolated as a solid by distilling a solvent off, or alternatively it may be subjected directly to a polymerization.

In the invention, as is discussed already in the first invention, a catalyst may be produced also by allowing at least one of a component (A) and a component (B) to be supported on a carrier within the system of polymerization.

The ratio of each component to a carrier is also similar to that in the first invention. The polymerization catalyst in this invention thus prepared usually has a mean particle size of 2 to 200 µm, preferably 10 to 150 µm, particularly 20 to 100 µm, and a specific surface area usually of 20 to 1000 m$^2$/g, preferably 50 to 500 m$^2$/g. In an inventive catalyst, the amount of a transition metal in 100 g of a carrier is usually 0.05 to 10 g, preferably 0.1 to 2 g. An amount of a transition metal departing from the range described above may result in a reduced activity.

A propylenic polymer employed in this invention can be produced using a polymerization catalyst described above by homopolymerizing a propylene or by copolymerizing propylene and ethylene and/or an α-olefin having 4 to 20 carbon atoms.

In such procedure, a polymerization method is not particularly limited and may be a slurry polymerization, a vapor phase polymerization, a bulk polymerization, a solution polymerization, a suspension polymerization and the like, and those particularly preferred are a slurry polymerization and a vapor phase polymerization.

A polymerization condition involves a polymerization temperature usually of –100 to 250° C., preferably –50 to 200° C., more preferably 0 to 130° C. The ratio of a catalyst to a reactant, represented as starting monomer/component (A) (molar ratio), is preferably 1 to 10$^8$, particularly 100 to $10^5$. A polymerization time usually of 5 minutes to 10 hours, and a reaction pressure preferably of atmospheric pressure to 200 kg/cm²G, particularly atmospheric pressure to 100 kg/cm²G are employed.

The molecular weight of a polymer may be adjusted by appropriately selecting the type and the amount of each catalyst component and the polymerization temperature, or by performing the polymerization in the presence of hydrogen.

When a polymerization solvent is employed, the types of the solvents may be similar to those in the first invention. A monomer such as an α-olefin may also be employed as a solvent. Some polymerization methods need no use of solvents.

Upon polymerization, a polymerization catalyst described above may be used to perform a preliminary polymerization. Such preliminary polymerization may be similar to that in the first invention.

As a crystalline propylenic polymer [II] described above, any propylenic polymer can be employed as far as it exhibits a crystallinity. Those which may be exemplified are a propylene homopolymer, a propylene-ethylene random copolymer, a propylene-ethylene-1-butene random copolymer, a propylene-ethylene block copolymer and the like. The molecular weight of a crystalline propylenic polymer [II] is selected based on a desired moldability, and a MI of 2 to 20 g/10 min is preferred for a T die cast film molding, while one of 1 to 10 g/10 min is preferred for a sheet molding. The selection can be made appropriately based on the intended use of a film or sheet. Specifically, when an intended use places a significance on the heat resistance and on the heat seal strength, then a highly crystalline propylene homopolymer is preferred, such as one described in JP-A-8-85711. Thus, one which can be exemplified is a propylenic resin which satisfies that:

(1) the % isotactic pentad (P) which is an index for the stereoregularity is 85.0% by mole, the amount of n-heptane-insoluble components (H) is 98.0 to 97.0% by weight, and P and H are in the relationship represented by the following formula:

$$0.750P+27.125<H;$$

and that (2) the melt index (MI) is 1 to 20 g/10 min and the relaxation time τ (sec) at the frequency ω0=10⁰ rad/sec based on the frequency distribution determination at 175° C. and the MI are in the relationship represented by the formula:

$$\tau \leq 0.65 - 0.025 MI.$$

More preferable polypropylenic polymer satisfies that: (1') the % isotactic pentad (P) which is an index for the stereoregularity is 85.0 to 92.0% by mole, the amount of n-heptane-insoluble components (H) is 86.0 to 97.0% by weight, and P and H are in the relationship represented by the following formula:

$$0.750P+26.000<H;$$

and that (2') the melt index (MI) is 1 to 25 g/10 min and the relaxation time τ (sec) at the frequency ω0=10⁰ rad/sec based on the frequency distribution determination at 175° C. and the MI are in the relationship represented by the formula:

$$\tau \leq 0.63 - 0.025 MI.$$

The meanings and the determination methods of P, H, MI, ω0 and τ described above and the method for producing a propylenic polymer are similar to those described in JP-A 8-85711.

For the purpose of improving the low temperature heat seal performance of a film or sheet, it is preferred that a crystalline propylenic polymer [II] is also a propylene-ethylene random copolymer or a propylene/ethylene/1-butene random copolymer which has an excellent low temperature heat seal performance, such as those described in JP-A-9-208629, JP-A-9-272718, JP-A-10-130336 and the like. Thus, a propylenic copolymer which can be mentioned is a copolymer of propylene and ethylene which satisfies the following requirements [1] to [5] (JP-A-9-208629):

[1] The ethylene unit content (χ(wt %)) in a copolymer is 3 to 10 wt %;
[2] The melt index (MI (g/10 min)) of a copolymer is 4 to 12 g/10 min;
[3] The boiling diethylether extract (E (wt %)) and χ are in the relationship represented the formula (I) or (II):

$$E \leq 0.25\chi + 1.1 \ (\chi = 3 \text{ to } 6 \text{ wt \%}) \quad (I)$$

$$E \leq 2.6 \ (\chi = 6 \text{ to } 10 \text{ wt \%}) \quad (II);$$

[4] The melting point (Tm(° C.)) determined by a differential scanning calorimeter and χ are in the relationship represented by the formula (III) or (IV):

$$Tm \leq 140 \ (\chi = 3 \text{ to } 5 \text{ wt \%}) \quad (III)$$

$$Tm \leq 165 - 5\chi \ (\chi = 5 \text{ to } 10 \text{ wt \%}) \quad (IV); \text{ and,}$$

[5] The % isotactic triad (mm (mol %)) of a PPP chain moiety determined by ¹³C-NMR is 98.0% by mole or higher.

Also exemplified is a propylenic random copolymer which is a random copolymer of propylene and ethylene which satisfies the following requirements [1] to [5] (JP-A-9-271718):

[1] The ethylene unit content (χ(wt %)) in a copolymer is 0.2 to 4 wt %;
[2] The melt index (MI (g/10 min)) of a copolymer is 4 to 12 g/10 min;
[3] The boiling diethylether extract (E (wt %)) and χ are in the relationship represented the formula (1):

$$E \leq 0.25\chi + 1.1 \quad (1);$$

[4] The melting point (Tm(° C.)) determined by a differential scanning calorimeter and χ are in the relationship represented by the formula (2):

$$Tm \leq 165 - 5\chi \quad (2); \text{ and,}$$

[5] The % isotactic triad (mm (mol %)) of a PPP chain moiety determined by ¹³C-NMR is 98.0% by mole or higher.

As an ethylene/1-butene/propylene copolymer, one described in JP-A-11-60639 may be exemplified. Thus, a propylenic random copolymer which is exemplified is a random copolymer of propylene, ethylene and 1-butene which satisfies the following requirements [1] to [6]:

[1] The ethylene unit content in a copolymer (α mol %) and the 1-butene unit content (β mol %) are in the relationship represented by the formula (1):

$$4 \leq (\alpha + \beta) \leq 15 \quad (1);$$

[2] The melt index of a copolymer (MI (g/10 min)) is 1 to 12 g/10 min;
[3] The boiling diethylether extract (E) and (α+β) are in the relationship represented by the formula (2) when (α+β)≤12 and by the formula (3) when (α+β)>12:

$$E \leq 0.2(\alpha + \beta) + 0.6 \quad (2)$$

$$E \leq 3.0 \quad (3)$$

[4] The melting point (Tm(° C.)) determined by a differential scanning calorimeter and (α+β) are in the relationship represented by the formula (4):

$$Tm \leq 164 - 3.6(\alpha + \beta) \quad (4)$$

[5] The stereoregularity index P (mol %) determined by $^{13}$C-NMR is 98% by mole or higher; and,

[6] The ratio (Mw/Mn) of the weight mean molecular weight (Mw) to the number mean molecular weight (Mn) determined by a gel permeation chromatography (GPC) is 6 or less (JP-A-11-60639).

The meaning and the determination method of each parameter are as described in the respective publication.

When as a crystalline propylenic polymer [II] in this invention one exhibiting no crystallinity is employed, the heat resistance of a film or sheet may be reduced.

In this invention, a propylenic polymer [I] and a crystalline propylenic polymer [II] may be dry-blended using a Henschel mixer and the like, or, alternatively, they may be kneaded using a single- or twin-screw extruder, Banbury mixer and the like. A component [I] is incorporated in an amount of 1 to 99% by weight, preferably 10 to 90% by weight, particularly 20 to 80% by weight. When an amount of a component [I] less than 1% by weight or less, the pliability may be reduced.

To a propylenic resin composition in this invention, various additives may be added if desired. Such additives may be antioxidant, neutralizing agent, slipperiness-imparting agent, anti-blocking agent, anti-frosting agent, antistatic agent and the like. Each of such additives may be employed alone or as a combination of two or more. For example, a phosphorus-based antioxidant, a phenol-based antioxidant and a sulfur-based antioxidant may be exemplified as an antioxidant.

A phosphorus-based antioxidant may for example be tris-nonylpheylphosphite, tris(2,4-di-t-butylphneyl)phosphite, distearylpentaerythritol diphosphite, bis(2,4-di-t-butylphenyl)pentaerythritol phosphite, bis(2,6-di-t-butyl-4-methylphenyl)pentaerythritol phosphite, 2,2-methylenebis(4,6-di-t-butylphenyl)octylphosphite, tetrakis(2,4-di-t-butylphenyl)-4,4-bophenylene-di-phosphite, ADECASTAB 1178 (ASAHI DENKA), SMILIZER TNP (SUMITOMO KAGAKU), JP-135 (JOHOKU KAGAKU), ADECASTAB 2112 (ASAHI DENKA), JPP-2000 (JOHOKU KAGAKU), Weston 618 (GE), ADECASTAB PEP-24G (ASAHI DENKA), ADECASTAB PEP-36 (ASAHI DENKA), ADECASTAB HP-10 (ASAHI DENKA), SandstabP-EPQ (SANDZ), phosphite 168 (Ciba-geigy) and the like.

A phenol-based antioxidant may for example be 2,6-di-t-butyl-4-methylphenol, n-octadecyl-3-(3',5'-di-t-butyl-4'-hydroxyphenyl)propionate, tetrakis[methylene-3-(3,5-di-t-butyl-4-hydroxyphenyl]methane, tris(3,5-di-t-butyl-4-hydroxybenzyl)isocyanurate, 4,4'-butylidenebis-(3-methyl-6-t-butylphenol), triethyleneglycol-bis[3-(3-t-butyl-4-hydroxy-5-methylphenyl)propionate], 3,9-bis{2-[3-(3-t-butyl-4-hydroxy-5-methylphenyl)propionyloxy]-1,1-dimethylethyl}-2,4,8,10-tetraoxaspiro[5,5]undecane, SMILIZER BHT (SUMITOMO KAGAKU), YOSHINOX BHT (YOSHITOMI PHARMACEUTICAL CO., LTD.), ANTAGE BHT (KAWAGUCHI KAGAKU), IRGANOX 1076 (Ciba-geigy), IRGANOX 1010 (Ciba-geigy), ADECASTAB AO-60 (ASAHI DENKA), SMILIZER BP-101 (SUMITOMO KAGAKU), TOMINOX TT (YOSHITOMI PHARMACEUTICAL CO., LTD.), TTHP (TORAY), IRGANOX 3114 (Ciba-geigy), ADECASTAB AO-40 (ASAHI DENKA), SMILIZER BBM-S (SUMITOMO KAGAKU), YOSHINOX BB (YOSHITOMI PHARMACEUTICAL CO., LTD.), ANTAGE W-300 (KAWAGUCHI KAGAKU), IRGANOX 245 (Ciba-geigy), ADECASTAB AO-70 (ASAHI DENKA), TOMINOX 917 (YOSHITOMI), ADECASTAB AO-80 (ASAHI DENKA), SMILIZER GA-80 (SUMITOMO KAGAKU) and the like.

A sulfur-based antioxidant may for example be dilauryl-3,3'-thiodipropionate, dimyristyl-3,3'-thiodipropionate, distearyl-3,3'-thiodipropionate, pentaerythritoltetrakis(3-laurylthiopropionate), SMILIZER TPL (SUMITOMO KAGAKU), YOSHINOX DLTP (YOSHITOMI), ANTIOX L (NIPPON YUSHI), SMILIZER TPM (SUMITOMO KAGAKU), YOSHINOX DMTP (YOSHITOMI), ANTIOX M (NIPPON YUSHI), SMILIZER TPS (SUMITOMO KAGAKU), YOSHINOX DSTP (YOSHITOMI), ANTIOX S (NIPPON YUSHI), ADECASTAB AO-412S (ASAHI DENKA), SEENOX 412S (CYPLO KASEI), SMILIZER TDP (SUMITOMO KAGAKU) and the like.

As an antioxidant for a film or sheet, IRGANOX 1010: general name: pentaerythrityl-tetrakis[3-(3,5-di-t-butyl-4-hydroxyphenyl)propionate], IRGAPHOS 168: general name: tris(2,4-di-t-butylphenyl)phosphite, IRGANOX 1076: general name: octadecyl-3-(3,5-di-t-butyl-4-hydroxyphenyl)propionate, IRGANOX 1330: general name: 1,3,5-trimethyl-2,4,6-tris(3,5-di-t-butyl-4-hydroxybenzyl)benzene, IRGANOX 3114: general name: tris(3,5-di-t-butyl-4-hydroxybenzyl)isocyanurate, P-EPQ: general name: tetrakis(2,4-di-t-butylphenyl)4,4'-biphenylene-di-phosphite are particularly preferred.

When an antioxidant is employed in this invention, it is added in an amount of 0.001 to 1 parts by weight to 100 parts by weight of a propylenic resin composition described above. As a result, a preferable effect such as prevention of yellowing is achieved.

Typically, an antioxidant listed above may be incorporated as follows.

| | |
|---|---|
| Case 1 | |
| IRGANOX 1010 | 1000 ppm |
| PEP-Q | 1000 ppm |
| Case 2 | |
| IRGANOX 1076 | 1200 ppm |
| PEP-Q | 600 ppm |
| IRGAPHOS 168 | 800 ppm |
| Case 3 | |
| IRGANOX 1010 | 400 to 1000 ppm |
| IRGAPHOS 168 | 750 to 1500 ppm |

A particularly preferred neutralizing agent for a film and sheet may for example be calcium stearate, zinc stearate, magnesium stearate, HYDROTALSITE (DHT-4A) empirical formula: $Mg4.5Al2(OH)13CO_3 3.5H_2O$ and the like.

A particularly preferred antiblocking agent for a film and sheet may for example be PSYLICIA: a synthesized silica-based material manufactured by FUJI SILICIA, MIZUKASIL: a synthesized silica-based material manufactured by MIZUSAWA KAGAKU KOGYO and the like.

A particularly preferred slipperiness-imparting agent for a film and sheet may for example be erucic acid amide, oleic acid amide, stearic acid amide, behenic acid amide, ethylene bisstearic acid amide, ethylene bis oleic acid amide, stearylerucaamide and oleylpalmitoamide.

When a nucleating agent is used in this invention, the amount of a nucleating agent to be added is 10 ppm or higher, preferably 10 to 10000 ppm, more preferably 10 to 5000 ppm, particularly 10 to 2500 ppm, based on a propylenic resin composition. An amount less than 10 ppm provides no improvement in the heat seal performance, while an amount exceeding 10000 ppm fails to exhibit corresponding increase in the effect and may rather lead to a poor appearance. A nucleating agent may be understood as is discussed in the first invention.

[VI] Sixth Invention

The sixth invention is detailed below.

[1] A resin composition in this invention is a polypropylenic resin composition comprising (A) 99 to 50% by weight of a propylene homopolymer having the following characteristics (a1) to (a4):
(a1) the intrinsic viscosity [η] is 0.5 to 5.0 dl/g;
(a2) the molecular weight distribution (Mw/Mn) is 3.5 or less;
(a3) the isotactic pentad fraction (mmmm (in percentage terms by mole)) is 40 to 99% by mole; and,
(a4) the isotactic pentad fraction (mmmm (in percentage terms by mole)) and the melting point (Tm(° C.)) are in the relationship represented by the following formula (I):

$$Tm \leq [mmmm]+65 \qquad (I);$$

and, (B) 1 to 50% by weight of a propylene homopolymer capable of forming an eutectic with a component (A) under a rapid cooling condition upon film formation.

Since a propylene homopolymer as a component (A) which has a narrow molecular weight distribution is analogous in its nature to a single component material, it has a smaller amount of a polymer having a different stereoregularity or a low molecular weight polymer which serves as a crystallization nucleus at the initial stage of the crystallization, resulting in a difficulty in the crystallization, which leads to an increase in the supercooling degree (difference in temperature between the melting point and the crystallization temperature) which is indicative of a crystallization profile.

In this invention, by means of an eutectic formation of a propylene homopolymer as a component (A) having a narrow molecular weight distribution with other propylene homopolymer as a component (B) under a rapid cooling condition upon film formation, an improvement in the moldability, which is difficult to be achieved with a single polypropylene, can be achieved, and a cast film whose rigidity and seal temperature are well-balanced can be obtained.

In general, a determination in an almost equilibrated process of a crystal growth such as in DSC may involve a difficulty in an eutectic formation and may exhibit a supercooling degree which is observed to be reduced only slightly.

On the contrary, a heat molding of a film or sheet employs a rapid cooling for setting (non-equilibrated process of a crystal growth) which allows an eutectic to be formed readily, and this eutectic formation contributes to the improvement in the physical characteristics and in the moldability.

Thus, a component (B) in this invention may be one capable of forming an eutectic with a component (A) under a rapid cooling condition upon film formation (on the basis of the resin temperature at the exit of a die of 191° C., the chill roll temperature of 30° C., the film thickness of 25μ, the haul-off speed of 6 mm/min).

A eutectic formation of a polymer in this invention is defined so when a single peak top is observed in a fusion endothermic curve obtained by raising the temperature immediately after conditioning a film, which has just been molded, as described later using a differential scanning calorimetry (DSC method). This eutectic formation of a polymer is understood to be a process in which one polymer undergoes an initial crystal formation utilizing the other polymer as a crystallization nucleus and a subsequent crystal growth takes place.

While a propylene homopolymer as a component (A) is a polypropylene which is polymerized with a homogeneous catalyst such as a metallocene catalyst, any catalyst having a performance close to that of a homogeneous system may be employed even if it is a supported catalyst such as a Ziegler-Natta catalyst. Thus, without limitation to a catalyst employed in a polymerization, a propylene homopolymer whose intrinsic viscosity [η] is 0.5 to 5.0 dl/g, molecular weight distribution (Mw/Mn) is 3.5 or less, % isotactic pentad (mmmm % by mole) is 40 to 99% by mole, preferably 80 to 99% by mole, and % isotactic pentad (mmmm % by mole) and melting point (Tm(° C.)) are in the relationship represented by the following formula (I):

$$Tm \leq [mmmm]+65 \qquad (I);$$

is acceptable.

An intrinsic viscosity [η] less than 0.5 dl/g results in a shortcoming in the mechanical strength of a film such as tensile strength and rigidity, while one higher than 5.0 dl/g results in a difficulty in extrusion moldings such as cast molding, and a molecular weight distribution (Mw/Mn) exceeding 3.5 results in an impairment in the balance between the rigidity and the heat seal performance of a film or a reduction in the anti-blocking performance. A % isotactic pentad (mmmm % by mole) less than 40% by mole results in a lower rigidity of a film, while one exceeding 90% by mole results in a disadvantageously poor impact resistance of a film.

The formula (I) representing the relationship between the isotactic pentad fraction (mmmm (in percentage terms by mole)) and the melting point (Tm ° C.) is defined for the purpose of excluding a polypropylene whose molecular weight distribution (Mw/Mn) of 3.5 or less obtained by means of a use of a peroxide for decomposing a polypropylene having a broad molecular weight distribution obtained by a conventional catalyst. While a propylene homopolymer as a component (A) in this invention has a stereoregularity [mmmm] and a molecular weight which are close to those of a single component material, one excluded as described above is a mixture of various components having different levels of the stereoregularity [mmmm] and tends to exhibits a higher melting point (Tm ° C.) inherent to a resin composition reflecting the presence of a component having a high stereoregularity [mmmm], because of which it is excluded by Formula (I). One departing from the relationship represented by Formula (I) provides a film having a poor balance between the rigidity and the heat seal temperature.

A propylene homopolymer as a component (B) may be one capable of forming an eutectic with a propylene homopolymer as a component (A).

In general, one having a stereoregularity and a molecular weight which are different from those of a propylene homopolymer as a component (A) can induce a crystallization nucleus and form an eutectic. Accordingly, a propylene homopolymer having a molecular weight which is smaller than that of a component (A) may be exemplified.

An inventive resin composition is a polypropylenic resin composition comprising 99 to 50% by weight, more preferably 99 to 80% by weight of a component (A), and 1 to 50% by weight, more preferably 1 to 20% by weight of a component (B).

An amount of a component (B) less than 1% by weight results in deteriorated heat seal performance and moldability, while that exceeding 50% by weight results in an impairment in the balance between the heat seal performance and the rigidity of a film.

A film produced by a cast molding using a resin composition whose crystallization profile is improved has a higher ability of improving the physical characteristics and a higher ability of improving the moldability, and a resultant cast-molded film has a tensile modulus in the direction of MD (TM(MPa)) and a heat seal temperature (HST(° C.)) are expected to be in the relationship represented by the following Formula (II):

$$TM \geq 22 \times HST - 1850 \qquad (II);$$

more preferably by the following Formula (II'):

$$TM \geq 22 \times HST - 1800 \qquad (II')$$

Formula [II] reflects the fact that the effect according to the invention serves to allow the heat seal temperature (HST(° C.)) to be further lowered (whereby achieving an intended seal pealing strength at a lower temperature) and also serves to allow the film tensile modulus (rigidity) to be improved.

[2] Also this invention is a polypropylenic resin composition which is included in a resin composition [1] described above and in which the crystallization temperature (TcB ° C.) of a component (B) determined by a differential scanning calorimeter is higher by 0 to 40° C. than that (TcA ° C.) of a component (A).

Thus, a component (B) capable of forming an eutectic with a component (A) exhibits a higher physical characteristics-improving effect when the difference in the crystallization temperature between the two components becomes greater, but a difference exceeding 40° C. results in a difficulty in forming an eutectic, which may lead to no physical characteristics-improving effect according to the invention to be expected. More preferably, TcB is higher by 10 to 40° C. than TcA.

[3] Furthermore, this invention is a polypropylenic resin composition comprising (A') 99 to 50% by weight of a propylenic polymer obtained by a polymerization using a metallocene catalyst which is a propylene homopolymer and has an isotactic pentad fraction (mmmm) of 80 to 99%, an intrinsic viscosity [η] of 1.0 to 2.0 dl/g and a molecular weight distribution (Mw/Mn ratio) of 3.5 or less, and, (B') 1 to 50% by weight of a propylenic polymer obtained by a polymerization using a metallocene catalyst which is a propylene homopolymer and has an intrinsic viscosity [η] of 0.01 to 1.0 dl/g and a molecular weight distribution (Mw/Mn ratio) of 3.5 or less.

(1) Component (A')

A component (A') may be a propylenic polymer which is a propylene homopolymer polymerized using a metallocene catalyst and also may be a propylenic polymer which has been subjected to a preliminary polymerization with a small amount (0.5% by mole or less) of ethylene or an α-olefin having 4 to 20 carbon atoms, wherein the % isotactic pentad (% mmmm), which is indicative of the stereoregularity of the polypropylene, is 80 to 99%, more preferably 85 to 97%, the intrinsic viscosity [ ] is 1.0 to 2.0 dl/g, more preferably 1.5 to 1.8 dl/g, and the molecular weight distribution (Mw/Mn ratio) is 3.5 or less, more preferably 3.0 or less.

A % isotactic pentad referred herein means the proportion (%) of the propylene structure units each having a meso-structure (mmmm structure in which 5 methyl groups are aligned in the same direction) in 5 propylene structure unit based on the assignment of the peaks in a $^{13}$C-NMR spectrum described by Chen H. N., Ewen J. A., Macromol. cem., 1989, 190, 1350. Such proportion is abbreviated as a % meso-pentad.

A % isotactic pentad described above which is less than 80% may result in an insufficient film rigidity, while that exceeding 99% may result a disadvantageous reduction in the impact resistance of a film.

An intrinsic viscosity [η] is usually preferable to be within the range from 1.0 to 2.0 dl/g for the purpose of a better film moldability, and one less than 1.0 dl/g results in insufficient tensile strength and rigidity of a film, while one exceeding 2.0 dl/g may cause a reduced flowability which may lead to a poor moldability.

Furthermore, a molecular weight distribution (Mw/Mn ratio) exceeding 3.5 may cause an impairment in the balance between the rigidity and the heat seal performance of a film or a reduction in the anti-blocking performance.

A propylenic polymer as a component (A') employed in this invention can be produced by a polymerization in the presence of a metallocene catalyst comprising a cyclopentadienyl group-carrying compound of a transition metal of Group IV in the periodic table and a methylaluminoxane or a compound capable of forming an ionic complex by reacting with a compound of a transition metal of Group IV in the periodic table and an organic aluminium compound.

A main catalyst, which is a cyclopentadienyl group-carrying compound of a transition metal of Group IV in the periodic table may be a compound of zirconium, titanium and hafnium having as a ligand a multi dentate coordination compound in which at least two groups selected from the group consisting of cycloalkadienyl groups or their substituted derivatives, typically, an indenyl group, a substituted indenyl group and its partially hydrogenated derivative are bound via a lower alkylene group or silylene group. Thus, a transition metal compound may be ethylene-bis-(indenyl)zirconium dichloride described by H. H. Brintzinger et al. In J. Organometal. Chem., 288, 63 (1985), or ethylene-bis-(indenyl) hafnium dichloride described in J. Am. Chem. Soc., 109, 6544 (1987), and a stereorigid chiral compound of zirconium and hafnium compounds such as dimethylsilylbis(2,4-dimethylcyclopentadienyl)zirconium dichloride, dimethylsilyl-bis(2,4,5-trimethylcyclopentadienyl)zirconium dichloride and hafnium dichlorides of the similar complexes, as described by H. Yamazaki et al. in Chemistry Letters, 1853 (1989).

Those exemplified typically are ethylenebis(indenyl)zirconium dichloride, ethylenebis(4,5,6,7-tetrahydro-1-indenyl) zirconium dichloride, ethylenebis(4-methyl-1-indenyl)zirconium dichloride, ethylenebis(5-methyl-1-indenyl)zirconium dichloride, ethylenebis(6-methyl-1-indenyl)zirconium dichloride, ethylenebis(7-methyl-1-indenyl)zirconium dichloride, ethylenebis(2,3-dimethyl-1-indenyl)zirconium dichloride, ethylenebis(4,7-dimethyl-1-indenyl)zirconium dichloride, ethylenebis(indenyl)hafnium dichloride, ethylenebis(4,5,6,7-tetrahydro-1-indenyl)hafnium dichloride, ethylenebis(4-methyl-1-indenyl)hafnium dichloride, ethylenebis(5-methyl-1-indenyl)hafnium dichloride, ethylenebis(6-methyl-1-indenyl)hafnium dichloride, ethylenebis(7-methyl-1-indenyl)hafnium dichloride, ethylenebis(2,3-dimethyl-1-indenyl)hafnium dichloride, ethylenebis(4,7-dimethyl-1-indenyl)hafnium dichloride, dimethylsilylenebis (indenyl)zirconium dichloride, dimethylsilylenebis(indenyl) hafnium dichloride, dimethylsilylenebis(4-methylindenyl) zirconium dichloride, dimethylsilylenebis(indenyl)hafnium dichloride, dimethylsilylenebis(2,4,5-trimethylcyclopentadienyl)zirconium dichloride, dimethylsilylenebis(2,4,5-trimethylcyclopentadienyl)hafnium dichloride, dimethylsilylenebis(2,4-dimethylcyclopentadienyl)zirconium dichloride, dimethylsilylenebis(2,4-dimethylcyclopentadienyl)hafnium dichloride, dimethylsilylenebis(3-methylcyclopentadienyl) zirconium dichloride, dimethylsilylenebis(3-methylcyclopentadienyl)hafnium dichloride, dimethylsilylenebis(2-methyl-4-phenylindenyl)zirconium dichloride, dimethylsilylenebis(benzoindenyl)zirconium dichloride and the like.

Those which may also be exemplified are (dimethylsilylene)(dimethylsilylene)-bis(indenyl)zirconium dichloride, (ethylene)(ethylene)-bis(indenyl)zirconium dichloride, (ethylene)(ethylene)-bis(3-methylindenyl)zirconium dichloride, (ethylene)(ethylene)-bis(4,7-dimethylindenyl)zirconium dichloride and the like, as well as those obtained by replacing zirconium in these compounds with hafnium or titanium.

As a compound capable of forming an ionic complex by reacting with a compound of a transition metal of Group IV in the periodic table which is a promoter, those employed preferably may for example be a tetra(pentafluorophenyl)borate anion-containing compound such as triphenylcarbynium tetrakis(pentafluorophenyl)borate, N,N-dimethylanilinium tetrakis(pentafluorophenyl)borate, lithium tetrakis(pentafluorophenyl)borate and the like, as well as a tetra(pentafluorophenyl)aluminate anion-containing compound such as triphenylcarbynium tetrakis(pentafluorophenyl)aluminate, N,N-dimethylanilinium tetrakis(pentafluorophenyl)aluminate, lithium tetrakis(pentafluorophenyl)aluminate.

An organic aluminium compound is one having at least one Al—C binding in its molecule. Typically, such organic aluminium compound may for example be a trialkylaluminium such as triethylaluminium, triisobutylaluminium, trihexylaluminium and the like, a dialkylaluminium halide such as diethylaluminium halide, diisobutylaluminium halide and the like, a mixture of a trialkylaluminium and dialkylaluminium halide, and an alkylalumoxane such as tetraethyldialumoxane, tetrabutylalumoxane and the like.

Among these organic aluminum compounds, those employed preferably are a trialkylaluminium, a mixture of a trialkylaluminium and a dialkylaluminium halide and an alkylalumoxane, with triethylaluminium, triisobutylaluminium, a mixture of triethylaluminium and diethylaluminium chloride and tetraethyldialumoxane being particularly preferred. As an organic aluminium, those employed preferably are triethylaluminium, triisobutylaluminium and the like.

These metallocene-based catalyst and/or promoter may be employed also as being supported on a carrier, and such carrier may for example be an organic compound such as polystyrene as well as an inorganic oxide such as silica, alumina and the like.

A polymerization method may be a bulk polymerization, a solution polymerization, a vapor phase polymerization, a suspension polymerization and the like, and may be performed as a batch process or a continuous process.

It is also possible that a small amount of α-olefin such as ethylene, propylene, 1-butene, 4-methyl-1-pentene and the like is used to perform a preliminary polymerization.

A polymerization is conducted at a temperature usually of −50 to 250° C., preferably 0 to 150° C., for a period usually of 1 to 10 hour(s), at a pressure usually of atmospheric pressure to 300 kg/cm$^2$-G.

(2) Component (B')

A component (B') may be a propylene homopolymer polymerized using a metallocene catalyst and also may be a propylenic polymer which has been subjected to a preliminary polymerization with a small amount (0.5% by mole or less) of ethylene or an α-olefin having 4 to 20 carbon atoms, wherein the intrinsic viscosity [η] is 0.01 to 1.0 dl/g, more preferably 0.1 to 0.8 dl/g and the molecular weight distribution (Mw/Mn ratio) is 3.5 or less, more preferably 3.0 or less.

An intrinsic viscosity [η] less than 0.01 dl/g may cause a stickiness in a film, while one exceeding 1.0 dl/g fails to improve the balance between the rigidity and the heat seal performance of a film.

On the other hand, a molecular weight distribution (Mw/Mn ratio) exceeding 3.5 results in an impairment in the balance between the rigidity and the heat seal performance of a film or a reduction in the anti-blocking performance.

While the % isotactic pentad (% mmmm) of a component (B') is not particularly limited, it is preferably 80 to 99% for the purpose of a better film rigidity. In addition, it is preferred that the crystallization temperature Tc of a component (B') is higher than that of a component (A').

A polymerization of a component (B') may basically use a metallocene-based catalyst and the promoter similar to those employed for the propylenic polymer as a compound (A') described above, and the production may be performed also by the similar polymerization method.

(3) Incorporation

An inventive propylenic polymer composition employs the incorporation ratio (ratio in % by weight) of a component (A') and a component (B') which is 99 to 50:1 to 50. More preferably, the ratio is 99 to 75:1 to 25, particularly 99 to 90:1 to 10.

A content of a component (B) less than 1% may results in a deteriorated heat seal performance, while that exceeding 50% by weight results in an impairment in the balance between the rigidity and the heat seal performance of a film.

When combining a component (A) with a component (B) or a component (A') with a component (B') according to the invention, various additives such as nucleating agent, heat stabilizing agent, antioxidant, weathering agent, neutralizing agent, slipperiness-imparting agent, anti-blocking agent, glidant, dye, pigment, filler, anti-frosting agent, antistatic agent and the like may be incorporated as desired.

A propylenic polymer composition can be obtained by mixing respective components described above using Henschel mixer, V blender, ribbon blender, tumbler blender and the like, followed by kneading the mixture using a kneading device such as single- or multi-screw extruder, kneader, Banbury mixer and the like.

[4] An inventive propylenic polymer composition can be applied also to an injection molding, a blow molding, an extrusion molding and the like, among which the application to a cast-molded or inflation-molded film is especially preferred. The thickness of a film may vary depending on the uses, and is usually about 5 to 500 μm. A film described above can not only be used as a single-layered film but can also be fabricated into a multi-layered film by means of a co-extrusion film forming process, and is used preferably also as an oriented film.

[VII] Seventh Invention

The seventh invention is detailed below.

[1] A resin composition in this invention is a propylenic resin comprising 99 to 50% by weight of a propylene-α-olefin copolymer (A') having the following characteristics (a1) to (a5):

(a1) the intrinsic viscosity [η] is 0.5 to 5 dl/g, preferably 0.7 to 2.5 dl/g, more preferably 1.0 to 2.0 dl/g;

(a2) the molecular weight distribution (Mw/Mn) is 3.5 or less, preferably 3.0 or less, more preferably 2.5 or less;

(a3) the stereoregularity index (P) is 5 to 99% by mole, preferably 55 to 95% by mole, more preferably 55 to 90% by mole;

(a4) it is a propylenic random copolymer produced by copolymerizing propylene and ethylene and/or an α-olefin having 4 to 20 carbon atoms, in which the ethylene and/or an α-olefin having 4 to 20 carbon atoms is contained in an amount of 1 to 30% by mole; and, (a5) the amount of the components which are dissolved out at 0° C. or lower in a temperature-raising fractional chromatography (TREF) is 10% by weight or less, preferably 8% by weight or less, more preferably 5% by weight or less; and, 1 to 50% by weight or a propylenic polymer (B') capable of forming an eutectic with a component (A') under a rapid cooling condition upon film formation.

Since a propylene-α-olefin copolymer as a component (A') which has a narrow molecular weight distribution is analogous in its nature to a single component material (a copolymer whose molecular weight and comonomer ratio are uniform), it has a smaller amount of a polymer having a different stereoregularity or a low molecular weight polymer which serves as a cystallization nucleus at the initial stage of the crystallization, resulting in a difficulty in the crystallization, which leads to an increase in the supercooling degree (difference in temperature between the melting point and the crystallization temperature) which is indicative of a crystallization profile.

In this invention, by means of an eutectic formation of a propylene-α-olefin copolymer as a component (A') having a narrow molecular weight distribution with other propylene polymer as a component (B') under a rapid cooling condition upon film formation, an improvement in the moldability, which is difficult to be achieved with a single propylene-α-olefin copolymer, can be achieved, and a cast film whose rigidity and seal temperature are well-balanced can be obtained.

In general, a determination of a crystallization temperature in an almost equilibrated process of a crystal growth such as in a differential scanning calorimetry (DSC) may involve a difficulty in an eutectic formation and may exhibit a supercooling degree which is observed to be reduced only slightly.

On the contrary, a heat molding of a film or sheet employs a rapid cooling for setting (non-equilibrated process of a crystal growth) which allows an eutectic to be formed readily, and this eutectic formation contributes to the improvement in the physical characteristics and in the moldability.

Thus, a component (B') in this invention may be one capable of forming an eutectic with a component (A') under a rapid cooling condition upon film formation (on the basis of the resin temperature at the exit of a die of 191° C., the chill roll temperature of 30° C., the film thickness of 25μ, the haul-off speed of 6 mm/min).

A eutectic formation of a polymer in this invention is defined so when the peak top observed in a fusion endothermic curve obtained by subjecting a film, which has just been molded, to a differential scanning calorimetry (DSC) is single and the crystallization temperature of this film is higher than that of a component (A') and lower than that of a component (B'). This eutectic formation of a polymer is understood to be a process in which one polymer undergoes an initial crystal formation utilizing the other polymer as a crystallization nucleus and a subsequent crystal growth takes place.

While a propylene-α-olefin copolymer as a component (A') employed in this invention is a polypropylene which is polymerized with a homogeneous catalyst such as a metallocene catalyst using a known production method such as vapor phase and solution polymerizations, any catalyst having a performance close to that of a homogeneous system, i.e., ability of providing a polymer having the parameters shown in the sections (a1) to (a5) described above, may be employed even if it is a supported catalyst such as a Ziegler-Natta catalyst. Typical catalysts and production examples are discussed later in above [4] [Examples of production of resins and films], and the methods for determining the parameters shown in the sections (a1) to (a5) described above are discussed later in the part of [Examples].

An intrinsic viscosity [η] less than 0.5 dl/g results in a shortcoming in the mechanical strength of a film such as tensile strength and rigidity, while one higher than 5.0 dl/g results in a difficulty in extrusion moldings such as cast molding, and a molecular weight distribution (Mw/Mn) exceeding 3.5 results in an impairment in the balance between the rigidity and the heat seal performance of a film or a reduction in the anti-blocking performance. A % isotactic pentad (mmmm % by mole), which is a stereoregularity index (P), less than 50% by mole results in a lower rigidity of a film, while one exceeding 90% by mole results in a disadvantageously poor impact resistance of a film.

This invention is also a propylenic random copolymer produced by copolymerizing propylene and ethylene and/or an α-olefin having 4 to 20 carbon atoms, and an α-olefin whose number of the constituent carbon atoms exceeds 20 exhibits a low activity which leads to a residual oil, and the amount of ethylene and/or an α-olefin having 4 to 20 carbon atoms less than 0.1% by mole gives a less improving effect, while that exceeding 30% by mole in results in a difficulty in the molding.

An amount of the components which are dissolved out at 0° C. or lower in a temperature-raising fractional chromatography (TREF) exceeding 10% by weight results in a disadvantageously apparent stickiness in a film. Thus, a polypropylene having a higher level of a copolymer of a low α-olefin content which may serve as a stickiness-impairing component in a film is intended to be excluded even if its molecular weight is adjusted to 3.5 or less by subjecting a propylene-α-olefin copolymer which is obtained using a conventional catalyst and has a broad molecular weight distribution and a broad range of the comonomer ratio in the copolymer (a mixture of copolymers having different comonomer ratio) to a decomposition using a peroxide.

A propylene homopolymer as a component (B') may be one capable of forming an eutectic with a propylene homopolymer as a component (A').

In general, one having a stereoregularity and a molecular weight which are different from those of a propylene-α-olefin copolymer as a component (A') can induce a crystallization nucleus and form an eutectic. Accordingly, a propylene homopolymer, a propylene-α-olefin copolymer, which has a molecular weight which is smaller than that of a component (A') may be exemplified. Among these, a propylenic polymer whose stereoregularity index (P) is preferably 85% by mole, more preferably 90% by mole, particularly 955 by mole is desirable.

Such component (B') may also be produced by a known method similarly to a component (A') discussed above. An inventive resin composition is a polypropylenic resin composition comprising 99 to 50% by weight, more preferably 99 to 80% by weight of a component (A'), and 1 to 50% by weight, more preferably 1 to 20% by weight of a component (B').

An amount of a component (B') less than 1% by weight results in deteriorated heat seal performance and moldability, while that exceeding 50% by weight results in an impairment in the balance between the heat seal performance and the rigidity of a film.

A film produced by a cast molding using a resin composition whose crystallization profile is improved has a higher ability of improving the physical characteristics and a higher ability of improving the moldability, and a resultant cast-molded film has a tensile modulus in the direction of MD (TM(MPa) and a heat seal temperature (HST(° C.)) are expected to be in the relationship represented by the following Formula (II):

$$TM \geq 22 \times HST - 1850 \quad (II);$$

more preferably by the following Formula (II'):

$$TM \geq \times HST - 1800 \quad (II').$$

Formula [II] reflects the fact that the effect according to the invention serves to allow the heat seal temperature (HST(° C.)) to be further lowered (whereby achieving an intended seal pealing strength at a lower temperature) and also serves to allow the film tensile modulus (rigidity) to be improved.

[2] Also this invention is a polypropylenic resin composition which is included in the invention [1] described above and in which the crystallization temperature (TcB ° C.) of a component (B) determined by a differential scanning calorimeter is higher by 0 to 40° C. than that (TcA ° C.) of a component (A).

Thus, a component (B) capable of forming an eutectic with a component (A) exhibits a higher physical characteristics-improving effect when the difference in the crystallization temperature between the two components becomes greater, but a difference exceeding 40° C. results in a difficulty in forming an eutectic, which may lead to no physical characteristics-improving effect according to the invention to be expected. More preferably, TcB is higher by 10 to 40° C. than TcA.

[3] Furthermore, this invention is a polypropylenic resin comprising a copolymer (A) of propylene and an α-olefin having 5 or more carbon atoms and a propylenic polymer (B) having a crystallization temperature determined by a differential scanning calorimetry which is higher than that of the component (A), wherein (A) is present in an amount of 55 to 99 parts by weight and (B) in an amount of 45 to 1 parts by weight.

In this invention, a copolymer (A) should be a copolymer of propylene and an α-olefin having 5 or more carbon atoms. A propylene homopolymer is not preferred since it gives an insufficient low temperature heat seal performance. An α-olefin having 5 or more carbon atoms is not particularly limited, and may typically be 1-pentene, 4-methyl-1-pentene, 1-hexene, 1-heptene, 1-octene, 1-nonene, 01-decene, 1-dodecene, 1-tridecene, 1-tetradecene, 1-pentadecene, 1-hexadecene, 1-heptadecene, 1-octadecene and the like. Among these α-olefins, at least one of 1-octene, 1-dodecene and 1-decene is employed to perform a preferable copolymerization with propylene. When an ethylene unit or a 1-butene unit is employed as an α-olefin, the ability of lowering the melting point of a polypropylene becomes lower than when an α-olefin having 5 or more carbon atom is employed, resulting in an insufficient ability of improving the low temperature heat seal characteristics.

Also in this invention, it is preferable that a copolymer (A) satisfies the following requirements (A-1) or (A-2):

(A-1) when the main elution peak temperature of a temperature-raising fractional chromatogram is Tp, the amount (W (A) p) of the components dissolved out within the temperature range from (Tp-5) ° C. to (Tp+5) ° C. is 70% by weight or more; and, (A-2) the amount (W(A)0) of the components dissolved out at 0° C. or lower in a temperature-raising fractional chromatography is 3% by weight or less.

In this context, W(A)p is more preferably 75% by weight or higher, particularly 80% by weight or higher. A W(A)p less than 70% by weight means a broad composition distribution, which allows the peaks other than the main elution peak to appear on a TREF curve or which allows the main elution peak to exhibit a long tailing in the direction of the high or low temperature. Such case is excluded from the preferable range because of the reasons described below. Thus, when the main elution peak exhibits a tailing in the direction of the high temperature or when a secondary peak is observed at a higher temperature than the temperature at which the main elution peak is observed, the heat seal performance tends to be insufficient. On the contrary, when the main elution peak exhibits a tailing in the direction of the low temperature or when a secondary peak is observed at a lower temperature than the temperature at which the main elution peak is observed, a resultant film, fiber, sheet or molded article exhibits a disadvantageous stickiness. W(A)0 is preferably 2% by weight or less. More preferably, it is 1.5% by weight or less. A value of W(A)0 exceeding 3% by weight results in a resultant film, fiber, sheet or molded article which may exhibit a disadvantageous stickiness.

Also in this invention, it is preferable that a copolymer (A) satisfies at least one of the following requirements (A-3), (A-4) or (A-5):

(A-3) a copolymer (A) contains an α-olefin unit having 5 or more carbon atoms in an amount (α % by mole) of 0.1 to 12% by mole;

(A-4) the stereoregularity index (P) of a copolymer (A) is 85% by mole or higher; and, (A-5) a copolymer (A) has an intrinsic viscosity [η] determined in a decalin at 135° C. ranges from 0.5 to 3.0 dl/g.

In this invention, it is preferable that a copolymer (A) contains an α-olefin unit having 5 or more carbon atoms in an amount (a % by mole) of 0.1 to 12% by mole. More preferably the amount is 0.2% by mole or higher and not more than 11% by mole. Particularly, the amount is 0.3% by mole or higher and not more than 10% by mole. An amount less than 0.1% by mole may result in an insufficient ability of improving the heat seal performance. On the other hand, an amount exceeding 12% by mole causes an reduction in the copolymer crystallinity which may lead to a disadvantageously poor rigidity. The stereoregurality index (P) is more preferably 90% by mole or higher. Particularly, it is 95% by mole or higher. A stereoregularity index (P) less than 85% by mole causes an reduction in the copolymer crystallinity which may lead to a poor rigidity. A stereoregularity index (P) is a % isotactic moiety in a triad unit determined by $^{13}$C-NMR, and the method for determination is detailed in Examples. The value of [η] is preferred to be within the range from 0.5 to 3.0 dl/g, a value departing from which may cause a poor molding performance.

In this invention, the melting point (Tma ° C.) of a copolymer (A) determined in a differential scanning calorimetry is in the relationship represented the following formula:

$$Tma \leq 140° \text{ C. and } Tma \leq 160 - 7\alpha \quad (2);$$

more preferably by the following formula:

$$Tma \leq 130° \text{ C. and } Tma \leq 155 - 7\alpha \quad (3);$$

further preferably by the following formula:

$$Tma \leq 120° \text{ C. and } Tma \leq 150 - 7\alpha \quad (4);$$

particularly by the following formula:

$$Tma \leq 115° \text{ C. and } Tma \leq 145 - 7\alpha \quad (5).$$

A value of Tma departing from the range specified above may result in an insufficient low temperature heat seal performance.

In this invention, a propylenic polymer (B) should has a crystallization temperature determined by a differential scanning calorimeter which is higher than that of a copolymer (A). The composition and the structure of a propylenic polymer (B) is not particularly limited, and one which may be employed is a polypropylene homopolymer or a copolymer of propylene with other α-olefin. As a polypropylene homopolymer, an isotactic polypropylene having a higher stereoregularity is preferred. Typically, one employed preferably has a % isotactic pentad, which is an index of the stereoregularity, of 85% by mole or higher, more preferably 90% by mole or higher, particularly 95% by mole or higher. A % isotactic pentad referred herein is a % isotactic moiety in a triad unit determined by $^{13}$C-NMR, and is a value obtained as a ratio of the signal intensity of 21.7 to 22.5 ppm to the total signal intensity of 19.8 to 22.5 ppm $^{13}$C-NMR is determined in the manner similar to that employed for determining the comonomer content (α) and the stereoregularity index (P) of a copolymer (A).

A copolymer of propylene with other α-olefin may for example be an ethylene/propylene copolymer, an ethylene/1-butene/propylene copolymer or a 1-butene/propylene copolymer. A preferred ethylene/propylene copolymer may for example be one described in JP-A-8-288052 or JP-A-8-313210.

A preferred ethylene/1-butene/propylene copolymer may for example be one described in JP-A-9-209210 or JP-A-9-222356. Each of these copolymers of propylene and other α-olefins is characterized by a high stereoregularity of a propylene chain and a higher crystallinity in spite of a low melting point.

The melt index of a propylenic polymer (B) is preferably 0.1 to 100 g/min. A propylenic polymer (B) having a crystallization temperature determined by a differential scanning calorimeter which is lower than that of a copolymer (A) fails to obtain the moldability-improving effect which is an objective of the present invention.

An inventive propylenic resin should consist of 55 to 99 parts by weight of a copolymer (A) and 45 to 1 part(s) by weight of a propylenic polymer (B). A copolymer (A) content less than 55 parts by weight results in an insufficient ability of improving the low temperature heat seal performance. A propylenic polymer (B) content less than 1 part by weight results in no moldability-improving effect. It is preferred to combine 65 to 98 parts by weight of a copolymer (A) with 35 to 2 parts by weight of a propylenic polymer (B). It is further preferred to combine 75 to 95 parts by weight of a copolymer (A) with 25 to 5 parts by weight of a propylenic polymer (B).

An inventive propylenic resin is preferred when the crystallization temperature (Tca ° C.) of a copolymer (A) and the crystallization temperature (Tcb ° C.) of a propylenic polymer (B), as determined by a differential scanning calorimetry, are in the relationship represented by the following formula:

$$Tcb-Tca \geq 20 \qquad (1);$$

more preferably by the following formula:

$$Tcb-Tca \geq 30 \qquad (6); \text{ and,}$$

most preferably by the following formula:

$$Tcb-Tca \geq 400 \qquad (7).$$

A small difference in the crystallization temperature between a copolymer (A) and a propylenic polymer (B) results in a low moldability-improving effect.

An inventive propylenic resin is preferred when a propylenic polymer (B) has the melting point (Tmb ° C.) and the crystallization temperature (Tcb ° C.), as determined by a differential scanning calorimetry, are in the relationship represented by the following formula:

$$Tmb-Tcb \leq 50 \qquad (8);$$

more preferably by the following formula:

$$Tmb-Tcb \leq 45 \qquad (9); \text{ and,}$$

most preferably by the following formula:

$$Tmb-Tcb \leq 40 \qquad (10).$$

A propylenic polymer (B) having a smaller difference between the melting point and the crystallization temperature may have a smaller adverse effect on the low temperature heat seal performance.

An inventive propylenic resin is preferred when it satisfies, upon being subjected to a temperature-raising fractional chromatography, the following requirements (1), (2) and (3):

(1) when the main elution peak temperature is Tp, the amount (W(H)p) of the components dissolved out within the temperature range from (Tp−5) ° C. to (Tp+5) ° C. is 65% by weight or more;

(2) the amount (W(H)0) of the components dissolved out at 0° C. or lower is 3% by weight or less; and, (3) the amount (W(H)1O) of the components dissolved out at Tp+10° C. or higher is 1 to 45% by weight, based on the total weight.

A more preferred W(H)p is 70% by weight or higher. A further preferred W(H)p is 75% by weight or higher. A particularly preferred W(H)p is 80% by weight or higher. A value of W(H)p less than 65% by weight makes the low temperature heat seal performance disadvantageously insufficient. A more preferred W(H)0 is 1% by weight or less. A further preferred W(H)0 is 1.5% by weight or less. A value of W(H)0 exceeding 3% by weight results in a disadvantageously reduced anti-blocking ability.

A more preferred W(H)10 is 2 to 35% by weight. A further preferred W(H)10 is 3 to 25% by weight. A particularly preferred W(H)10 is 4 to 20% by weight. A value less than 1% by weight may cause a poor molding phenomenon, while one exceeding 45% by weight makes the low temperature heat seal performance disadvantageously insufficient.

An inventive propylenic resin is preferred when the peak top temperature on the side of the maximum temperature on the crystallization curve, as determined by a differential scanning calorimetry, is 85° C. or higher.

A more preferable peak top temperature is 90° C. or higher. A further preferable peak top temperature is 95° C. or higher. A particularly preferable peak top temperature is 100° C. or higher. A peak top temperature below 85° C. results in a lower moldability-improving effect.

An inventive propylenic resin is preferred when the peak top temperature on the side of the minimum temperature on the crystallization curve, as determined by a differential scanning calorimetry, is 150° C. or lower.

A more preferable peak top temperature is 140° C. or lower. A further preferable peak top temperature is 130° C. or lower. A particularly preferable peak top temperature is 120° C. or lower. A peak top temperature exceeding 150° C. results in an insufficient low temperature heat seal performance.

[4] [Method for Producing Resins and Films]

In a propylenic resin according to the invention, a copolymer (A') or (A') can be obtained by a polymerization in the manner described in Examples, which is not limiting, and any method for producing a copolymer specified above may be employed.

A catalyst employed preferably in the production is a metallocene catalyst obtained by combining a metallocene-based transition metal compound with an organic aluminium compound or a boron compound. In this context, a metallocene-based transition metal compound may for example be a compound of a transition metal selected from Group IVB, such as titanium, zirconium and hafnium, to which one or two cyclopentadienyl, substituted cyclopentadienyl, indenyl, substituted indenyl, tetrahydroindenyl, substituted tetrahydroindenyl, fluorenyl or substituted fluorenyl, groups are bound, or to which two of these groups crosslinked covalently to each other are bound, and which further contains hydrogen atom, oxygen atom, halogen atom, alkyl, alkoxy, aryl, acetylacetonato, carbonyl group, nitrogen-, oxygen-, sulfur-, phosphorus-silicon-containing ligand.

An organic aluminium compound may be any of various aluminoxane compounds. One preferred particularly is methylaluminoxane. Otherwise, an organic aluminium compound such as trimethylaluminium, triethylaluminium, tri-isobutylaluminium and the like may be used in combination.

A boron compound can preferably be used as an ionizing agent. Such boron compound may for example be a trialkyl-substituted ammonium salt such as triethylammonium tetrapgenylborate, or an N,N-dialkylanilinium salt such as N,N-dimethyltetraphenylborate, a phenylboron compound such as trispentafluorophenylboron and the like.

Such metallocene catalyst and/or an organic aluminium compound may be employed also as being supported on a carrier. In such case, a carrier may for example be an organic compound such as styrene as well as an inorganic compound such as silica, alumina and the like.

It is also possible that a small amount of α-olefin such as ethylene, propylene, 1-butene, an α-olefin having 5 or more carbon atoms and the like is subjected to a preliminary polymerization before use.

A copolymerization of propylene and ethylene or an α-olefin having 4 to 20 carbon atoms, i.e., a component (A') or a copolymerization of propylene and an α-olefin having 5 or more carbon atoms, i.e., a component (A) may not particularly be limited, and may be a bulk polymerization, a solution polymerization, a vapor phase polymerization, a suspension polymerization and the like, and may be performed as a batch process or a continuous process.

A method for feeding each monomer to a reaction system is not particularly limited, and various methods can be employed. The monomer ratio in a reaction system may not necessarily be constant always, and respective monomers may be fed at a certain ratio, or such ratio may vary depending on the timings of feeding. A certain monomer may be added portionwise considering the copolymer reactivity ratio. Alternatively, a gas mixture having a constant monomer ratio is introduced continuously to a reaction system, from which an excessive gas is removed using a exhaustion valve, whereby maintaining a constant monomer ratio in the reaction system. Hydrogen is also used as a molecular weight adjusting agent.

A polymerization condition is not particularly limited and may be similar to that employed in a known method. For example, the polymerization temperature is usually −50 to 250° C., preferably 0 to 150° C. The reaction pressure is atmospheric pressure to 300 kg/cm$^2$g. The polymerization time is 1 minute to about 10 hours.

In a propylenic resin according to the invention, a propylenic polymer (B') or (B) can be obtained by a polymerization in the manner described in Examples, which is not limiting, and any method for producing a propylenic polymer specified above may be employed.

A catalyst employed preferably is a catalyst formed from a solid catalyst component whose essential component is magnesium, titanium and halogen, an organic metal compound catalyst component such as an organic aluminium compound, and an electron donor compound catalyst component such as a silane compound. In addition, a metallocene-based transition metal compound described above combined with an organic aluminium compound, a borane compound and the like, which is referred to as a metallocene catalyst, may also be employed preferably.

A polymerization condition is not particularly limited and may be similar to that employed in a known method. For example, the polymerization temperature is 20 to 150° C., and the reaction pressure is atmospheric pressure to 40 kg/cm$^2$. The polymerization time is 1 minute to about 10 hours. Hydrogen is also used as a molecular weight adjusting agent. A comonomer such as ethylene, 1-butene, an α-olefin having 5 or more carbon atoms and the like may be copolymerized as desired.

An inventive propylenic resin can be obtained by incorporating a copolymer (A') or (A) with a propylenic polymer (B') or (B), in a manner which is not limited. While the examples described later employ the separate productions of a copolymer (A') or (A) and a propylenic polymer (B') or (B) followed by a incorporating step, to which no limitation is made. For example, the first step reactor is used to polymerize a propylenic polymer (B), which is then transferred to the second step reactor, in which propylene and an α-olefin having 5 or more carbon atoms are polymerized. In such case, the catalyst in the second step is not necessarily identical to that in the first step, and any suitable catalysts may be selected.

To a propylenic resin in this invention, customary additives such as antioxidant, neutralizing agent, slipperiness-imparting agent, anti-blocking agent and anti-static agent may be incorporated as desired.

An inventive propylenic resin may be molded into a film using a melt extrusion molding method. For example, in a T die cast film-forming process, it can be used preferably to form a film having a thickness of 10 to 500 μm even in a fast film-forming condition at a haul-off speed of 50 mm/min or even higher. It can also be employed preferably as at least one layer in a laminated film production by means of a co-extrusion film-forming process.

While as a film forming method a T die cast film-forming process in which a large film-forming machine is used to effect a high speed film-forming is employed preferably, no limitation is made thereto, and with any film-forming process capable of producing a film by a melt extrusion molding, an inventive propylenic resin can preferably be employed.

[VIII] Eighth Invention

The eighth invention relates to a novel transition metal compound having a double crosslinking ligand useful as an olefin polymerization catalyst, an olefin polymerization catalyst comprising a compound capable of forming an ionic complex by reacting said transition metal compound and a method for producing an olefinic polymer. An inventive transition metal compound [I], an olefin polymerization catalyst [II] comprising a compound capable of forming an ionic complex by reacting said transition metal compound, and a method for producing an olefinic polymer [III] are detailed below.

[I] Transition Metal Compound

An inventive transition metal compound is a double crosslinking compound of a transition metal of Group 3 to Group 10 or of lanthanoids in the periodic table, which has the structure represented by Formula (VIII):

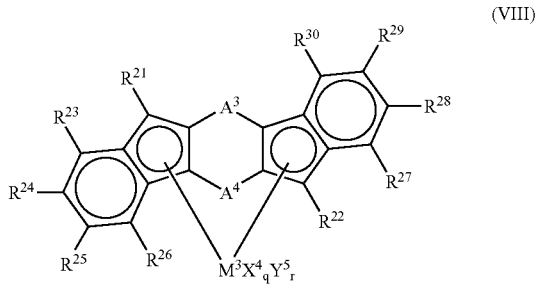

(VIII)

wherein each of $A^3$ and $A^4$ denotes a crosslinking consisting of Group XIV metal (C, Si, Ge, Sn) and may be same to or different from each other, $X^4$ denotes a σ-binding or π-binding ligand, and when two or more $X^4$ are present they may be same or different, $Y^5$ is a Lewis base and when two or more $Y^5$ are present they may be same or different, and each $Y^5$ may be crosslinked with other $Y^5$ or $X^4$, q is an integer of 1 to 5 and represents [(valency of M3)−2], r is an integer of 0 to 3, each of $R^{21}$ to $R^{30}$ denotes a hydrogen atom, a halogen atom, a hydrocarbon group having 1 to 20 carbon atom(s), a silicon-containing group and a heteroatom-containing group, and $M^3$ denotes a metal element of Group 3 to Group 10 or of lanthanoids in the periodic table.

In Formula (VIII) shown above, each of $A^3$ and $A^4$ forms a crosslinking group consisting of Group IVX element (C, Si, Gen) and may be same to or different from each other. $A^3$ or $A^4$ may for example be a crosslinking group represented by Formula (VIV):

(VIV)

wherein E denotes C, Si, Ge, Sn, each of $R^{31}$ and $R^{32}$ denotes a hydrogen atom, a halogen atom, a hydrocarbon group having 1 to 20 carbon atom(s) or a halogen-containing hydrocarbon group having 1 to 20 carbon atom(s), and each may be same to or different from each other, or the both may be taken together to form a ring.

A halogen atom in Formula (VIV) may for example be a chlorine, fluorine, bromine or iodine atom. Examples of a hydrocarbon group having 1 to 20 carbon atom(s) are an alkyl group such as methyl, ethyl, propyl, butyl, hexyl, cyclohexyl, octyl groups and the like, an alkenyl group such as vinyl, propenyl, cyclohexenyl groups and the like; an arylalkyl group such as benzyl, phenylethyl, phenylpropyl groups and the like; and an aryl group such as phenyl, tolyl, dimethylphenyl, trimetnylphenyl, ethylphenyl, propylphenyl, biphenyl, naphthyl, methylnaphthyl, anthracenyl, phenanthnyl groups and the like. Among those listed above, an alkyl group such as methyl, ethyl, propyl groups and the like and an aryl group such as phenyl group are preferred. A halogenated hydrocarbon having 1 to 20 carbon atom(s) may for example be one of the hydrocarbon groups listed above which is substituted with a halogen atom. Among these, those preferred are a halogenated alkyl group such as trifluoromethyl, trichloromethyl groups and the like.

A crosslinking group consisting of a carbon atom in Formula (VIV) may for example be methylene, dimethylmethylene group; an alkylidene group such as ethylidene, propylidene, isopropylidene, cyclohexylidene and the like; as well as 1,1-cyclohexylene and vinylidene groups. A crosslinking group consisting of a silicon atom may for example be an alkylsilylene group such as methylsilylene, dimethylsilylene, diethylsilylene, di(n-propyl)silylene, di(i-propyl)silylene, di(cyclohexyl)silylene and the like; an alkylarylsilylene group methylphenylsilylene, ethylphenylsilylene and the like; and arylsilylene group such as diphenylsilylene, di(p-tolyl)silylene, di(p-chlorophenyl)silylene and the like. A crosslinking group consisting of a germanium atom may for example be a germylene group obtained by replacing a silicon atom in a crosslinking group consisting of a silicon atom listed above with a germanium atom. A crosslinking group consisting of a tin atom may for example be a stannylene group obtained by replacing a silicon atom in a crosslinking group consisting of a silicon atom listed above with a tin atom. One preferred as $A^3$ or $A^4$ is a crosslinking group consisting of a carbon atom or a crosslinking group consisting of a silicon atom.

$X^4$ is a σ-binding or π-binding ligand, and such σ-binding ligand may for example be a halogen atom, a hydrocarbon group having 1 to 20 carbon atoms, an alkoxy group having 1 to 20 carbon atoms, an aryloxy group having 6 to 20 carbon atoms, an amide group having 1 to 20 carbon atoms, a silicon-containing group having 1 to 20 carbon atoms, a phosphide group having 1 to 20 carbon atoms, a sulfide group having 1 to 20 carbon atoms, a sulfoxide group having 1 to 20 carbon atoms and an acyl group having 1 to 20 carbon atoms, among which a halogen atom and a hydrocarbon group having 1 to 20 carbon atoms are preferred. A halogen atom and a hydrocarbon group having 1 to 20 carbon atoms may be those described above. An alkoxy group having 1 to 20 carbon atoms may for example be an alkoxy group such as methoxy, ethoxy, propoxy, butoxy groups and the like; and an aryloxy group such as phenoxy, methyphenoxy, dimethylphenoxy, naphthoxy groups and the like. An aryloxy group having 6 to 20 carbon atoms may for example be phenylmethoxy, phenylethoxy groups and the like. An amide group having 1 to 20 carbon atoms may for example be an alkylamide group such as dimethylamide, diethylamide, dipropylamide, dibutylamide, dicyclohexylamide, methylethylamide groups and the like, an alkenylamide group such as divinylamide, dipropenylamide, dicyclohexenylamide groups and the like; an arylalkylamide group such as dibenzylamide, phenylethylamide, phenylpropylamide groups and the like; and arylamide group such as diphenylamide, dinaphtylamide groups and the like. A silicon-containing group having 1 to 20 carbon atoms may for example be a monohydrocarbon-substituted silyl group such as methylsilyl, phenylsilyl groups and the like; a dihydrocarbon-substituted silyl group such as dimethylsilyl, diphenylsilyl groups and the like; a trihydrocarbon-substituted silyl group such as trimethylsilyl, triethylsilyl, tripropylsilyl, tricyclohexylsilyl, triphenylsilyl, dimethylphenylsilyl, methylphenyldisilyl, tritolylsilyl, trinaphthylsilyl groups and the like; a silyl ether group of a hydrocarbon-substituted silyl group such as trimethylsilylether group; a silicon-substituted alkyl group such as trimethylsilylmethyl group; and a silicon-substituted aryl group such as trimethylsilylphenyl group and the like. Among those listed above, trimethylsilyl, phenethyldimethylsilyl groups are preferred. A sulfide group having 1 to 20 carbon atoms may for example be an alkylsulfide group such as methylsulfide, ethylsulfide, propylsulfide, butylsulfide, hexylsulfide, cyclohexylsulfide, octylsulfide groups and the like and an alkenylsulfide group such as vinylsulfide, propenyl sulfide, cyclohexenylsulfide groups and the like; an arylalkylsulfide group such as benzylsulfide, phenylethylsulfide, phenylpropylsulfide groups and the like; and an arylsulfide group such as phenylsulfide, tolylsulfide, dimethylsulfide, trimethylphenylsulfide, ethylphenylsulfide, propylphenylsulfide, biphenylsulfide, naphthylsulfide, methylnaphthylsulfide, anthracenylsulfide, phenanthnylsulfide groups and the like. A sulfoxide group having 1 to 20 carbon atoms may for example be an alkylsulfoxide group such as methylsulfoxide, methylsulfoxide, propylsulfoxide, butylsulfoxide, hexylsulfoxide, cyclohexylsulfoxide, octylsulfoxide groups and the like and an alkenylsulfoxide group such as vinylsulfoxide, propenylsulfoxide, cyclohexenylsulfoxide groups and the like; an arylalkylsulfoxide group such as benzyl sulfoxide, phenylethylsulfoxide, phenylpropylsulfoxide groups and the like; and an arylsulfoxide such as phenylsulfoxide, tolylsulfoxide, dimethylphenylsulfoxide, trimethylphenylsulfoxide, ethylphenylsulfoxide, propylphenylsulfoxide, biphenylsulfoxide, naphthylsulfoxide, methylnaphthylsulfoxide, anthracenylsulfoxide, phenanthnylsulfoxide groups and the like. An acyl group having 1 to 20 carbon atoms may for example be an alkylacyl group such as formyl, acethyl, propionyl, butyryl, valeryl, palmitoyl, thearoyl, oleoyl groups and the like; an arylacyl group such as benzoyl, toluoyl, salicyloyl, cinnamoyl, naphthoyl, phthaloyl groups and the like; oxalyl, malonyl and succinyl groups derived from dicarboxylic acids such as oxalic acid, malonic acid and succinic acid, respectively, and the like.

A π-binding ligand may for example be a conjugated diene bond-carrying compound having 4 to 20 carbon atoms, a non-conjugated diene bond-carrying compound having 5 to 20 carbon atoms and the like. A conjugated diene bond-carrying compound having 4 to 20 carbon atoms may for example be 1,3-butadiisoprene, chloroprene, 1,3-pentadiene, 1,3-hexadiene, 1,3,5-hexatriene, 1,3-heptadiene, 1,3,6-heptatriene, 1,4-diphenylbutadiene and the like. A non-conjugated diene bond-carrying compound having 5 to 20 carbon atoms may for example be 1,4-pentadiene, 1,4-hexadiene and the like.

Characteristically, a σ-binding ligand in $X^4$ gives an enhanced reactivity with $M^3$. On the other hand, a π-binding ligand gives an increased activity.

$Y^5$ is a Lewis base and when two or more Y5 are present they may be same or different. Each Y5 may be crosslinked with other $Y^5$ or $X^4$. $Y^5$ may optionally be crosslinked with a cyclopentadienyl ring in Formula (VIII). Examples of $Y^5$ are amines, ethers, phosphines, thioethers and the like. Amines may for example be an amine having 1 to 20 carbon atoms, and typically an alkylamine such as methylamine, ethylamine, propylamine, butylamine, cyclohexylamine, methylethylamine, dimethylamine, diethylamine, dipropylamine, dibutylamine, dicyclohexylamine, methylethylamine and the like and an alkenylamine such as vinylamine, propenylamine, cyclohexenylamine, divinylamine, dipropenylaine, dicyclohexenylamine and the like; an arylalkylamine such as phenylamine, phenylethylamine, phenylpropylamine and the like; and arylamine such as diphenylamine, dinaphthylamine and the like. Ethers may for example be an aliphatic monoether compound such as methylether, ethylether, propylether, isopropylether, butylether, isobutylether, n-amylether, isoamylether and the like; an aliphatic mixed ether compound such as methylethylether, methylpropylether, methylisopropylether, methyl-n-amylether, methylisoamylether, ethylpropylether, ethylisopropylether, ethylbutylether, ethyliobutylether, ethyl-n-amylether, ethylisoamylether and the like; an aliphatic unsaturated ether compound such as vinylether, allylether, methylvinylether, methylallylether, ethylvinylether, ethylallylether and the like; an aromatic ether compound such as anisol, phenethol, phenylether, benzylether, phenylbenzylether, α-naphthylether, β-naphthylether and the like, as well as a cyclic ether compound such as ethylene oxide, propylene oxide, trimethylene oxide, tetrahydrofuran, tetrahydropyrane, dioxane and the like. An example of the phosphines may be a phosphine having 1 to 20 carbon atoms. Those included typically are an alkylphosphine including a monohydrocarbon-substituted phosphine such as methylphosphine, ethylphosphine, propylphosphine, butylphosphine, hexylphosphine, cyclohexylphosphine, octylphosphine and the like; a dihydrocarbon-substituted phosphine such as dimethylphosphine, diethylphosphine, dipropylphosphine, dibutylphosphine, dihexylphosphine, dicyclohexylphosphine, dioctylphosphine and the like; a trihydrocarbon-substituted phosphine such as dimethylphosphine, triethylphosphine, tripropylphosphine, tributylphosphine, trihexylphosphine, tricyclohexylphosphine, trioctylphosphine and the like and a monoalkenylphosphine such as vinylphosphine, propenylphosphine, cyclohexenylphosphine and the like as well as a dialkenyl phosphine whose hydrogen atoms on the phosphorus were replaced with two alkenyl groups; a trialkenyl phosphine whose hydrogen atoms on the phosphorus were replaced with three alkenyl groups; an arylalkylphosphine such as benzylphosphine, phenylethylphosphine, phenylpropylphosphine and the like; a diarylalkyl phosphine or an aryldialkylphosphine whose hydrogen atoms on the phosphorus were replaced with three aryl or alkenyl groups; phenylphosphine, tolylphosphine, dimethylphenylphosphine, trimethylphenylphosphine, ethylphenylphosphine, propylphenylphosphine, biphenylphosphine, naphthylphosphine, methylnaphthylphosphine, anthracenylphosphine, phenanthracenyl phosphine; a di(alkylaryl)phosphine whose hydrogen atoms on the phosphorus were replaced with 2 aklkylaryl groups; a tri(alkylaryl)phosphine whose hydrogen atoms on the phosphorus were replaced with 3 aklkylaryl groups, and the like. An example of the thioethers may be a sulfide mentioned above.

Each of $R^{21}$ to $R^{30}$ denotes a hydrogen atom, a halogen atom, a hydrocarbon group having 1 to 20 carbon atoms, a silicon-containing group and a heteroatom-containing group, and a halogen atom may for example be chlorine, fluorine, bromine, iodine atoms. A hydrocarbon group having 1 to 20 carbon atoms may for example be an alkyl group such as methyl, ethyl, propyl, butyl, hexyl, cyclohexyl, octyl groups and the like and an aryl group such as phenyl, naphthyl groups and the like; an arylalkyl group such as benzyl, phenylethyl, phenylpropyl groups and the like; an alkylaryl group such as tolyl, xylyl groups and the like. A silicon-containing group may for example be a silicon-containing group having 1 to 20 carbon atoms, typical examples of which are trimethylsilyl, trimethylsilylmethyl, triphenylsilyl groups and the like. A heteroatom-containing group may for example be a heteroatom-containing group having 1 to 20 carbon atoms, typical examples of which are a nitrogen-containing group such as dimethylamino, diethylamino, diphenylamino groups and the like, a sulfur-containing group such as phenylsulfide, methylsulfide groups and the like; a phosphorus-containing group such as dimethylphosphino, diphenylphosphino groups and the like; an oxygen-containing group such as methoxy, ethoxy, phenoxy groups and the like. Those employed preferably as $R^{21}$ to $R^{30}$ are a hydrogen atom or a hydrocarbon group having 1 to 20 carbon atoms.

M3 denotes a metal element of Group 3 to Group 10 or of lanthanoids in the periodic table, and is typically titanium, zirconium, hafnium, vanadium, chromium, manganese, nickel, cobalt, palladium and lanthanoid metals. A metal element of Group IV in the periodic table is preferable as $M^3$ since it gives a higher activity.

A preferred representative of a transition metal compound represented by Formula (VIII) shown above is one wherein $A^3$ and $A^4$ denotes a crosslinking group consisting of a carbon atom or a silicon atom which may be same to or different from each other; $X^4$ denotes a σ-binding or π-binding ligand, and when two or more $X^4$ are present they may be same or different; $Y^5$ is a Lewis base and when two or more $Y^5$ are present they may be same or different; each $Y^5$ may be crosslinked with other $Y^5$ or $X^4$; q is an integer of 1 to 5 and represents [(valency of $M^3$)−2], r is an integer of 0 to 3, each of $R^{21}$ to $R^{30}$ denotes a hydrogen atom or a hydrocarbon group having 1 to 20 carbon atoms; and $M^3$ denotes a metal element of Group IV in the periodic table.

A transition metal compound represented by Formula (VIII) shown above, when those of Group IV in the periodic table are exemplified, includes (1,2'-dimethylsilylene)(2,1'-dimethylsilylene)bis(indenyl)zirconium dichloride, (1,2'-dimethylsilylene)(2,1'-dimethylsilylene)bis(3-methylindenyl)zirconium dichloride, (1,2'-dimethylsilylene)(2,1'-dimethylsilylene)bis(3-ethylindenyl)zirconium dichloride, (1,2'-dimethylsilylene)(2,1'-dimethylsilylene)bis(3-isopropylindenyl)zirconium dichloride, (1,2'-dimethylsilylene)(2,1'-dimethylsilylene)bis(3-trimethylsilylmethylindenyl)zirconium dichloride, (1,2'-dimethylsilylene)(2,1'-dimethylsilylene)bis(3-butylindenyl)zirconium dichloride, (1,2'-dimethylsilylene)(2,1'-dimethylsilylene)bis(4-methylindenyl)zirconium dichloride, (1,2'-dimethylsilylene)(2,1'-dimethylsilylene)bis(4,7-dimethylindenyl)zirconium dichloride, (1,2'-dimethylsilylene)(2,1'-dimethylsilylene)bis(5,6-dimethylindenyl)zirconium dichloride, (1,2'-phenylmethylsilylene)(2,1'-phenylmethylsilylene)bis(indenyl)zirconium dichloride, (1,2'-phenylmethylsilylene)(2,1'-phenylmethylsilylene)bis(3-methylindenyl)zirconium dichloride, (1,2'-dimethylsilylene)(2,1'-isopropylidene)bis(indenyl)zirconium dichloride, (1,2'-dimethylsilylene)(2,1'-isopropylidene)bis(3-methylindenyl)zirconium dichloride, (1,2'-dimethylsilylene)(2,1'-isopropylidene)bis(3-isopropylindenyl)zirconium dichloride, (1,2'-dimethylsilylene)(2,1'-isopropylidene)bis(3-n-butylindenyl)zirconium, dichloride, (1,2'-dimethylsilylene)(2,1'-isopropylidene)bis(3-trimethylsilylmethylindenyl)zirconium dichloride, (1,2'-dimethylsilylene)(2,1'-isopropylidene)bis(3-trimethylsilylindenyl)zirconium dichloride, (1,2'-dimethylsilylene)(2,1'-isopropylidene)bis(3-phenylindenyl)zirconium dichloride, (1,2'-dimethylsilylene)(2,1'-methylene)bis(indenyl)zirconium dichloride, (1,2'-dimethylsilylene)(2,1'-methylene)bis(3-methylindenyl)zirconium dichloride, (1,2'-dimethylsilylene)(2,1'-methylene)bis(3-isopropylindenyl)zirconium dichloride, (1,2'-dimethylsilylene)(2,1'-methylene)bis(3-n-butylindenyl)zirconium dichloride, (1,2'-dimethylsilylene)(2,1'-methylene)bis(3-trimethylsilylmethylindenyl)zirconium dichloride, (1,2'-dimethylsilylene)(2,1'-methylene)bis(3-trimethylsilylindenyl)zirconium dichloride, (1,2'-diphenylsilylene)(2,1'-methylene)bis(indenyl)zirconium dichloride, (1,2'-diphenylsilylene)(2,1'-methylene)bis(3-methylindenyl)zirconium dichloride, (1,2'-diphenylsilylene)(2,1'-methylene)bis(3-n-butylindenyl)zirconium dichloride, (1,2'-diphenylsilylene)(2,1'-methylene)bis(3-trimethylsilylmethylindenyl)zirconium dichloride, (1,2'-diphenylsilylene)(2,1'-methylene)bis(3-trimethylsilylindenyl)zirconium dichloride as well as the compounds obtained by replacing zirconium in the compounds listed above with titanium or hafnium, while they are not limiting. An analogous compound of a metal element of Groups other than Group IV or of lanthanoids. Preferably, a compound of a transition metal of Group IV in the periodic table, especially of zirconium is employed.

[II] Olefin Polymerization Catalyst

An inventive olefin polymerization catalyst consists of (A) a transition metal element of Group 3 to Group 10 or of lanthanoids in the periodic table represented by Formula (VIII) and (B) a compound capable of forming an ionic complex by reacting with a transition metal compound as a component (A), optionally with (C) an organic aluminium compound.

In an inventive polymerization catalyst, a component (A) and a compound capable of forming an ionic complex by reacting with a transition metal compound as a component (A).

One exemplified preferably as a component (B) is (B-1) an ionic compound capable of forming an ionic complex by reacting with a transition metal compound as a component (A) (B-2) an aluminoxane, or (B-3) a Lewis acid, because of its high polymerization activity and low catalyst cost.

A component (B-1) described above may be any ionic compound capable of forming an ionic complex by reacting with a transition metal compound as a component (A), and may for example be one exemplified as a component (B-1) in the first invention.

An ionic compound, which is a component (B-1), capable of forming an ionic complex by reacting with a transition metal compound as a component (A) may be employed alone or in a combination with one or more.

An aluminoxane as a component (B-2) may be any substance such as those described in the first invention as a component (B-2). Such aluminoxane may be employed alone or in a combination with one or more.

A Lewis acid as a component (B-3) is not particularly limited, and may be an organic compound or a solid inorganic compound. An organic compound employed preferably is a boron compound, an aluminium compound and the like, while an inorganic compound employed preferably is a magnesium compound, an aluminium compound and the like, because of their ability of forming an active center efficiently. Such aluminium compound may for example be bis(2,6-di-t-butyl-4-methylphenoxy)aluminium methyl, (1,1-bi-2-naphthoxy)aluminium methyl and the like, while a magnesium compound may for example be magnesium chloride, diethoxymagnesium and the like, and an aluminium compound may for example be aluminium oxide, aluminium chloride and the like, and a boron compound may for example be triphenylboron, tris(pentafluorophenyl)boron, tris[3,5-bis(trifluoromethyl)phenyl]boron, tris[(4-fluoromethyl)phenyl]boron, trimethylboron, triethylboron, tri-n-butylboron, tris(fluoromethyl)boron, tris(pentafluoroethyl)boron, tris(nonafluorobutyl)boron, tris(2,4,6-trifluorophenyl)boron, tris(3,5-difluoro)boron, tris[3,5-bis(trifluoromethyl)phenyl]boron, bis(pentafluorophenyl)fluoroboron, diphenylfluoroboron, bis(pentafluorophenyl)chloroboron, dimethylfluoroboron, diethylfluoroboron, di-n-butylfluoroboron, pentafluorophenyldifluoroboron, phenyldifluoroboron, pentafluorophenyldichloroboron, methyldifluoroboron, ethyldifluoroboron, n-butyldifluoroboron and the like.

Such Lewis acid may be employed alone or in a combination with one or more.

The molar ratio of a catalyst component (A) to a catalyst component (B) when employing a compound (B-1) as a catalyst component (B) is preferably 10:1 to 1:100, more preferably 2:1 to 1:10, and a ratio departing from this range is not advantageous industrially because of an increased catalyst cost per unit weight of a polymer. When a compound (B-2) is employed, the molar ratio is preferably 1:1 to 1:1000000, more preferably 1:10 to 1:10000. A ratio departing from this range is not advantageous industrially because of an increased catalyst cost per unit weight of a polymer.

The molar ratio of a catalyst component (A) to a catalyst component (B-3) is preferably 10:1 to 1:2000, more preferably 5:1 to 1:1000, particularly 2:1 to 1:500, and a ratio departing from this range is not advantageous industrially because of an increased catalyst cost per unit weight of a polymer. As a component (B), any one of, or, a combination of two or more of components (B-1), (B-2) and (B-3) may be employed.

A polymerization catalyst according to the invention may comprise as main components a component (A) and a component (B) described above, or may comprise as main components a component (A), a component (B) and an organic aluminium compound (C).

An organic aluminium compound as a component (C) may be one listed as a component (C) in the first invention.

Such organic aluminium compound may be employed alone or in a combination of two or more.

The molar ratio of a catalyst component (A) to a catalyst component (C) is preferably 1:1 to 1:10000, more preferably 1:5 to 1:2000, particularly 1:10 to 1:1000. By employing a catalyst component (C), the polymerization activity per unit weight of a transition metal can be increased, but a too excessive amount, especially one departing from the range specified above, is of no use, and results in a large amount of residue remaining in a polymer, while a too small amount may fail to obtain a sufficient catalyst activity.

Upon contact or after contact between components in this invention, a polymer such as polyethylene, polypropylene and the like, or an inorganic oxide such as silica, alumina and the like, is allowed to exist simultaneously or to be in contact. A support on a carrier may be effected preferably as a support on a polymer, and such polymeric carrier has a particle size of 1 to 300 μm, preferably 10 to 200 μm, more preferably 20 to 100 μm. A particle size smaller than 1 μm results in increased microparticles in a polymer, while one exceeding 300 μm results in increased coarse particles in a polymer, which leads to a problematic reduction in the bulk density and a plugging of a hopper in a manufacturing process. The specific surface area of a carrier when employed as discussed above is 1 to 1,000 m$^2$/g, preferably 50 to 500 m$^2$/gm, and a micropore void volume is 0.1 to 5 m$^3$/g, preferably 0.3 to 3 m$^3$/g.

A contact may be effected in an atmosphere of an inert gas such as nitrogen, and in a hydrocarbon such as pentane, hexane, heptane, toluene, xylene and the like. While an addition or a contact of each component may of course be effected at a polymerization temperature, a temperature of −30° C. to a boiling point of a solvent, especially room temperature to a boiling point of a solvent is preferred.

[III] Method for Producing Olefin Polymer

An inventive method for producing an olefin polymer is a method for producing a polymer wherein An olefin is homopolymerized or copolymerized in the presence of an olefin-polymerizing catalyst obtained by bringing (A) a transition metal element of Group 3 to Group 10 or of lanthanoids in the periodic table represented by Formula (VIII) into contact with (B) a compound capable of forming an ionic complex by reacting with a transition metal compound as a component (A) optionally together with (C) an organic aluminium compound. As an organic aluminium compound (C), a compound represented by Formula (VII) shown above is employed, and is preferably a trialkylaluminium compound. Those particularly preferred are trimethylaluminium and triisobutylaluminium. In an inventive method for producing an olefin polymer, an organic aluminium compound (C) may be employed as being brought into contact preliminarily with a component (A) and/or a component (B), or may be introduced first into a reactor and then brought into contact with a component (A) and a component (B). The amount of a component (C) employed is similar to that described above in the section of the olefin polymerization catalyst. According to an inventive method for producing an olefin polymer, a polymerization catalyst described above is used preferably to effect a homopolymerization of an olefin or a copolymerization of an olefin with other olefins and/or other monomers (a copolymerization between different olefins, a copolymerization between olefins and other monomers, or a copolymerization between different olefins together with other monomers).

While such olefin is not particularly limited, an α-olefin having 2 to 20 carbon atoms is preferred. Such α-olefin may for example be α-olefins such as ethylene, propylene, 1-butene, 1-pentene, 1-hexene, 1-heptene, 1-octene, 1-nonene, 1-decene, 4-phenyl-1-butene, 6-phenyl-1-hexene, 3-methyl-1-butene, 4-methyl-1-butene, 3-methyl-1-pentene, 4-methyl-1-hexene, 5-methyl-1-hexene, 3,3-dimethyl-1-pentene, 3,4-dimethyl-1-pentene, 4,4-dimethyl-1-pentene, vinylcyclohexane and the like, diens such as 1,3-butadiene, 1,4-pentadiene, 1,5-hexadiene, and the like, a halogenated α-olefin such as hexafluoropropene, tetrafluoroethylene, 2-fluoropropene, fluororthylene, 1,1-difluoroethylene, 3-fluoropropene, trifluoroethylene, 3,4-dichloro-1-butene and the like, cyclic olefins such as cyclopentene, cyclohexene, norbornene, 5-methylnorbornene, 5-ethylnorbornene, 5-propylnorbornene, 5,6-dimethylnorbornene, 5-benzylnorbornene and the like, styrenic substances including alkylstyrenes such as styrene, p-methylstyrene, p-ethylstyrene, p-propylstyrene, p-isopropylstyrene, p-butylstyrene, p-tert-butylstyrene, p-phenylstyrene, o-methylstyrene, o-ethylstyrene, o-propylstyrene, o-isopropylstyrene, m-methylstyrene, m-ethylstyrene, m-isopropylstyrene, m-butylstyrene, mesitylstyrene, 2,4-dimethylstyrene, 2,5-dimethylstyrene, 3,5-dimethylstyrene and the like, alkoxystyrenes such as p-methoxystyrene, o-methoxystyrene, m-methoxystyrene and the like, halogenated styrenes such as p-chlorostyrene, m-chlorostyrene, o-chlorostyrene, p-bromostyrene, m-bromostyrene, o-bromostyrene, p-fluorostyrene, m-fluorostyrene, o-fluorostyrene, o-methyl-p-fluorostyrene and the like, as well as trimethylsilylstyrene, vinyl benzoate, divinylbenzene and the like. Other olefins described above may appropriately selected from the olefins listed above.

In this invention, any one of, or a combination of two or more of the olefins listed above may be employed. When two or more olefins is copolymerized, any combination of the olefins listed above may be employed.

Also in this invention, the olefins listed above may be copolymerized with other monomers, and such monomers are linear diolefins such as butadiene, isoprene, 1,4-pentadiene, 1,5-hexadiene and the like, polycyclic olefins such as norbornene, 1,4,5,8-dimethano-1,2,3,4,4a,5,8,8a-octahydronaphthalene, 2-norbornene and the like, cyclic olefins such as norbornadiene, 5-ethylidenenorbornene, 5-vinylnorbornene, dicyclopentadiene and the like, unsaturated esters such as ethyl acrylate, methyl methacrylate and the like.

In this invention, one preferred particularly as such olefin is propylene.

A method for polymerizing olefins is not particularly limited, and may be a slurry polymerization, a solution polymerization, a vapor phase polymerization, a bulk polymerization, a suspension polymerization.

When a polymerization solvent is employed, such solvent may for example be a hydrocarbon and a halogenated hydrocarbon such as benzene, toluene, xylene, n-hexane, n-heptane, cyclohexane, methylene chloride, chloroform, 1,2-dichloroethane, chlorobenzene and the like. Any one of, or a combination of two or more of those listed above may be employed. A certain monomer subjected to a polymerization may be used also as a solvent.

The amount of a catalyst employed in a polymerization reaction is selected so that a component [A] is within the range usually of 0.5 to 100 micromoles, preferably 2 to 25 micromoles per 1 liter of a solvent, for the purpose of advantageous polymerization activity and reactor efficiency.

A polymerization condition involves a polymerization pressure usually of atmospheric pressure to 2000 kg/cm$^2$G. The reaction temperature is usually −50 to 250° C. The molecular weight of a polymer may be adjusted by appropriately selecting the types and amounts of respective catalyst components, and the polymerization temperature, or by introducing hydrogen.

Also in a polymerization process of an olefin according to the invention, a catalyst described above is used to effect a preliminary polymerization. Such preliminary polymerization can be effected by bringing a solid catalyst component into contact with a small amount of an olefin, at a reaction temperature of −20 to 100° C., preferably −10 to 70° C., particularly 0 to 50° C. While an inert hydrocarbon, an aliphatic hydrocarbon, an aromatic hydrocarbon or a monomer is employed as a solvent for this preliminary polymerization, an aliphatic hydrocarbon is particularly preferred. This preliminary polymerization may be effected also in the absence of a solvent. In a preferably adjusted condition, a preliminary polymerization product has an intrinsic viscosity [η] (at 135° C. in decalin) of 0.2 dl/g, preferably 0.5 dl/g, and an amount of a preliminary polymerization product per 1 millimole of a transition metal component in a catalyst is 1 to 10,000 g, preferably 10 to 1,000 g.

The present invention is further described in the following the examples which is not intended to restrict the invention.

[First Invention]

A method for evaluating a propylenic polymer and a method for evaluating a film are described below.

(A) Method for Evaluating Resin Characteristics (1) Intrinsic viscosity [η]

An automatic viscometer model VMR-053 available from RIGOSHA (KK) was used in a decalin solvent at 135° C.

(2) Molecular Weight Distribution (Mw/Mn).

Measurement was made in accordance with the method described in the detailed description of the invention.

(3) % Isotactic Pentad and % Abnormal Insertion

Measurement was made in accordance with the method described in the detailed description of the invention.

(4) Melting Point (Tm) and Crystallization Temperature (Tc)

Using a differential scanning calorimeter (Perkin Elmer, DSC-7), 10 mg of a sample was fused for 3 minutes at 230° C. under a nitrogen atmosphere and then the temperature was lowered to 0° C. at the rate of 10° C./minutes. The peak top of the maximum peak in the crystallization exothermic curve obtained during this course was regarded as the crystallization temperature. After holding at 0° C. for 3 minutes, the temperature was raised at the rate of 10° C./minute to obtain a fusion endothermic curve, in which the peak top of the maximum peak was regarded as the melting point.

(5) Boiling Ether Extraction

Soxlet extractor was used under the conditions specified below.

Extraction sample: 5 to 6 g

State of sample: Powder (a pellet should be pulverized into a powder before use)

Extraction solvent: Diethylether

Extraction duration: 10 hours

Extraction times: 180 times or more

Calculation of extract: As shown below

[Amount extracted into diethylether (g)]/Charged powder weight (g)]×100

(6) Temperature-Raising Fractional Chromatography (TREF)

A peak top temperature Tp(° C.) of a main elution peak in an elution curve, and an amount (% by weight based on the entire copolymer) of the components which are dissolved out, instead of adsorbed onto a packing, at the TREF column temperature of 25° C. were obtained as described below.

(a) Operating Procedure

A sample solution was introduced into a TREF column adjusted at 135° C. and then the temperature was lowered gradually at the lowering rate of 5° C./hour to 25° C. to allow the sample to be adsorbed on the packing. Thereafter, the column temperature was raised at the raising rate of 40° C./hour to 135° C. to obtain an elution curve.

(b) Instruments

TREF column: Manufactured by GL SCIENCE, Silica gel column (4.6φ×150 mm)

Flow cell: Manufactured by GL SCIENCE, pathlength 1 mm, KBr cell

Feed pump: Manufactured by SENSHU KAGAKU, Pump Model SSC-3100

Valve oven: Manufactured by GL SCIENCE, Oven model 554 (high temperature type)

TREF oven: Manufactured by GL SCIENCE

Dual-system thermostat: Manufactured by RIKAGAKU KOGYO, Thermostat model REX-C100

Detector: Infrared detector for HPLC, Manufactured by FOXBORO CORP., Model MIRAN 1A CVF 10-way valve: Manufactured by VALCO, Electric valve Loop: Manufactured by VALCO, 500 μL Loop (C) Operating Conditions Solvent: o-Dichlorobenzene Sample concentration: 7.5 g/L Injection volume: 500 μL Pumping rate: 2.0 mL/min Detection wavenumber: 3.41 μm Column packing: CHROMOSOLVE P (30 to 60 mesh)

Column temperature deviation: Within ±0.2° C.

(7) Comonomer Unit (α-Olefin Unit) Content (α(% by Mole)) in Copolymer and Stereoregularity Index (β(% by Mole))

A $^{13}$C NMR spectrum was obtained using Nippon Densi Model JNM-EX400 $^{13}$C-NMR device under the conditions specified below and calculation was made also as shown below.

Concentration: 220 mg/NMR Solvent 3 ml

Solvent: 1,2,4-Trichlorobenzene/benzene-d6 (90/10% by volume)

Temperature: 130° C.

Pulse gap: 45°

Pulse interval: 10 seconds

Number of cycles: 4000 times (a) 1-Butene Unit

The 1-butene unit content (α(% by mole)) in the copolymer was obtained in accordance with the following equation from the spectrum determined by the $^{13}$C-NMR.

$$\alpha = \frac{(I(2)/2 + I(4))}{\{I(1) + I(2) + I(3) + I(4) + 2 \times I(9)\}} \times 100$$

Also in accordance with the following equation, a stereoregularity index (P (% by mole)) of the copolymer was obtained.

$$P = \frac{(I(12))}{\{I(12) + I(13) + I(14)\}} \times 100$$

wherein (1), (2) and the like represent the signals of a spectrum of a copolymer of propylene and 1-butene determined by $^{13}$C-NMR. I(1), I(2) and the like represent the respective signal intensities. The signals of a spectrum of a copolymer of propylene and 1-butene determined by $^{13}$C-NMR are indicated in the table shown below.

Instead of the signal intensity of a PPP chain Sαβ carbon, the signal intensity of a PPP chain Sαβ carbon (signal intensity of (9)) was indicated as an alternative.

TABLE 1

| Number | Chemical shift | Assignment |
|---|---|---|
| 1 | 45.7-47.4 | PP Sαα |
| 2 | 43.0-44.9 | PB Sαα |
| 3 | 42.3 | PPP Sαα |
| 4 | 40.3 | BB Sαα |
| 5 | 36.6 | PPP Tαγ |
| 6 | 36.0 | PPP Sαβ and PPP Sαβ |
| 7 | 35.5 | B unit Tββ |
| 8 | 31.6 | PPP Tβγ |
| 9 | 30.6 | PPP Sαβ |
| 10 | 28.6-29.8 | P unit Tββ |
| 11 | 27.8-28.4 | B unit side chain methylene carbon |
| 12 | 21.2-22.7 | Pββ PPP(mm), PPB(mm), BPB(mm) |
| 13 | 20.6-21.2 | Pββ PPP(mr), PPB(mr), BPB(mr), PPB(rr), BPB(rr) |
| 14 | 19.8-20.6 | Pββ PPP(rr) |
| 15 | 17.6 | Pαβ |
| 16 | 17.2 | Pαγ |
| 17 | 11.1 | B unit side chain methyl carbon |

NOTE)
B denotes a 1-butene unit.

(8) Tensile Modulus

A propylenic polymer was press-molded to obtain a test piece, which was subjected to the tensile test in accordance with JIS K-7113 under the conditions specified below.

Crosshead speed: 50 mm/min

Test piece form: JIS No. 2 dumb-bell test specimen, 1 mm in thickness (9) Izod Impact Strength Using a test piece having the thickness of 3 mm prepared as described above was subjected to the test in accordance with JIS K110 at 23° C.

(10) Transparency

A test piece described above was evaluated visually. The result was indicated as O when the transparency was judged to be satisfactory, while it was indicated as Δ when judged to be somewhat poor.

(11) Internal Haze

A propylenic polymer was press-molded to obtain a test piece whose thickness was 1 mm, and after applying a silicone oil (manufactured by SHINETSU SILICONE, KF56) onto the surface of the test piece, the haze was determined in accordance with JIS K7105.

(B) Film-Forming Method

From a propylenic polymer composition obtained in Examples and Comparatives described later, a film whose thickness was 50 μm was formed using a 20 mmφ molding machine manufactured by TSUKADA JUKISEISAKUSHO under the molding conditions specified below.

T die exit resin temperature: 192° C.

Haul-off speed: 6.0 m/min

Chill roll temperature: 40° C.

Chill roll: Mirror (C) Film Qualification

A film once formed was subjected to aging at 40° C. for 24 hours followed by conditioning at a temperature of 23±2° C. and a humidity of 50±10% for 16 hours or longer and then qualified at the same temperature and humidity.

(1) Tensile Modulus

A tensile test was conducted under the conditions specified below in accordance with JIS K-7127.

Crosshead speed: 500 mm/min

Load cell: 15 kg

Direction: Machine direction (2) Impact Resistance

Film impact tester manufactured by TOYOSEKI SEISAKUSHO was used together with a ½ inch impact head to evaluate a impact destruction strength.

(3) Haze

A test was conducted in accordance with JIS K-7105.

(4) Heat Seal Temperature

A test was conducted in accordance with JIS Z-1707. The fusing conditions were as indicated below. The temperature of the heat seal bar was corrected as being read by a surface thermometer. After sealing followed by allowing to stand at room temperature overnight, the peeling strength was determined by a type-T peeling method at the peeling speed of 200 mm/min at room temperature. The heat seal temperature was obtained as a temperature at which the peeling strength was 300 g/15 mm by calculating on the basis of a curve of a seal strength vs peeling strength. Seal duration: 2 seconds Seal area: 15×10 mm Seal pressure: 5.3 kg/cm² G Seal temperature: Several temperatures over the range which include the heat seal temperature to be calculated later

EXAMPLE I-1

[1] Catalyst Preparation (1) Preparation of (1,2'-ethylene) (2,1'-ethylene)-bis(3-methylindene)

Under nitrogen flow, 1.12 g (3.94 mmol) of (1,2'-ethylene) (2,1'-ethylene)-bis(indene) was dissolved in 50 ml of anhydrous ether. After cooling to −78° C., 5.01 mL of a 1.57 mol/L solution of n-butyllithium in hexane (n-butyllithium: 7.87 mmol) was added dropwise over 30 minutes, and then the mixture was warmed to room temperature and stirred for 8 hours. The ether solvent was distilled off under reduced pressure and the residue was washed with hexane to obtain 1.12 g (3.02 mmol) of a dilithium salt as an ether adduct. This dilithium salt was dissolved in 50 mL of anhydrous tetrahydrofuran and cooled to −78° C. To this solution, 10 mL of a tetrahydrofuran solution containing 0.42 mL (6.74 mmol) of methyl iodide was added dropwise over 20 minutes, and the mixture was warmed to room temperature and stirred for 8 hours. After distilling the solvent off under reduced pressure, the residue was extracted with ethyl acetate. This extract was washed with water, and the organic phase was dried over anhydrous magnesium sulfate and filtered, and the filtrate was evaporated to dryness under reduced pressure to obtain 0.87 g (2.78 mmol) of the desired substance, (1,2'-ethylene)(2,1'-ethylene)-bis(3-methylindene) (Yield: 70.5%). This substance was present as a mixture of the isomers with regard to the double bonds in the 5-membered ring.

(2) Preparation of (1,2'-ethylene) (2,1'-ethylene)-bis(3-methylindene) dilithium salt 0.87 g (2.78 mmol) of (1,2'-ethylene)(2,1'-ethylene)-bis(3-methylindene) was dissolved in 35 mL of ether and cooled to −78° C. To this solution, 3.7 mL of a 1.57 mol/L solution of n-butyllithium in hexane (n-butyllithium: 5.81 mmol) was added dropwise over 30 minutes and then the mixture was warmed to room temperature and stirred for 8 hours. After distilling the solvent off under reduced pressure, the residue was washed with hexane to obtain 1.03 g (2.58 mmol) of a dilithium salt as an ether adduct (yield: 92.8%).

This substance was subjected to ¹H-NMR analysis and the following results were obtained.

¹H-NMR (THF-d8) (δ, ppm): 2.20 (6H, s), 3.25 (8H,s), 6.0-7.4 (8H, m)

(3) Preparation of (1,2'-ethylene) (2,1'-ethylene)-bis(3-methylindenyl)zirconium dichloride 1.03 g (2.58 mmol) of an ether adduct of (1,2'-ethylene) (2,1'-ethylene)-bis(3-methylindene) dilithium salt was suspended in 25 mL of toluene and cooled to −78° C. To this, a suspension of 0.60 g (2.58 mmol) of zirconium tetrachloride in toluene (20 mL) was added over 20 minutes and the mixture was warmed to room temperature and stirred for 8 hours, and then the toluene supernatant was filtered. The residue was extracted twice with 50 ml of dichloromethane. The solvent was distilled off under reduced pressure and the residue was recrystallized from dichloromethane/hexane to obtain 0.21 g (yield: 17.3%) of (1,2'-ethylene) (2,1'-ethylene)-bis(3-methylindenyl)zirconium dichloride.

This substance was subjected to ¹H-NMR analysis and the following results were obtained.

¹H-NMR (CDCl3):2.48 (6H, s), 3.33-3.85 (8H, m), 6.9-7 (8H, m)

[2] Polymerization

To a 10 L stainless steel autoclave, 5 L of heptane, 5 mmol of triisobutylaluminium and a catalyst component, which had been obtained by bringing 19 mmol as aluminum of a methyl aluminoxane (manufactured by Albemarle) into preliminary contact with 19 mmol of (1,2'-ethylene) (2,1'-ethylene)-bis (3-methylindenyl)zirconium dichloride prepared in Step [1] described above in toluene for 30 minutes, were charged and the mixture was heated to 40° C. and a propylene gas was introduced until the total pressure became 8.0 kg/cm²G. During polymerization, the propylene gas was supplied using a pressure controller to keep a constant pressure, and after 1 hour the content was recovered and dried under reduced pressure to obtain polypropylene.

[3] Evaluation of Physical Characteristics

The physical characteristics were evaluated by the methods described above. The results are shown in Table I-1.

EXAMPLE I-2

The procedure similar to that in Example I-1 was employed except for charging 50 g of 1-butene (comonomer) additionally in Step [2] in Example I-1 and the physical characteristics were evaluated. The results are shown in Table I-1.

EXAMPLE I-3

(1) Catalyst Preparation (1) Production of 2-chlorodimethylsilylindene

Under nitrogen flow, a 1 L three-necked flask received 50 mL of THF (tetrahydrofuran) and 2.5 g (41 mmol) of magnesium and further received 0.1 mL of 2-diburomoethane, and the mixture was stirred for 30 minutes to activate the magnesium. After stirring, the solvent was removed, and 50 mL of THF was newly added. To the mixture, a solution of 5.0 g (25.6 mmol) of 2-bromoindene in THF (200 mL) was added dropwise over 2 hours. After the addition was completed, the mixture was stirred at room temperature for 2 hours and then cooled to −78° C., and a solution of 3.1 mL (25.6 mmol) of dichlorodimethylsilane in THF (100 mL) was added dropwise over 1 hour and the mixture was stirred for 15 hours and then the solvent was distilled off. The residue was extracted with 200 mL of hexane, and the solvent was distilled off to obtain 6.6 g (24.4 mmol) of 2-clorodimethylsilylindene (yield: 94%).

(2) Preparation of (1,2'-dimethylsilylene)(2,1'-dimethylsilylene)-bis(indene)

Under nitrogen flow, a 1 L three-necked flask received 400 mL of THF and 8 g of 2-chlorodimethylsilylindene and the mixture was cooled to −78° C. To this solution, 38.5 mL (38.5 mmol) of a THF solution (1.0 M) of LiN(SiMe₃)₂ was added dropwise. After stirring at room temperature for 15 hours, the solvent was distilled off, and the residue was extracted with 300 mL of hexane. The solvent was distilled off to obtain 2.2 g (6.4 mmol) of (1,2'-dimethylsilylene)(2,1'-dimethylsilylene)-bis(indene) (yield: 33.4%).

(3) Preparation of (1,2'-dimethylsilylene)(2,1'-dimethylsilylene)-bis(indenyl)zirconium dichloride A Schlenk's bottle received 2.2 g (6.4 mmol) of (1,2'-dimethylsilylene)(2,1'-dimethylsilylene)-bis(indene) and 100 mL of ether and the mixture was cooled to −78° C. and combined with 9.6 mL (15.4 mmol) of n-butyllithium (solution in hexane: 1.6 M) and then stirred at room temperature for 12 hours. The solvent was distilled off and the solid obtained was washed with 20 mL of hexane to obtain a lithium salt (this lithium salt can be obtained quantitatively.). The lithium salt thus obtained was dissolved in 100 mL of toluene and a separate Schlenk's bottle received 1.5 g (6.4 mmol) of zirconium tetrachloride and 100 mL of toluene. A 500 mL three-necked flask received 100 mL of toluene, which was cooled to 0° C. and to which the equivalent amounts of the lithium salt obtained above and zirconium tetrachloride were added dropwise using a cannula over 1 hours. After the addition was completed, the mixture was stirred at room temperature overnight. The solution was filtered and the solvent in the filtrate was distilled off. The solid obtained was recrystallized from dichloromethane to obtain 1.2 g (2.4 mmol) of (1,2'-dimethylsilylene)(2,1'-dimethylsilylene)-bis(indenyl)zirconium dichloride (yield: 37%). This substance was subjected to $^1$H-NMR analysis and the following results were obtained. $^1$H-NMR CDCl3):0.85, 1.08 (6H, s),7.11 (2H, s), 7.2-7.7 (8H, m)

[2] Polymerization

To a 10 L stainless steel autoclave, 5 L of heptane, 5 mmol of triisobutylaluminium and a catalyst component, which had been obtained by bringing 10 mmol as aluminum of a methyl aluminoxane (Albemarle) into preliminary contact with 10 μmol of (1,2'-dimethylsilylene)(2,1'-dimethylsilylene)-bis(indenyl)zirconium dichloride prepared in Step [1] described above in toluene for 5 minutes, were charged and the mixture was heated to 50° C. and a propylene gas was introduced until the total pressure became 8.0 kg/cm$^2$ G. During polymerization, the propylene gas was supplied using a pressure controller to keep a constant pressure, and after 2.5 hours the content was recovered and dried under reduced pressure to obtain polypropylene.

[3] Formulation and Kneading

The polypropylene thus obtained was combined with the following additives and extruded by a single-screw extruder (TSUKADA JUKISEISAKUSHO: Model TLC35-20) to granulate into a pellet.

Antioxidants
IRGANOX 1010, Ciba Specialty Chemicals: 1000 ppm; and,
IRGAPHOS 168, Ciba Specialty Chemicals: 1000 ppm

[4] Evaluation of Physical Characteristics

The evaluation was made by the methods described above. The results are shown in Table I-1.

TABLE I-1

|  |  | Example I-1 | Example I-2 | Example I-3 |
|---|---|---|---|---|
| Resin analysis | Intrinsic viscosity [η] (dl/g) | 1.2 | 1.2 | 1.7 |
|  | Molecular weight distribution Mw/Mn | 1.8 | 2.1 | 2.2 |
|  | % Isotactic pentad (mol %) | 63.5 | — | 64.8 |
|  | Boiling ether extract (wt/%) | 5 | 8 | 5 |
|  | TREF peak | 63(s) | 58(s) | 67(s) |
|  | TREF elution (W25) (wt %) | 1.7 | 2.0 | 1.6 |
|  | Comonomer content (mol %) | — | 0.9 | — |
|  | Stereoregularity (P) (mol %) | — | 76 | — |
| Nucleating agent | GELOL MD (ppm) | — | — | — |
| Resin characteristics | Melting point Tm (° C.) | 102 | 98 | 111 |
|  | Crystallization temperature (Tc) (° C.) | 63 | 56 | 72 |
| Press performance | Tensile modulus (Mpa) | 250 | 180 | 260 |
|  | Izod impact strength (kJ/m$^2$) | NB | NB | NB |
|  | Transparency | ⊚ | ⊚ | ⊚ |
|  | Internal haze | 14 | 12 | 14 |
|  | 0.75 × Tm − 15 | 61.5 | 58.5 | 68.3 |

(Note)
TREF peak: s; Sharp, b; Broad
N.B.: Not broken
⊚: Excellent,
○: Satisfactory,
Δ: Poor

EXAMPLE I-4

[1] Catalyst Preparation (1,2'-dimethylsilylene)(2,1'-dimethylsilylene)-bis(indenyl)zirconium dichloride was obtained similarly as in Example I-3.

[2] Polymerization

To a 10 L stainless steel autoclave, 6 L of heptane, 6 mmol of triisobutylaluminium and a catalyst component, which had been obtained by bringing 500 μmol as aluminum of a methyl aluminoxane (Albemarle) into preliminary contact with 5 μmol of (1,2'-dimethylsilylene)(2,1'-dimethylsilylene)-bis(indenyl)zirconium dichloride prepared in Step [1] described above in toluene for 5 minutes, were charged and the mixture was heated to 50° C. and a propylene gas was introduced until the total pressure became 8.0 kg/cm$^2$ G. During polymerization, the propylene gas was supplied using a pressure controller to keep a constant pressure, and after 60 minutes the content was recovered and dried under reduced pressure to obtain polypropylene.

[3] Formulation and Kneading

The procedure employed in Example I-3 was followed.

[4] Evaluation of Physical Characteristics

The evaluation was made by the methods described above. The results are shown in Table I-2.

EXAMPLE I-5

The procedure similar to that in Example I-3 was employed except for adding GELOL MD (SHINIPPON RIKASHA). The results of the evaluation of the physical characteristics are shown in Table I-2.

COMPARATIVE EXAMPLE I-1

[1] Catalyst Preparation (1) Preparation of Magnesium Compound

A glass reactor (about 6 L in capacity) fitted with a stirrer was purged sufficiently with a nitrogen gas and received about 2430 g of ethanol, 16 g of iodine and 160 g of elemental magnesium, and the reaction was continued under pressure with stirring under reflux until the evolution of a hydrogen gas from the reaction system was terminated to obtain a solid reaction product. The fluid reaction mixture containing this solid product was dried under reduced pressure to obtain a magnesium compound.

[2] Preparation of Solid Catalyst Component

A three-necked flask (capacity of 500 mL) purged sufficiently with a nitrogen gas received 16 g of the magnesium compound obtained above (not pulverized), 80 mL of a purified heptane, 2.4 mL of silicon tetrachloride and 2.3 mL of diethyl phthalate. The reaction system was kept at 90° C., and 77 mL of titanium tetrachloride was added with stirring and the reaction was continued at 110° C. for 2 hours and then the solid components were separated and washed with a purified heptane at 80° C. Addition of 122 mL of titanium tetrachloride followed by the reaction at 110° C. for 2 hours followed by a sufficient washing with a purified heptane yielded a solid catalyst component.

[2] Polymerization

A 5 L stainless steel autoclave received 20 g of a polypropylene powder, 2.5 mmol of triisobutylaluminium (TIBA), 0.125 mmol of 1-allyl-3,4-dimethoxybenzene (ADMB), 0.2 mmol of dipheyldimethoxysilane (DPDMS) and 20 mL of a heptane solution containing 0.05 mmol as titanium atom of the solid catalyst component obtained above, and the reaction system was vented for 5 minutes, and then a propylene gas was supplied until the total pressure became 28 kg/cm² G, whereby effecting a vapor phase polymerization for 1.7 hours to obtain a polymer.

[3] Evaluation f Physical Characteristics

Evaluation was made similarly as in Example I-1. The results are shown in Table I-2.

TABLE I-2

| | | Example I-4 | Example I-5 | Comparative Example I-1 |
|---|---|---|---|---|
| Resin analysis | Intrinsic viscosity [η] (dl/g) | 2.1 | 1.7 | 4.3 |
| | Molecular weight distribution Mw/Mn | 2.3 | 2.2 | 4.7 |
| | % Isotactic pentad (mol %) | 65.0 | 64.8 | 65.3 |
| | Boiling ether extract (wt/%) | 4 | 5 | 12 |
| | TREF peak | 67(s) | 67(s) | 113(b) |
| | TREF elution (W25) (wt %) | 1.4 | 1.6 | 30 |
| | Comonomer content (mol %) | — | — | — |
| | Stereoregularity (P) (mol %) | — | — | — |
| Nucleating agent | GELOL MD (ppm) | — | 1000 | — |
| Resin characteristics | Melting point Tm (° C.) | 111 | 112 | 161 |
| | Crystallization temperature (Tc) (° C.) | 71 | 80 | 100 |
| Press performance | Tensile modulus (Mpa) | 264 | 278 | 480 |
| | Izod impact strength (kJ/m²) | NB | NB | NB |
| | Transparency | ◯ | ◯◯ | Δ |
| | Internal haze | 15 | 8 | 47 |
| | 0.75 × Tm − 15 | 68.3 | 69.0 | 105.8 |

(Note)
TREF peak: s; Sharp, b; Broad
N.B.: Not broken
◯◯: Excellent,
◯: Satisfactory,
Δ: Poor

EXAMPLE I-6

The polypropylene obtained similarly as in Example I-1 was combined with the following additives and extruded by a single-screw extruder (TSUKADAJUKISEISAKUSHO: Model TLC35-20) to granulate into a pellet.

Antioxidants

IRGANOX 1010, Ciba Specialty Chemicals: 1000 ppm; and,

IRGAPHOS 168, Ciba Specialty Chemicals: 1000 ppm

Neutralizing agent . . . Calcium stearate: 1000 ppm

Anti-blocking agent . . . Silica-based agent: 2300 ppm

Slipperiness-imparting (slipping) agent . . . Erucic acid amide: 2500 ppm

Nucleating Agent

GELOL MD available from SHINNIPPON RIKASHA (dimethylbenzylidene sorbitol): 2300 ppm The pellet obtained above was subjected to a film-forming process described above and the film was qualified by the methods described above. The results are shown in Table I-3.

EXAMPLE I-7

A propylene/butene copolymer obtained in a manner similar to that in Example I-2 was combined with the following additives and extruded by a single-screw extruder (TSUKADA JUKISEISAKUSHO: Model TLC35-20) to granulate into a pellet.

Antioxidants

IRGANOX 1010, Ciba Specialty Chemicals: 1000 ppm; and,

IRGAPHOS 168, Ciba Specialty Chemicals: 1000 ppm

Neutralizing agent . . . Calcium stearate: 1000 ppm

Anti-blocking agent . . . Silica-based agent: 2300 ppm

Slipperiness-imparting (slipping) agent . . . Erucic acid amide: 2500 ppm

Nucleating Agent

GELOL MD available from SHINNIPPON RIKASHA (dimethylbenzylidene sorbitol):2300 ppm The pellet obtained above was subjected to a film-forming process described above and the film was qualified by the methods described above. The results are shown in Table I-3.

EXAMPLE I-8

A polypropylene obtained in a manner similar to that in Example I-1 was combined with the following additives and extruded by a single-screw extruder (manufactured by TSUKADA JUKISEISAKUSHO: Model TLC35-20) to granulate into a pellet.

Antioxidants

IRGANOX 1010, Ciba Specialty Chemicals: 1000 ppm; and,

IRGAPHOS 168, Ciba Specialty Chemicals: 1000 ppm.

Neutralizing agent . . . Calcium stearate: 1000 ppm

Anti-blocking agent . . . Silica-based agent: 2300 ppm

Slipperiness-imparting (slipping) agent . . . Erucic acid amide: 2500 ppm

Nucleating Agent

GELOL MD available from SHINNIPPON RIKASHA (dimethylbenzylidene sorbitol):500 ppm The pellet obtained above was subjected to a film-forming process described above and the film was qualified by the methods described above. The results are shown in Table I-3.

TABLE I-3

| | | Example I-6 | Example I-7 | Example I-8 |
|---|---|---|---|---|
| Resin analysis | Intrinsic viscosity [η] (dl/g) | 1.2 | 1.2 | 1.2 |
| | Molecular weight distribution Mw/Mn | 1.8 | 2.1 | 1.8 |
| | % Isotactic pentad (mol %) | 63.5 | — | 63.5 |
| | Boiling ether extract (wt/%) | 5 | 8 | 5 |
| | TREF peak | 63(s) | 58(s) | 63(s) |
| | TREF elution (W25) (wt %) | 1.7 | 2.0 | 1.7 |
| | Comonomer content (mol %) | — | 0.9 | — |
| | Stereoregularity (P) (mol %) | — | 76 | — |
| Nucleating agent | GELOL MD (ppm) | 2300 | 2300 | 500 |
| Resin characteristics | Melting point Tm (° C.) | 102 | 98 | 102 |
| | Crystallization temperature (Tc) (° C.) | 78 | 74 | 78 |
| Film performance | Tensile modulus (Mpa) | 613 | 552 | 442 |
| | Impact resistance, Impact destruction strength (J/m) | 9900 | 9900 | 9900 |
| | Haze | 2.1 | 2.0 | 2.5 |
| | Heat seal temperature (° C.) | 106 | 100 | 108 |
| | 0.75 × Tm − 15 | 61.5 | 58.5 | 61.5 |

(Note)
TREF peak: s; Sharp, b; Broad

COMPARATIVE EXAMPLE I-21

The procedure similar to that employed in Example I-6 was followed except for adding no nucleating agent, but the film could not be formed because of an extremely poor roll release performance upon the film-forming process.

COMPARATIVE EXAMPLE I-3

The procedure similar to that employed in Example I-6 was followed except for using a propylenic polymer E2900 available from IDEMITSU SEKYU KAGAKU which is produced using a non-metallocene catalyst (titanium/magnesium-based catalyst) and also except for adding no nucleating agent. The performance of the film thus obtained is shown in Table I-4.

COMPARATIVE EXAMPLE I-4

The procedure similar to that employed in Example I-6 was followed except for using a propylenic polymer E2900 available from IDEMITSU SEKYU KAGAKU which is produced using a non-metallocene catalyst (titanium/magnesium-based catalyst). The performance of the film thus obtained is shown in Table I-4.

COMPARATIVE EXAMPLE I-5

[1] Catalyst Preparation
Similarly as in Example I-1, (1,2'-ethylene) (2,1'-ethylene)-bis(3-methylindenyl)zirconium dichloride.

[2] Polymerization

A 10 L stainless steel autoclave was charged sequentially with 5 L of toluene, 20 mmol as aluminum of a methyl aluminoxane (Albemarle) and then 20 μmol of (1,2'-ethylene)(2,1'-ethylene)-bis(3-methylindenyl)zirconium dichloride obtained in Example I-1, and heated to 50° C., and a propylene gas was introduced until the total pressure became 8.0 kg/cm$^2$ G. During polymerization, the propylene gas was supplied using a pressure controller to keep a constant pressure, and after 1 hour the content was recovered and dried under reduced pressure to obtain polypropylene.

[3] Formulation and Kneading

The procedure employed in Example I-8 was followed.

[4] Evaluation of Physical Characteristics

The evaluation was made by the methods described above, but the film could not be formed because the film was broken during the film-forming process.

the integrated intensity of each peak. A value (m-2, 1) was obtained by calculating the ratio of the integrated intensity of a peak assigned to Pα,γ threo observed near 17.2 ppm to the integrated intensity in all methyl carbon region as a % meso-2,1 insertion content. A value (r-2, 1) was obtained by calculating the ratio of the integrated intensity of a peak assigned to Pα,γ threo observed near 15.0 ppm to the integrated intensity in all methyl carbon region as a % rasemi-2,1 insertion content. A value (1, 3) was obtained by calculating the ratio of the integrated intensity of a peak assigned to Tβ,γ+observed near 31.0 ppm to the integrated intensity in all methine carbon region as a % 1,3 insertion content. When a peak to be assigned to a meso-2, 1 insertion, a racemi-2, 1 insertion or a 1, 3 insertion could not be distinguished because of, for example, being overlapped with noises, then each heterogeneous binding content (m-2, 1), (r-2, 1) or (1, 3) was regarded as a zero value.

TABLE I-4

|  |  | Comparative Example I-3 | Comparative Example I-4 | Comparative Example I-5 |
|---|---|---|---|---|
| Resin analysis | Intrinsic viscosity [η] (dl/g) | 1.9 | 1.9 | 0.7 |
|  | Molecular weight distribution Mw/Mn | 2.6 | 2.6 | 2.0 |
|  | % Isotactic pentad (mol %) | 72.2 | 72.2 | 59.2 |
|  | Boiling ether extract (wt/%) | 12 | 12 | 6 |
|  | TREF peak | 112(b) | 112(b) | 58(s) |
|  | TREF elution (W25) (wt %) | 30 | 30 | 1.5 |
|  | Comonomer content (mol %) | — | — | — |
|  | Stereoregularity (P) (mol %) | — | — | — |
| Nucleating agent | GELOL MD (ppm) | — | 2300 | 500 |
| Resin characteristics | Melting point Tm (° C.) | 160 | 160 | — |
|  | Crystallization temperature (Tc) (° C.) | 102 | 103 | — |
| Film performance | Tensile modulus (Mpa) | 512 | 514 | — |
|  | Impact resistance, Impact destruction strength (J/m) | 9800 | 9800 | — |
|  | Haze | 15.5 | 15.8 | — |
|  | Heat seal temperature (° C.) | 151 | 151 | — |
|  | 0.75 × Tm − 15 | 105 | 105 | — |

(Note)
TREF peak: s; Sharp, b; Broad

[Second Invention]

A method for evaluating the resin characteristics and the physical characteristics of a polymer according to the invention are described below.

(1) Intrinsic viscosity [η]

An automatic viscometer model VMR-053 available from RIGOSHA (KK) was used in a tetralin solvent at 135° C.

(2) % Pentad and % Abnormal Insertion

Measurement was made in accordance with the method described in the detailed description of the invention. Thus, a % meso-pentad (% mmmm) and a % racemi-pentad (% rrrr) referred herein were obtained in accordance with the method proposed by A. Zambelli et al in Macromolecules, 6, 925 (1973) by determining the methyl signal in a $^{13}$C-NMR spectrum and calculating % meso and % racemi levels, in a polypropylene molecule chain, as represented in pentad as a unit. The calculation was made in accordance with the method described in the detailed description of the invention.

With regard to (m-2, 1), (r-2, 1) and (1,3), the peaks in a $^{13}$C-NMR spectrum were assigned in accordance with the report by Grassi et al (Macromolecules, 21, p. 617 (1988)) and the report by Busico et al (Macromolecules, 27, p. 7538 (1994)) and each % insertion content was calculated based on A $^{13}$C NMR spectrum was obtained using the following instruments under the conditions specified below.

Instrument: Nippon Densi Model JNM-EX400 $^{13}$C-NMR device

Method: Proton complete decoupling method

Concentration: 220 mg/milliliter

Solvent: A 90/10 solvent mixture (by volume) of 1,2,4-Trichlorobenzene and benzene-d6

Temperature: 130° C.

Pulse gap: 45°

Pulse interval: 4 seconds

Number of cycles: 10000 times (3) Comonomer Unit Content (% by Mole) in Copolymer A $^{13}$C NMR spectrum was obtained using Nippon Densi Model JNM-EX400 $^{13}$C-NMR device under the conditions specified below and the calculation was made as described below.

Sample concentration: 220 mg/3 ml NMR solvent

NMR Solvent: 1,2,4-Trichlorobenzene/benzene-d6 (90/10 v/v)

Determination temperature: 130° C.

Pulse gap: 45°

Pulse interval: 10 seconds

Number of cycles: 4000 times (a) Ethylene Unit

A random copolymer of propylene and ethylene, when subjected to $^{13}$C-NMR, exhibited the spectrum whose signals had the chemical shifts and the assignments indicated in Table II-1

TABLE II-1

Assignments of signals in $^{13}$C-NMR spectrum of ethylene-propylene copolymer

| Number | Chemical shift | Assignment |
|---|---|---|
| 1 | 45.1-47.3 | PPP S$\alpha\alpha$ |
| 2 | 42.3 | PPP S$\alpha\alpha$ |
| 3 | 38.6 | PPP T$\alpha\gamma$ |
| 4 | 38.0 | S$\alpha\gamma$ |
| 5 | 37.5 | S$\alpha\delta$ |
| 6 | 36.0 | PPP S$\alpha\beta$ |
| 7 | 36.0 | PPP T$\alpha\beta$ |
| 8 | 34.9 | EPP, PEP S$\alpha\beta$ |
| 9 | 34.6 | EPP, PEP S$\alpha\beta$ |
| 10 | 34.1 | EPP T$\gamma\gamma$ |
| 11 | 33.7 | EEPP T$\gamma\delta$ |
| 12 | 33.3 | EPE T$\delta\delta$ |
| 13 | 31.6 | PPP T$\beta\gamma$ |
| 14 | 31.4 | EPP T$\beta\gamma$ |
| 15 | 31.0 | PPE T$\beta\delta$ |
| 16 | 30.7 | PPP S$\alpha\beta$ |
| 17 | 30.5 | PEEE S$\gamma\delta$ |
| 18 | 30.0 | EEE S$\delta\delta$ |
| 19 | 29.0 | PPP T$\beta\beta$ |
| 20 | 27.3 | PEE S$\beta\delta$ |
| 21 | 24.6 | PEP S$\alpha\beta$ |
| 22 | 21.3-22.7 | P$\beta\beta$ |
| 23 | 20.6-21.3 | P$\beta\beta$ |
| 24 | 19.8-20.6 | P$\beta\beta$ |
| 25 | 17.6 | P$\alpha\beta$ |
| 26 | 17.2 | P$\alpha\gamma$ |

(NOTE)
E represents an ethylene unit. A chemical shift is represented in ppm.

The ethylene unit content in the copolymer ($\alpha$(% by mole)) was obtained in accordance with the following equation (1) based on the spectrum determined by the $^{13}$C-NMR.

$$\alpha = E/S \times 100 \quad (1)$$

wherein S and E are each represented as follows:

S=IEPE+IPPE+IEEE+IPPP+IPEE+IPEP

E=IEEE+2/3(IPEE+IEPE)+1/3(IPPE+IPEP)

wherein:

IEPE=I(12)

IPPE=I(15)+I(11)+(I(14)−I(11))/2+I(10)

IEEE=I(18)/2+I(17)/4

IPPP=I(19)+(I(6)+I(7))/2+I(3)+I(13)+I(11)+(I(14)−I(11))/2

IPEE=I(20)

IPEP=(I(8)+I(9)−2×(I(11))/4+I(21).

A % isotactic triad of a PPP chain was obtained as a stereoregularity index (P (% by mole)) according to the equation (2) shown below.

$$P = Im/I \times 100 \quad (2)$$

wherein Im and I are each represented as follows:

Im=I(22)

I=I(22)+I(23)+I(24)−{(I(8)+I(9))/2+I(10)+3/2×I(11)+I(12)+I(13)+I(15)}.

In the equation shown above, I(1), I(2) and the like represent the intensities of signal [1], signal [2] and the like, respectively.

(4) Molecular Weight Distribution (Mw/Mn)

Measurement was made in accordance with the method described in the detailed description of the invention.

(5) DSC Analysis

Analysis was made in accordance with the method described in the detailed description of the invention.

(6) Temperature-Raising Fractional Chromatography

Measurement was made by the method described in the first invention.

(7) Tensile Modulus

Measurement was made by the method described in the first invention.

(8) Internal Haze

A propylenic polymer was press-molded to obtain a test piece which was subjected to the test in accordance with JIS K7105.

Test piece: 15 cm×15 cm×1 mm (test piece thickness=1 mm)

(9) % Elasticity Recovery

The method described in JP-A-5-132590 was followed. Thus, a propylenic polymer was press-molded and a JIS No. 2 dumb-bell test specimen was prepared. The constant-width region of the dumb-bell was marked at 25 mm interval, which was designated as L0. The specimen was stretched using a tensile test device from 80 mm to 160 mm of the inter-chuck distance at the stretching speed of 50 mm/min, and then the inter-chuck distance was allowed to become the initial length, and then after one minute the distance between the marks was determined and designated as L1. A % elasticity recovery was calculated by the equation shown below. When the value obtained was zero then the result was judged as "No recovery".

$$[(2L0-L1)/L0] \times 100$$

L0: Initial distance between marks on dumb-bell

L1: Distance between marks on dumb-bell after stretching

(10) Anti-Blocking Ability

A propylenic polymer was press-molded to obtain a test piece, which was bound in the conditions described below and examined for its peeling strength by a tensile test device.

Test piece: 15 cm×62.5 mm×2 mm

Binding conditions: Bound at 40° C. over the area of 15 mm×31 mm under the pressing load of 0.7 kg for 3 hours.

Shear peeling conditions: Crosshead speed of 50 mm/min

(11) Izod Impact Strength

A propylenic polymer was press-molded to obtain a test piece which was subjected to the test in accordance with JIS K-7110 with the test piece thickness of 3 mm at the ambient temperature of −5° C.

(12) Amount of Components Dissolved Out into Hexane (H25)

A value of H 25 was determined under the conditions specified below.

Sample size: 0.1 to 5 g

State of sample: Powder (a pellet should be pulverized into a powder before use)

Solvent: Hexane

Elution conditions: Allowing to stand at 25° C. for 3 days or longer

Calculation of amount eluted: According to the following equation:

$$H25=[(W0W1)/W0] \times 100(\%)$$

(13) Boiling Diethylether Extract

The method similar to that in the first invention was employed except that the sample size was 1 to 2 g.

EXAMPLE II-1

Propylene Homopolymer (1) Catalyst Preparation

Synthesis of (Dimethylsilylene) 2(3-n-butylindenyl) 2 zirconium dichloride

A Schlenk's bottle receives 0.83 g (2.4 mmol) of (1,2'-dimethylsilylene)(2,1'-dimethylsilylene)(indene)2 and 50 mL of ether. The mixture is cooled to −78° C. and combined with 3.1 mL (5.0 mmol) of n-BuLi (1.6 M solution in hexane) and then stirred at room temperature for 12 hours. The solvent is distilled off to obtain a solid which is washed with 20 mL of hexane to obtain 1.1 g (2.3 mmol) of a lithium salt as an ether adduct. This lithium salt is dissolved in 50 mL of THF, and cooled to −78° C., 0.57 mL (5.3 mmol) of n-butyl bromide is added dropwise slowly and the mixture is stirred at room temperature for 12 hours. After distilling the solvent off followed by extraction with 50 ml of hexane followed by removing the solvent, 0.81 g (1.77 mmol) of (1,2'-dimethylsilylene) (2,1'-dimethylsilylene) (3-n-butylindene)2 was obtained (yield: 74%).

0.81 g (1.77 mmol) of (1,2'-dimethylsilylene) (2,1'-dimethylsilylene) (3-n-butylindene)2 thus obtained is placed in a Schlenk's bottle under nitrogen flow together with 100 mL of ether. The mixture is cooled to −78° C. and combined with 2.7 mL (4.15 mmol) of n-BuLi (1.54 M solution in hexane) and then stirred at room temperature for 12 hours. The solvent was distilled off to obtain a solid which is washed with hexane to obtain 0.28 g (1.43 mmol) of a lithium salt as an ether adduct.

The lithium salt thus obtained is dissolved in 50 mL of toluene under nitrogen flow. The mixture is cooled to −78° C. and treated dropwise with 0.33 g (1.42 mmol) of zirconium tetrachloride suspended in toluene (50 mL) which has previously been cooled to −78° C. After the dropwise treatment, the mixture is stirred at room temperature for 6 hours. After filtration, the solvent of the filtrate is distilled off. Recrystallization from dichloromethane yielded 0.2 g (0.32 mmol) of (1,2'-dimethylsilylene) (2,1'-dimethylsilylene) (3-n-butylindenyl)2 zirconium dichloride (yield: 22%).

The results of $^1$H-NMR (90 MHz, CDCl3) analysis are as follows: δ 0.88, 0.99 (12H, dimethylsilylene), 0.7-1.0. 1.1-1.5 (18H, n-Bu), 7.0-7.6 (8H, benzene ring proton).

(2) Propylene Polymerization

A 10 L stainless steel autoclave received 6 L of heptane, 6 mmol of triisobutylaluminium and a catalyst component which had been obtained by bringing 5 mmol of a methyl aluminoxane (manufactured by Albemarle) into preliminary contact with 5 µmol of (1,2'-dimethylsilylene) (2,1'-dimethylsilylene) (3-n-butylindenyl) 2 zirconium dichloride in toluene for 5 minutes. After introducing hydrogen at 0.5 kg/cm$^2$ G, a propylene gas was introduced until the total pressure became 8.0 kg/cm$^2$ G, and the propylene gas was supplied using a pressure controller to keep a constant pressure during polymerization. After polymerizing at 50° C. for 30 minutes, the content was recovered and dried under reduced pressure to obtain a propylene homopolymer.

(3) Formulation and Kneading

The polypropylene homopolymer thus obtained was combined with the following additives and extruded by a single-screw extruder (manufactured by TSUKADA JUKISEI-SAKUSHO: Model TLC35-20) to granulate into a pellet.

(Formulation of Additives)

Antioxidants
  Phenolic antioxidant: IRGANOX 1010 available from Ciba Specialty Chemicals, 1000 ppm
  Phosphorus-based antioxidant: P-EPQ 500 ppm
  Neutralizing agent: Calcium stearate: 500 ppm
  Neutralizing agent: DHT-4A: 500 ppm (4) Evaluation of Resin Characteristics and Physical Characteristics Evaluation was made by the methods described above. The results are shown in Table II-2 and Table II-3. In these tables, Example 1 means Example II-1. The same applies analogously to Example 2 or later as well as Comparatives. The description further thereafter is also handled similarly.

EXAMPLE II-2

Propylene Homopolymer

The method similar to that in Example II-1 was employed except for producing a propylene homopolymer without hydrogenation. The results are shown in Tables II-2 and II-3.

EXAMPLE II-3

(1) Synthesis of (dimethylsilylene)2(3-methylindenyl)2 zirconium dichloride

A Schlenk's bottle receives 2.2 g (6.4 mmol) of (1.2'-dimethylsilylene) (2,1'-dimethylsilylene) (indene) and 100 mL of ether. The mixture is cooled to −78° C. and combined with 9.6 mL (15.4 mmol) of n-BuLi (1.6 M solution in hexane) and then stirred at room temperature for 12 hours. The solvent is distilled off to obtain a solid which is washed with 20 ml of hexane to obtain a lithium salt quantitatively. This lithium salt is dissolved in 100 mL of THF and cooled to −78° C. 7.4 g (52.0 mmol) of methyl iodide was added dropwise slowly and the mixture is stirred at room temperature for 12 hours. After distilling the solvent off followed by extraction with 50 ml of hexane followed by removing the solvent off, 4.5 g (12 mmol) of (1.2-dimethylsilylene)(2,1'-dimethylsilylene) (3-methylindene)2 was obtained (yield: 94%)

Subsequently, a Schlenk's bottle receives under nitrogen flow 2.0 g (5.4 mmol) of (1,2'-dimethylsilylene)(2,1'-dimethylsilylene)(3-methylindene)2 and 100 mL of ether. The mixture is cooled to −78° C. and combined with 13.5 mL (21.6 mmol) of n-BuLi (1.6 M solution in hexane) and then stirred at room temperature for 12 hours. The solvent is distilled off to obtain a solid which is washed with hexane to obtain 1.1 g (2.9 mmol) of a lithium salt. Under nitrogen flow, the lithium salt obtained above is dissolved in 100 mL of toluene. The mixture is cooled to −78° C., and treated dropwise with 0.7 g (3.0 mmol) of zirconium tetrachloride suspended in toluene (100 ml) which has previously been cooled to −78° C. After completion of the addition, the mixture is stirred for 6 hours at room temperature. After filtration, the precipitate was extracted with dichloromethane. Recrystallization from dichloromethane/hexane yielded 0.5 g (0.94 mmol) of (1.2′-dimethylsilylene)(2,1′-dimethylsilylene) (3-methylindenyl)2 zirconium dichloride (yield: 32%).

The results of $^1$H-NMR (CDCl3) analysis are as follows: δ 0.95, 1.05 (12H, dimethylsilylene), 2.50 (6H, CH3), 7.2-7.7 (8H, Ar—H).

(2) Propylene Polymerization

A 1 L stainless steel autoclave received 400 mL of heptane, 0.5 mmol of triisobutylaluminium and a catalyst component which had been obtained by bringing 0.5 mmol of a methyl aluminoxane (manufactured by Albemarle) into preliminary contact with 0.5 μmol of (1,2′-dimethylsilylene) (2,1′-dimethylsilylene) (3-methylindenyl) 2 zirconium dichloride in toluene for 5 minutes. After introducing hydrogen at 0.3 kg/cm$^2$ G, a propylene gas was introduced until the total pressure became 8.0 kg/cm$^2$G, and the propylene gas was supplied using a pressure controller to keep a constant pressure during polymerization. After polymerizing at 70° C. for 1 hour, the content was recovered and dried under reduced pressure to obtain a propylene homopolymer.

(3) Formulation and Kneading

Except for combining the polypropylene homopolymer thus obtained with the following additives shown below, the procedure similar to that in Example II-1 was employed.
(Formulation of Additives)
Phenolic antioxidant: IRGANOX 1010 available from Ciba Specialty Chemicals, 1000 ppm
Phosphorus-based antioxidant: IRGAPHOS 168 available from Ciba Specialty Chemicals: 1000 ppm (4) Evaluation of Resin Characteristics and Physical Characteristics Evaluation was made similarly as in Example II-1 (4). The results are shown in Tables II-2 and II-3.

EXAMPLE II-4

Propylenic Copolymer (1) Preparation of (1,2′-ethylene) (2,1′-ethylene)-bis(3-methylindenyl)zirconium dichloride The method similar to that described in Example I-1 was employed.

(2) Propylene/Ethylene Copolymerization

A 2 L stainless steel autoclave received 1.2 L of toluene, 1.5 mmol of triisobutylaluminium, 10 (Al) mmol of a methyl aluminoxane (Albemarle) and 20 μmol of (1,2′-ethylene)(2, 1′-ethylene)bis(3-methylindenyl)zirconium dichloride and the mixture was warmed to 30° C., and then an ethylene/propylene gas mixture (molar ratio of ethylene/propylene=1/100) was introduced. An excessive gas was vented so that the total pressure became 7.0 kg/cm$^2$ G, and the polymerization was effected for 60 minutes while keeping a constant gas composition in the reaction system, and then the content was recovered and dried under reduced pressure to obtain a propylenic copolymer. The formulation and the kneading, and the evaluation of the resin characteristics and the physical characteristics were performed in the manner similar to that in Example II-1. The results are shown in Tables II-1 and II-3.

COMPARATIVE EXAMPLE II-1

Propylene Homopolymer (1) Preparation of Magnesium Compound
The method similar to that in Comparative I-1 was employed.

(2) Preparation of Solid Catalyst Component (A)

A glass reactor whose capacity was 5 L and which has sufficiently been purged with a nitrogen gas was charged with 160 g of the magnesium compound obtained in Step (1) described above (not pulverized), 800 ml of a purified heptane, 24 ml of silicon tetrachloride and 23 ml of diethyl phthalate and then the reaction system was kept at 80° C. and admixed with 770 ml of titanium tetrachloride with stirring, and the reaction was continued at 110° C. for 2 hours and then the solid components wer separated and washed with a purified heptane at 90° C. 1220 ml of titanium tetrachloride was further added, and the reaction at 110° C. for 2 hours followed by a thorough washing with a purified heptane yielded a solid catalyst component (A).

(3) Vapor Phase Polymerization of Propylene

A polymerization chamber whose capacity was 200 L was fed with 6.0 g/h of the solid catalyst component obtained in Step (2) described above, 0.2 mol/h of triisobutylaluminium (TIBA), 0.012 mol/h of 1-allyl-3,4-dimethoxybenzene (ADMB), 0.012 mol/h of cyclohexylmethyldimethoxysilane (CHMDMS) and 37 kg/h of propylene, and the polymerization was effected at 70° C. under 28 kg/cm$^2$ G.

(4) Formulation and Kneading

The polypropylene powder thus obtained was admixed with 2,5-dimethyl-2,5-di-(t-butylperoxy)-hexane and then combined with the additives as described in Example II-1 and extruded via a 40 mmφ die to obtain a pellet.

(5) Evaluation of Resin Characteristics and Physical Characteristics

The method similar to that in Example II-1 (4) was employed. The results are shown in Tables II-2 and II-3.

REFERENCE EXAMPLE

Affinity PL1880

The pellet of Affinity PL1880 (trade name) available from Dow Chemical Japan (K.K.9 was subjected to the evaluation of the physical characteristics as described in Example II-1 (4). The results are shown in Table II-3.

COMPARATIVE EXAMPLE II-2

Propylene Homopolymer

A stainless steel autoclave whose capacity was 1 L was charged with 400 mL of heptane, 0.5 mmol of triisobutylaluminium and a catalyst component which had been obtained by bringing 2 μmol of dimethylanilinium (pentafluorophenyl)borate into preliminary contact with 1 μmol of (t-butylamide)dimethyl(tetramethyl-$\eta^5$-cyclopentadienyl)silane titanium dichloride in toluene for 5 minutes. After introducing hydrogen at 0.3 kg/cm² G, a propylene gas was introduced until the total pressure became 8.0 kg/cm² G, and the propylene gas was supplied using a pressure controller to keep a constant pressure during polymerization. After polymerizing at 70° C. for 1 hour, the content was recovered and dried under reduced pressure to obtain a propylene homopolymer. The formulation and the kneading, and the evaluation of the resin characteristics and the physical characteristics were performed in the manner similar to that in Example II-1. The results are shown in Tables II-2 and II-3.

EXAMPLE II-5

Addition of Nucleating Agent

Except for combining the propylene homopolymer obtained in Example II-1 with the following additives shown below, the procedure similar to that in Example II-1 was employed. The results are shown in Table II-4.
(Formulation of Additives)
Phenolic antioxidant: IRGANOX 1010 available from Ciba Specialty Chemicals, 1000 ppm
Phosphorus-based antioxidant: P-EPQ, 500 ppm
Neutralizing agent: Calcium stearate: 500 ppm
Neutralizing agent: DHT-4A: 500 ppm
Nucleating agent: GELOL MD available from SHINNIPPON RIKAGAKUSHA: 1000 ppm

EXAMPLE II-6

Addition of Nucleating Agent

Except that the amount of GELOL MD available from SHINNIPPON RIKGAKUSHA which was added was 2000 ppm, the method similar to that in Example II-5 was employed. The results are shown in Table II-4.

EXAMPLE II-7

Addition of Nucleating Agent

Except for combining the propylene homopolymer obtained in Example II-1 with the following additives shown below, the procedure similar to that in Example II-1 was employed. The results are shown in Table II-4.
Phenolic antioxidant: IRGANOX 1010 available from Ciba Specialty Chemicals, 1000 ppm
Phosphorus-based antioxidant: IRGAPHOS 168 available from Ciba Specialty Chemicals: 1000 ppm
Nucleating agent: GELOL MD available from SHINNIPPON RIKAGAKUSHA: 5000 ppm

EXAMPLE II-8

Addition of Nucleating Agent

Except that the amount of GELOL MD available from SHINNIPPON RIKAGAKUSHA which was added was 10000 ppm, the method similar to that in Example II-7 was employed. The results are shown in Table II-4.

EXAMPLE II-9

ADDITION OF NUCLEATING AGENT

Except for employing 2000 ppm of NA-11 available from DENKASHA instead of 5000 ppm of GELOL MD available from SHINNIPPON RIKAGAKUSHA, the method similar to that in Example II-7 was employed. The results are shown in Table II-4.

EXAMPLE II-10

Effect of Modifier

Polypropylene E105 GM manufactured by IDEMITSU SEKIYU KAGAKU was combined with the pellet obtained in Example II-1 and extruded by a single-screw extruder (manufactured by TSUKADA JUKISEISAKUSHO: Model TLC35-20) to granulate into a pellet. The physical characteristics were evaluated similarly as in Example II-1 (4). The results are shown in Table II-5.

EXAMPLE II-11

Effect of Modifier

Except for changing the ratio of the pellet obtained in Example II-1 into 60% by weight, the procedure similar to that in Example II-10 was employed. The results are shown in Table II-5

EXAMPLE II-12

Effect of Modifier

Except for changing the ratio of the pellet obtained in Example II-1 into 30% by weight, the procedure similar to that in Example II-10 was employed. The results are shown in Table II-5.

COMPARATIVE EXAMPLE II-3

Polypropylene E105 GM manufactured by IDEMITSU SEKIYU KAGAKU was subjected to the evaluation of the physical characteristics similarly as in Example II-1 (4). The results are shown in Table II-5.

COMPARATIVE EXAMPLE II-4

Except for combining 50% by weight of the polymer obtained in Comparative II-2 with Polypropylene E105 GM manufactured by IDEMITSU SEKIYU KAGAKU, the procedure similar to that in Example II-10 was employed. The results are shown in Table II-5.

TABLE II-2

| Item | Example 1 | Example 2 | Example 3 | Example 4 | Comparative Example 1 | Comparative Example 2 |
|---|---|---|---|---|---|---|
| Comonomer content, % by mole | — | — | — | 10 | — | — |
| W25, % by weight | 93 | 90 | 80 | 56 | 30 | 99 |
| H25, % by weight | 17 | 15 | 15 | 42 | 6 | 100 |
| Tm ° C. | nd | nd | 70 | 76 | 159 | nd |
| ΔH J/mol | nd | nd | 7 | 19 | 61 | nd |
| 6 × (Tm−140) | nd | nd | −420 | −384 | 111.6 | nd |

TABLE II-2-continued

| Item | Example 1 | Example 2 | Example 3 | Example 4 | Comparative Example 1 | Comparative Example 2 |
|---|---|---|---|---|---|---|
| % mmmm, % by mole | 41 | 41 | 46 | — | 65 | 2 |
| P, % by mole | — | — | — | 76 | — | — |
| rrrr/(1−mmmm) | 0.04 | 0.04 | 0.04 | — | 0.23 | 0.11 |
| Mw/Mn | 2.4 | 2.0 | 2.5 | 6.1 | 2.7 | 2.2 |
| [η] dl/g | 2.5 | 4.4 | 2.5 | 0.7 | 2.1 | 1.9 |
| % 2, 1 insertion, % by mole | 0 | 0 | 0 | — | 0 | 4.4 |
| % 1, 3 insertion, % by mole | 0 | 0 | 0 | — | 0 | 0 |
| Boiling diethylether extract % by weight | 30 | 29 | 25 | 56 | 12 | 63 |
| Tc ° C. | nd | nd | nd | 18 | 104 | nd |

(NOTE)
n.d: Not detected,

Example 1 means Example II-1. The same applies analogously hereinafter.

TABLE II-3

| Item | Example 1 | Example 2 | Example 3 | Example 4 | Comparative Example 1 | Comparative Example 2 | Reference Example |
|---|---|---|---|---|---|---|---|
| Tensile modulus Mpa | 31 | 34 | 52 | 60 | 330 | 2 | 85 |
| Internal haze % | 4 | 3 | 4 | 10 | 60 | 4 | 10 |
| % Elasticity recovery % | 69 | 78 | 33 | 28 | No recovery | 79 | No recovery |
| Anti-blocking ability kg/cm$^2$ | 5 | 5 | 4 | 6 | 0 | No peeling | 3 |
| Izod impact strength KJ/m$^2$ | 2.8 | 3.4 | 2.5 | 5.0 | 2.1 | 4.3 | No break |

(Note)
Izod impact strength: Determined at −5° C. with notches being formed

TABLE II-4

| Item | Example 1 | Example 5 | Example 6 | Example 7 | Example 8 | Example 9 |
|---|---|---|---|---|---|---|
| Nucleating agent | — | GELOL MD | GELOL MD | GELOL MD | GELOL MD | NA-11 |
| Nucleating agent level ppm | — | 1000 | 2000 | 5000 | 10000 | 2000 |
| Tm ° C. | nd | nd | 64 | 65 | 64 | 64 |
| Tc ° C. | nd | nd | nd | nd | nd | nd |
| Tensile modulus Mpa | 30 | 32 | 35 | 41 | 42 | 32 |
| Internal haze % | 4 | 5 | 5 | 5 | 4 | 5 |
| % Elasticity recovery % | 69 | 70 | 72 | 75 | 76 | 76 |
| Izod impact strength KJ/m$^2$ | 2.8 | 3.2 | 2.9 | 5.0 | 2.9 | 7.1 |

(NOTE)
Izod impact strength: Determined at −5° C. with notches being formed

TABLE II-5

| Item | Example 10 | Example 11 | Example 12 | Comparative Example 1 | Comparative Example 3 | Comparative Example 4 |
|---|---|---|---|---|---|---|
| Tensile modulus Mpa | 190 | 230 | 560 | 330 | 1500 | 240 |
| Internal haze % | 33 | 43 | 54 | 60 | 44 | 71 |
| % Elasticity recovery % | 20 | 1 | No recovery | No recovery | No recovery | No recovery |
| Izod impact strength KJ/m$^2$ | 2.5 | 2.4 | 1.9 | 2.1 | 1.9 | 1.6 |

(NOTE)
Izod impact strength: Determined at −5° C. with notches being formed

[Third Invention]

A method for evaluating the resin characteristics and the physical characteristics of a polymer according to the invention are described below.

(1) Intrinsic Viscosity [η]

Measurement was made by the method described in the first invention.

(2) % Pentad and % Abnormal Insertion

Measurement was made by the method described in the second invention.

(3) Comonomer Unit Content (% by Mole) in Copolymer

Measurement was made by the method described in the second invention.

(4) Molecular Weight Distribution (Mw/Mn)

Measurement was made by the method described in the first invention.

(5) DSC Analysis

Measurement was made by the method described in the second invention.

(6) Temperature-Raising Fractional Chromatography

Measurement was made by the method described in the first invention.

(7) Amount of Components Dissolved Out into Hexane (H25)

Measurement was made by the method described in the second invention.

(8) Boiling Diethylether Extract

Measurement was made by the method described in the first invention.

(9) Frequency Distribution Determination of Melt Viscoelasticity

A value of (η*)(Pa·s) is obtained using a rotary rheometer (ARES) manufactured by RHEOMETRIX together with a parallel plate (25 mm in diameter, 1mm in gap) at the temperature of 230° C. and at the initial strain of 20% or less.

(10) Tensile Modulus

Measurement was made by the method described in the second invention.

EXAMPLE III-1

Propylene Homopolymer (1) Catalyst Preparation (1,2'-dimethylsilylene)(2,1'-dimethylsilylene)-bis(3-n-butylindenyl)zirconium dichloride A Schlenk's bottle receives 0.83 g (2.4 mmol) of (1,2'-dimethylsilylene) (2,1'-dimethylsilylene)-bis(indene) and 50 mL of ether. The mixture is cooled to −78° C. and combined with 3.1 mL (5.0 mmol) of n-BuLi (1.6 M solution in hexane) and then stirred at room temperature for 12 hours. The solvent is distilled off to obtain a solid which is washed with 20 mL of hexane to obtain 1.1 g (2.3 mmol) of a lithium salt as an ether adduct. This lithium salt is dissolved in 50 mL of THF and cooled to −78° C. 0.57 mL (5.3 mmol) of n-butyl bromide is added dropwise slowly and the mixture is stirred at room temperature for 12 hours. After distilling the solvent off followed by extraction with 50 mL of hexane, followed by removing the solvent, 0.81 g (1.77 mmol) of (1,2'-dimethylsilylene) (2,1'-dimethylsilylene)-bis(3-n-butylindene) (yield: 74%).

Subsequently, 0.81 g (1.77 mmol) of (1,2'-dimethylsilylene)(2,1'-dimethylsilylene)-bis(3-n-butylindene) obtained above and 100 mL of ether are placed in a Schlenk's bottle. The mixture is cooled to −78° C. and combined with 2.7 mL (4.15 mmol) of n-BuLi (1.54M solution in hexane) and then stirred at room temperature for 12 hours. The solvent is distilled off to obtain a solid which is washed with hexane to obtain 0.28 g (1.43 mmol) of a lithium salt as an ether adduct.

Under nitrogen flow, the lithium salt obtained above is dissolved in 50 mL of toluene. The mixture is cooled to −78° C. and treated dropwise with 0.33 g (1.42 mmol) of zirconium tetrachloride suspended in toluene (50 mL) which has previously been cooled to −78° C. After dropwise treatment, the mixture is stirred at room temperature for 6 hours. Subsequently the mixture is filtered and the solvent of the filtrate is distilled off. Recrystallization from dichloromethane yielded 0.2 g (0.32 mmol) of (1,2'-dimethylsilylene) (2,1'-dimethylsilylene)-bis(3-n-butylindenyl)zirconium dichloride (yield 22%).

The results of $^1$H-NMR (90 MHz, CDCl3) analysis are as follows: δ 0.88, 0.99 (12H, dimethylsilylene), 0.7-1.0. 1.1-1.5 (18H, n-Bu), 7.0-7.6 (8H, benzene ring proton).

(2) Propylene Homopolymerization

A 1 L stainless steel, pressure-resistant autoclave fitted with a stirrer was heated to 80° C. and dried under reduced pressure thoroughly, and then it was allowed to be at atmospheric pressure with a dry nitrogen and allowed to cool to room temperature. Under dry nitrogen flow, 400 mL of dried deoxygenated heptane and 0.5 mL (1.0 mmol) of a solution of triisobutylaluminium (2.0 M) in heptane were added and stirred at 350 rpm for a while. On the other hand, a thoroughly nitrogen-purged 50 mL Schlenk's bottle were charged under nitrogen flow with toluene (10 mL) and a solution of triisobutylaluminiumheptane (2M, 0.5 mL, 1.0 mmol) and then with a solution of a methyl aluminoxane in toluene (1.43 M, 0.35 mL, 0.5 mmol) and a slurry of (1,2'-dimethylsilylene) (2,1'-dimethylsilylene)-bis(3-n-butylindenyl)zirconium dichloride obtained in Step (1) described above in heptane (5 μmol/mL, 0.1 mL, 0.5 μmol), which were stirred at room temperature for 5 minutes. The catalyst slurry was placed rapidly in the autoclave.

(First Step Polymerization)

Subsequently, the stirring was initiated at 400 rpm, and the propylene pressure was raised slowly to 8.0 kg/cm$^2$ as a total pressure, and at the same time the temperature was raised slowly to 70° C. The polymerization was effected for 20 minutes.

(Second Step Polymerization)

Subsequently, the temperature was lowered to 30° C. over a period of 5 minutes, and after the completion of additional 35-minute polymerization, unreacted propylene was removed by depressurization. The reaction mixture was poured into 2 L of methanol to precipitate polypropylene, which was filtered and dried to obtain 17 g of polypropylene. The resin characteristics and the physical characteristics described above were determined and the results are shown in Table III-1. In this table, Example 1 means Example III-1. The same applies analogously to Example 2 or later as well as Comparatives. [Example III-2] Propylene homopolymerization (Hydrogenation upon second step polymerization)

(Catalyst Preparation)

The method similar to that in Example III-1 was employed.

(First Step Polymerization)

Subsequently, the stirring was initiated at 400 rpm, and the propylene pressure was raised slowly to 8.0 kg/cm² G as a total pressure, and at the same time the temperature was raised slowly to 50° C. The polymerization was effected for 20 minutes.

(Second Step Polymerization)

Subsequently, unreacted propylene was depressurized to 1.0 kg/cm² G. Hydrogen was then introduced at the pressure of 0.3 kg/cm² G. The propylene pressure was then raised slowly to 8.0 kg/cm² G as a total pressure, and the temperature was raised slowly to 70° C., and the polymerization was effected for 30 minutes. After completion of the reaction, unreacted propylene was removed by depressurization. The reaction mixture was poured into 2 L of methanol to precipitate polypropylene, which was filtered and dried to obtain 32 g of polypropylene. The resin characteristics and the physical characteristics described above were determined and the results are shown in Table III-1.

EXAMPLE III-3

Propylenic Copolymer (1) Preparation of (1,2'-ethylene) (2,1'-ethylene)-bis(3-methylindenyl)zirconium dichloride The method similar to that in Example I-1 in the first invention was employed.

(2) Propylene/ethylene copolymerization

A 2 L stainless steel autoclave received 1.2 L of toluene, 1.5 mmol of triisobutylaluminium, 10 (Al) mmol of a methyl aluminoxane (Albemarle) and 20 μmol of (1,2'-ethylene)(2,1'-ethylene)bis(3-methylindenyl)zirconium dichloride and the mixture was warmed to 30° C., and then an ethylene/propylene gas mixture (molar ratio of ethylene/propylene=1/100) was introduced. An excessive gas was vented so that the total pressure became 7.0 kg/cm² G, and the polymerization was effected for 60 minutes while keeping a constant gas composition in the reaction system, and then the content was recovered and dried under reduced pressure to obtain a propylenic copolymer. The evaluation of the resin characteristics and the physical characteristics described above were examined and the results are shown in Table III-1.

COMPARATIVE III-1

Single Step Polymerization of Propylene (Hydrogenation)

(Catalyst Preparation)

The method similar to that in Example III-1 was employed.

(Polymerization)

Subsequently, hydrogen was introduced until the pressure became 1.0 kg/cm² G, and the stirring was initiated at 400 rpm. Then the propylene pressure was raised slowly to 8.0 kg/cm² G as a total pressure, and at the same time the temperature was raised slowly to 50° C., and the polymerization was effected for 60 minutes. After completion of the reaction, unreacted propylene was removed by depressurization. The reaction mixture was poured into 2 L of methanol to precipitate polypropylene, which was filtered and dried to obtain 38 g of polypropylene. The resin characteristics and the physical characteristics described above were determined and the results are shown in Table III-1.

COMPARATIVE III-2

Propylene Homopolymer (Non-Hydrogenation)

(Catalyst Preparation)

The method similar to that in Example III-1 was employed.

(Polymerization)

Subsequently, the stirring was initiated at 400 rpm. Then the propylene pressure was raised slowly to 8.0 kg/cm² G as a total pressure, and at the same time the temperature was raised slowly to 30° C., and the polymerization was effected for 60 minutes. After completion of the reaction, unreacted propylene was removed by depressurization. The reaction mixture was poured into 2 L of methanol to precipitate polypropylene, which was filtered and dried to obtain 13 g of polypropylene. The resin characteristics and the physical characteristics described above were determined and the results are shown in Table III-1.

TABLE III-1

|  | Item | Example 1 | Example 2 | Example 3 | Comparative Example 1 | Comparative Example 2 |
|---|---|---|---|---|---|---|
| Resin characteristics/ physical characteristics | Comonomer content, % by mole | — | — | 10 | — | — |
| | H25, % by weight | 15 | 17 | 42 | 17 | 15 |
| | Tm ° C. | nd | nd | 76 | nd | nd |
| | ΔH J/mol | nd | nd | 19 | nd | nd |
| | 6 × (Tm−140) | — | — | −384 | — | — |
| | % mmmm, % by mole | 40 | 41 | — | 41 | 42 |
| | P, % by mole | — | — | 76 | — | — |
| | rrrr/(1−mmmm) | 0.04 | 0.04 | — | 0.04 | 0.04 |
| | Mw/Mn | 9.6 | 4.5 | 6.1 | 2.1 | 2.2 |
| | [η] dl/g | 10.3 | 2.8 | 0.7 | 3.0 | 13.7 |
| | W25, % by weight | 94 | 93 | 56 | 93 | 94 |
| | η* Pa · s | 1590 | 920 | 840 | 1230 | 2930 |
| | 159η + 743 | 2381 | 1185 | 854 | 1218 | 2921 |
| | % 2, 1 insertion, % by mole | 0 | 0 | 0 | 0 | 4.4 |
| | % 1, 3 insertion, % by mole | 0 | 0 | 0 | 0 | 0 |
| | Boiling diethylether extract, % by weight | 25 | 30 | 56 | 31 | 23 |
| | Tc ° C. | nd | nd | nd | nd | nd |
| | Tensile modulus MPa | 37 | 30 | 60 | 26 | 47 |

(NOTE)
nd: Not detected

[Fourth Invention]

A method for evaluating the resin characteristics and the physical characteristics of a polymer according to the invention are described below.

(1) Intrinsic Viscosity [η]

Measurement was made by the method described in the second invention.

(2) % Pentad and % Abnormal Insertion

Measurement was made by the method described in the second invention.

(3) Comonomer Unit Content (% by Mole) in Copolymer

Measurement was made by the method described in the second invention.

(4) Molecular Weight Distribution (Mw/Mn)

Measurement was made by the method described in the first invention.

(5) DSC Analysis

Measurement was made by the method described in the second invention.

(6) Temperature-Raising Fractional Chromatography

Measurement was made by the method described in the first invention.

(7) Tensile Modulus

Measurement was made by the method described in the second invention.

(8) Internal Haze

Measurement was made by the method described in the second invention.

(9) % Elasticity Recovery

The method described in JP-A-5-132590 was followed. Thus, a propylenic polymer was press-molded and a JIS No. 2 dumb-bell test specimen was prepared. The constant-width region of the dumb-bell was marked at 25 mm interval, which was designated as L0. The specimen was stretched using a tensile test device from 80 mm to 160 mm of the inter-chuck distance at the stretching speed of 50 mm/min, and then the inter-chuck distance was allowed to become the initial length, and then after one minute the distance between the marks was determined and designated as L1. A % elasticity recovery was calculated by the equation shown below. When the value obtained was zero then the result was judged as "No recovery".

$[(2L0-L1)/L0] \times 100$

L0: Initial distance between marks on dumb-bell
L1: Distance between marks on dumb-bell after stretching

(10) Anti-Blocking Ability

A propylenic polymer was press-molded to obtain a test piece, which was bound in the conditions described below and examined for its peeling strength by a tensile test device.

Test piece: 15 cm×62.5 mm×2 mm

Binding conditions: Bound at 40° C. over the area of 15 mm×31 mm under the pressing load of 0.7 kg for 3 hours.

Shear peeling conditions: Crosshead speed of 50 mm/min

(11) Izod Impact Strength

A propylenic polymer was press-molded to obtain a test piece which was subjected to the test in accordance with JIS K-7110 with the test piece thickness of 3 mm at the ambient temperature of −5° C.

(12) Amount of Components Dissolved Out into Hexane (H25)

Measurement was made by the method described in the second invention.

(13) Boiling Diethylether Extract

Measurement was made by the method described in the first invention.

(14) Density

A density was determined in accordance with JIS K7112.

(15) Glass transition temperature (Tg)

A glass transition temperature (Tg) was determined in accordance with JIS K7198 (Tensile oscillation method) under the conditions specified below.

Frequency 10 Hz
Load 300 g
Temperature range −140° C. to 80° C.

(16) Vicat Softening Point

A Vicat softening point was determined in accordance with JIS K7206.

EXAMPLE IV-1

(1) Preparation of Methyl Aluminoxane/Silica Carrier

A thoroughly nitrogen-purged 500 mL glass contained fitted with a dropping funnel was charged with toluene (500 mL) and then with 4.04 g of a silica (indicated also as $SiO_2$) manufactured by FUJI SILICIA which had previously been sintered at 200° C. for 3 hours under nitrogen flow and the mixture was stirred at 400 rpm. At 0° C., a solution (29.8 mL) of a methyl aluminoxane (indicated also as MAO) manufactured by Albemarle in toluene was added slowly over 45 minutes. The stirring was continued further for 1 hour at 0° C., 1 hour at room temperature and then 4 hours at 0.80° C. After completion of the reaction, the mixture was allowed to cool to 60° C. at which point the supernatant was washed by means of decantation three times with toluene (200 mL) and three times with heptane (200 mL) to obtain an intended product. The product was stored as a heptane slurry in a Schlenk's bottle. The amount of aluminum supported was 12.06% when determined by an UV quantification method.

(2) Synthesis of (Dimethylsilylene) 2 (3-N-Butylindenyl)2 Zirconium Dichloride

The method similar to that described in Example II-1 in the second invention was employed.

(3) Synthesis of rac-Me2 Si (2-Et-4,5-BenzInd)2ZrCl2 [racemi-dimethylsilylene bis(2-ethyl-4,5-benzoindenyl)zirconium dichloride]

According to the description in JP-A-6-184179 and JP-A-7-196734, the procedures of (I) to (VI) were employed for the synthesis.

Synthesis of diethyl-ethyl(2-naphthylmethyl)malonate (I)

7.63 g (320 mmol) of sodium is dissolved in 200 mL of absolute ethanol with heating, and treated dropwise with 58.1 ml (310 mmol) of diethylethyl malonate at room temperature. A solution of 64 g (310 mmol) of 2-bromonaphthalene dissolved in 300 mL of ethanol is added dropwise slowly at 0° C., and the reaction mixture is heated under reflux for 5 hours. This is poured into an ice water, and extracted with ethyl acetate. The organic phase is dried over anhydrous sodium sulfate and the solvent is distilled off. To the oily residue, 50 mL of hexane was added and cooled to 0° C. to obtain 7.12 g of Compound (I) (yield: 70%).

Synthesis of 2-ethyl-3-naphthylpropionic acid (II)

A solution of 33.8 g (603 mmol) of potassium hydroxide dissolved in 100 mL of water is added dropwise to 49.3 g (150 mmol) of Compound (I) in 150 mL of ethanol, and the reaction mixture is heated under reflux for 4 hours. After distilling the solvent off, the solid obtained is combined with ethyl acetate and water and adjusted at pH1 with hydrochloric acid. After drying over anhydrous magnesium sulfate, the solvent of the organic phase is distilled off. The residue is combined with hexane and stirred. The brown solid thus obtained is placed in a flask, which is heated at 175° C. After heating until termination of gas evolution followed by cooling to room temperature, 30 g of Compound (II) was obtained as a brown solid (yield: 87%)

Synthesis of 2-ethyl-6,7-benzoindan-1-on (III)

30 g (131 mmol) of Compound (II) is admixed with 29 mL of thionyl chloride, and the mixture is heated under reflux for 30 minutes. Subsequently, an excessive thionyl chloride is distilled off under reduced pressure. To the residue, 50 mL of methylene chloride is added. The solution is added dropwise slowly to a suspension of 35 mg (262 mmol) of aluminum trichloride in 100 mL of methylene chloride, and after completion of the addition the mixture is further heated under reflux for 30 minutes. The mixture is poured onto an ice, and extracted with methylene chloride. The organic phase is dried over anhydrous sodium sulfate and the solvent is distilled off. The brackish-brown oil is subjected to a column chromatography on silica gel using hexane/ethyl acetate=8/2 as an eluent to obtain 11.3 g of Compound (III) (yield: 41%).

Synthesis of 2-ethyl-4,5-benzoindene (IV)

In 400 mL of a solvent mixture of THF/methanol (2:1), 11.3 g (53.7 mmol) of indanone (III) is dissolved and admixed with 3.0 g (80.5 mmol) of sodium borohydride in portions. The reaction mixture is stirred for 12 hours at room temperature. The solution is poured onto an ice and hydrochloric acid is added. After extraction with ether, the organic phase is washed with water and dried over anhydrous sodium sulfate. After distilling the solvent off, an orange oil is dissolved in 300 mL of toluene, and the solution is heated together with 0.77 g (4.26 mmol) of p-toluenesulfonic acid at 80° C. for 15 minutes. After allowing to cool to room temperature followed by washing several times with water followed by drying over anhydrous sodium sulfate, the solvent is distilled off. The residue was subjected to a column chromatography on silica gel using hexane/ethyl acetate=20/1 as an eluent to obtain 6.2 g of Compound (IV) as a colorless oil (yield: 59%).

Synthesis of dimethylbis(2-ethyl-4,5-benzoindenyl)silane (V)

6.2 g (31.7 mmol) of indene (IV) is dissolved in 50 m of THF, and 20.7 mL (31.7 mmol, 1.53M solution in hexane) of n-butyllithium is added dropwise. The reaction mixture is heated under reflux for 1 hour. The solution is added dropwise to a solution of 1.93 g (15 mmol) of dimethyldichlorosilane in 10 mL of THF, and the mixture is heated under reflux for 6 hours. The reaction solution is hydrolyzed and extracted with ether. The organic phase is dried over anhydrous sodium sulfate and the solvent is distilled off. The residue is subjected to a column chromatography on silica gel using hexane/ethyl acetate 3% as an eluent to obtain 2.8 g of Compound (V) (yield: 41%)

Synthesis of rac-Me2 Si(2-Et-4,5-BenzInd)2ZrCl2 [racemi-dimethylsilylene bis(2-ethyl-4,5-benzoindenyl)zirconium dichloride] (VI)

2.8 g (6.3 mmol) of Compound (V) is admixed with 20 mL of THF and treated dropwise with 10.3 mL (15.8 mmol, 1.53 M solution in hexane) of n-butyllithium. The reaction mixture is stirred for 12 hours at room temperature. After distilling the solvent off, the residue is washed with hexane. The powder thus obtained is dried under reduced pressure. This is suspended in 25 mL of methylene chloride and combined with 1.5 g (6.3 mmol) of zirconium tetrachloride suspended in 25 mL of methylene chloride. The reaction mixture is stirred for 12 hours at room temperature, and the solvent is distilled off and the residue is extracted with 20 mL of toluene. The residue of the toluene extract is extracted with methylene chloride, and the extract is concentrated and stored in a refrigerator to obtain 1.3 g of a metallocene (VI) (yield: 35%).

(4) Preparation of Co-Supporting Catalyst

A thoroughly nitrogen-purged 50 mL Schlenk's tube was charged under nitrogen flow with heptane (5 mL) and tri-isobutylaluminium (2M, 0.25 mL, 0.5 mmol) followed by a slurry of MAO/SiO$_2$ carrier obtained above (0.37 mol/L, 13.6 mL, 5 mmol, as Al) in heptane and a slurry of bis-(dimethylsilylene)-bis-(3-n-butylindenyl)zirconium dichloride [(SiM2) (SiMe2) (3-n-BuInd)2ZrCl2] (5 µmol/mL, 2.5 mL, 12.5 µmol) in heptane, a slurry of dimethylsilylene-bis(2-ethyl-4,5-benzoindenyl)zirconium dichloride [SiMe2 (2-Et-4,5-BzInd)2ZrCl2] (10 µmol/mL, 0.25 mL, 2.5 µmol) in heptane, and stirred at room temperature for 30 minutes to obtain a co-supporting catalyst (1).

(5) Vapor Phase Polymerization of Propylene

A 5 L autoclave was charged with 100 g of a polypropylene powder (homo-PP, 720 µm of greater in particle size) as a catalyst dispersant and dried under vacuum for 20 minutes at 70° C. After allowing to be at an atmospheric pressure with nitrogen, triisobutylaluminium (2M, 1.25 mL, 25 mmol) was added under nitrogen flow with stirring (200 rpm). After stirring for 15 minutes, the co-supporting catalyst (1) prepared in Step (3) was added and the mixture was stirred for 5 minutes. Beginning at this time point (50° C., atmospheric pressure, 200 rpm), the temperature and the pressure were raised over 30 minutes to the reactor temperature of 70° C. and the propylene pressure of 28 kg/cm$^2$ G with stirring at 350 rpm, and then the vapor phase polymerization was continued further for 60 minutes. As a result, a powdery polymer undergoing no adhesion onto the wall was obtained. The yield was 260 g. The polymer thus obtained was extracted with diethylether as described above and the resin characteristics were measured. The results are shown in Table IV-1. In this table, Example 1 means Example IV-1. The same applies analogously to Example 2 or later as well as Comparatives.

EXAMPLE IV-2

(1) Preparation of Supporting Catalyst (1)

A thoroughly nitrogen-purged 50 mL Schlenk's tube was charged under nitrogen flow with heptane (5 mL) and tri-isobutylaluminium (2M, 0.25 mL, 0.5 mmol) followed by a slurry of MAO/SiO2 carrier obtained in Example IV-1, Step (1) (0.37 mol/L, 13.6 mL, 5 mmol, as Al) in heptane and a slurry of dimethylsilylene-bis(2-ethyl-4,5-benzoindenyl)zirconium dichloride [SiMe2 (2-Et-4,5-BzInd)2ZrCl2] obtained in Example IV-1, Step (3) (10 µmol/mL, 0.25 mL, 2.5 µmol) in heptane, and stirred at room temperature for 30 minutes to obtain a co-supporting catalyst (1).

(2) Vapor Phase Two-Step Polymerization Employing High Stereoregular Supported Metallocene Catalyst in First Step and Low Stereoregular Supported Metallocene Catalyst in Second Step <First Step Polymerization>

A 5 L autoclave was charged with 100 g of a polypropylene powder (homo-PP, 720 µm of greater in particle size) as a catalyst dispersant and dried under vacuum for 20 minutes at 70° C. After allowing to be at an atmospheric pressure with nitrogen, triisobutylaluminium (2M, 1.25 mL, 25 mmol) was added under nitrogen flow with stirring (200 rpm). After stirring for 15 minutes, the co-supporting catalyst (1) prepared in Step (1) was added and the mixture was stirred for 5 minutes. Beginning at this time point (50° C., atmospheric pressure, 200 rpm), the temperature and the pressure were raised over 30 minutes to the reactor temperature of 70° C. and the propylene pressure of 28 kg/cm$^2$ G with stirring at 350 rpm, and then the vapor phase polymerization was continued further for 20 minutes.

<Second Step Polymerization>

Subsequently, a thoroughly nitrogen-purged 50 mL Schlenk's tube was charged under nitrogen flow with toluene (10 mL) and a solution of triisobutylaluminium (2M, 0.25 mL, 0.5 mmol) in heptane followed by a slurry of MAO/SiO2 carrier obtained in Example IV-1, Step (1) (0.37 mol/L, 6 mL, 2.5 mmol, as Al) in heptane and a slurry of bis-(dimethylsilylene)-bis-(3-n-butylindenyl)zirconium dichloride [(SiM2)(SiMe2)(3-n-BuInd)2ZrCl2] obtained in Example IV-1, Step (2) (5 mmol/mL, 0.1 mL, 0.5 µmol) in heptane, and stirred at room temperature for 5 minutes to obtain a co-supporting catalyst (2). This solution was introduced in an autoclave using a catalyst-introducing tube. Then the polymerization was effected until the total pressure became 28 kg/cm$^2$ G at 70° C. for 30 minutes. As a result, a powdery polymer undergoing no adhesion onto the wall was obtained. The yield was 200 g. The polymer thus obtained was examined for the diethyl-characteristics described above were measured. The results are shown in Table IV-1.

EXAMPLE IV-3

(1) Preparation of Solid Catalyst Component

After purging a 5 L three-necked flask fitted with a stirrer with a nitrogen gas, 500 mL of dehydrated heptane and 160 g (1.4 M) of diethoxymagnesium were added. The mixture was heated to 40° C., combined with 28.5 mL (225 mM) of silicon tetrachloride, stirred for 20 minutes, and then admixed with 25.2 mL (127 mM) of diethyl phthalate. The solution was heated to 80° C. and treated dropwise with 461 mL (4.2 M) of titanium tetrachloride using a dropping funnel, and then stirred at the internal temperature of 110° C. for 2 hours to allow the catalyst to be supported. Thereafter, the catalyst was washed thoroughly with dehydrated heptane. 768 ml (7M) of titanium tetrachloride was further added and stirred at the internal temperature of 110° C. for 2 hours whereby effecting the second supporting procedure. Thereafter, the catalyst was washed thoroughly with dehydrated heptane to obtain Solid Component A (supported Ti content—3.0% by weight).

(2) Preliminary Polymerization of Solid Catalyst Component

A nitrogen-purged 5 L three-necked flask fitted with a stirrer was charged with a slurry of 60 g of the solid catalyst component (37.6 mM-Ti) obtained above in heptane and also with dehydrated heptane to make the entire volume 500 mL. The solution was stirred with being kept at 10° C., and combined with 24.8 mM of triethylaluminium and 12.4 mM of cyclohexylmethyldimethoxysilane. While still keeping the temperature at 10° C., a predetermined amount of propylene was allowed to be absorbed for 40 minutes, and the residual monomer was washed thoroughly with heptane with being purged with nitrogen, whereby obtaining 65 g of a preliminary polymerized catalyst B (seal level=0.083 g PP/g solid catalyst).

(3) Two-Step Slurry Polymerization of Propylene Employing Preliminarily Polymerized Mg—Ti-Based Catalyst in First Step and Low Stereoregular Metallocene Catalyst in Second Step <First Step Polymerization>

A 1 L stainless steel autoclave fitted with a stirrer was dried thoroughly, purged with nitrogen, and then charged with 400 ml of dehydrated heptane. 2 mM of triethylaluminium and 8.6 mg of Catalyst B were added, and hydrogen was introduced at 1 kg/cm$^2$ G, and then propylene was introduced with raising the temperature and the pressure to 80° C. and 8 Kg/cm$^2$ G as a total pressure, followed by effecting polymerization for 20 minutes. Thereafter, the temperature was lowered to 50° C. and the system was depressurized.

<Second Step Polymerization.

Subsequently, a thoroughly nitrogen-purged 50 mL Schlenk's tube was charged under nitrogen flow with toluene (10 mL) and a solution of triisobutylaluminium in heptane (2M, 0.5 mL, 1.0 mmol) followed by a solution of MAO in toluene (1.43M, 0.35 mL, 0.5 mmol) and a slurry of bis-(dimethylsilylene)-bis-(3-n-butylindenyl)zirconium dichloride [(SiMe$_2$) (SiMe$_2$) (3-n-BuInd)2ZrCl$_2$] in heptane (5 µmol/mL, 0.5 mL, 2.5 µmol), and stirred at room temperature for 5 minutes to obtain Catalyst (3). This solution of catalyst was fed to an autoclave using a catalyst-introducing tube. The pressure of propylene was raised slowly to 80 kg/cm$^2$ G as a total pressure, and the polymerization was effected at 70° C. for 40 minutes. After completion of the reaction, unreacted propylene was removed by depressurization. The reaction mixture was poured into 2 L of methanol to precipitate polypropylene, which was filtered and dried to obtain 21 g of polypropylene. The polymer thus obtained was extracted with diethylether as described above and the resin characteristics were measured. The results are shown in Table IV-1.

EXAMPLE IV-4

Two-Step Vapor Phase Polymerization of Propylene Employing Preliminarily Polymerized Mg—Ti-Based Catalyst in First Step and Low Stereoregular Metallocene Catalyst in Second Step <First Step Polymerization>

A 5 L autoclave was charged with 30 g of a polypropylene powder (homo-PP, 720 µm of greater in particle size) as a catalyst dispersant and dried under vacuum for 20 minutes at 70° C. After allowing to be at an atmospheric pressure with nitrogen, triethylaluminium (2M, 1.8 mL, 3.6 mmol) was added under nitrogen flow with stirring (200 rpm) After stirring for 15 minutes, the reaction system was depressurized. Thereafter, hydrogen was introduced at 3 kg/cm$^2$ G, and propylene gas was introduced until the total pressure became 28 kg/cm$^2$ G. Then a mixture of heptane (10 mL), triethylaluminium (2M, 0.2 mL, 0.4 mmol) and Catalyst B (17.3 mg, Ti:0.01 mmol) was added via a catalyst-introducing tube, and the vapor phase polymerization was effected for 20 minutes at 400 rpm.

<Second Step Polymerization>

Subsequently, the solution of Catalyst (3) prepared similarly as in Example IV-3, Step (3) was placed in the autoclave. The polymerization was effected further for 40 minutes at 70° C. and the total pressure of 28 kg/cm$^2$ G. As a result, a powdery polymer undergoing no adhesion onto the wall was obtained. The yield was 270 g. The polymer thus obtained was extracted with diethylether as described above and the resin characteristics were measured. The results are shown in Table IV-1.

EXAMPLE IV-5

Two-Step Slurry Polymerization of Propylene Employing High Stereoregular Metallocene Catalyst in First Step and Low Stereoregular Metallocene Catalyst in Second Step <First Step Polymerization>

A 1 L stainless steel, pressure-resistant autoclave fitted with a stirrer was heated to 80° C. and dried under reduced pressure thoroughly, and then it was allowed to be at atmospheric pressure with a dry nitrogen and allowed to cool to room temperature. Under dry nitrogen flow, 400 mL of dried deoxygenated heptane and a solution of triisobutylaluminium in heptane (2.0M, 0.5 mL, 1.0 mmol) were added and stirred at 350 rpm for a while. On the other hand, a thoroughly nitrogen-purged 50 mL Schlenk's bottle were charged under nitrogen flow with toluene (10 mL) and a solution of triisobutylaluminiuminheptane (2M, 0.5 mL, 1.0 mmol) and then with a solution of a MAO in toluene (1.43 M, 0.35 mL, 0.5 mmol) and a slurry of dimethylsilylene-bis-(2-ethyl-4,5-benzoindenyl)zirconium dichloride [SiMe2 (2-Et-4,5-BzInd) 2ZrCl2] obtained in Example IV-1, Step (3) in heptane (1 µmol/mL, 0.1 mL, 0.1 µmol), which were stirred at room temperature for 5 minutes. The catalyst slurry was placed rapidly in the autoclave. Subsequently, the stirring was initiated at 1200 rpm, and the propylene pressure was raised slowly to 8.0 kg/cm$^2$ G as a total pressure, and at the same time the temperature was raised slowly to 50° C. The polymerization was effected for 20 minutes. Subsequently, unreacted propylene was removed by depressurization.

(Second Step Polymerization)

A solution of Catalyst (3) prepared similarly as in Example IV-3, Step (3) was placed in the autoclave. Then the propylene pressure was raised slowly to 8.0 kg/cm$^2$ G as a total pressure to effect polymerization for 40 minutes at 50° C. After completion of the reaction, unreacted propylene was removed by depressurization. The polymer thus obtained was poured into 2 L of methanol to precipitate polypropylene, which was filtered and dried to obtain 31 g of polypropylene. The polymer thus obtained was extracted with diethylether as described above and the resin characteristics were measured. The results are shown in Table IV-1.

EXAMPLE IV-6

Polymerization of Propylene Using Co-Catalyst

A 1 L stainless steel, pressure-resistant autoclave fitted with a stirrer was heated to 80° C. and dried under reduced pressure thoroughly, and then it was allowed to be at atmospheric pressure with a dry nitrogen and allowed to cool to room temperature. Under dry nitrogen flow, 400 mL of dried deoxygenated heptane and 1.0 mL (2.0 mmol) of a solution of triisobutylaluminium in heptane (2.0M) were added and stirred at 350 rpm for a while. On the other hand, a thoroughly nitrogen-purged 50 mL Schlenk's bottle were charged under nitrogen flow with toluene (10 mL) and a solution of triisobutylaluminium in heptane (2M, 0.5 mL, 1.0 mmol) and then with a solution of an MAO in toluene (1.43 M, 0.35 mL, 0.5 mmol), an slurry of bis-(dimethylsilylene)-bis-(3-n-butylindenyl)zirconium dichloride [(SiM2)(SiMe2)(3-n-BuInd) 2ZrCl2] obtained in Example IV-1, Step (2) in heptane (5 µmol/mL, 0.1 mL, 0.5 µmol), and a slurry of dimethylsilylene-bis-(2-ethyl-4,5-benzoindenyl)zirconium dichloride [SiMe2 (2-Et-4,5-BzInd)2ZrCl2] obtained in Example IV-1, Step (3) in heptane (1 µmol/mL, 0.1 mL, 0.1 µmol), which were stirred at room temperature for 5 minutes. The catalyst slurry was placed rapidly in the autoclave.

Subsequently, the stirring was initiated at 1200 rpm, and the propylene pressure was raised slowly to 8.0 kg/cm$^2$ as a total pressure, and at the same time the temperature was raised slowly to 50° C. The polymerization was effected for 20 minutes. After completion of the reaction, unreacted propylene was removed by depressurization. The reaction mixture was poured into 2 L of methanol to precipitate polypropylene, which was filtered and dried to obtain 22 g of polypropylene. The polymer thus obtained was extracted with diethylether as described above and the resin characteristics were measured. The results are shown in Table IV-1.

EXAMPLE IV-7

Propylenic Copolymer (1) Preparation of (1,2'-ethylene) (2,1'-ethylene)-bis(3-methylindenyl)zirconium dichloride The method described in Example I-1 in the first invention was employed.

(2) Propylene/Ethylene Copolymerization

A 2 L stainless steel autoclave received 1.2 L of toluene, 1.5 mmol of triisobutylaluminium, 10 (Al) mmol of a methyl aluminoxane (manufactured by Albemarle) and 20 µmol of (1,2'-ethylene) (2,1'-ethylene)bis(3-methylindenyl)zirconium dichloride and the mixture was warmed to 30° C., and then an ethylene/propylene gas mixture (molar ratio of ethylene/propylene=1/100) was introduced. An excessive gas was vented so that the total pressure became 7.0 kg/cm$^2$ G, and the polymerization was effected for 60 minutes while keeping a constant gas composition in the reaction system, and then the content was recovered and dried under reduced pressure to obtain a propylenic copolymer. The polymer thus obtained was extracted with diethylether as described above and the resin characteristics were measured. The results are shown in Table IV-1.

EXAMPLE IV-8

(1) Propylene Polymerization

A 10 L stainless steel autoclave received 6 L of heptane, 6 mmol of triisobutylaluminium, and a catalyst component obtained by bringing 5 mmol of a methyl aluminoxane (manufactured by Albemarle) into preliminary contact with 5 µmol of (1,2'-dimethylsilylene)(2,1'-dimethylsilylene)bis(3-n-butylindenyl)2 zirconium dichloride in toluene for 5 minutes. After introducing hydrogen at 0.5 kg/cm$^2$ G, a propylene gas was introduced until the total pressure became 8.0 kg/cm$^2$, and the propylene gas was supplied using a pressure controller to keep a constant pressure during polymerization. After polymerizing at 50° C. for 30 minutes, the content was recovered and dried under reduced pressure to obtain a propylene homopolymer.

(3) Formulation and Kneading

30 Parts by weight of the polypropylene homopolymer obtained above and 70 parts by weight of a PE-based resin, EG8100 available from Dow Chemical (glass transition temperature Tg=−100° C.) were combined with the following additives and extruded by a single-screw extruder (TSUKADAJUKISEISAKUSHO: Model TLC35-20) to granulate into a pellet.

(Formulation of Additives)

Phenolic antioxidant: IRGANOX 1010 available from Ciba Specialty Chemicals, 1000 ppm Phosphorus-based antioxidant: IRGAPHOS 168 available from Ciba Specialty Chemicals: 1000 ppm (4) Evaluation of Resin Characteristics and Physical Characteristics Evaluation was made by the methods described above. The results obtained are shown in Tables VI-2 and VI-3.

EXAMPLE IV-9

Resin Blend

The procedure similar to that in Example IV-8 was employed except for changing the amounts of the propylene homopolymer of Example IV-8 and the PE-based resin, EG8100 available from Dow Chemical (glass transition temperature Tg=−100° C.), to 60 parts by weight and 40 parts by weight, respectively. The results obtained are shown in Tables VI-3.

EXAMPLE IV-10

Resin Blend

The procedure similar to that in Example IV-8 was employed except for using 30 parts by weight of the propylene homopolymer of Example IV-8, 40 parts by weight of Polypropylene E105GM available from IDEMITSU SEKIYU KAGAKU (Tc=110° C.) and 40 parts by weight a PE-based resin, EG8100 available from Dow Chemical (glass transition temperature Tg=−100° C.). The results obtained are shown in Tables VI-3.

TABLE IV-1

| | Item | Example 1 | Example 2 | Example 3 | Example 4 | Example 5 | Example 6 | Example 7 |
|---|---|---|---|---|---|---|---|---|
| Entire polymer | Comonomer content, % by mole | — | — | — | — | — | — | 10 |
| | [η] dl/g | 2.6 | 2.1 | 1.4 | 2.4 | 3.2 | 3.4 | 0.7 |
| | Boiling diethylether extract, % by weight | 25 | 19 | 9 | 22 | 27 | 15 | 56 |
| Diethylether extract components | % mmmm, % by mole | 40 | 39 | 41 | 39 | 42 | 39 | — |
| | P, % by mole | — | — | — | — | — | — | 76 |
| | rrrr/(1−mmmm) | 0.04 | 0.04 | 0.04 | 0.04 | 0.04 | 0.04 | — |
| | W25, % by weight | 95 | 96 | 94 | 95 | 94 | 95 | 56 |
| | Mw/Mn | 2.3 | 2.2 | 2.4 | 2.2 | 2.3 | 2.3 | 6.1 |
| | [η] dl/g | 2.6 | 2.5 | 3.9 | 2.6 | 4.1 | 3.8 | 0.8 |
| | Tm ° C. | nd | nd | nd | nd | nd | nd | 76 |
| | ΔH J/mol | nd | nd | nd | nd | nd | nd | 19 |
| | Tc ° C. | nd | nd | nd | nd | nd | nd | 18 |
| | % 2,1 insertion, % by mole | 0 | 0 | 0 | 0 | 0 | 0 | — |
| | % 1,3 insertion, % by mole | 0 | 0 | 0 | 0 | 0 | 0 | — |

(NOTE)
nd: Not detected

TABLE IV-2

| Propylene homopolymer produced in Example 8(a) | |
|---|---|
| Item | (a) |
| Comonomer content, % by mole | — |
| W25, % by weight | 93 |
| H25, % by weight | 17 |
| Tm ° C. | nd |
| ΔH J/mol | nd |
| 6 × (Tm − 140) | — |
| [η] dl/g | 2.5 |
| Boiling diethylether extract, % by weight | 30 |
| % mmmm, % by mole | 41 |
| P, % by mole | — |
| rrrr/(1 − mmmm) | 0.04 |
| Mw/Mn | 2.4 |
| % 2,1 insertion, % by mole | 0 |
| % 1,3 insertion, % by mole | 0 |
| Tc ° C. | nd |

(NOTE)
nd: Not detected

TABLE IV-3

| | Item | Example 8 | Example 9 | Example 10 |
|---|---|---|---|---|
| Formulation ratio | Component (a), % by weight | 30 | 60 | 30 |
| | EG8100, % by weight | 70 | 40 | 30 |
| | E105GM, % by weight | — | — | 40 |
| Resin composition | Comonomer content, % by mole | — | — | — |
| | [η] dl/g | 2.6 | 2.1 | 1.4 |
| | Boiling diethylether extract, % by weight | 25 | 19 | 9 |

TABLE IV-3-continued

| | Item | Example 8 | Example 9 | Example 10 |
|---|---|---|---|---|
| Physical characteristics | Tensile modulus MPa | 20 | 25 | 150 |
| | % Elasticity recovery % | 69 | 64 | 10 |
| | Izod impact strength KJ/m$^2$ | No break | No break | No break |
| | Vicat softening point ° C. | 42 | 50 | 90 |

(NOTE)
Izod impact strength: Determined at −30° C. with notches being formed

[Fifth Invention]

A method for evaluating the resin characteristics and the film performance in this invention are described below.

(1) Intrinsic Viscosity [η]

Measurement was made by the method described in the second invention.

(2) % Pentad and % Abnormal Insertion

Measurement was made by the method described in the second invention.

(3) Molecular Weight Distribution (Mw/Mn)

Measurement was made by the method described in the first invention.

(4) DSC Analysis

Measurement was made by the method described in the second invention.

(5) Temperature-Raising Fractional Chromatography

Measurement was made by the method described in the first invention.

(6) Tensile Modulus

Measurement was made by the method described in the first invention.

(7) Amount of Components Dissolved Out into Hexane (H25)

Measurement was made by the method described in the second invention.

"Film Qualification"

A film once formed was annealed at 40° C. for 24 hours and then conditioned at a temperature of 23±2° C. and a humidity of 50±10% for 16 hours or longer and subsequently qualified at the same temperature and humidity.

(1) Heat Seal Temperature and Heat Seal Strength

A test was conducted in accordance with JIS Z-1707. Typically, under the conditions specified below, a heat seal bar whose temperature was corrected as being read by a surface thermometer was used to seal a film which was then allowed to stand at room temperature overnight and examined for the peeling strength (heat seal strength) by a type-T peeling method at the peeling speed of 200 mm/min at room temperature. The heat seal temperature was defined as the temperature at which the peeling strength was 300 g/15 mm, and calculated on the basis of a curve of a seal strength vs peeling strength.

Sealing Conditions

Seal surface: Metal roll surface/metal roll surface

Seal area: 15×10 mm

Seal pressure: 2.0 kg/cm$^2$

Seal duration: 1 second

Seal temperature: Several temperatures over the range which include the heat seal temperature to be calculated later (2) Haze A test was conducted in accordance with JIS K-7105.

(3) Tensile Modulus

A tensile test was conducted under the conditions specified below in accordance with JIS K-7127.

Crosshead speed: 500 mm/min

Load cell: 10 kg

Direction: Machine direction (4) Frequency Distribution Determination of Melt viscoelasticity A rotary rheometer manufactured by RHEOMETRIX is used together with a cone plate (25 mm in diameter, 0.10 radian in cone angle) at the temperature of 175° C. with the initial strain of 20% to perform the frequency distribution determination of the melt viscosity. A complex modulus of elasticity G* (iω) at a frequency (ω(rad/sec)) can be represented by a stress σ* and a strain γ* as shown below.

$$G^*(i\omega)=\sigma^*/\gamma^*=G'(\omega)+iG''(\omega)$$

wherein i is an imaginary number unit.

EXAMPLE V-1

(1) Catalyst Preparation

Synthesis of (dimethylsilylene) 2 (3-n-butylindenyl) 2 zirconium dichloride

The method described in Example II-1 in the second invention was employed.

(2) Propylene Polymerization

A 10 L stainless steel autoclave received 6 L of heptane, 6 mmol of triisobutylaluminium, and a catalyst component obtained by bringing 5 mmol of a methyl aluminoxane (Albemarle) into preliminary contact with 5 μmol of (1,2'-dimethylsilylene)(2,1'-dimethylsilylene)bis(3-n-butylindenyl)2 zirconium dichloride in toluene for 5 minutes. After introducing hydrogen at 0.5 kg/cm$^2$ G, a propylene gas was introduced until the total pressure became 8.0 kg/cm$^2$, and the propylene gas was supplied using a pressure controller to keep a constant pressure during polymerization. After polymerizing at 50° C. for 30 minutes, the content was recovered and dried under reduced pressure to obtain a propylene homopolymer (B-1).

(3) Formulation and Kneading

The polypropylene homopolymer (B-1) obtained above was combined with the following additives and extruded by a single-screw extruder (manufactured by TSUKADA JUKISEISAKUSHO: Model TLC35-20) to granulate into a pellet.

(Formulation of Additives)

Phenolic antioxidant: IRGANOX 1010 available from Ciba Specialty Chemicals, 1000 ppm Phosphorus-based antioxidant: P-EPQ available from Ciba Specialty Chemicals: 500 ppm Neutralizing agent: Calcium stearate: 500 ppm Neutralizing agent: DHT-4A: 500 ppm (4) Production of Resin Composition 15 Parts by weight of the propylenic polymer [a-1] produced as described above as a propylenic polymer [I] and 85 parts by weight of IDEMITSU POLYPRO F-704NP as a crystalline propylenic polymer [II] were placed in a blender and mixed thoroughly, and then extruded by a single-screw extruder (manufacture by TSUKADA JUKISEISAKUSHO: Model TLC35-20) whereby effecting granulation.

(5) Film Forming

From the pellet of the propylenic resin composition thus obtained, a film whose thickness was 50 μm was formed using a 20 mmφ molding machine manufactured by TSUKADA JUKISEISAKUSHO with the T die exit resin temperature of 190° C., the chill roll temperature of 30° C. and the haul-off speed of 6 m/min.

(6) Evaluation of Resin Characteristics and Physical Characteristics

Evaluation was made by the methods described above. The results obtained are shown in Tables V-1 and V-2. In these tables, Example 1 means Example V-1. The same applies analogously to Example 2 or later as well as Comparative Examples.

EXAMPLE V-2

The method similar to that in Example V-1 was employed except for changing the blend ratios of the propylenic polymer [a-1] and IDEMITSU POLYPRO F-704 NP to 30 parts by weight and 70 parts by weight, respectively. The results are shown in Table V-2.

EXAMPLE V-3

The method similar to that in Example V-1 was employed except for changing the blend ratios of the propylenic polymer [a-1] and IDEMITSU POLYPRO F-704 NP to 60 parts by weight and 40 parts by weight, respectively. The results are shown in Table V-2.

COMPARATIVE EXAMPLE V-1

The method similar to that in Example V-1 was employed except for using an ethylene-propylene copolymer rubber available from NIPPON SYNTHETIC RUBBER KK (Grade: EP913Y) instead of the propylenic polymer [a-1]. The results are shown in Table V-2.

COMPARATIVE EXAMPLE V-2

The method similar to that in Example V-2 was employed except for using an ethylene-propylene copolymer rubber available from NIPPON SYNTHETIC RUBBER KK (Grade: EP913Y) instead of the propylenic polymer [a-1]. The results are shown in Table V-2.

COMPARATIVE EXAMPLE V-3

The method similar to that in Example V-3 was employed except for using an ethylene-propylene copolymer rubber available from NIPPON SYNTHETIC RUBBER KK (Grade: EP913Y) instead of the propylenic polymer [a-1]. The results are shown in Table V-2.

COMPARATIVE EXAMPLE V-4

The method similar to that in Example V-1 was employed except for using only IDEMITSU POLYPROF-704NP without blending a propylenic polymer [I]. The results are shown in Table V-2.

COMPARATIVE EXAMPLE V-5

The method similar to that in Example V-1 was employed except for using only IDEMITSU POLYPRO F-454NP without blending a propylenic polymer [I]. The results are shown in Table V-2.

COMPARATIVE EXAMPLE V-6

The method similar to that in Example V-1 was employed except for using only IDEMITSU TPO E2900 without blending a propylenic polymer [I]. The results are shown in Table V-2.

TABLE V-1

| Propylenic polymer (I) | (a-1) |
|---|---|
| W25, % by weight | 93 |
| H25, % by weight | 17 |
| ΔH J/mol | nd |
| 6 × (Tm − 140) | — |
| % mmmm, % by mole | 41 |
| rrrr/(1 − mmmm), % by mole | 4 |
| % 2,1 insertion, % by mole | 0 |
| % 1,3 insertion, % by mole | 0 |
| Mw/Mn | 2.4 |
| [η] dl/g | 2.5 |
| Tm ° C. | nd |
| Tc ° C. | nd |
| Tensile modulus MPa | 31 |

(NOTE)
n.d.: Not detected

TABLE V-2

| | | Example-1 | Example-2 | Example-3 | Comparative Example-1 | Comparative Example-2 | Comparative Example-3 | Comparative Example-4 | Comparative Example-5 | Comparative Example-6 |
|---|---|---|---|---|---|---|---|---|---|---|
| Formulation ratio | Propylenic polymer (I), (% by weight) | (a-1) | (a-1) | (a-1) | EP913Y | EP913Y | EP913Y | — | — | — |
| | Crystalline propylenic polymer (II), (% by weight) | 15 | 30 | 60 | 15 | 30 | 60 | 0 | 0 | 0 |

TABLE V-2-continued

|  |  | Example-1 | Example-2 | Example-3 | Comparative Example-1 | Comparative Example-2 | Comparative Example-3 | Comparative Example-4 | Comparative Example-5 | Comparative Example-6 |
|---|---|---|---|---|---|---|---|---|---|---|
| Resin characteristics | ΔHm (J/g) | F-704NP | F-704NP | F-704NP | F-704NP | F-704NP | F-704NP | F-704NP | F-454NP | E2900 |
|  | Tc (° C.) | 85 | 70 | 40 | 85 | 70 | 40 | 100 | 100 | 100 |
|  | (1/4)ΔHm + 90 | 88 | 73 | 41 | 83 | 62 | 38 | 100 | 87 | 72 |
|  | ω(G' = G") (rad/sec) | 115.2 | 112.3 | 106.1 | 111.9 | 111.9 | 112.2 | 112.4 | 113.8 | 106.4 |
|  | (1/10)ΔHm + 15 | 112.1 | 108.3 | 100.3 | 110.7 | 105.5 | 99.6 | 115.1 | 111.7 | 108.1 |
| Film performance | Haze (%) | 1.8 | 1.8 | 3.6 | 2.1 | 11.0 | 5.5 | 1.6 | 61.0 | 13.5 |
|  | Tensile modulus (Mpa) | 741 | 518 | 166 | 873 | 612 | 343 | 1040 | 856 | 486 |
|  | Heat seal temperature (° C.) | 152 | 144 | 130 | 145 | 138 | 129 | 155 | 154 | 158 |
|  | Heat seal strength (gf/15 mm) |  |  |  |  |  |  |  |  |  |
|  | Seal temperature 115° C. |  |  |  |  |  | 63 |  |  |  |
|  | Seal temperature 120° C. |  |  |  |  |  | 116 |  |  |  |
|  | Seal temperature 125° C. |  |  |  |  |  | 199 |  |  |  |
|  | Seal temperature 130° C. |  |  | 269 |  |  | 322 |  |  |  |
|  | Seal temperature 135° C. |  |  | 628 |  | 298 | 293 |  |  |  |
|  | Seal temperature 140° C. |  | 111 | 1031 | 209 | 302 | 344 |  |  |  |
|  | Seal temperature 145° C. |  | 333 | 1289 | 303 | 306 | 372 |  |  |  |
|  | Seal temperature 150° C. | 137 | 695 | 1505 | 455 | 329 | 339 | 155 | 124 | 88 |
|  | Seal temperature 155° C. | 494 | 1359 | 1699 | 971 | 389 | 381 | 256 | 345 | 99 |
|  | Seal temperature 160° C. | 1449 | 2920 | 2020 | 916 | 486 | 461 | 1052 | 600 | 443 |
|  | Seal temperature 165° C. | 3900 | 3087 | 2147 | 939 | 411 | 444 | 2484 | 1682 | 1553 |
|  | Seal temperature 170° C. | 3453 | 3353 |  |  |  | 483 | 3105 | 2646 | 3641 |
|  | Seal temperature 175° C. | 3662 |  |  |  |  | 525 | 3690 |  | 3479 |

[Sixth Invention]

Respective tests and evaluations were made as described below.

[1] Intrinsic Viscosity [η]

Measurement was made by the method described in the first invention.

[2] Molecular Weight Distribution (Mw/Mn)

Measurement was made by the method described in the first invention.

[3] % Isotactic Pentad

A % isotactic pentad (% mmmm, % by mole) means the proportion (%) of the propylene structure units each having a meso-structure (mmmm structure in which 5 methyl groups are aligned in the same direction) in 5 propylene structure units based on the assignment of the peaks in a $^{13}$C-NMR spectrum as described by Cheng H. N., Ewen J. A., Macromol. cem., 1989, 19O, 1350, and was determined using the following device and the conditions.

Instrument: Nippon Densi Model JNM-EX400 NMR device

Sample concentration: 220 mg/NMR Solvent 3 ml

NMR Solvent: 1,2,4-Trichlorobenzene/benzene-d6 (90/10 vol %)

Temperature: 130° C.

Pulse gap: 45°

Pulse interval: 4 seconds

Number of cycles: 10000 times

[4] when a % Isotactic Pentad (% mmmm, % by Mole) and a Melting point (Tm° C.) are in the Relationship Represented by Formula (I):

$$Tm \leq [mmmm] + 65 \qquad (I)$$

then the result was judged as OK, and when not the result was judged as NO.

[5] Tensile Modulus

A tensile test in accordance with JIS K-7127NI was employed. The test was conducted at the crosshead speed of 500 mm/min in the machine direction (MD).

[6] When a Tensile Modulus (TM (MPa)) and a Heat Seal Temperature (HST(° C.)) are in the Relationship Represented by Formula (II):

$$TM \geq 22 \times HST - 1850 \qquad (II)$$

then the result was judged as OK, and when not the result was judged as NO.

[7] Film Impact (F.I.)

A film impact means a impact destruction strength, and was determined using a film impact tester produced by TOYOSEIKI together with a 1-inch impact head.

[8] Heat Seal Temperature (HST)

A heat seal temperature (HST) was determined in accordance with JIS K-1707. After sealing under the fusing conditions described below followed by allowing to stand at room temperature overnight, the peeling strength was determined by a type-T peeling method at the peeling speed of 200 mm/min at room temperature to obtain a curve of a seal strength vs peeling strength, from which the temperature at which the peeling strength became 300 g/15 mm was calculated and designated as the heat seal temperature.

Fusing Condition

Seal duration: 2 seconds

Seal area: 15×10 mm

Seal pressure: 5.3 kg/cm$^2$

Seal temperature: Several temperatures over the range which include the heat seal temperature to be calculated later The temperature of a heat seal bar is corrected to the value read by a surface thermometer.

[9] Melting Point (Tm° C.) and Crystallization Temperature (Tc° C.) of Resin

Using a differential scanning calorimeter (Perking Elmer, DSC-7), 10 mg of a sample is fused for 3 minutes at 230° C. under a nitrogen atmosphere and then the temperature is lowered to 0° C. at the rate of 10° C./minute. The peak top of the maximum peak in the crystallization exothermic curve obtained during this course was regarded as the crystallization temperature (Tc° C.). After holding at 0° C. for 3 minutes, the temperature is raised at the rate of 10° C./minute to obtain a fusion endothermic curve, in which the peak top of the maximum peak was regarded as the melting point (Tm° C.).

[10] Criteria for Eutectic Based on Direct Fusion Endothermic Curve of Film Sample A eutectic formation of a polymer in this invention is judged to have taken place when the peak top, observed in a fusion endothermic curve obtained by subjecting 10 mg of a film sample which had just been cast-molded to a differential scanning calorimetry (Perking Elmer, DSC-7) under nitrogen atmosphere in which the temperature was kept at 0° C. for 3 minutes and then raised at 10° C./min, is single.

In an actual determination, the peak observed may have two or more resolved peak tops derived from melting points of resin components as the constituents of the film, or may have a single peak top associated optionally with the shoulder or trace peaks possibly derived from the components other than the resin components. Accordingly, the result is indicated as: O: which indicates the eutectic formation when a single peak top with or without overlapping shoulders or traces is observed; and, x: which indicates no eutectic formation when two or more peak tops with or without overlapping shoulders or traces is observed.

EXAMPLE VI-1

(1) Production of Component (A-1)

A 10 L stainless steel autoclave was charged with 4.0 L of toluene, 8 mmol of triisobutylaluminium and 20 μmol of tetrakis-pentafluorophenylborate dimethylanilinium salt, and the mixture was heated to 40° C. and combined with 10 mmol of hydrogen, and then propylene was introduced until the total pressure became 7.0 kg/cm$^2$-G. At this point, 5 μmol of (1,2'-ethylene)(2,1'-ethylene)-bis(indenyl)hafnium dichloride was added and the polymerization was initiated. Propylene was supplied via a pressure controller to keep a constant pressure. After 2 hours, the content was recovered, dried under reduced pressure to obtain 820 g of polypropylene.

The polypropylene thus obtained had the meso-pentad fraction (mmmm (in percentage terms by mole)) of 91%, the intrinsic viscosity [η] of 1.5 dl/g and the molecular weight distribution (Mw/Mn ratio) of 1.9.

(2) Production of Component (B-1)

A 1 L stainless steel autoclave was charged with 400 mL of toluene, 1 mmol of triisobutylaluminium and 4 μmol of tetrakis-pentafluorophenylborate dimethylanilinium salt and the mixture was heated to 55° C. and combined with 4 mmol of hydrogen, and then propylene was introduced until the total pressure became 7.0 kg/cm$^2$-G. At this point, 1 μmol of (1,2'-ethylene) (2,1'-ethylene)-bis(indenyl)hafnium dichloride was added and the polymerization was initiated. Propylene was supplied via a pressure controller to keep a constant pressure. After 1 hours, the content was recovered, and poured into a large amount of methanol, filtered and dried to obtain 75 g of polypropylene.

The polypropylene thus obtained had the meso-pentad fraction (mmmm (in percentage terms by mole)) of 90%, the intrinsic viscosity [η] of 0.5 dl/g and the molecular weight distribution (Mw/Mn ratio) of 2.0.

(3) Formulation and Kneading 91 parts by weight of the component A-1 and 9 parts by weight of the component B-1, in combination with antioxidants, namely, 750 ppm by weight of IRGANOX 1010 (manufacture by Ciba Specialty Chemicals, trade name) and 750 ppm by weight of IRGANOX 168 (manufactured by Ciba Specialty Chemicals, trade name), and 500 ppm by weight of calcium stearate as a neutralizing agent, 1000 ppm by weight of erucic acid amide as a slipping agent, and 1800 ppm by weight of a silica-based anti-blocking agent as an anti-blocking agent were kneaded by a single-screw extruder (manufactured by TSUKAD AJUKISEISAKUSHO: Model TLC35-20) to obtain a resin composition.

(4) Film Forming

By means of a T die cast molding method and using a 20 mmφ T die cast molding machine manufactured by TSUKADA JUKISEISAKUSHO, a film whose thickness was 25 μm was formed under the conditions specified below. After a film was formed at the T die exit temperature of 191° C., the chill roll temperature of 30° C., and the haul-off speed of 6 m/min, it was aged at 40° C. for 24 hours.

The film thus obtained was examined for the tensile modulus, the film impact and the heat seal temperature together with the film molding stability, and the results are shown in Table VI-1. In this table, Example 1 means Example VI-1. The same applies analogously to Example 2 or later as well as Comparative Examples. The film molding stability was very satisfactory, and adverse events such as neck-in were not observed.

EXAMPLE VI-2

A resin was prepared and a film was formed and evaluated similarly as in Example VI-1 except for using the component (A-1) in the amount of 90% by weight instead of 91% by weight and using 10 parts by weight of the component (B-2) instead of 9 parts by weight of the component (B-1). The results are shown in Table VI-1.

The film molding stability was very satisfactory, and adverse events such as neck-in were not observed. No blisters were observed.

Production of Component (B-2)

1) Preparation of Magnesium Compound

A reaction chamber fitted with a stirrer (whose capacity was 500 L) was purged thoroughly with a nitrogen gas, and charged with 97.2 kg of ethanol, 640 g of iodine and 6.4 kg of elemental magnesium, and the mixture was reacted under reflux with stirring until the evolution of a hydrogen gas from the reaction system ceased, whereby obtaining a solid reaction product. The fluid reaction mixture containing this solid product was dried under reduced pressure to obtain an intended magnesium compound.

2) Preparation of Solid Catalyst Component

A reaction chamber fitted with a stirrer (whose capacity was 500 L) purged sufficiently with a nitrogen gas was charged with 30 kg of the magnesium compound obtained above (not pulverized), 150 L of purified heptane (n-heptane), 4.5 L of silicon tetrachloride and 5.4 L of di-n-butyl phthalate. The reaction system was kept at 90° C., and 144 L of titanium tetrachloride was added with stirring and the reaction was continued at 110° C. for 2 hours and then the solid components were separated and washed with a purified heptane at 80° C. Addition of 288 L of titanium tetrachloride followed by the reaction at 110° C. for 2 hours followed by a sufficient washing with a purified heptane at 80° C. yielded a solid catalyst component.

3) Pretreatment

A 500 L reaction chamber fitted with a stirrer was charged with 230 L of a purified heptane (n-heptane), and fed with 25 kg of the solid catalyst component obtained above, and 1.0 mol/mol of triethylaluminium and 1.8 mol/mol of dicyclopentyldimehtoxysilane, both per titanium atom of the solid catalyst component. Subsequently, propylene was introduced at the partial pressure of 0.3 kg/cm$^2$ G, and the reaction was continued for 4 hours at 25° C. After completion of the reaction, the solid catalyst component was washed several times with a purified heptane, and fed further with carbon dioxide and stirred for 24 hours.

4) Main Polymerization

A 200 L polymerization reactor fitted with a stirrer was charged with propylene, and also fed with 3=mol/kg-PP, as titanium atom in the solid catalyst component, of the catalyst component, 4 mmol/kg-PP of triethylaluminium and 1 mmol/kg-PP of dicyclopentyldimethoxysilane, and then the mixture was reacted at the polymerization temperature of 80° C. and the polymerization pressure (total pressure) of 28 kg/cm$^2$ G. In this Example, the hydrogen supply was adjusted so that the intended molecular weight was achieved. The polymer (B) thus obtained had the % isotactic pentad of 97.6 mol % and the melt index of 5.9 g/10 minutes. Analysis (gas chromatography) of the composition of the gas in the polymerization reactor during polymerization revealed that the hydrogen concentration was 4.2% by mole.

EXAMPLE VI-3

A resin was prepared and a film was formed and evaluated similarly as in Example VI-1 except for using 90% by weight of the component (A-2) instead of 91% by weight of the component (A-1) and also using 10 parts by weight of the component (B-2) instead of 9 parts by weight of the component (B-1). The results are shown in Table VI-1.

The film molding stability was very satisfactory, and the release from the chill roll was also satisfactory. No blisters were observed.

Production of Component (A-2)

1) (1,2'ethylene)(2,1'-ethylene)-bis(3-methylindenyl)zirconium dichloride

The method similar to that in Example I-1 in the first invention was employed.

2) Polymerization

A 10 L stainless steel autoclave was charged with 5 L of heptane, 5 mmol of triisobutylaluminium, and a catalyst component obtained by bringing 19 mmol as Al of a methyl aluminoxane (manufactured by Albemarle) into preliminary contact with 19 μmol of (1,2'-ethylene)(2,1'-ethylene)-bis(3-methylindenyl)zirconium dichloride prepared above in toluene for 30 minutes, and the temperature was raised to 40° C. and the propylene gas was introduced until the total pressure became 8.0 kg/cm$^2$ G. During polymerization, the propylene gas was supplied using a pressure controller to keep a constant pressure, and after 1 hour the content was recovered and dried under reduced pressure to obtain polypropylene.

COMPARATIVE EXAMPLE VI-1

A resin was prepared and a film was formed and evaluated similarly as in Example VI-1 except for using only the component (A-1) without incorporating the component (B-1). The results are shown in Table VI-1. Upon film-forming, neck-in was observed.

COMPARATIVE EXAMPLE VI-2

A resin was prepared and a film was formed and evaluated similarly as in Example VI-1 except for using only the component (A-2) without incorporating the component (B-1). The results are shown in Table VI-1. The release of the film from the chill roll was very poor, and the film could not be molded.

COMPARATIVE EXAMPLE VI-3

A resin was prepared and a film was formed and evaluated similarly as in Example VI-1 except for using E2900 produced by IDEMITSU SEKIYU KAGAKU which was obtained using a non-metallocene catalyst (titanium/magnesium-based catalyst) instead of the components (A-1) and (B-1). The results are shown in Table VI-1. Although the film molding could be performed satisfactorily, the chill roll tended to be spotted.

COMPARATIVE EXAMPLE VI-4

A resin was prepared and a film was formed and evaluated similarly as in Example VI-1 except for using 50% by weight of the component (A-2) instead of 91% by weight of the component (A-1) and also using 50 parts by weight of the component (B-2) instead of 9 parts by weight of the component (B-1). The results are shown in Table VI-1.

Although the film molding could be performed satisfactorily without exhibiting particular adverse events, several blisters were observed.

COMPARATIVE VI-5

A resin was prepared and a film was formed and evaluated similarly as in Example VI-1 except for using the component (A-1) in the amount of 95% by weight instead of 91% by weight and using 5 parts by weight of a high density polyethylene (manufactured by IDEMITSU SEKIYU KAGAKU, IDEMITSUHDPE 640UF) instead of 9 parts by weight of the component (B-1). The results are shown in Table VI-1.

Although the film molding could be performed satisfactorily without exhibiting particular adverse events, substantial blisters formed made the determination of the physical characteristics impossible.

TABLE VI-1

| | | Example 1 | Example 2 | Example 3 | Comparative Example 1 | Comparative Example 2 | Comparative Example 3 | Comparative Example 4 | Comparative Example 5 | Reference Example | | |
|---|---|---|---|---|---|---|---|---|---|---|---|---|
| Composition (%) | Component A (A-1) | 91 | 90 | | 100 | | | | 95 | | | |
| | Component A (A-2) | | | 90 | | 100 | | 45 | | | | |
| | Component B (B-1) | 9 | | | | | | | | 100 | | |
| | Component B (B-2) | | 10 | 10 | | | | 55 | | | 100 | |
| | Others (E2900) | | | | | | 100 | | | | | |
| | HDPE (640UF) | | | | | | | | 5 | | | 100 |
| Component A | | | | | | | | | | | | |
| Intrinsic viscosity [η] dl/g | | 1.5 | 1.5 | 1.2 | 1.5 | 1.2 | 1.9 | 1.2 | 1.5 | — | — | — |
| Molecular weight distribution [Mw/Mn] | | 1.9 | 1.9 | 1.8 | 1.9 | 1.8 | 2.6 | 1.8 | 1.9 | — | — | — |
| % mmmm, % by mole | | 91.0 | 91.0 | 63.5 | 91.0 | 63.5 | 72.7 | 63.5 | 91.0 | — | — | — |
| Melting point (Tm ° C.) | | 146.5 | 146.5 | 104.0 | 146.5 | 104.0 | 160.0 | 104.0 | 146.5 | — | — | — |
| Tm ≦ [mmmm] + 65 | | OK | OK | OK | OK | OK | NO | OK | OK | | | |
| Component B | | | | | | | | | | | | |
| Intrinsic viscosity [η] dl/g | | 0.5 | 1.7 | 1.7 | — | — | — | 1.7 | 3.4 | 0.5 | 1.7 | 3.4 |
| Molecular weight distribution [Mw/Mn] | | 2.0 | 4.2 | 4.2 | — | — | — | 4.2 | 22 | 2.0 | 4.2 | 22 |
| Resin composition and film | | | | | | | | | | | | |
| Melting point (Tm ° C.) | | 146.3 | 147.0 | 108.0/16 | 146.5 | 104.0 | 160.0 | 163.5/11 | 146/130 | 145.5 | 165.5 | 130 |
| Crystallization temperature (Tc ° C.) | | — | — | — | 107.0 | 63.5 | 117.0 | — | — | 109.8 | 117.0 | 116 |
| Tensile modulus (TM: Mpa) | | 1100 | 1100 | 550 | 1100 | — | 514 | 880 | — | — | — | — |
| Heat seal temperature (HST: ° C.) | | 130 | 130 | 102 | 135 | — | 151 | 130 | — | — | — | — |
| TM ≧ 22 × HST − 1850 | | OK | OK | OK | NO | — | NO | NO | — | — | — | — |
| Film impact (1 inch) J/m | | 29000 | 28000 | NB | 29000 | — | NB | 2700 | — | — | — | — |
| Moldability | | No neck-in | No neck-in | Molding possible | Neck-in | Molding impossible | Molding possible | Molding possible | Molding possible | — | — | — |
| Eutectic formation | | ○ | ○ | ○ | ○ | ○ | ○ | ○ | X | — | — | — |

[Seventh Invention]

The methods for evaluating the resin characteristics, for film-forming and for qualifying a film are discussed below.

(a) Method for Evaluating Resin Characteristics 1) 1-Octene Unit Content (% by Mole) in Copolymer and Stereoregularlity Index (P(% by Mole))

The 1-octene unit content (% by mole)) in the copolymer was obtained in accordance with the following equation (1) from the spectrum determined by the $^{13}$C-NMR.

$$\text{1-Octene unit content} = \frac{(I[2]/2 + I[4])}{\{I[1] + I[2] + I[3] + I[4] + 2 \times I[11]\}} \times 100 \quad (1)$$

Also in accordance with the following equation (2), a stereoregularity index (P (% by mole)) of the copolymer was obtained.

$$P = \frac{(I[16]) \times 100}{\{I[16] + I[17] + I[18]\}} \quad (2)$$

wherein [1], [2] and the like represent the signals of a spectrum of a random copolymer of propylene and 1-octene determined by $^{13}$C-NMR. I[1], I[2] and the like represent the respective signal intensities. The signals of a spectrum of a random copolymer of propylene and 1-octene determined by $^{13}$C-NMR are indicated in Table VII-1.

Instead of the signal of a PPP chain Sαβ carbon which was difficult to be determined because of the overlapping signal of PPP chain Tαβ carbon, the signal intensity of a PPP chain Sαβ carbon was indicated as an alternative.

A $^{13}$C-NMR spectrum was obtained using Nippon Densi Model JNM-EX400 NMR device under the conditions specified below.

Sample concentration: 220 mg/3 ml NMR solvent

NMR Solvent: 1,2,4-Trichlorobenzene/benzene-d6 (90/10 vol)

Determination temperature: 130° C.

Pulse gap: 45° C.

Pulse interval: 4 seconds

Number of cycles: 4000 times 2) 1-Dodecene Unit Content (% by Mole) in Copolymer and Stereoregularlity Index (P(% by Mole))

The 1-dodecene unit content (% by mole)) in the copolymer was obtained in accordance with the following equation (3) from the spectrum determined by the $^{13}$C-NMR.

$$\text{1-Dodecene unit content} = \frac{(I[2]/2 + I[4]) \times 100}{\{I[1] + I[2] + 3 \times I[3] + I[4]\}} \quad (3)$$

Also in accordance with the following equation (4), a stereoregularity index (P (% by mole)) of the copolymer was obtained.

$$P = \frac{(I[5]) \times 100}{\{I[5] + I[6] + I[7]\}} \quad (4)$$

wherein [1], [2] and the like represent the signals of a spectrum of a random copolymer of propylene and 1-dodecene determined by $^{13}$C-NMR. I[1], I[2] and the like represent the respective signal intensities. The signals of a spectrum of a random copolymer of propylene and 1-dodecene determined by $^{13}$C-NMR are indicated in Table VII-2.

Because of the difficulty in resolving the signal of a PPP chain Sαβ carbon from the overlapping signal of PPP chain Tαβ carbon and the signal of a PPP chain Sαβ carbon from the overlapping signal of the side chain methylene carbon of a 1-dodecene unit, the signal intensity of a PPP chain Sαα carbon was employed as a substitute.

3) 1-Decene Unit Content (% by Mole) in Copolymer and Stereoregularlity Index (P(% by Mole))

The 1-decene unit content (% by mole)) and the stereoregularlity index (P(% by mole)) of the copolymer were obtained by the method similar to that in above 2) except for using Table VII-3 indicating the signals of a spectrum of a random copolymer of propylene and 1-decene by the $^{13}$C-NMR instead of Table VII-2.

Because of the difficulty in resolving the signal of a PPP chain Sαβ carbon from the overlapping signal of PPP chain Tαβ carbon and the signal of a PPP chain Sαβ carbon from the overlapping signal of the side chain methylene carbon of a 1-decene unit, the signal intensity of a PPP chain Sαα carbon was employed as a substitute.

4) Ethylene Unit Content (% by Mole) in Copolymer and Stereoregularlity Index (P(% by Mole))

The ethylene unit content (% by mole)) in the copolymer was obtained in accordance with the following equation (5) from the spectrum determined by the $^{13}$C-NMR.

$$\text{Ethylene unit content} = E/S \times 100 \tag{5}$$

wherein S and E are each represented as follows:

S=IEPE+IPPE+IEEE+IPPP+IPEE+IPEP

E=IEEE+2/3(IPEE+IEPE)+1/3(IPPE+IPEP)

wherein:

IEPE=I(12)

IPPE=I(15)+I(11)+(I(14)−I(11))/2+I(10)

IEEE=I(18)/2+I(17)/4

IPPP=I(19)+(I(6)+I(7))/2+I(3)+I(13)+I(11)+(I(14)−I(11))/2

IPEE=I(20)

IPEP=(I(8)+I(9)−2×(I(11))/4+I(21).

A stereoregularity index (P (% by mole)) of the copolymer was obtained according to the equation (6) shown below.

$$P = Im/I \times 100 \tag{6}$$

wherein Im and I are each represented as follows:

Im=I(22)

I=I(22)+I(23)+I(24)−{(I(8)+I(9))/2+I(10)+3/2×I(11)+I(12)+I(13)+I(15)}.

In the equation shown above, (1), (2) and the like are the signals of a spectrum of a random copolymer of propylene and ethylene obtained by 13C-NMR, and I(1), I(2) and the like represent the intensities of respective signals. The signals of a spectrum of a random copolymer of propylene and ethylene determined by $^{13}$C-NMR are shown in Table VII-4.

5) 1-Butene Unit Content (% by Mole) in Copolymer and Stereoregularlity Index (P(% by Mole))

The 1-butene unit content (% by mole)) in the copolymer was obtained in accordance with the following equation (7) from the spectrum determined by the $^{13}$C-NMR.

$$\text{1-Butene unit content} = \frac{(I[2]/2 + I[4])}{\{I[1] + I[2] + I[3] + I[4] + 2 \times I[9]\}} \times 100 \tag{7}$$

Also in accordance with the following equation (8), a stereoregularity index (P (% by mole)) of the copolymer was obtained.

$$P = \frac{(I[12]) \times 100}{\{I[12] + I[13] + I[14]\}} \tag{8}$$

wherein [1], [2] and the like represent the signals of a spectrum of a random copolymer of propylene and 1-butene determined by $^{13}$C-NMR. I[1], I[2] and the like represent the respective signal intensities. The signals of a spectrum of a random copolymer of propylene and 1-butene determined by $^{13}$C-NMR are indicated in Table VII-5.

The signal of a PPP chain Sαβ carbon was substituted with the signal intensity of a PPP chain Sαβ carbon.

6) Main Elution Peak Temperature (Tp), Half of Main Elution Peak Temperature (Th), Elution Level at 0° C. (W0) and Elution Level in Temperature Range from (Tp−5)° C. to (Tp+5)° C.

A temperature-raising fractional chromatography (TREF) obtained using the devices, the procedure and the conditions specified below.

Tp: Peak top temperature of main elution peak in elution curve

W0: % By weight of component which are dissolved out instead of being adsorbed onto a packing at the column temperature of 0° C. based on the total weight WP: % By weight of component which are dissolved out instead of being adsorbed onto a packing in the temperature range of (Tp−5)° C. to (Tp+5)° C. based on the total weight PPP W(TP+10): % By weight of component which are dissolved out instead of being adsorbed onto a packing at a column temperature not lower than (Tp+10)° C. based on the total weight A) Operating Procedure A sample solution is introduced into a TREF column adjusted at 135° C. and then the temperature is lowered gradually at the lowering rate of 5° C./hour to 0° C. to allow the sample to be adsorbed onto the packing. Subsequently, the column temperature was raised at the raising rate of 40° C./hour to 135° C. to obtain an elution curve.

B) Instruments

TREF column: Manufactured by GL SCIENCE, Silica gel column (4.6φ×150 mm)

Flow cell: Manufactured by GL SCIENCE, pathlength 1 mm, KBr cell

Feed pump: Manufactured by SENSHU KAGAKU, Pump Model SSC-3100

Valve oven: Manufactured by GL SCIENCE, Oven model 554

TREF oven: Manufactured by GL SCIENCE

Dual-system thermostat: Manufactured by RIKAGAKU KOGYO, Thermostat model REX-C100

Detector: Infrared detector for HPLC, Manufactured by FOXBORO CORP., Model MIRAN 1A CVF 10-way valve: Manufactured by VALCO, Electric valve Loop: Manufactured by VALCO, 500 µL Loop C) Operating Conditions Solvent: o-Dichlorobenzene Sample concentration: 7.5 g/L Injection volume: 500 L Pumping rate: 2.0 mL/min Detection wavenumber: 3.41 µm Column packing: CHROMOSOLVE P (30 to 60 mesh)

Column temperature deviation: Within 0.2° C.

7) Intrinsic Viscosity ($[\eta]$ dl/g) Determined in Decalin at 135° C.

Measurement was made by the method described in the first invention.

8) Crystallization Temperature ($Tc(°C.)$) and Melting Point ($Tm(°C.)$) Determined by Differential Scanning Microscopy Measurement was made by the method described in the first invention.

9) Criteria for Eutectic Based on Crystallization Exothermic Curve of Film Sample A eutectic formation of a polymer in this invention is judged to have taken place when the peak top of the maximum peak, observed in a crystallization exothermic curve obtained as described in above 8) by subjecting a film sample which had just been cast-molded to a differential scanning calorimetry (Perkin Elmer, DSC-7), is a single peak and at the same time the crystallization temperature of this film is higher than that of a component (A') and lower than that of a component (B').

10) Molecular Weight Distribution Mw/Mn Ratio

Measurement was made by the method described in the first invention.

(B) Film-Forming Method

From a pellet of the propylenic resin in Examples and Comparatives described below, a film whose thickness was 30 µm was formed using a 20 mmφ molding machine manufactured by TSUKADAJUKISEISAKUSHO under the molding conditions specified below.

T die exit resin temperature: 192° C.

Haul-off speed: 6.0 m/min

Chill roll temperature: 30° C.

Chill roll: Mirror (C) Film Qualification

A film once formed was subjected to aging at 40° C. for 24 hours followed by conditioning at a temperature of 23±2° C. and a humidity of 50±10% for 16 hours or longer and then qualified at the same temperature and humidity.

1) Heat Seal Performance

A test was conducted in accordance with JIS Z-1707. The fusing conditions were as indicated below. The temperature of the heat seal bar was corrected as being read by a surface thermometer. After sealing followed by allowing to stand at room temperature overnight, the peeling strength was determined by a type-T peeling method at the peeling speed of 200 mm/min at room temperature. The heat seal temperature was obtained as a temperature at which the peeling strength was 300 g/15 mm by calculating on the basis of a curve of a seal strength vs peeling strength.

Seal duration: 1 second

Seal area: 15 mm×15 mm

Seal pressure: 2.0 kg/cm$^2$

Seal temperature: Several temperatures over the range which include the heat seal temperature to be calculated later 2) Anti-Blocking Ability A rectangular film (30 cm×15 cm) was fixed on a mount whose size was 10 cm×10 cm and fused under the conditions specified below, and subsequently the peeling strength was determined.

Fusing condition 1, Temperature: 60° C., Duration: 3 hours, Load: 36 g/cm$^2$, Area: 10 cm×10 cm Fusing condition 2, Temperature: 50° C., Duration: 1 week, Load: 15 g/cm$^2$, Area: 10 cm×10 cm The peeling test was conducted under the conditions shown below.

Test speed: 20 mm/min

Load cell: 2 kg

3) Slipperiness

A sled on which a film was applied was allowed to stand on a glass plate on which the film was also applied, and then the glass plate was tilted and the tangent of the angle θ at which the sled began to slip was determined. The friction angle meter manufactured by TOYOSEIKI was employed in the test under the conditions specified below.

Slipping surface: Metal roll surface/metal roll surface

Tilting speed: 2.7°/sec

Sled weight: 1 kg

Sled sectional area: 65 cm$^2$

Interface pressure: 15 g/cm$^2$

4) Haze

A test was conducted in accordance with JIS K-7105.

5) Tensile Modulus

A tensile test was conducted under the conditions specified below in accordance with JIS K-7127.

Crosshead speed: 500 mm/min

Load cell: 10 kg

Direction: Machine direction (MD)

6) When a Tensile Modulus (TM (MPa)) and a Heat Seal Temperature (HST(° C.)) are in the Relationship Represented by Formula (II):

$$TM \geq 22 \times HST - 1850 \quad (II)$$

then the result was judged as OK, and when not the result was judged as NO.

EXAMPLE VII-1

<Production of Copolymer (A'-1)>

[1] Preparation of (1,2'-ethylene) (2,1'-ethylene)-bis(3-methylindenyl)zirconium dichloride The method similar to that in Example I-1 in the first invention was employed.

[2] Polymerization (propylene-1-butene copolymer)

A 10 L stainless steel autoclave was charged with 5 L of heptane, 5 mmol of triisobutylaluminium, 50 g of 1-butene, and a catalyst component obtained by bringing 19 mmol, as aluminum, of a methyl aluminoxane (Albemarle) into preliminary contact with 19 μmol of (1,2'-ethylene) (2,1'-ethylene)-bis(3-methylindenyl)zirconium dichloride in toluene for 30 minutes, and the mixture was heated to 40° C. and the propylene gas was introduced until the total pressure became 8.0 kg/cm$^2$ G. During polymerization, the propylene gas was supplied using a pressure controller to keep a constant pressure, and after 1 hour the content was recovered and dried under reduced pressure to obtain a propylenic copolymer.

The copolymeric powder thus obtained was combined with the following additives and extruded by a kneader into a pellet.

1) Antioxidant

IRGANOX 1010 available from Ciba-geigy: 1000 ppm and,

IRGAPHOS 168 available from Ciba-geigy: 1000 ppm

2) Neutralizing agent . . . Calcium stearate: 1000 ppm

3) Anti-blocking agent . . . Silica-based agent: 1800 ppm

4) Slipping agent . . . Erucic acid amid: 500 ppm

A copolymer pellet thus obtained was examined for its resin characteristics by the method in Section (A) described above.

<Propylenic Polymer (B')>

1) Preparation of Magnesium Compound

A reaction chamber fitted with a stirrer (whose capacity was 500 L) was purged thoroughly with a nitrogen gas, and charged with 97.2 kg of ethanol, 640 g of iodine and 6.4 kg of elemental magnesium, and the mixture was reacted under reflux with stirring until the evolution of a hydrogen gas from the reaction system ceased, whereby obtaining a solid reaction product. The fluid reaction mixture containing this solid product was dried under reduced pressure to obtain an intended magnesium compound.

2) Preparation of Solid Catalyst Component

A reaction chamber fitted with a stirrer (whose capacity was 500 L) purged sufficiently with a nitrogen gas was charged with 30 kg of the magnesium compound obtained above (not pulverized), 150 L of purified heptane (n-heptane), 4.5 L of silicon tetrachloride and 5.4 L of di-n-butyl phthalate. The reaction system was kept at 90° C., and 144 L of titanium tetrachloride was added with stirring and the reaction was continued at 110° C. for 2 hours and then the solid components were separated and washed with a purified heptane at 80° C. Addition of 288 L of titanium tetrachloride followed by the reaction at 110° C. for 2 hours followed by a sufficient washing with a purified heptane at 80° C. yielded a solid catalyst component.

3) Pretreatment

A 500 L reaction chamber fitted with a stirrer was charged with 230 L of a purified heptane (n-heptane), and fed with 25 kg of the solid catalyst component obtained above, and 1.0 mol/mol of triethylaluminium and 1.8 mol/mol of dicyclopentyldimehtoxysilane, both per titanium atom of the solid catalyst component. Subsequently, propylene was introduced at the partial pressure of 0.3 kg/cm$^2$ G, and the reaction was continued for 4 hours at 25° C. After completion of the reaction, the solid catalyst component was washed several times with a purified heptane, and fed further with carbon dioxide and stirred for 24 hours.

4) Main Polymerization

A 200 L polymerization reactor fitted with a stirrer was charged with propylene, and also fed with 3 mmol/kg-PP, as titanium atom in the solid catalyst component, of the catalyst component, 4 mmol/kg-PP of triethylaluminium and 1 mmol/kg-PP of dicyclopentyldimethoxysilane, and then the mixture was reacted at the polymerization temperature of 80° C. and the polymerization pressure (total pressure) of 28 kg/cm$^2$. In this Example, the hydrogen supply was adjusted so that the intended molecular weight was achieved. The polymer (B) thus obtained had the % isotactic pentad of 97.6 mol % and the melt index of 5.9 g/10 minutes. Analysis (gas chromatography) of the composition of the gas in the polymerization reactor during polymerization revealed that the hydrogen concentration was 4.2% by mole.

The propylenic polymer powder thus obtained was combined with the following additives and extruded by a kneader into a pellet.

1) Antioxidant

IRGANOX 1010 available from Ciba-geigy: 1000 ppm and,

IRGAPHOS 168 available from Ciba-geigy: 1000 ppm

2) Neutralizing agent . . . Calcium stearate: 1000 ppm

3) Anti-blocking agent . . . Silica-based agent: 1000 ppm

4) Slipping agent . . . Erucic acid amid: 1000 ppm

A propylenic polymer pellet thus obtained was examined for its resin characteristics by the method in Section (A) described above.

90 Parts by weight of the copolymer (A'-1) thus obtained was mixed thoroughly with 10 parts by weight of the propylenic polymer (B') by a dry blender. The propylenic resin thus obtained was formed into a film by the method in Section (B) described above, and qualified by the method in Section (C) described above. The results are shown in Table VII-6. In this table, Example 1 means Example VII-1. The same applies analogously to Example 2 or later as well as Comparatives.

COMPARATIVE VII-1

A film was formed and evaluated by the method similar to that in Example VII-1 except for using only the component (A'-1) without using the component (B'). The results are shown in Table VII-6.

EXAMPLE VII-2

<Production of Copolymer (A'-2)>

[1] Catalyst Preparation

[1] Production of Ethyl(2-indenyl)acetate

Under nitrogen flow, 3.3 g of sodium hydride was suspended in 300 mL of tetrahydrofurane and cooled to 10° C. To this suspension, a solution of 28.3 g of ethyldiethylphosphonoacetate in 200 mL of tetrahydrofuran was added dropwise over 1 hour. Then the mixture was stirred at room temperature for 30 minutes and then cooled on ice, and then treated dropwise with a solution of 16.33 g of 2-indanone in 75 mL of tetrahydrofuran over 1 hour. Subsequently, the mixture was stirred at room temperature for 30 minutes and then combined with water to effect hydrolysis followed by extraction with 500 mL of diethylether to separate the organic phase, whose solvent was distilled off under reduced pressure. The residue was distilled under reduced pressure to obtain a pale yellow oil.

The oil obtained was identified as ethyl(2-indenyl)acetate on the basis of $^1$H-NMR. The yield was 11.06

[2] Production of 2-(2-indenyl)-ethanol

Under nitrogen flow, 2.2 g of lithium aluminum hydride was suspended in 100 mL of dietylether. To this suspension, a solution of 11 g of ethyl(2-indenyl)acetate obtained in Step [1] described above in 50 mL of diethylether was added dropwise over 1 hour. After stirring for 30 minutes at room temperature followed by cooling on ice, 50 mL of water was added portionwise, and then a dilute hydrochloric acid was added to dissolve insolubles. The organic phase was separated and the solvent was distilled off under reduced pressure to obtain a white solid.

The compound obtained was identified as 2-(2-indenyl)-ethanol on the basis of $^1$H-NMR. The yield was 7.89

[3] Production of 1-bromo-2-(2-indenyl)ethane

Under nitrogen flow, 4.61 g of 2-(2-indenyl)-ethanol obtained in Step [2] described above was dissolved in 65 mL of dichloromethane. To this solution, 7.66 g of triphenylphosphine was added and then 5.19 g of N-bromosuccinimide was added portionwise. After stirring at room temperature for 30 minutes followed by addition of water, the organic phase was separated and dried over anhydrous magnesium sulfate. The solvent was distilled off under reduced pressure and the residue was purified on a silica gel column (eluted with hexane) to obtain a colorless oil.

This colorless oil was identified as 1-bromo-2-(2-indenyl) ethane on the basis of $^1$H-NMR. The yield was 5.07 g.

[4] Production of (1,2'-ethylene) (2,1'-ethylene)-bis(indene)

Under nitrogen flow, 50 mL of tetrahydrofuran was combined with 6.87 mL of diisopropylamine and cooled to −78° C. TO this solution, 1.96 mL of a 1.64 mol/L solution of n-butyllithium in hexane was added dropwise over 10 minutes. Subsequently, the reaction mixture was allowed to warm to 0° C., whereby obtaining a lithium diisopropylamide (LDA) solution.

Subsequently, under nitrogen flow, 500 mL of tetrahydrofuran was combined with 11.69 g of 1-bromo-2-(2-indenyl) ethane obtained in Step [3] described above and stirred for dissolution followed by cooling to −78° C. This solution was treated dropwise over 30 minutes with the LDA solution obtained above which had been cooled to −78° C., and then allowed to warm to room temperature and then stirred for 12 hours.

To this reaction mixture, 500 mL of water was added to wash the organic phase, which was then dried over anhydrous magnesium sulfate. Then the solvent was distilled off under reduced pressure to obtain a solid, which was purified by sublimation at 0.2 Torr at 150° C. to obtain a white solid.

The compound thus obtained was identified as (1,2'-ethylene)(2,1'-ethylene)-bis(indene) on the basis of a field desorption mass spectrum (FD-MS) and $^1$H-NMR.

[5] Production of Dilithium Salt of (1,2'-ethylene)(2,1'-ethylene)-bis(indene)

Under nitrogen flow, 0.6 g of (1,2'-ethylene)(2,1'-ethylene)-bis(indene) obtained in Step [4] described above was combined with 100 mL of diethylether and stirred and cooled to −78° C. This was treated dropwise with 2.6 mL of a 1.64 mol/L solution of n-butyllithium in hexane over 30 minutes.

The reaction mixture was allowed to warm to room temperature, stirred for 12 hours, and the solvent was distilled off under reduced pressure to obtain a residue, which was washed twice with 50 mL of hexane and dried under reduced pressure to obtain a dilithium salt of (1,2'-ethylene)(2,1'-ethylene)-bis(indene) as a pale yellow powder.

[6] Production of (1,2'-ethylene) (2,1'-ethylene)-bis(indene) Hafnium Dichloride Under nitrogen flow, 0.58 g of hafnium tetrachloride was suspended in 100 mL of toluene and cooled to −78° C. Then this suspension was treated over 30 minutes with 0.54 g of the dilithium salt of (1,2'-ethylene) (2,1'-ethylene)-bis(indene), obtained in Step [5] described above, suspended in 50 mL of toluene at −78° C.

This reaction mixture was allowed to warm to room temperature and stirred for 12 hours, and then toluene supernatant was filtered off and the filter cake was extracted twice with 50 mL of dichloromethane and the solvent was distilled off under reduced pressure. The residue was recrystallized from dichloromethane/hexane to obtain (1,2'-ethylene)(2,1'-ethylene)-bis(indene) hafnium dichloride. The yield was 0.18 g.

This compound was subjected to $^1$H-NMR analysis and the following results were obtained.

$^1$H-NMR (CDCl3):3.66 (8H), 6.37 (s, 2H), 6.90-7.60 (m, 8H)

This compound had the structure shown below.

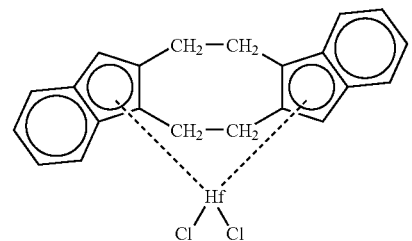

[2] Polymerization (Propylene-Ethylene Copolymer)

A 10 L stainless steel autoclave was charged with 6 L of toluene, 6 mmol of triisobutylaluminium, 20 µmol of tetrakis-pentafluorophenylborate dimethylanilinium salt and 5 µmol of (1,2'-ethylene) (2,1'-ethylene)-bis(indene) hafnium dichloride, and the mixture was heated to 50° C. and the gas mixture of ethylene/propylene=10/100 was introduced until the total pressure became 7.0 kg/cm$^2$ G. During polymerization, the propylene was supplied using a pressure controller to keep a constant pressure, and after 3 hours the content was recovered and dried under reduced pressure to obtain a propylenic copolymer.

The copolymeric powder thus obtained was combined with the following additives and extruded by a kneader into a pellet.

1) Antioxidant

IRGANOX 1010 available from Ciba-geigy: 1000 ppm and,

IRGAPHOS 168 available from Ciba-geigy: 1000 ppm

2) Neutralizing agent . . . Calcium stearate: 1000 ppm

3) Anti-blocking agent . . . Silica-based agent: 1800 ppm

4) Slipping agent . . . Erucic acid amid: 500 ppm

A copolymer pellet thus obtained was examined for its resin characteristics by the method in Section (A) described above.

80 Parts by weight of the copolymer (A'-2) thus obtained was mixed thoroughly with 20 parts by weight of the propylenic polymer (B'-1) by a dry blender.

The propylenic resin thus obtained was formed into a film by the method similar to that in Section (B) described above except for setting the chill roll temperature at 60° C., and the film was qualified by the method in Section (C) described above. The results are shown in Table VII-6.

COMPARATIVE VII-2

A film was formed and evaluated by the method similar to that in Example VII-2 except for using only the component (A'-2) without using the component (B'). The results are shown in Table VII-6.

EXAMPLE VII-3

<Production of Copolymer (A)>
A 10 L stainless steel autoclave received 5.0 L of toluene, 6 mmol of triisobutylaluminium and 500 mL of 1-octene, and charged with 40 μmol of tetrakis-pentafluorophenylborate dimethylanilinium salt and 20 μmol of racemi-dimethylsilyl-bis-2-ethyl-4,5-benzoindenylzirconium dichloride and the mixture was heated to a propylene gas was introduced until the total pressure became 8.0 kg/cm² G whereby initiating polymerization. During polymerization, the propylene was supplied using a pressure controller to keep a constant pressure. After 3 hours, the content was recovered and dried under reduced pressure to obtain a copolymer.

The copolymeric powder thus obtained was combined with the following additives and extruded by a kneader into a pellet.

1) Antioxidant

IRGANOX 1010 available from Ciba-geigy: 1000 ppm and,

IRGAPHOS 168 available from Ciba-geigy: 1000 ppm

2) Neutralizing agent . . . Calcium stearate: 1000 ppm

3) Anti-blocking agent . . . Silica-based agent: 1800 ppm

4) Slipping agent . . . Erucic acid amid: 500 ppm

A copolymer pellet thus obtained was examined for its resin characteristics by the method in Section (A) described above.

<Production of Propylenic Polymer (B)>
The method similar to that for the propylenic polymer (B') in Example VII-1 was employed.

80 Parts by weight of the copolymer (A) thus obtained was mixed thoroughly with 20 parts by weight of the propylenic polymer (B) by a dry blender.

The propylenic resin thus obtained was formed into a film by the method similar to that in Section (B) described above and the film was qualified by the method in Section (C) described above. The results are shown in Table VII-6.

EXAMPLE VII-4

The propylenic polymer (B) was produced by the method similar to that for the propylenic polymer (B') in Example VII-1, except for adjusting the amounts of ethylene and hydrogen supplied so that the predetermined ethylene content and molecular weight were achieved in the main polymerization. The polymer (B) thus obtained had the ethylene content of 3.0% by mole, the % isotactic pentad of 99.2% by mole and the melt index of 8.5 g/10 min. In this example, analysis (gas chromatography) of the composition of the gas in the polymerization reactor during polymerization revealed that the ethylene concentration was 1.2% by mole and the hydrogen concentration was 4.3% by mole. Thereafter, the procedure similar to that in Example VII-3 was conducted except for changing the amounts of the copolymer (A) and the propylenic polymer (B), obtained above, into 90 parts by weight and 10% by weight, respectively. The results are shown in Table VII-6.

EXAMPLE VII-5

The method similar to that in Example VII-4 was employed except for setting the chill roll temperature at 60° C. upon film-forming. The results are shown in Table VII-6.

EXAMPLE VII-6

The copolymer (A) was produced by the method similar to that in Example VII-3 except for changing the amount of 1-octene from 500 mL to 300 mL, the polymerization temperature from 50° C. to 40° C. and using n-heptane instead of toluene with regard to the copolymer (A), and otherwise the procedure in Example VII-3 was followed entirely. The results are shown in Table VII-6.

EXAMPLE VII-7

The copolymer (A) was produced by the method similar to that in Example VII-3 except for using 500 mL of 1-dodecene instead of 1-octene, changing the polymerization temperature from 50° C. to 40° C. and using n-heptane instead of toluene with regard to the copolymer (A), and otherwise the procedure in Example VII-3 was followed entirely. The results are shown in Table VII-6.

EXAMPLE VII-8

The copolymer (A) was produced by the method similar to that in Example VII-3 except for using 500 mL of 1-decene instead of 1-octene, changing the polymerization temperature from 50° C. to 40° C. and using n-heptane instead of toluene with regard to the copolymer (A), and otherwise the procedure in Example VII-3 was followed entirely. The results are shown in Table VII-6.

COMPARATIVE EXAMPLE VII-3

The procedure similar to that in Example VII-3 was conducted except for using 45 parts by weight of the copolymer (A) produced in Example VII-3 and 55 parts by weight of the propylenic polymer (B) produced in Example VII-3. The results are shown in Table VII-6.

COMPARATIVE EXAMPLE VII-4

A film was formed at the chill roll temperature of 60° C. using only the copolymer (A) produced in Example VII-3 without using the propylenic polymer (B). As a result, the release from the chill roll was poor and a film having good appearance could not be obtained.

COMPARATIVE EXAMPLE VII-5

Except for setting the chill roll temperature upon film-forming at 30° C. similarly as in Example VII-3, the procedure similar to that in Comparative Example VII-4 was followed.

EXAMPLE VII-9

The copolymer (A) was produced by the method similar to that in Example VII-3 except for using 500 mL of 1-butene instead of 1-octene and using n-heptane instead of toluene with regard to the copolymer (A), and otherwise the procedure in Example VII-3 was followed entirely. The results are shown in Table VII-6.

EXAMPLE VII-10

Except for subjecting a propylenic resin obtained from the same amounts of the copolymer (A) instead of the copolymer (A'-2) produced in Example VII-2 and the propylenic polymer (B) instead of the propylenic polymer (B-1) used in Example VII-2 to the chill roll temperature of 30° C., the procedure similar to that in Example VII-2 was followed. The results are shown in Table VII-6.

REFERENCE EXAMPLE

A commercially available linear low density polyethylene (manufactured by IDEMITSU MORETEC V0398CN) was combined with the additives similarly as in Example VII-3, and evaluated similarly as in Example VII-3. The results are shown in Table VII-6.

TABLE VII-1

Assignments of signals of $^{13}$C—NMR of 1-octene/PP copolymer

| Number | Chemical shift | Assignment | |
|---|---|---|---|
| 1 | 46.0-47.6 | PP Sαα | |
| 2 | 43.8-44.4 | PO Sαα | |
| 3 | 42.3 | PPP Sαα | |
| 4 | 41.5 | OO Sαα | |
| 5 | 38.6 | PPP Tαγ | |
| 6 | 36.2 | C6 | |
| 7 | 36.0 | PPP Sαβ and PPP Tαβ | |
| 8 | 34.0 | O unit Tββ, | 2,1 insertion of propylene unit (indicated as PPP chain) |
| 9 | 32.2 | C3 | |
| 10 | 31.6 | PPP Tβγ | °     20 19 |
| 11 | 30.6 | PPP Sαβ | \|    \| \| |
| 12 | 30.2 | C4 | 10 - 7 - 11 - 5 - 7 - 3 |
| 13 | 28.2-29.8 | P unit Tββ | |
| 14 | 27.1 | C5 | Side chain methylene carbon of 1-octene unit |
| 15 | 22.9 | C2 | |
| 16 | 21.2-22.7 | Pββ | \| |
| 17 | 20.6-21.2 | Pββ | ° - 15 - 9 - 12 - 14 - 6 - • |
| 18 | 19.8-20.6 | Pββ | C2 C3 C4 C5 C6 \| |
| 19 | 17.6 | Pαβ | |
| 20 | 17.2 | Pαγ | ° methyl carbon, • methine carbon |
| 21 | 14.1 | Oββ | |

(NOTE)
P represents a propylene unit, and
P represents a reversed propylene unit,
O represents a 1-octene unit.
(NOTE)
A chemical shift is represented in ppm.

TABLE VII-2

Chemical shifts and assignments of signals used in calculation of α and P of 1-dodecene/PP copolymer

| Number | Chemical shift | Assignment |
|---|---|---|
| 1 | 46.0-47.6 | PP Sαα |
| 2 | 43.8-44.4 | PD Sαα |
| 3 | 42.3 | PPP Sαα |
| 4 | 41.5 | DD Sαα |
| 5 | 21.2-22.7 | Pββ |
| 6 | 20.6-21.2 | Pββ |
| 7 | 19.8-20.6 | Pββ |

(Note)
D represents a 1-dodecene unit.
(Note)
A chemical shift is represented in ppm.

TABLE VII-3

Chemical shifts and assignments of signals used in calculation of α and P of 1-decene/PP copolymer

| Number | Chemical shift | Assignment |
|---|---|---|
| 1 | 46.0-47.6 | PP Sαα |
| 2 | 43.8-44.4 | PD Sαα |
| 3 | 42.3 | PPP Sαα |
| 4 | 41.5 | DD Sαα |
| 5 | 21.2-22.7 | Pββ |

TABLE VII-3-continued

Chemical shifts and assignments of signals used in calculation of α and P of 1-decene/PP copolymer

| Number | Chemical shift | Assignment |
|---|---|---|
| 6 | 20.6-21.2 | Pββ |
| 7 | 19.8-20.6 | Pββ |

(Note) D represents a 1-dodecene unit.
(Note) A chemical shift is represented in ppm.

TABLE VII-4

Assignments of signals of 13C-NMR spectrum of ethylene/PP copolymer

| Number | Chemical shift | Assignment |
|---|---|---|
| 1 | 45.1-47.3 | PPP Sαα |
| 2 | 42.3 | PPP Sαα |
| 3 | 38.6 | PPP Tαγ |
| 4 | 38.0 | Sαγ |
| 5 | 37.5 | Sαδ |
| 6 | 36.0 | PPP Sαβ |
| 7 | 36.0 | PPP Tαβ |
| 8 | 34.9 | EPP, PEP Sαβ |
| 9 | 34.6 | EPP, PEP Sαβ |
| 10 | 34.1 | EPP Tγγ |
| 11 | 33.7 | EEPP Tγδ |
| 12 | 33.3 | EPE Tδδ |
| 13 | 31.6 | PPP Tβγ |
| 14 | 31.4 | EPP Tβγ |
| 15 | 31.0 | PPE Tβδ |
| 16 | 30.7 | PPP Sαβ |
| 17 | 30.5 | PEEE Sγδ |
| 18 | 30.0 | EEE Sδδ |
| 19 | 29.0 | PPP Tββ |
| 20 | 27.3 | PEE Sβδ |
| 21 | 24.6 | PEP Sαβ |
| 22 | 21.3-22.7 | Pββ |
| 23 | 20.6-21.3 | Pββ |
| 24 | 19.8-20.6 | Pββ |

TABLE VII-4-continued

Assignments of signals of 13C-NMR spectrum of ethylene/PP copolymer

| Number | Chemical shift | Assignment |
|---|---|---|
| 25 | 17.6 | Pαβ |
| 26 | 17.2 | Pαγ |

(Note) E represents an ethylene unit.
(Note) A chemical shift is represented in ppm.

TABLE VII-5

Assignments of signals of $^{13}$C-NMR spectrum of 1-butene/PP copolymer

| Number | Chemical shift | Assignment |
|---|---|---|
| 1 | 45.7-47.4 | PP Sαα |
| 2 | 43.0-44.9 | PB Sαα |
| 3 | 42.3 | PPP Sαα |
| 4 | 40.3 | BB Sαα |
| 5 | 38.6 | PPP Tαγ |
| 6 | 36.0 | PPP Sαβ and PPP Tαβ |
| 7 | 35.5 | B unit Tββ |
| 8 | 31.6 | PPP Tβγ |
| 9 | 30.6 | PPP Sαβ |
| 10 | 28.6-29.8 | P unit Tββ |
| 11 | 27.8-28.4 | B unit side chain methylene carbon |
| 12 | 21.2-22.7 | Pββ PPP(mm), PPB(mm), PBP(mm) |
| 13 | 20.6-21.2 | Pββ PPP(mr), PPB(mr), BPB(mr), PPB (rr), BPB(rr) |
| 14 | 19.8-20.6 | Pββ PPP(rr) |
| 15 | 17.6 | Pαβ |
| 16 | 17.2 | Pαγ |
| 17 | 11.1 | B unit side chain methyl carbon |

(NOTE) B denotes a 1-butene unit.
(NOTE) A chemical shift is represented in ppm.

TABLE VII-6

| | | Example 1 | Example 2 | Example 3 | Example 4 | Example 5 | Example 6 | Example 7 | Example 8 |
|---|---|---|---|---|---|---|---|---|---|
| Resin characteristics of copolymer A or A' | Comonomer type | 1-Butene | Ethylene | 1-Octene | 1-Octene | 1-Octene | 1-Octene | 1-Dodecene | 1-Decene |
| | α mol % | 0.9 | 8.7 | 4.0 | 4.0 | 4.0 | 3.2 | 3.8 | 4.4 |
| | [η] dl/g | 1.2 | 1.7 | 1.5 | 1.5 | 1.5 | 1.7 | 1.9 | 1.9 |
| | Tm °C. | 100.1 | 110.9 | 108.0 | 108.0 | 108.0 | 114.0 | 108.7 | 103.9 |
| | Tc °C. | 59.1 | 75.8 | 67.8 | 67.8 | 67.8 | 74.6 | 67.0 | 63.2 |
| | P mol % | 76.0 | 97.8 | 96.4 | 96.4 | 96.4 | 97.5 | 97.0 | 97.4 |
| | Tp °C. | 60.2 | 71.6 | 64.7 | 64.7 | 64.7 | 70.6 | 64.3 | 61.4 |
| | Wo wt % | 1.10 | 0.64 | 0.69 | 0.69 | 0.69 | 0.59 | 1.08 | 1.06 |
| | Wp wt % | 75.3 | 68.7 | 90.8 | 90.8 | 90.8 | 91.7 | 88.2 | 89.1 |
| | Mw/Mn | 2.1 | 2.0 | — | — | — | — | — | — |
| B or B' | Tm °C. | 165.9 | 165.9 | 165.9 | 150.6 | 150.6 | 165.9 | 165.9 | 165.9 |
| | Tc °C. | 117.0 | 117.0 | 117.0 | 106.9 | 106.9 | 117.0 | 117.0 | 117.0 |

| | | Example 1 | Example 2 | Example 3 | Example 4 | Example 5 | Example 6 | Example 7 | Example 8 |
|---|---|---|---|---|---|---|---|---|---|
| Ratio A/B | | 90/10 | 80/20 | 80/20 | 90/10 | 90/10 | 80/20 | 80/20 | 80/20 |
| Chill roll temperature ° C. | | 30 | 60 | 30 | 30 | 60 | 30 | 30 | 30 |
| Film performance | Heat seal temperature (HST: ° C.) | 105 | 110 | 102 | 100 | 103 | 108 | 101 | 100 |
| | Anti-blocking, Condition 1 (N/m$^2$) | 48 | 82 | 45 | 46 | 41 | 38 | 39 | 43 |
| | Anti-blocking, Condition 2 (N/m$^2$) | 23 | 45 | 24 | 26 | 21 | 19 | 20 | 24 |
| | Slipperiness tan θ | 0.35 | 0.39 | 0.26 | 0.21 | 0.19 | 0.38 | 0.29 | 0.31 |
| | Haze % | 1.9 | 1.8 | 1.0 | 1.1 | 1.6 | 1.5 | 1.2 | 1.0 |
| | Tensile modulus (TM: MPa) | 370 | 360 | 540 | 510 | 560 | 670 | 530 | 480 |

TABLE VII-6-continued

| | | | | | | | | | |
|---|---|---|---|---|---|---|---|---|---|
| TM ≧ 22xHST-1850 | ○ | ○ | ○ | ○ | ○ | ○ | ○ | ○ | |
| Moldability | No neck-in | No neck-in | No neck-in | No neck-in | No neck-in | No neck-in | No neck-in | No neck-in | |
| resence/absence of eutectic formation Tc ° C. | ○ 86.0 | ○ 104.7 | ○ 98.3 | ○ 96.2 | ○ 96.2 | ○ 103.8 | ○ 98.0 | ○ 94.2 | |

| | | Comparative Example 1 | Comparative Example | Comparative Example | Comparative Example | Comparative Example | Example 9 | Example 10 | Reference Example |
|---|---|---|---|---|---|---|---|---|---|
| Resin characteristics of copolymer A or A' | Comonomer type | 1-Butene | Ethylene | 1-Octene | 1-Octene | 1-Octene | 1-Butene | Ethylene | Commercially available LL |
| | α mol % | 0.9 | 8.0 | 4.0 | 4.0 | 4.0 | 9.0 | 8.7 | 4.1 |
| | [η] dl/g | 1.2 | 1.7 | 1.5 | 1.5 | 1.5 | 2.2 | 1.7 | 1.3 |
| | Tm ° C. | 100.1 | 110.9 | 108.0 | 108.0 | 108.0 | 121.9 | 110.9 | 102.7 |
| | Tc ° C. | 59.1 | 75.8 | 67.8 | 67.8 | 67.8 | 84.3 | 75.8 | 88.5 |
| | P mol % | 76 | 97.8 | 96.4 | 96.4 | 96.4 | 97.6 | 97.8 | — |
| | Tp ° C. | — | — | 64.7 | 64.7 | 64.7 | 79.1 | 71.6 | 69.3 |
| | Wo wt % | 2.0 | 0.64 | 0.69 | 0.69 | 0.69 | 0.34 | 0.64 | 2.64 |
| | Wp wt % | — | — | 90.8 | 90.8 | 90.8 | 86.8 | 68.7 | 57.4 |
| | Mw/Mn | 2.1 | 2.0 | — | — | — | 2.1 | 2.0 | — |
| B or B' | Tm ° C. | — | — | 165.9 | — | — | 165.9 | 165.9 | — |
| | Tc ° C. | — | — | 117.0 | — | — | 117.0 | 117.0 | — |

| | | Comarative Example 1 | Comarative Example 2 | Comarative Example 3 | Comarative Example 4 | Comarative Example 5 | Example 9 | Example 10 | Reference Example |
|---|---|---|---|---|---|---|---|---|---|
| Ratio A/B | | 100/0 | 100/0 | 45/55 | 100/0 | 100/0 | 80/20 | 80/20 | 100/0 |
| Chill roll temperature C. | | | | 30 | 60 | 30 | 30 | 30 | 30 |
| Film performance | Heat seal temperature (HST: ° C.) | — | — | 135 | — | 100 | 118 | 108 | 99 |
| | Anti-blocking, Condition 1 (N/m²) | — | — | 25 | — | 42 | 40 | 87 | 129 |
| | Anti-blocking, Condition 2 (N/m²) | — | — | 5 | — | 20 | 19 | 49 | 53 |
| | Slipperiness tan θ | — | — | 0.29 | — | 0.29 | 0.24 | 0.41 | 0.87 |
| | Haze % | — | — | 3.8 | — | 1.0 | 3.6 | 1.3 | 1.4 |
| | Tensile modulus (TM: MPa) | — | — | 900 | — | 490 | 600 | 310 | 110 |
| | TM ≧ 22xHST-1850 | — | — | x | — | ○ | x | x | x |
| | Moldability | Molding impossible | Molding impossible | No neck-in | Molding impossible | No neck-in | No neck-in | No neck-in | No neck-in |
| | resence/absence of eutectic formation Tc ° C. | — | — | ○ 114.3 | — | — | ○ 105.5 | ○ 104.7 | — |

(NOTE)
Anti-blocking ability
Condition 1: Fusing condition involving the temperature of 60° C., the duration of 3 hours and the load of 36 g/cm² G, Anti-blocking ability
Condition 2: Fusing condition involving the temperature of 50° C., the duration of 1 week and the load of 15 g/cm² G
(1) (2)Example 9, (3)Reference Example, (4)Resin characteristics of copolymer A or A', (5)Comonomer type, (6)B or B', (7), (8), (9), (10), (11)

[Eighth Invention]

The present invention is discussed specifically in the following examples.

Production Example 1

Synthesis of (dimethylsilylene) 2 (indene) 2

Under nitrogen flow, a 1 L three-necked flask receives 50 mL of THF and 2.5 g (41 mmol) of Mg. To this 0.1 mL of 1,2-dibromoethane is added and the mixture is stirred to activate Mg. After stirring for 30 minutes, the solvent is removed and 50 mL of THF is newly added. To this, a solution of 5.0 g (25.6 mmol) of 2-bromoindene in THF (200 mL) is added dropwise over 2 hours. After completion of the addition followed by stirring at room temperature for 2 hours followed by cooling to −78° C., a solution of 3.1 mL (25.6 mmol) of dichlorodimethylsilane in THF (100 mL) is added dropwise over 1 hour. After stirring for 15 hours, the solvent is evaporated off. The residue was extracted with 200 mL of hexane and the solvent was distilled off to obtain 6.6 g (24.2 mmol) of 2-chloromethylsilylindene (yield: 94%).

Under nitrogen flow, a 1 L three-necked flask receives 400 mL of THF and 8 g of 2-chloromethylsilylindene and the mixture is cooled to −78° C. To this, 38.5 mL (38.5 mmol) of a solution (1.0M) of LiN(trimethylsilylene)2 in THF is added dropwise. After stirring at room temperature for 15 hours, the solvent is distilled off and the residue is extracted with 300 mL of hexane. The solvent was distilled off to obtain 2.2 g (6.4 mmol) of (1,2'-dimethylsilylene)(2,1'-dimethylsilylene)(indene) 2 (yield: 33.4%). The results of $^1$H-NMR analysis (90 MHz, CDCl3) are as follows: δ−0.69, 0.73 (12H, dimethylsilylene), 3.66 (4H, —CH2-), 7.17 (8H, Ar—H).

EXAMPLE VIII-1

Synthesis of (Dimethylsilylene) 2 (Indenyl) 2 Zirconium Dichloride

A Schlenk's bottle receives 22.2 g (6.4 mmol) of (1,2'-dimethylsilylene)(2,1'-dimethylsilylene)(indene) 2 obtained above and 10 mL of ether. After cooling to −78° C. and adding 9.6 mL (15.4 mmol) of n-BuLi (1.6 M solution in hexane), the mixture is stirred for 12 hours at room temperature. The solvent is distilled off to obtain a solid which is washed with 20 mL of hexane to obtain a lithium salt quantitatively. This lithium salt is dissolved in 100 mL of toluene. A separate Schlenk's bottle receives 1.5 g (6.4 mmol) of zirconium tetrachloride and 100 mL of toluene. A 500 mL three-necked flask receives 100 mL of toluene, which is cooled to 0° C. To this, the lithium salt and zirconium tetrachloride in equal amounts are added dropwise using a cannula over 1 hour. After completion of the addition, the mixture is stirred at room temperature overnight. The solution is filtered, and the solvent in the filtrate is distilled off. The solid thus obtained was recrystallized from dichloromethane to give 1.2 g (2.4 mmol) of (1,2'-dimethylsilylene) (indenyl)2 zirconium dichloride (yield: 37%).

The results of $^1$H-NMR analysis (90 MHz, CDCl3) are as follows: δ 0.85, 1.08 (12H, dimethylsilylene), 7.18 (2H, —CH—), 7.2-7.4, 7.6-7.7 (8H, Ar—H).

EXAMPLE VIII-2

Synthesis of (dimethylsilylene)2(3-methylindenyl)2 zirconium dichloride

A Schlenk's bottle receives 2.2 g (6.4 mmol) of (1,2'-dimethylsilylene)(2,1'-dimethylsilylene)(indene)2 obtained above and 100 mL of ether. After cooling to −78° C. and adding 9.6 mL (15.4 mmol) of n-BuLi (1.6 M solution in hexane), the mixture is stirred at room temperature for 12 hours. The solvent is distilled off to obtain a solid, which is washed with 20 mL of hexane to obtain a lithium salt quantitatively. This lithium salt is dissolved in 100 mL of THF and cooled to −78° C. 7.4 g (52.0 mmol) of methyl iodide is added dropwise slowly and the mixture is stirred at room temperature for 12 hours. After distilling the solvent off followed by extraction with 50 mL of hexane, the solvent is removed to obtain 4.5 g (12 mmol) of (1,2'-dimethylsilylene)(2,1'-dimethylsilylene)(3-methylindene)2 (yield: 94%).

Subsequently, a Schlenk's bottle receives under nitrogen flow 2.0 g (5.4 mmol) of (1,2'-dimethylsilylene)(2,1'-dimethylsilylene)(3-methylindene)2 obtained above and 100 mL of ether. After cooling to −78° C. and adding 13.5 mL (21.6 mmol) of n-BuLi (1.6M solution in hexane), the mixture is stirred at room temperature for 12 hours. The solvent is distilled off to obtain a solid which was washed with hexane to obtain 1.1 g (2.9 mmol) of a lithium salt. This lithium salt is dissolved under nitrogen flow in 100 mL of toluene. The mixture is cooled to −78° C. and treated dropwise with a suspension of 0.7 g (3.0 mmol) of zirconium tetrachloride in toluene (100 mL) which has previously been cooled to −78° C. After completion of the addition, the mixture is stirred at room temperature for 6 hours. Thereafter, the mixture is filtered to obtain a filtrate, whose solvent is distilled off. Recrystallization from dichloromethane gave 0.5 g (0.94 mmol) of (1,2'-dimethylsilylene)(2,1'-dimethylsilylene)(3-methylindenyl) 2 zirconium dichloride (yield: 32%). The results of $^1$H-NMR analysis (90 MHz, CDCl3) are as follows: δ 0.90, 1.00 (12H, dimethylsilylene), 2.89 (6H, CH3), 7.2-7.7 (BH, Ar—H).

EXAMPLE VIII-3

Synthesis of (dimethylsilylene) 2)-3-n-butylindenyl) 2 zirconium dichloride

A Schlenk's bottle receives 0.83 g (2.4 mmol) of (1,2'-dimethylsilylene)(2,1'-dimethylsilylene)(indene)2 and 50 mL of ether. After cooling to −78° C. and adding 3.1 mL (5.0 mmol) of n-BuLi (1.6 M solution in hexane), the mixture is stirred at room temperature for 12 hours. The solvent is distilled off to obtain a solid, which is washed with 20 mL of hexane to obtain 1.1 g (2.3 mmol) of a lithium salt as an ether adduct. This lithium salt is dissolved in 50 mL of THF and cooled to −78° C. 0.57 mL (5.3 mmol) of n-butylbromide is added dropwise slowly and the mixture is stirred at room temperature for 12 hours. After distilling the solvent off followed by extraction with 50 mL of hexane, the solvent was removed to obtain 0.81 g (1.77 mmol) of (1,2'-dimethylsilylene) (2,1'-dimethylsilylene) (3-n-butylindene)2 (yield: 74%).

Subsequently, a Schlenk's bottle receives under nitrogen flow 0.81 g (1.77 mmol) of (1,2'-dimethylsilylene) (2,1'-dimethylsilylene) (3-n-butylindene)2 obtained above and 100 mL of ether. After cooling to −78° C. and adding 2.7 mL (4.15 mmol) of n-BuLi (1.54 M solution in hexane), the mixture is stirred at room temperature for 12 hours. The solvent is distilled off to obtain a solid which was washed with hexane to obtain 0.28 g (1.43 mmol) of a lithium salt as an ether adduct.

The lithium salt obtained above is dissolved under nitrogen flow in 50 mL of toluene. The mixture is cooled to −78° C. and treated dropwise with a suspension of 0.33 g (1.42 mmol) of zirconium tetrachloride in toluene (50 mL) which has previously been cooled to −78° C. After completion of the addition, the mixture is stirred at room temperature for 6 hours. Thereafter, the mixture is filtered to obtain a filtrate, whose solvent is distilled off. Recrystallization from dichloromethane gave 0.2 g (0.32 mmol) of (1,2'-dimethylsilylene)(2,1'-dimethylsilylene) (3-n-butylindenyl) 2 zirconium dichloride (yield: 22%).

The results of $^1$H-NMR analysis (90 MHz, CDCl3) are as follows: δ 0.88, 0.99 (12H, dimethylsilylene), 0.7-1.0, 1.1-1.5 (18H, n-Bu), 7.0-7.6 (8H, Ar—H).

EXAMPLE VIII-4

Synthesis of (1,2'-dimethylsilylene) (2,1'-dimethylsilylene)bis(indenyl) 2 zirconium (diphenylbutadiene)

0.2 g (0.40 mmol) of (1,2'-dimethylsilylene) (2,1'-dimethylsilylene)bis(indenyl) 2 zirconium dichloride and 0.09 g (0.42 mmol) of 1,4-diphenylbutadiene are combined with 20 mL of toluene. To this solution, 0.5 mL of n-BuLi (1.6 M solution in hexane) is added dropwise at −78° C. After completion of the addition, the solution is extracted with 50 mL of dichloromethane. The extract is concentrated to 10 mL, and cooled to 0° C. whereby obtaining 0.1 g of the desired product as a dark red solid (yield: 40%).

EXAMPLE VIII-5

A 1 L autoclave, which had been dried by heating, was charged under nitrogen flow at room temperature with 400 mL of toluene and 3 mmol of a methyl aluminoxane. After heating to 60° C. with stirring, 3 μmol of (1,2'-dimethylsilylene) (2,1'-dimethylsilylene) (3-methylindenyl)2 zirconium dichloride obtained in Example VIII-2 was added. Subsequently, the pressure was kept at 7 kg/cm$^2$ G with propylene to effect polymerization for 1 hour. After completion of the polymerization, the reaction product was poured into methanol-hydrochloric acid solution, stirred thoroughly and filtered, and then washed thoroughly with methanol, dried to obtain 35.0 g of an isotactic polypropylene. The polymer thus obtained had the melting point of 76.4° C., the intrinsic viscosity of 2.45 dl/g, the weight mean molecular weight Mw of 342,000, the molecular weight distribution Mw/Mn of 1.80 and the % meso-pentad [mmmm] of 40.7%.

A % meso-pentad was determined as a % area occupied by the signal at 21.8 ppm assigned to the pentad-meso based on the total area of the 9 signals appearing within the range from 19 to 22 ppm in 13C-NMR of the polymer.

A melting point was determined using the following device under the following conditions.

Instrument: DSC of Perkin Elmer 7 Series

Temperature raising rate: 10° C./min

Temperature range: −50° C. to 150° C.

An intrinsic viscosity [η] was determined at 135° C. in decalin.

A molecular weight and a molecular weight distribution were determined by a gel permeation chromatography (GPC) and represented as polystyrene.

Instrument: WATERS ALC/GPC150C

Column: TOSO, TSK HM+GMH6×2

Solvent: 1,2,4-trichlorobenzene

Flow rate: 1 mL/min

EXAMPLE VIII-6

A 1 L autoclave, which had been dried by heating, was charged under nitrogen flow at room temperature with 400 mL of toluene, 0.5 mmol of TIBA and 1 mmol of a methyl aluminoxane. After heating to 50° C. with stirring, 1 μmol of (1,2'-dimethylsilylene) (2,1'-dimethylsilylene) (3-n-butylindenyl)2 zirconium dichloride obtained in Example VIII-3 was added. Subsequently, the pressure was kept at 7 kg/cm$^2$ with propylene to effect polymerization for 1 hour. After completion of the polymerization, the reaction product was poured into methanol-hydrochloric acid solution, stirred thoroughly and filtered, and then washed thoroughly with methanol, dried to obtain 19.5 g of an isotactic polypropylene. The polymer thus obtained had the melting point of 71.5° C., the intrinsic viscosity of 3.18 dl/g, the weight mean molecular weight Mw of 499,000, the molecular weight distribution Mw/Mn of 1.97 and the % meso-pentad [mmmm] of 44.5%.

EXAMPLE VIII-7

The procedure similar to that in Example VIII-6 was followed except for setting the polymerization temperature at 40° C. to obtain 20.1 g of an isotactic polypropylene. The polymer thus obtained had the melting point of 69.9° C., the intrinsic viscosity of 6.05 dl/g, the weight mean molecular weight Mw of 914,000, the molecular weight distribution Mw/Mn of 1.95 and the % meso-pentad [mmmm] of 48.0%.

EXAMPLE VIII-8

The procedure similar to that in Example VIII-3 was followed except for using (1,2'-dimethylsilylene) (2,1'-dimethylsilylene) (indenyl) 2 zirconium dichloride instead of (1,2'-dimethylsilylene) (2,1'-dimethylsilylene) (3-methylindenyl)2 zirconium dichloride to obtain 30.0 g of an isotactic polypropylene. The polymer thus obtained had the melting point of 111.8° C., the intrinsic viscosity of 0.83 dl/g, the weight mean molecular weight Mw of 90,000, the molecular weight distribution Mw/Mn of 1.74 and the % meso-pentad [mmmm] of 66.1%.

COMPARATIVE EXAMPLE VIII-1

The procedure similar to that in Example VIII-3 was followed except for using (1,2'-dimethylsilylene) (2,1'-dimethylsilylene) (tetrahydroindenyl)2 zirconium dichloride instead of (1,2'-dimethylsilylene) (2,1'-dimethylsilylene) (3-n-butylindenyl) 2 zirconium dichloride to obtain 15.6 g of an isotactic polypropylene. The polymer thus obtained had the melting point of 116.0° C., the intrinsic viscosity of 0.17 dl/g, the weight mean molecular weight Mw of 15,000, the molecular weight distribution Mw/Mn of 1.7 and the % meso-pentad [mmmm] of 75.7%.

INDUSTRIAL APPLICABILITY

A propylenic polymer which has an excellent melt flowability, contains a less amount of stickiness-causing components, has a low modulus and is pliable, and is capable of providing a transparent molded article, thus being useful as a substitute for a pliable vinyl chloride resin and a composition thereof are thus provided. They are excellent also in terms of the heat seal performance at a low temperature, as well as the transparency and the rigidity.

What is claimed is:

1. A propylene homopolymer satisfying the following requirements (1) to (5):
    (1) the amount of the components which are dissolved out into hexane at 25° C. (H25) ranges from 0 to 80% by weight;
    (2) the melting temperature Tm and the heat of fusion ΔH(J/g) satisfy a relationship represented by the following formula:

$\Delta H \geq 3 \times (Tm-120)$;

(3) the meso-pentad fraction (mmmm (in percentage terms by mole)) ranges from 20 to 60% by mole;
    (4) the racemi-pentad fraction (rrrr) and (1-mmmm) satisfy a relationship represented by the following formula:

$[rrrr/(1-mmmm)] \leq 0.1$;

wherein the racemi-pentad fraction (rrrr) and the meso-pentad fraction (mmmm) are expressed as a decimal; and,
    (5) the amount of the components which are dissolved out at 25° C. or lower (W25) in temperature-raising chromatography ranges from 20 to 100% by weight.

2. A propylene homopolymer of claim 1 having a molecular weight distribution (Mw/Mn) determined by gel permeation chromatography (GPC) of 4 or less and/or an intrinsic viscosity [η] determined in tetralin solvent at 135° C. of 0.5 to 15.0 dl/g.

3. A copolymer of propylene and ethylene satisfying the following requirements (1) to (4):
    (1) the amount of the components which are dissolved out into hexane at 25° C. (H25) ranges from 0 to 80% by weight;
    (2) the melting point (Tm( °C.)) is 100° C. or less;
    (3) the stereoregularity index (P) determined by $^{13}$C-NMR ranges from 55 to 90% by mole;
    wherein said stereoregularity index (P), in % by mole, is obtained according to the following equation $P = Im/I \times 100$;

wherein Im and I are each represented as follows:

$Im = I(22)$, $I = I(22)+I(23)+I(24)-\{(I(8)+I(9))/2+I(10)+3/2 \times I(11)+I(12)+I(13)+I(15)\}$, wherein I(8), I(9), I(10), I(11), I(12), I(13), I(15), I(22), I(23) and I(24) represent the intensities of signal [8], [9], [10], [11], [12], [13], [15], [22], [23] and [24], respectively; and,
    (4) the amount of the components which are dissolved out at 25° C. or lower (W25) in temperature-raising chromatography ranges from 20 to 100% by weight.

* * * * *